US010786525B2

(12) United States Patent
Dobson

(10) Patent No.: US 10,786,525 B2
(45) Date of Patent: *Sep. 29, 2020

(54) METHOD FOR TREATING HAEMORRHAGE, SHOCK AND BRAIN INJURY

(71) Applicant: Hibernation Therapeutics, A KF, LLC, Camden, DE (US)

(72) Inventor: Geoffrey Phillip Dobson, Wulguru (AU)

(73) Assignee: HIBERNATION THERAPEUTICS A KF LLC, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/000,727

(22) Filed: Jan. 19, 2016

(65) Prior Publication Data
US 2016/0271161 A1 Sep. 22, 2016

Related U.S. Application Data

(63) Continuation-in-part of application No. PCT/AU2014/050130, filed on Jul. 17, 2014, and a continuation-in-part of application No. PCT/AU2014/050128, filed on Jul. 17, 2014, and a continuation-in-part of application No. PCT/AU2014/050133, filed on Jul. 17, 2014.

(30) Foreign Application Priority Data

Jul. 17, 2013 (AU) .................................. 2013902656
Jul. 17, 2013 (AU) .................................. 2013902657
Jul. 17, 2013 (AU) .................................. 2013902658
Jul. 17, 2013 (AU) .................................. 2013902659
Sep. 23, 2013 (AU) .................................. 2013903644

(51) Int. Cl.
*A01N 43/00* (2006.01)
*A01N 43/46* (2006.01)
*A61K 31/55* (2006.01)
*A61K 31/7076* (2006.01)
*A61K 31/167* (2006.01)
*A61K 45/06* (2006.01)
*A61K 9/00* (2006.01)
*A61K 31/519* (2006.01)
*A61K 31/7004* (2006.01)
*A61K 47/26* (2006.01)
*A61K 33/06* (2006.01)
*A61K 31/194* (2006.01)
*A61K 9/08* (2006.01)
*A61K 31/05* (2006.01)
*A61K 31/19* (2006.01)

(52) U.S. Cl.
CPC ........ *A61K 31/7076* (2013.01); *A61K 9/0019* (2013.01); *A61K 9/08* (2013.01); *A61K 31/05* (2013.01); *A61K 31/167* (2013.01); *A61K 31/19* (2013.01); *A61K 31/194* (2013.01); *A61K 31/519* (2013.01); *A61K 31/7004* (2013.01); *A61K 33/06* (2013.01); *A61K 45/06* (2013.01); *A61K 47/26* (2013.01)

(58) Field of Classification Search
None
See application file for complete search history.

(56) References Cited

U.S. PATENT DOCUMENTS

| 3,795,581 | A | | 3/1974 | Brake |
|---|---|---|---|---|
| 4,112,070 | A | | 9/1978 | Harmening |
| 4,798,824 | A | | 1/1989 | Belzer et al. |
| 4,968,675 | A | * | 11/1990 | Su .................. A61K 9/0019 |
| | | | | 514/176 |
| 5,006,512 | A | | 4/1991 | Ohnishi |
| 5,145,771 | A | | 9/1992 | Lemasters et al. |
| 5,206,222 | A | | 4/1993 | Forman et al. |
| 5,256,770 | A | | 10/1993 | Glaser et al. |
| 5,370,989 | A | | 12/1994 | Stern et al. |
| 5,407,793 | A | | 4/1995 | Del Nido et al. |
| 5,432,053 | A | | 7/1995 | Berdyaev et al. |
| 5,514,536 | A | | 5/1996 | Taylor |
| 5,656,420 | A | | 8/1997 | Chien |
| 5,679,706 | A | | 10/1997 | D'Alonzo et al. |
| 5,693,462 | A | | 12/1997 | Raymond |

(Continued)

FOREIGN PATENT DOCUMENTS

| CN | 1176738 A | 3/1998 |
|---|---|---|
| CN | 101019529 A | 8/2007 |

(Continued)

OTHER PUBLICATIONS

Ar-Rajab, et al., "Improved Liver Preservation for Transplantation Due to Calcium Channel Blockade", Transplantation, 51(5):965-967, May 1991.

Beyersdorf, F., "The use of controlled reperfusion strategies in cardiac surgery to minimize ischaemia/reperfusion damage" Cardiovascular Research, 83, 262-268 (2009).

Brett, CL et al., "Evolutionary origins of eukaryotic sodium/proton exchangers" Am J Physiol Cell Physiol, 288, C223-C239 (2005).

Canyon, SJ, et al., "Protection Against Ventricular Arrhythmias and Cardiac Death Using Adenosine and Lidcaine During Regional Ischemia in the in Vivo Rat," Am J. Physiol Heart Circ Physiol 287:H1286-H1295; American Physiological Society 2004.

(Continued)

*Primary Examiner* — Layla Soroush
(74) *Attorney, Agent, or Firm* — Keith Haddaway; Miguel A. Lopez; Venable LLP

(57) ABSTRACT

The invention relates to a composition and method for increasing blood pressure, including a low pain or analgesic state or hypotensive anaesthesia in a subject that has suffered a life threatening hypotension or shock or reducing hypofusion in the whole body of a subject. The composition comprises (i) a compound selected from at least one of a potassium channel opener, a potassium channel agonist and an adenosine receptor agonist; and (ii) an antiarrhythmic agent or a local anaesthetic.

6 Claims, 44 Drawing Sheets

(56) References Cited

U.S. PATENT DOCUMENTS

| | | | |
|---|---|---|---|
| 5,939,394 | A | 8/1999 | Fleming et al. |
| 6,011,017 | A | 1/2000 | Marangos et al. |
| 6,187,756 | B1 | 2/2001 | Lee et al. |
| 6,358,208 | B1 | 3/2002 | Lang et al. |
| 6,372,723 | B1 | 4/2002 | Martin et al. |
| 6,569,615 | B1 | 5/2003 | Thatte et al. |
| 6,586,413 | B2 | 7/2003 | Liang et al. |
| 6,921,633 | B2 | 7/2005 | Baust et al. |
| 6,955,814 | B1 | 10/2005 | Dobson |
| 6,992,075 | B2 | 1/2006 | Hill et al. |
| 7,223,413 | B2 | 5/2007 | Dobson |
| 7,749,522 | B2 | 7/2010 | Dobson |
| 2001/0041688 | A1 | 11/2001 | Waeber et al. |
| 2003/0060415 | A1 | 3/2003 | Hung |
| 2003/0216775 | A1 | 11/2003 | Hill et al. |
| 2004/0229780 | A1 | 11/2004 | Olivera |
| 2005/0176763 | A1 | 8/2005 | Boy et al. |
| 2006/0034941 | A1 | 2/2006 | Dobson |
| 2009/0198145 | A1 | 8/2009 | Chow |
| 2013/0122108 | A1 | 5/2013 | Matheny |

FOREIGN PATENT DOCUMENTS

| | | |
|---|---|---|
| CN | 101496512 A | 8/2009 |
| CN | 102726366 A | 10/2012 |
| DE | 39 26 287 A1 | 2/1991 |
| GB | 2 436 255 A | 9/2007 |
| JP | 09-151134 | 10/1997 |
| SU | 0878297 A1 | 11/1981 |
| WO | WO-92/20346 A1 | 11/1992 |
| WO | WO-98/37886 A1 | 9/1998 |
| WO | WO-00/03716 A1 | 1/2000 |
| WO | WO-00/24378 A1 | 5/2000 |
| WO | WO-00/056145 A1 | 9/2000 |
| WO | WO-2001/045684 | 6/2001 |
| WO | WO-01/54679 A2 | 8/2001 |
| WO | WO-01/82914 A2 | 11/2001 |
| WO | WO-03/063782 A2 | 8/2003 |
| WO | WO-03/088978 A1 | 10/2003 |
| WO | WO-2004/000331 A1 | 12/2003 |
| WO | WO-2004/056180 A1 | 7/2004 |
| WO | WO-2004/056181 A1 | 7/2004 |
| WO | WO-2004/060286 A2 | 7/2004 |
| WO | WO-2004/108666 A2 | 12/2004 |
| WO | WO-2006/069170 A2 | 6/2006 |
| WO | WO-2007/030198 A2 | 3/2007 |
| WO | WO-2007/137321 A1 | 12/2007 |
| WO | WO-2008/011670 A1 | 1/2008 |
| WO | WO-2008/040094 A1 | 4/2008 |
| WO | WO-2008/106724 A1 | 9/2008 |
| WO | WO-2009/012534 A1 | 1/2009 |
| WO | WO-2011/075391 A1 | 6/2011 |

OTHER PUBLICATIONS

Canyon, SJ, et al., "Pretreatment with an Adenosine Al Receptor Agonist and Lidocaine: A Possible Alternative to Myocardial Ischemic Preconditioning," The Journal of Thoracic and Cardiovascular Surgery, vol. 130, No. 2, pp. 371-377, 2005.

Canyon, SJ, et al., "The Effect of Adenosine and Lidocaine Infusion on Myocardial High-Energy Phosphates and pH During Regional Ischemia in the Rat Model in vivo", Canadian Journal of Physiology and Pharmacology, vol. 84, 903-912, Oct. 18, 2006.

Chien, S, et al., "Extension of Tissue Survival Time in Multiorgan Block Preparation With a Delta Opioid DADLE (D-Ala2, D-Leu5)-enkephalin)," The Journal of Thoracic and Cardiovascular Surgery, 107:965967, 1994.

Corvera, JS, et al., "Polarised Arrest With Warm or Cold Adenosine/Lidocaine Blood Cardioplegia is Equivalent to Hypothermic Potassium Blood Cardioplegia," The Journal of Thoracic and Cardiovascular Surgery, 129(3):599-606, May 2005.

Das, et al., "Myocardial preservation during cardiac surgery", Annals of Cardiac Anaesthesia, vol. 5, pp. 25-32, 2002.

Dobson, G.P., "Organ Arrest, Protection and Preservation: Natural Hibernation to Cardiac Surgery," Comparative Biochemistry and Physiology, 139 (Part B):469-485; Elsevier Inc., 2004.

Dobson, G.P., et al., "Adenosine and Lidocaine: A New Concept in Nondepolarizing Surgical Myocardial Arrest, Protection and Preservation," The Journal of Thoracic and Cardiovascular Surgery 127:794-805, Mar. 2004.

Ely, S.W., et al., "Protective Effects of Adenosine in Myocardial Ischemia", Circulation, 85(3): 893-904, Mar. 1992.

Forman, et al., "Mechanisms and Therapy of Myocardial Reperfusion Injury". Circulation, 81(3 Suppl):IV69-78, Mar. 1990.

Forman, et al., "Adenosine Therapy at Reperfusion on Myocardial Infarct Size," Cardiovascular Research, 33:497-498, 1997.

Garratt, et al., "Intravenous Adenosine and Lidocaine in Patients with Acute Myocardial Infarction," American Heart Journal, 136(2): 196-204, Aug. 1998.

Goto, et al., "Adenosine Infusion During Early Reperfusion Failed to Limit Myocardial Infarct Size in a Collateral Deficient Species" Cardiovascular Research, 25(11):943-9, Nov. 1991.

Granger, C.B., "Adenosine for Myocardial Protection in Acute Myocardial Infarction", The American Journal of Cardiology, 79(12A): 44-48, Jun. 1997.

Hearse, et al., "Protection of the Myocardium during ischemic arrest," J. Thorac. Cardiovasc. Surg., vol. 81, No. 6, pp. 873-879, 1981.

Hicks, et al., "ATP-Sensitive Potassium Channel Activiation Mimics the Protective Effect of Ischaemic Preconditioning in the Rat Isolated Working Heart After Prolonged Hypothermic Storage," Clinical and Experimental Pharmacology and Physiology 26:20-25, 1999.

Homeister, et al., "Combined Adenosine and Lidocaine Administration Limits Myocardial Reperfusion Injury," Circulation, 82(2):595-608, Aug. 1990.

Huang, T.F., "Drug Effects on the Ischemia- and Reperfusion-induced Arrhythmias in the Conscious Rats", Chinese Journal of Physiology 35(1): 9-19,1992.

International Preliminary Examination Report, dated Mar. 5, 2001, issued in related International Application No. PCT/AU00/00226.

International Preliminary Examination Report, dated Oct. 12, 2004, issued in related International Application No. PCT/AU2003/000771.

International Preliminary Report on Patentability, dated Dec. 3, 2008, issued in related International Application No. PCT/AU2006/000717.

International Preliminary Report on Patentability, dated Jan. 27, 2009, issued in related International Application No. PCT/AU2007/001029.

International Preliminary Report on Patentability, dated Sep. 8, 2009, issued in related International Application No. PCT/AU2008/000289.

International Preliminary Report on Patentability, dated Jan. 26, 2010, issued in related International Application No. PCT/AU2008/001086.

International Search Report dated Jun. 9, 2000, issued in related International Application No. PCT/AU00/00226.

International Search Report dated Aug. 4, 2003, issued in related International Application No. PCT/AU03/00771.

International Search Report dated Feb. 13, 2004, issued in related International Application No. PCT/AU2003/001710.

International Search Report dated Feb. 13, 2004, issued in related International Application No. PCT/AU2003/001711.

International Search Report dated Jul. 21, 2006, issued in related International Application No. PCT/AU2006/000717.

International Status Report, dated Sep. 25, 2007, issued in related International Application No. PCT/AU2007/001029.

International Search Report, dated May 7, 2008, issued in related International Application No. PCT/AU2008/000289.

International Search Report dated Sep. 25, 2008, issued in related International Application No. PCT/AU2008/001086.

Jakosben, et al., "Adenosine instead of supranormal potassium in cardioplegic solution improves cardioprotection," European Journal of Cardio-thoracic Surgery, vol. 32, pp. 493-500, 2007.

(56) References Cited

OTHER PUBLICATIONS

Jakosben, et al., "Adenosine instead of supranormal potassium in cardioplegic solution preserves endothelium-derived hyperpolarization factor-dependent vasodilation", European Journal of Cardiothoracic Surgery, vol. 33, pp. 18-24, 2008.

Jayawant, et al., "Advantages of Continuous Hyperpolarized Arrest with Pinacidil Over St. Thomas' Hospital Solution During Prolonged Ischemia," J. Thoracic and Cardiovascular Surgery, 11(1): 131-138, 1998.

Jayawant, Am et al "Potassium-channel opener cardioplegia is superior to St. Thomas' solution in the intact animal" Ann Thorac Surg, 68, 67-74 (1999).

Jin, et al, "The myocardial protective effects of a moderate-potassium adenosine-lidocaine cardioplegia in pediatric cardiac surgery", The Journal of Thoracic and Cardiovascular Surgery, vol. 136, No. 6, pp. 1450-1455, 2008.

Karck, M., et al, "Myocardial protection by ischemic preconditioning and -opioid receptor activation in the isolated working rat heart" The Journal of Thoracic and Cardiovascular Surgery, 122, 986-992 (2001).

Kinoshita, H., et al "Mild alkalinisation and acidification deifferentially modify the effects of lidocaine or mexiletine on vasorelaxation mediated by ATP-sensitive K+ channels" Anesthesiology, 95, 200-206 (2001).

Kusano T. et al., "Organ Preserving Effect of lidocaine Administration in the Model of Orthopic Liver Transplantation from Non-heart Beating Donors", Transplantation Proceedings, 28(3): 1928-1929, Jun. 1996.

Lee et al., "Retrograde infusion of liocaine or L-arginine before reperfusion reduces myocardial infarct size", Ann. Thorac. Surg 65:1353-1359, 1998.

Mahaffey, et al., "Adenosine as an Adjunct to Thrombolytic Therapy for Acute Myocardial Infarction," JACC 34(6): 1711-20, Nov. 1999.

Neely, et al., "A1 Adenosine Receptor Antagonist Block lschemia-reperfusion Injury of the Heart", Circulation, Supplement 94(9):11376-11380, 1996, abstract.

O'Rullian, et al., "Excellent Outcomes in a Case of complex Re-do Surgery Requiring Prolonged Cardioplegia Using a New Cardioprotective Approach: Adenocaine," The Journal of ExtraCorporeal Technology, vol. 40, pp. 203-205, 2008.

Rogriguez-Reynoso, et al "Effect of exogenous melatonin on hepatic energetic status during ischemia/reperfusion: possible role of tumor necrosis factor-a and nitric oxide" J Surgical Research, 100(2), 141-149 (2001).

Rudd, DM, et al. "Toward a New Cold and Warm Nondepolarizing, Normokalemic Arrest Paradigm for Orthotopic Heart Transplantation", Journal of Thoracic and Cardiovascular Surgery, 137(1): 198-207, Jan. 2009.

Schubert, et al., "Adenosine cardioplegia," J. Thorac. Cardiovasc. Surg., vol. 98, No. 6, pp. 1057-1065, 1989.

Segal, et al., "On the Natriuretic Effect of Verapamil: Inhibition of EnaC and Transephithelial Sodium Transport", Am J. Physiol Renal Physiol, 283: F765-F770, 2002.

Sigg, et al "Role of d-opioid receptor agonists on infarct size reduction in swine" Am. J. Physiol. Heart Circ. Physiol, 282, H1953-H1960 (2002).

Silber, et al "A rapid hemodynamic monitor of acute ischemia during cardiac procedures: changes in relaxation via a continuous left ventricular pressure-derivative loop" J Surg Res, 134(1), 107-113 (2006) with Medline entry Acc No. 2006367738.

Sloots, K, et al, "Warm nondepolarizing adenosine and lidocaine cardioplegia: Continuous versus intermittent delivery," The Journal of Thoracic and Cardiovascular Surgery, vol. 133, No. 5, pp. 1171-1178. 2007.

Su, T-P., "Delta Opioid Peptide [D-Ala2, D-Leu5] Enkephalin Promotes Cell Survival," J. Biomed. Sci., 7:195-199, 2000.

Sultan, et al., "Heart Preservation: Analysis of Cardioprotective Infusate Characteristics, Membrane Stabilization, Calcium Antagonism, and Protease Inhibition on Myocardial Viability: A Biochemical, Ultrastructural, Functional Study," The Journal of Heart and Lung Transplantation 11(4):607-18, 1992.

Takeuchi, et al. "Prolonged Preservation of the Blood-Perfused Canine Heart with Glycolysis-Promoting Solution," Ann Thorac Surgery 68:903-7, 1999.

Thourani Vinod H et al: "Myocardial protection with adenosine given at reperfusion is superior to adenosine-enhanced cardioplegia", Circulation, vol. 98, No. 17 Supply., Oct. 27, 1998 (Oct. 27, 1998), p. 1612, XP009177883, & 71st Scientific Sessions of the American Heart Association, Dallas, Texas, USA; Nov. 8-11, 1998 ISSN: 009-7322.

Ulusal, et al., "The Effect of A2a Adenosine Receptor Agonist on Composite Tissue Allotransplant Survival: An In Vitro Preliminary Study", J. Surgical Research 131: 261-266, 2006.

Vander Heide, et al., "Adenosine Therapy at Reperfusion and Myocardial Infarct Size," Cardiovascular Research, 33:499-500, 1997.

Vinten-Johansen, J., et al. "Preconditioning and postconditioning: innate cardioprotection from ischemia-reperfusion injury." Journal of Applied Physiology, 103(4). pp. 1441-1448, 2007.

Wu, et al., "Mechanism of cardiac protection by preconditioning and postconditioning for hypoxia-reoxygenation injury is different" Jpn J Physiol, 54, S96, item 127 (2004).

Bryland et al "Citrate treatment reduces endothelial death and inflammation under hyperglycaemic conditions" Diabetes and Vascular Disease Research 9(1) 42-51 2011.

Djabir, Y, et al., "60 Minutes of Cardiac Rescue and Stabilization with a Small Intravenous Bolus of Adenocaine Following 8 Minutes of Asphyxial Hypoxia in the Rat in Vivo: Effect of Therapeutic Hypothermia." Circulation, 124 (21 Supplement). p. 1, 2011.

Djabir, Y, et al., "Adenosine, Lidocaine, and Mg2+ (ALM) Increases Survival and Corrects Coagulopathy After Eight-Minute Asphyxial Cardiac Arrest in the Rat." Shock, 40(3):222-32, Sep. 2013.

Dobson GP & Jones MW "Adenosine and Lignocaine: a New Concept in Cardiac Arrest and Preservation" Ann Thorac Surg 75 S746 (Abstract) 2003.

Dobson, G.P., "Membrane polarity: A target for myocardial protection and reduced inflammation in adult and pediatric cardiothoracic surgery," The Journal of Thoracic and Cardiovascular Surgery, vol. 140, No. 6, pp. 1213-1217, 2010.

Dobson, G.P., "Bloody Battle" Australian Science, pp. 14-16, Sep. 2011.

Dobson, G.P., "Small animal model species are not created equal." Critical Care Medicine, 40 (2). p. 711, 2012.

Dobson, G.P., "Hyperkalemic cardioplegia for adut and pediatric surgery: end of an era?", Front Physiol. Aug. 28;4:228. Review, 2013.

Dobson GP "Addressing the global burden of trauma in major surgery" Fontiers in Surgery 2(43) 1-26 Sep. 2015.

Dobson GP & Letson HL "Adenosine, lidocaine, and Mg2+ (ALM): From cardiac surgery to combat casualty care—Teaching old drugs new tricks" J Trauma Acute Care Surg 80(1) 135-145 2015.

Donohue DM et al "Erythrocyte Preservation. VI The storage of blood with purine nucleosides" Journal of Clinical Investigation 562-567 May 1956.

Fukihiro Y et al "Cardioplegic strategies for calcium control Low Ca2 , High Mg2 , Citrate, or Na /H Exchange Inhibitor HOE-642" Circulation 102:III319-III325 2000.

Gao et al Journal of Huazhong University of Science and Technology [Med Sci] 2003; 23(4): 407-410.

Giangrande PLF "The history of blood transfusion" British Journal of Haematology 110 758-767 2000.

Granfeldt, A., et al. "Resuscitation with adenocaine and magnesium reduces fluid requirement and improves cardiac function following 72% blood loss in the pig." Circulation 124 (21 Supplement). p. 1, 2011.

Granfeldt, A., et al., "Adenocaine and Mg2+ reduce fluid requirement to maintain hypotensive resuscitation and improve cardiac and renal function in a porcine model of severe hemorrhagic shock" Crit Care Med, 40(11), 3013-3025, (2012).

Gross G.J and Peart J.N. "Opioids and myocardial reperfusion injury" Archives des Maladies du cœur et des vaissaeux, tome 100, No. 3, Mar. 2007.

(56) References Cited

OTHER PUBLICATIONS

Hammon, JW, "Why change?", The Journal of Thoracic and Cardiovascular Surgery 140:1218-1219, 2010.
International Preliminary Report on Patentability, dated Jan. 19, 2016, issued in related International Application No. PCT/AU2014/050132.
International Preliminary Report on Patentability, dated Jan. 19, 2016, issued in related International Application No. PCT/AU2014/050128.
International Preliminary Report on Patentability, dated Jan. 19, 2016, issued in related International Application No. PCT/AU2014/050130.
International Preliminary Report on Patentability, dated Jan. 19, 2016, issued in related International Application No. PCT/AU2014/050131.
International Preliminary Report on Patentability, dated Jan. 19, 2016, issued in related International Application No. PCT/AU2014/050133.
International Search Report dated Sep. 25, 2014, issued in related International Application No. PCT/AU2014/050132.
International Search Report dated Sep. 10, 2014, issued in related International Application No. PCT/AU2014/050128.
International Search Report dated Sep. 24, 2014, issued in related International Application No. PCT/AU2014/050130.
International Search Report dated Sep. 16, 2014, issued in related International Application No. PCT/AU2014/050131.
International Search Report dated Sep. 16, 2014, issued in related International Application No. PCT/AU2014/050133.
Kato R et al "Fentanyl protects the heart against ischaemic injury via opioid receptors, adenosine A1 receptors and KATP channel linked mechanisms in rats" British Journal of Anaesthesia 84(2):204-14 2000.
Letson, H.L., & Dobson G.P. "Ultra-small intravenous bolous of 7.5% NaCl/Mg2+ with adenosine and lidocaine improves early rescusctation outcome in the rat after severe hemorrhagic shock in vivo." Journal of Trauma, 71(3). pp. 708-719, 2011.
Letson, H.L., & Dobson G.P., "Small vol. 7.5% NaCl with 6% dextran-70 or 6% and 10% hetastarch are associated with arrhythmias and death after 60 minutes of severe hemorrhagic shock in the rat in vivo." Journal of Trauma, 70(6), pp. 1444-1452, 2011.
Letson, H.L., & Dobson G.P, "Unexpected 100% survival following 60% blood loss using small-vol. 7.5% NaCl with Adenocaine and Mg2+ in the rat model of extreme hemorrhagic shock." Shock, 36(6). pp. 586-594, 2011.
Letson, H.L., et al. "Reversal of acute coagulopathy using small-volume 7.5% NaCl with adenocaine and Mg2+ resuscitation in a rat model of severe hemorrhagic shock." Circulation, 124 (21 Supplement). p. 1, 2011.
Letson, H.L., et al "Reversal of acute coagulopathy during hypotensive resuscitation using small-volume 7.5% NaCl adenocaine and Mg2+ in the rat model of severe hemorrhagic shock." Critical Care Medicine, 40(8). pp. 2417-2422, 2012.
Letson, H.L., & Dobson, G.P., "Acute coagulopathy of trauma in the rat." Shock 39: 440-446, 2013.
McAllister et al (Abstract), "Abstract 1419: Ischemic Postconditioning Against Ischemia/Reperfusion Injury Beyond the Myocardium" American Heart Association, Inc., Circulation 2006, 114:11_271, 231-2237.
Morabito S et al "Regional citrate anticoagulation in cardiac surgery patients at high risk of bleeding: a continuous veno-venous hemofiltration protocol with a low concentration citrate solution" Critical Care 16:R111 2012.
Morabito S et al "Continuous venovenous hemodiafiltration with a low citrate dose regional anticoagulation protocol and a phosphate-containing solution: effects on acid-base status and phosphate supplementation needs" BMC Nephrology 14:232 2013.
Noera G " When and why CDP in continous warm blood cardioplegia?" Ann Thorac Surg 56:1214-20 1993.
O'Neill LAJ "A critical role in citrate metabolism in LPS signalling" Biochem J 439 e5-e6 2011.

Onorati F "Polarizing microplegia improves cardiac cycle efficiency after CABG for unstable angina" International Journal of Cardiology 167: 2739-2746 2013.
Patel NN et al "Phosphodiesterase-5 Inhibition Prevents Postcardiopulmonary Bypass Acute Kidney Injury in Swine" Ann Thorac Surg 92:2168-76 2011.
Rosenkranz ER & Buckberg GD "Myocardial protection during surgical coronary reperfusion" J Am Coll Cardiol 1(5)1235-46 1983.
Rudd, DM, et al., "Early reperfusion with warm, polarizing adenosine-lidocaine cardioplegia improves functional recovery after 6 hours of cold static storage," The Journal of Thoracic and Cardiovascular Surgery, vol. 141, No. 4, pp. 1044-1055, 2011.
Rudd, D.M., & Dobson, G.P., "Eight hours of cold static storage with adenosine and lidocaine (Adenocaine) heart preservation solutions: towards therapeutic suspended animation." Journal of Thoracic and Cardiovascular Surgery, 142(6). pp. 1552-1561, 2011.
Sawynok J et al "Antidepressants as analgesics: an overview of central and peripheral mechanisms of action" Journal of Psychiatry & Neuroscience 26(1): 21-29 Jan. 2001.
Shi "The novel non-depolarizing, normokalemic cardioplegia formulation based on the combination of adenosine-lidocaine (Adenocaine™) exerts superior anti-neutrophil effects by synergistic actions of its components" FASEB J lb548 (Abstract) 2010.
Shi, W, et al., "The nondepolarizing, normokalemic cardioplegia formulation adenosine-lidocain (adenocaine) exerts anti-neutrophil effects by synergistic actions of its components." The Journal of Thoracic and Cardiovascular Surgery, 143(5), pp. 1167-1175, 2012.
Sloots, K., & Dobson G., "Normokalemic adenosine-lidocaine cardioplegia: importance of maintaining a polarized myocardium for optimal arrest and reanimation." Journal of Thoracic and Cardiovascular Surgery, 139(6). pp. 1576-1586, 2010.
STN File CAplus Abstact 147:317797. (Abstract of CN1176728 (Zheng) 1998).
STN File CAplus Abstract 132:242003. (Abstract of CN101019529 (Sun) 2007).
Vinten-Johansen J et al "Polarized arrest with adenosine-lidocaine blood cardioplegia: A new paradigm in myocardial protection" Journal of Molecular and Cellular Cardiology 35:A7 (Abstract) 2003.
Vinten-Johansen, J., & Dobson G.P., "Adenosine-procaine cardioplegia and adenosine-lidocaine cardioplegia: Two sides of the same coin?" J Thorac Cardiovasc Surg. Jun.: 145(6): 1684-5, 2013.
Vinten-Johansen, J., "Adenosine-lidocaine-magnesium non-depolarizing cardioplegia: Moving forward from bench to bedside" International Journal of Cardiology, (2012).
Granfeldt, A.: "Organ dysfunction following regional and global ischemia/reperfusion. Intervention with Postconditioning and Adenocaine", Danish Medical Journal, vol. 59, No. 8, p. B4496, ZP055308455 (Aug. 2012).
Joao et al., "Immediate post-operative care following cardiac surgery," Jornal de Pediatria, vol. 79, Supl2, pp. S213-5222 (2003).
Joyce K. Lee-Iannotti et al.: "New-onset Atrial Fibrillation in Severe Sepsis and Risk of Stroke and Death", Neurologist, vol. 18, No. 4, pp. 239-243 (Jul. 1, 2012).
Karnatovskia et al., "Sepsis: A Review for the Neurohospitalist," The Neurohospitalist, 2(4): pp. 144-153 (2012).
LaRosa, "Sepsis," Cleveland Clinic, Center for Continuing Eduation, published Aug. 2010 (13 pages), (http://www.clevelandclinicmeded.com/medicalpubs/diseasemanagement/infectious-disease/sepsis).
Ozkan Candan et al.: "Aorto-right atrial fistula secondary to infective endocarditis presenting with cardiogenic shock", Journal of Cardiovascular Medicine, vol. 13, No. 1, pp. 65-67 (Jan. 1, 2012).
Schmidt et al., "Influence of Lidocaine on Endotoxin-induced Leukocyte-Endothelial Cell Adhesion and Macromolecular Leakage in Vivo," Anesthesiology, (87): pp. 617-624 (1997).
Toledo, "Life After Traumatic Injury: How the Body Responds," National Institutes of Health, Sep. 2012 (3 pp.), (http://www.livescience.com/23415-life-after-traumatic-injury-how-the-body-responds.html).
Rizzon, P. et al. "Class 1B agents lidocaine, mexiletine, tocainide, phenytoin", European Heart Journal (1987) 8 (Supplement A), 21-25.

(56) References Cited

OTHER PUBLICATIONS

Lanshen et al., "Assay, Analysis and Comparison of Potassium Salt in Cardiac Arrest Solution", 1998, pp. 95-96 (copy of original article in Chinese provided as well as English translation).

Beutler et al., "The Storage of Hard-Packed Red Blood Cells in Citrate-Phosphate_Dextrose (CPD) and CPD-Adenin (cpda-1)", Blood, vol. 54, No. 1, Jul. 1979, pp. 280-284.

Jesperson et al., "Femoral Arterial and Venous Catheterization for Blood Sampling, Drug Administration and Conscious Blood Pressure and Heart Rate Measurements," (Published Jan. 24, 2012) Journal of Visualized Experiments, 59(e3496):1-8.

Luo et al., "Vascular Catheter Locking Solutions in Rats: Sodium Citrate as an Alternative to Heparin," Charles River Laboratories Informational poster from AALAS, San Antonio, TX (Oct. 2014).

"Removal of Blood from Laboratory Mammals and Birds, First Report of the BVA/FRAME/RSPCA/UFAW Joint Working Group on Refinement," (1993) Laboratory Animals 27:1-22.

\* cited by examiner

Figure 8 : Inducing a pulseless electrical activity (PEA) State and Whole body arrest following 60 min Severe Shock in the Rat (~40% blood loss): HR = heart rate. MAP = mean arterial

Bolus-Infusion (One-Two) Treatment Strategy
A: Mean Arterial Blood Pressure
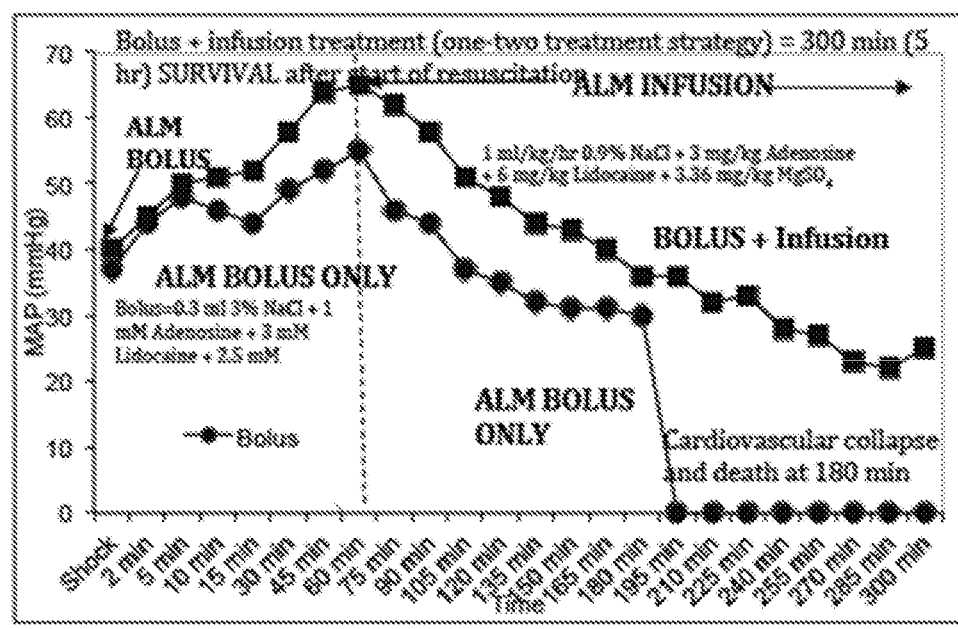
B: Heart Rate
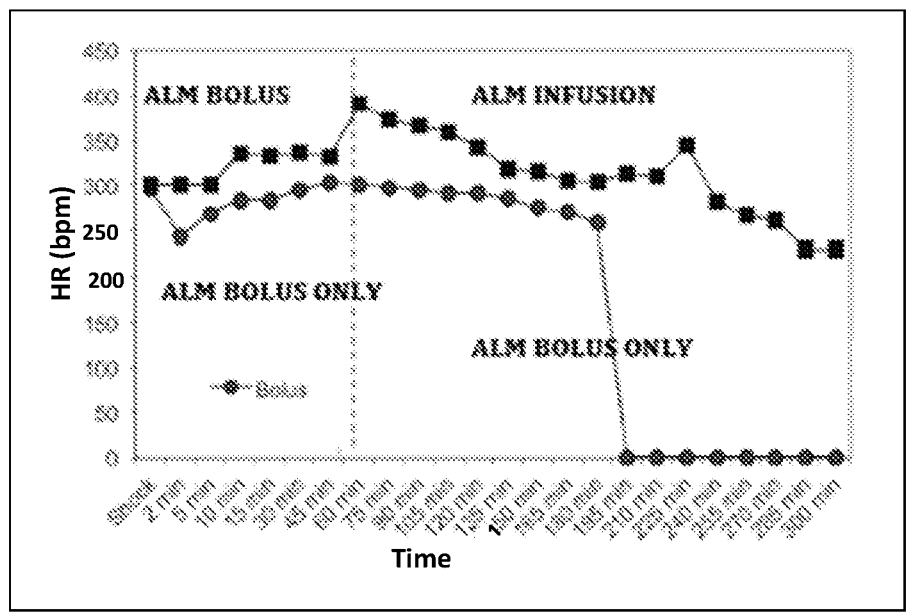
Figure 10

Fig12. Addition of Valproic Acid

Fig 13 Nitric Oxide Involvement in Hypotensive Resuscitation Addition of L-NAME (NOS Inhibitor) to 7.5% NaCl/ALM

A.
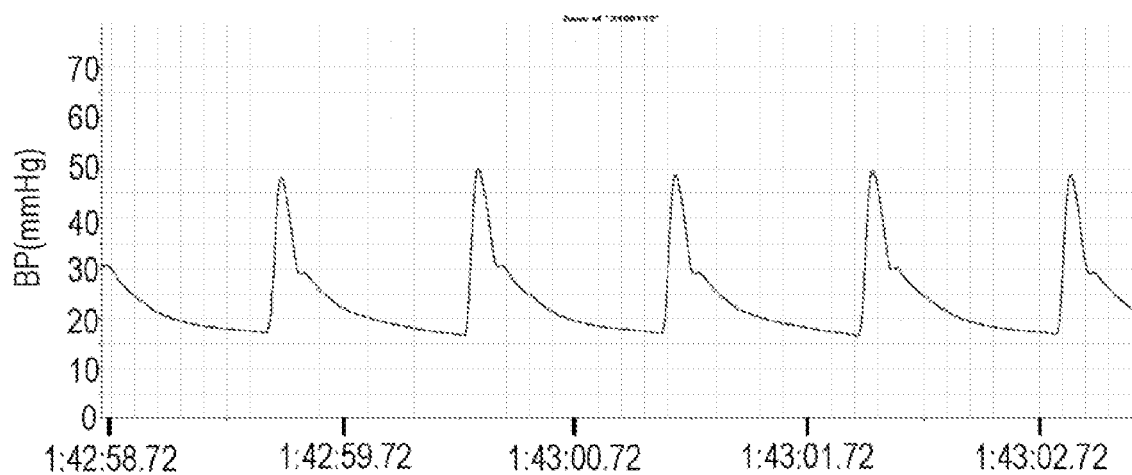
B.
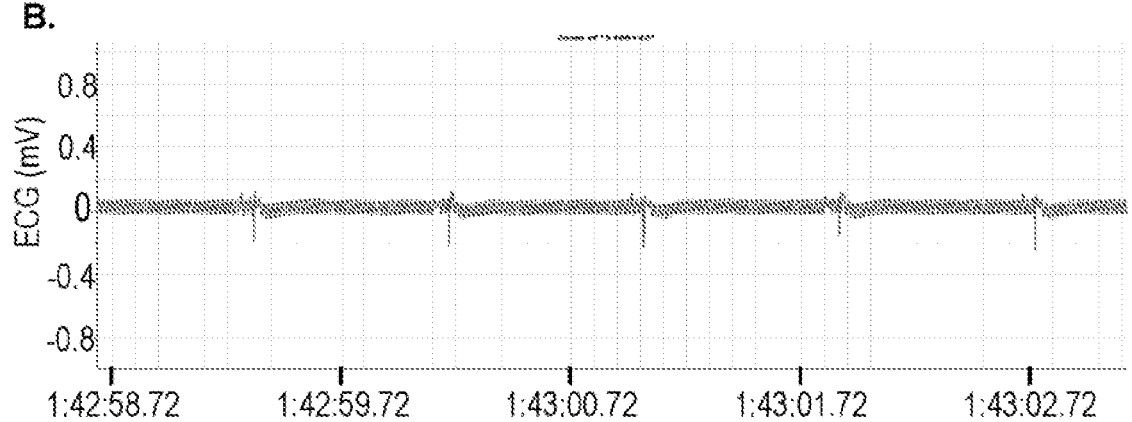
Figure 19

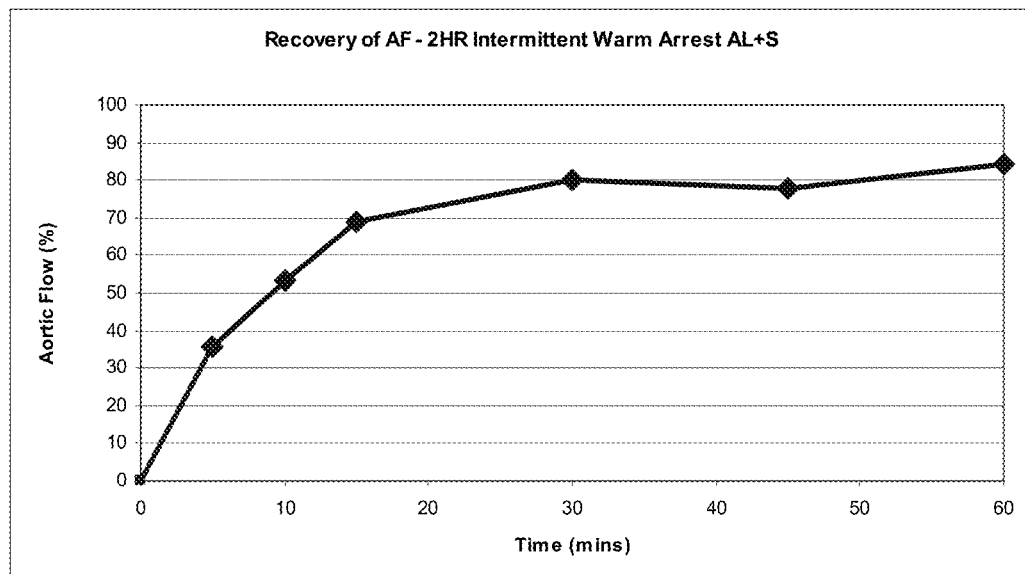
A
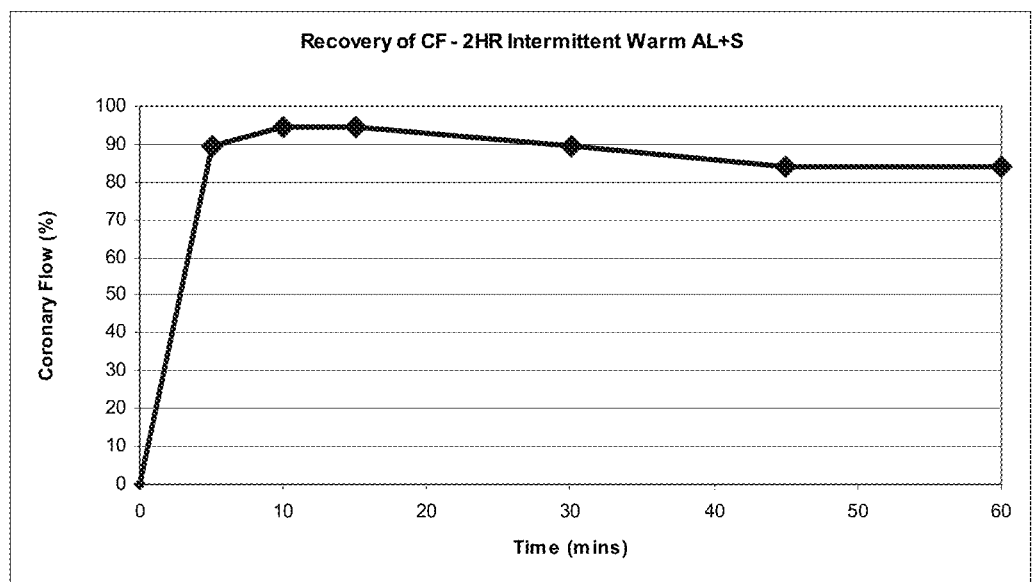
B
Figure 24

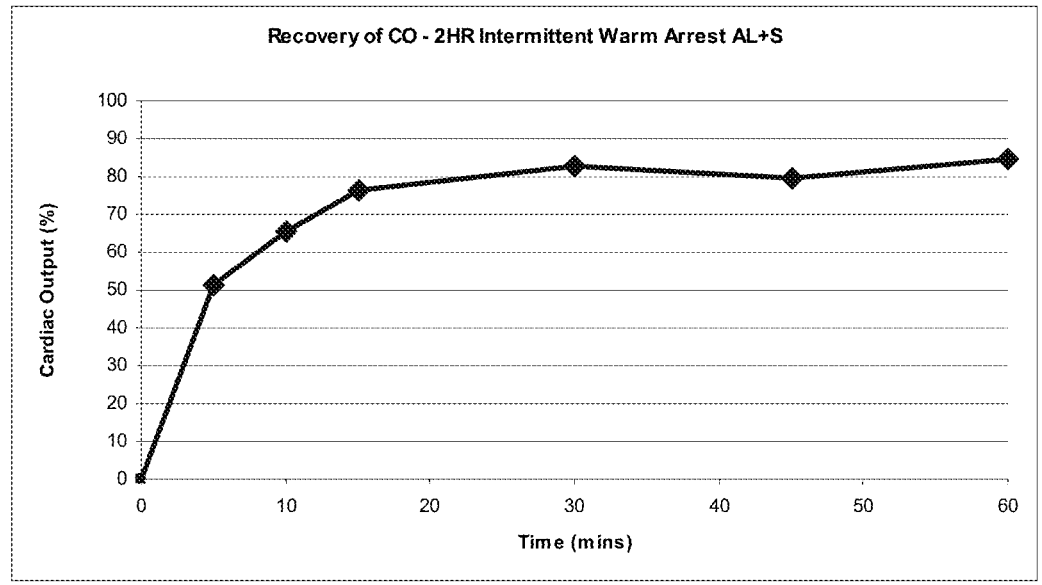
C
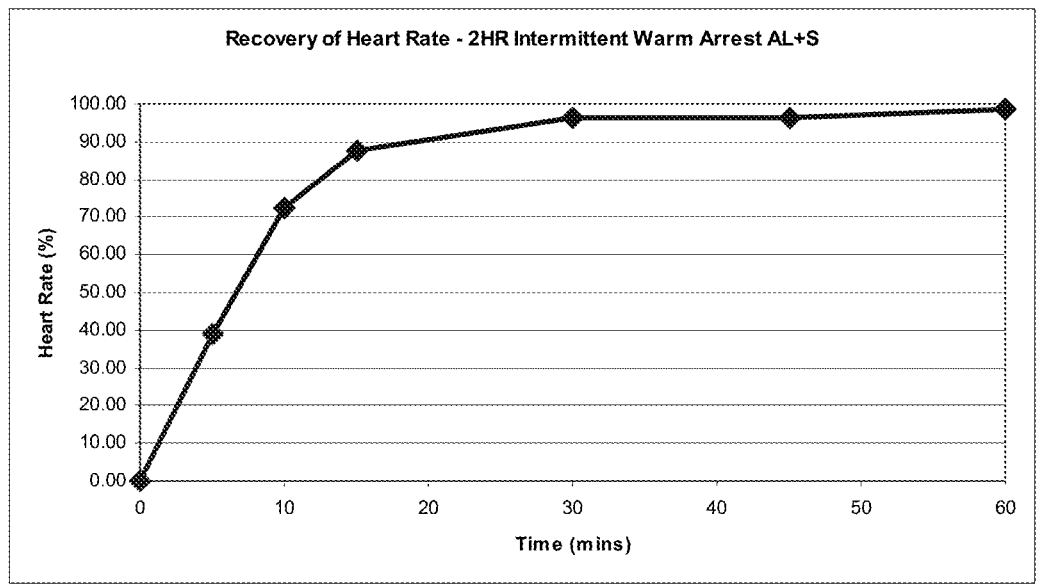
D
Figure 25

TABLE 1. Effect of 0.9% NaCl ALM on Hemodynamics and Rectal Temperature During 5 Hours Following CLP in a Rat Model of Severe Sepsis

| Groups (n = 8) | Baseline | | | | | 30 min | | | | 240 min | | | | 300 min | | | |
|---|---|---|---|---|---|---|---|---|---|---|---|---|---|---|---|---|---|
| | MAP, mm Hg | SAP, mm Hg | DAP, mm Hg | HR, beats/min | Temperature, °C | MAP, mm Hg | HR, beats/min | Temperature, °C | MAP, mm Hg | HR, beats/min | Temperature, °C | MAP, mm Hg | HR, beats/min | Temperature, °C |
| Sham | 115.5 ± 4.2 | 134.0 ± 14.8 | 105.8 ± 4.2 | 389.5 ± 13.6 | 35.6 ± 0.2 | 110.5 ± 3.4 ↓3.9% | 376.9 ± 10.8 ↓3.1% | 34.8 ± 0.2 ↓2.3% | 83.6 ± 3.0 ↓27.1%* | 301.3 ± 9.5 ↓22.2%* | 34.0 ± 0.3 ↓4.4% | 83.3 ± 3.0 ↓27.4%* | 300 ± 10.8 ↓22.4%* | 33.8 ± 0.4 ↓5.1%* |
| Control | 101.1 ± 7.1 | 107.8 ± 7.2 | 97.8 ± 5.3 | 332.1 ± 15.8 | 35.3 ± 0.2 | 87.5 ± 6.3 ↓13.4% | 262.7 ± 13.6 ↓19.1% | 34.3 ± 0.2 ↓3.0% | 68.1 ± 5.1 ↓31.0%* | 244.1 ± 13.0 ↓24%* | 32.3 ± 0.5 ↓8.7%* | 61.1 ± 5.6 ↓39%* | 251.7 ± 14.6 ↓25.7%* | 32.0 ± 0.6 ↓25.7%* |
| ALM | 111.0 ± 3.6 | 132.8 ± 7.0 | 98.8 ± 3.7 | 345.5 ± 7.4 | 36.0 ± 0.2 | 73.3 ± 3.5 ↓34.0%* | 271.3 ± 6.8 ↓21.5%* | 35.3 ± 0.3 ↓1.9% | 59.3 ± 4.0 ↓46.2%* | 211.0 ± 10.8 ↓39.1%* | 33.6 ± 0.5 ↓6.7%* | 75.8 ± 5.1 ↓31.1%* | 251.0 ± 9.7 ↓27.4%* | 33.2 ± 0.5 ↓7.6%* |

*$p < 0.05$ compared with baseline.
Values expressed as mean ± SEM and % change from baseline.
MAP = HR × SV × TPR.

Figure 41

METHOD FOR TREATING HAEMORRHAGE, SHOCK AND BRAIN INJURY

CROSS-REFERENCE TO RELATED APPLICATIONS

This application is a Continuation-in-Part of International Application No. PCT/AU2014/050128, filed Jul. 17, 2014, International Application No. PCT/AU2014/050130, filed Jul. 17, 2014, and International Application No. PCT/AU2014/050133, filed Jul. 17, 2014, all claiming priority to Australian Application No. 2013902656, filed Jul. 17, 2013, Australian Application No. 2013902657, filed Jul. 17, 2013, Australian Application No. 2013902658, filed Jul. 17, 2013, Australian Application No. 2013902659, filed Jul. 17, 2013, and Australian Application No. 2013903644, filed Sep. 23, 2013, the entire contents of all of which are hereby incorporated by reference.

FIELD

The invention relates to a method of increasing blood pressure to an optimal level in a subject that has suffered a life threatening hypotension or shock. The invention also relates to a method of increasing blood pressure in a subject that is in a shocked state, particularly after circulatory collapse or infection or burn shock or disease. The methods of the invention relates to protecting the brain of a subject following injury. The invention also relates to a method for reducing the harmful effects of hypoperfusion in the whole body prior to further resuscitation or definitive care. The invention also includes a method for reducing the harmful effects brain injury without blood loss prior to definitive care. The present application claims priority from Australian Provisional Patent Application Nos. 2013902656, 2013902657, 2013902658, 2013902659 and 2013903644, and PCT applications PCT/AU2014/050128, PCT/AU2014/050130 and PCT/AU2014/050133, the entire disclosures of which are incorporated into the present specification by this cross-reference.

BACKGROUND

Most battlefield deaths occur within the first 10 minutes of wounding and called the "platinum 10 minutes", rather than the "golden hour". Around 50% of all deaths are due to acute hemorrhage and traumatic brain injury (TBI), and it has been estimated that 25% may be salvageable. In the civilian pre-hospital setting, hemorrhage is responsible for over 35% of pre-hospital deaths following TBI and over 40% of deaths within the first 24 hours. Since a large percentage of hemorrhaging casualties suffer TBI and visa versa there is an urgent need for new methods to treat hemorrhage with suspected TBI. While promising neuroprotective drugs have been identified as being effective in animal TBI models to reduce neuronal and vascular tissue damage, they all have failed in Phase II or Phase III clinical trials.

The unmet need is a double-edged sword: A high mean arterial blood pressure (MAP) is not recommended for uncontrolled blood loss as it promotes further bleeding, and a low MAP is not recommended for TBI because it reduces brain blood flow and causes brain damage. In 1982 it was reported that hypotension (systolic blood pressure <90 mm Hg) worsened outcome after TBI. In 1993 it was also reported that there was a correlation between hypotension and increased morbidity and mortality after TBI in humans, with hypotension (and hypoxia) being the most critical parameter. It was also found that a single episode of hypotension during the period from injury through resuscitation was associated with an approximate doubling of mortality and a parallel increase in morbidity in survivors. The association persists when age and the presence or absence of hypoxia and extra-cranial injuries are taken into account. During surgery, if intra-operative hypotension occurs there is a three-fold increase in mortality. The precise mechanism for the enhanced susceptibility of the injured brain to hypotension is not clear, however, up to 90% of head-injured deaths have evidence of ischemic damage at autopsy. These secondary injuries from TBI lead to alterations in cell function and propagation of injury through processes such as depolarization, excitotoxicity, disruption of calcium homeostasis, free-radical generation, blood-brain barrier disruption, ischemic injury, edema formation, and intracranial hypertension. In addition to the adverse effects of hypotension, if TBI is associated with hemorrhagic, cardiogenic and septic shock, cardiac instability, CNS biorhythm disorders (heart rate variability), or coagulation, inflammatory imbalances the condition is worsened with increased mortality.

In some resuscitation therapies for brain protection have used hypertonic saline. Mostly hypertonic saline has been used to reduce brain swelling. The literature suggests all hypertonic solutions from 3% to 23.5% NaCl have favourable effects when administered as either a bolus or continuous infusion (drip) and appear to be more effective than mannitol in reducing acute episodes of elevated intracranial pressure. However, it was shown in a pre-hospital human trauma and hemorrhage shock trial that 7.5% NaCl hypertonic solutions led to a higher early-mortality rate compared with the group receiving 0.9% sodium chloride injection and the trial was halted. Another recent study assessed the effect of hypertonic resuscitation on outcome for patients with both hypotension and severe TBI. This study enrolled 229 patients, randomized to 250 cc 7.5% saline vs. LR solution as the initial prehospital resuscitation fluid and assessed neurologic outcome using the extended Glasgow coma score 6 months after injury. This trial failed to identify any difference in neurologic outcome. Resuscitation with hypertonic (3%) saline solution is accompanied by lower intracranial pressure values and less cerebral edema than is isotonic saline or colloid resuscitation in beagle dogs after 40% blood loss, the blood brain barrier function is not restored by hypertonic saline solution resuscitation.

Currently there is no effective global treatment strategy for the hypotensive support of non-compressible bleeding in combatants or civilians with or without suspected TBI. In "resource poor" environments such as the battlefield and civilian rural and remote areas, diagnosing TBI is extremely difficult so an invention that treats blood loss and suspected brain injury at the same time would be an important advance in the area of pre-hospital military and civilian resuscitation medicine and retrieval.

The present invention is directed toward overcoming or at least alleviating one or more of the difficulties of the prior art.

SUMMARY

The present invention provides a method of increasing blood pressure in a subject that has suffered a life threatening hypotension or shock comprising the administration of (i) a compound selected from at least one of a potassium channel opener, a potassium channel agonist and an adenosine receptor agonist; and (ii) an antiarrhythmic agent or a local anaesthetic to the subject. Preferably the method also includes administration of an elevated source of magnesium ions. The method may also include the administration of an anti-inflammatory agent and/or metabolic fuel.

The present invention is also directed to use of (i) a compound selected from at least one of a potassium channel opener, a potassium channel agonist and an adenosine receptor agonist; and (ii) an antiarrhythmic agent or a local anaesthetic in the manufacture of a medicament for increasing blood pressure in a subject that has suffered a life threatening hypotension or shock.

The present invention is also directed to use of (i) a compound selected from at least one of a potassium channel opener, a potassium channel agonist and an adenosine receptor agonist; and (ii) an antiarrhythmic agent or a local anaesthetic for increasing blood pressure in a subject that has suffered a life threatening hypotension or shock.

The present invention is also directed to (i) a compound selected from at least one of a potassium channel opener, a potassium channel agonist and an adenosine receptor agonist; and (ii) an antiarrhythmic agent or a local anaesthetic for use in increasing blood pressure in a subject that has suffered a life threatening hypotension or shock.

Preferably, the composition is administered by bolus followed by iv drip.

Preferably, the anti-inflammatory agent is BOH.

Preferably, the metabolic fuel is citrate.

Preferably, the antiarrhythmic agent is lidocaine.

Preferably, the potassium channel opener or agonist and/or adenosine receptor agonist is adenosine.

The present invention also provides a composition which may be used in increasing blood pressure in a subject that has suffered a life threatening hypotension or shock comprising (i) a compound selected from at least one of a potassium channel opener, a potassium channel agonist and an adenosine receptor agonist; and (ii) an antiarrhythmic agent or a local anaesthetic. Preferably the composition includes an elevated source of magnesium ions. The composition may also include or be administered with an anti-inflammatory agent and/or metabolic fuel.

In another aspect the present invention is directed to a method of inducing a low pain or analgesic state in a subject that has suffered a life threatening hypotension or shock comprising the administration of (i) a potassium channel opener or agonist and/or adenosine receptor agonist; (ii) an antiarrhythmic agent or a local anaesthetic; and (iii) an elevated source of magnesium ions to the subject. The composition may also include or be administered with an anti-inflammatory agent and/or metabolic fuel.

In yet another aspect the present invention is directed to a method of inducing hypotensive anaesthesia in a subject that has suffered a life threatening hypotension or shock comprising the administration of (i) a potassium channel opener or agonist and/or adenosine receptor agonist; (ii) an antiarrhythmic agent or a local anaesthetic; and (iii) an elevated source of magnesium ions to the subject. The composition may also include or be administered with an anti-inflammatory agent and/or metabolic fuel.

In a further aspect, the present invention is directed to a method for reducing hypofusion in the whole body of a subject, particularly prior to further resuscitation or definitive care comprising the administration of (i) a compound selected from at least one of a potassium channel opener, a potassium channel agonist and an adenosine receptor agonist; and (ii) an antiarrhythmic agent or a local anaesthetic to the subject. Preferably the method also includes administration of an elevated source of magnesium ions. The method may also include the administration of an anti-inflammatory agent and/or metabolic fuel.

The present invention is also directed to use of (i) a compound selected from at least one of a potassium channel opener, a potassium channel agonist and an adenosine receptor agonist; and (ii) an antiarrhythmic agent or a local anaesthetic in the manufacture of a medicament for inducing a low pain or analgesic state or hypotensive anaesthesia or reducing hypofusion in the whole body of a subject that has suffered a life threatening hypotension or shock.

The present invention is also directed to (i) a compound selected from at least one of a potassium channel opener, a potassium channel agonist and an adenosine receptor agonist; and (ii) an antiarrhythmic agent or a local anaesthetic for use in inducing a low pain or analgesic state or hypotensive anaesthesia or reducing hypofusion in the whole body of a subject that has suffered a life threatening hypotension or shock.

The present invention is also directed to use of (i) a compound selected from at least one of a potassium channel opener, a potassium channel agonist and an adenosine receptor agonist; and (ii) an antiarrhythmic agent or a local anaesthetic for inducing a low pain or analgesic state or hypotensive anaesthesia or reducing hypofusion in the whole body in a subject that has suffered a life threatening hypotension or shock.

The present invention also provides a composition which may be used in inducing a low pain or analgesic state or hypotensive anaesthesia or for reducing hypofusion in the whole body of a subject that has suffered a life threatening hypotension or shock comprising (i) a compound selected from at least one of a potassium channel opener, a potassium channel agonist and an adenosine receptor agonist; and (ii) an antiarrhythmic agent or a local anaesthetic. Preferably the method also includes administration of an elevated source of magnesium ions. The method may also include the administration of an anti-inflammatory agent and/or metabolic fuel.

In one embodiment, the compositions described above further comprise a pharmaceutically acceptable carrier.

In another embodiment, the composition is a pharmaceutical composition.

In a further embodiment, the composition may be in the form of a kit in which components (i) and (ii) are held separately. The kit may be adapted to ensure simultaneous, sequential or separate administration of components (i) and (ii) when used in the methods described above.

The present invention is directed to methods, uses and compositions for inducing whole-body arrest, a coma-like state or sleep state, a hypotensive state or a low pain or analgesic state in a subject.

The present invention is directed to a method of inducing whole-body arrest in a subject comprising the administration of (i) a compound selected from at least one of a potassium channel opener, potassium channel agonist and an adenosine receptor agonist; (ii) an antiarrhythmic agent or a local anaesthetic; and (iii) at least one of a citrate and a general anaesthetic to the subject. Components (i), (ii), and (iii) can also be administered in the form of a composition. Preferably, the composition also includes an elevated source of magnesium ions. Preferably, the composition includes 800 mM magnesium. Preferably, the subject has suffered an injury to the body.

In another aspect the present invention is directed to a method of inducing a coma-like state or sleep state in a subject comprising the administration of (i) a compound selected from at least one of a potassium channel opener, a potassium channel agonist and an adenosine receptor agonist; (ii) an antiarrhythmic agent or a local anaesthetic; and (iii) at least one of a citrate and a general anaesthetic to the subject. Components (i), (ii), and (iii) can also be administered in the form of a composition. Preferably, the composition also includes an elevated source of magnesium ions. Preferably, the subject has suffered an injury to the body.

The present invention is also directed to use of (i) a compound selected from at least one of a potassium channel opener, potassium channel agonist and an adenosine receptor agonist; (ii) an antiarrhythmic agent or a local anaesthetic; and (iii) at least one of a citrate and a general anaesthetic in the manufacture of a medicament for inducing whole-body arrest or a coma-like state or sleep state in a subject.

The present invention is also directed to use of (i) a compound selected from at least one of a potassium channel opener, potassium channel agonist and an adenosine receptor agonist; (ii) an antiarrhythmic agent or a local anaesthetic; and (iii) at least one of a citrate and a general anaesthetic for inducing whole-body arrest or a coma-like state or sleep state in a subject.

The present invention is also directed to (i) a compound selected from at least one of a potassium channel opener, potassium channel agonist and an adenosine receptor agonist; (ii) an antiarrhythmic agent or a local anaesthetic; and (iii) at least one of a citrate and a general anaesthetic for use in inducing whole-body arrest or a coma-like state or sleep state in a subject.

Compounds (i), (ii) and (iii) can also be administered in the form of a composition.

Preferably the general anaesthetic is a GABA(A) receptor agonist or NMDA antagonist, or both GABA(A) receptor agonist and NMDA antagonist.

Preferably, the anti-inflammatory agent is BOH.

Preferably, the antiarrhythmic agent is lidocaine.

Preferably, the potassium channel opener, potassium channel agonist or adenosine receptor agonist is adenosine.

In another aspect, the present invention is directed to a method of inducing whole-body arrest in a subject comprising the administration of (i) a compound selected from at least one of a potassium channel opener, a potassium channel agonist and an adenosine receptor agonist; (ii) an antiarrhythmic agent or a local anaesthetic; (iii) at least one of a citrate and a general anaesthetic; and (iv) magnesium ions, preferably an elevated source of magnesium ions to the subject.

In yet another aspect the present invention is directed to a method of inducing a coma-like state or sleep state in a subject comprising the administration of (i) a compound selected from at least one of a potassium channel opener, a potassium channel agonist and an adenosine receptor agonist; (ii) an antiarrhythmic agent or a local anaesthetic; (iii) at least one of a citrate and a general anaesthetic; and (iv) magnesium ions, preferably an elevated source of magnesium ions to the subject.

In another aspect, the present invention is directed to a method of inducing whole-body arrest in a subject comprising the administration of (i) a compound selected from at least one of a potassium channel opener, a potassium channel agonist and an adenosine receptor agonist; (ii) an antiarrhythmic agent or a local anaesthetic; (iii) at least one of a citrate and a general anaesthetic; and (iv) magnesium ions, preferably an elevated source of magnesium ions to the subject.

In yet another aspect the present invention is directed to a method of inducing a coma-like state or sleep state in a subject comprising the administration of (i) a compound selected from at least one of a potassium channel opener, a potassium channel agonist and an adenosine receptor agonist; (ii) an antiarrhythmic agent or a local anaesthetic; (iii) at least one of a citrate and a general anaesthetic; and (iv) magnesium ions, preferably an elevated source of magnesium ions to the subject.

In yet another aspect the present invention is directed to a method of inducing a hypotensive state in a subject comprising the administration of (i) a compound selected from at least one of a potassium channel opener, potassium channel agonist and an adenosine receptor agonist; (ii) an antiarrhythmic agent or a local anaesthetic; (iii) at least one of a citrate and a general anaesthetic; and (iv) magnesium ions, preferably an elevated source of magnesium ions to the subject.

In another aspect, the present invention is directed to a method of inducing a hypotensive state in a subject comprising the administration of (i) a compound selected from at least one of a potassium channel opener, a potassium channel agonist and an adenosine receptor agonist; (ii) an antiarrhythmic agent or a local anaesthetic; (iii) at least one of a citrate and a general anaesthetic; and (iv) magnesium ions, preferably an elevated source of magnesium ions to the subject.

In yet another aspect the present invention is directed to a method of inducing a low pain or analgesic state in a subject comprising the administration of (i) a compound selected from at least one of a potassium channel opener, a potassium channel agonist and an adenosine receptor agonist; (ii) an antiarrhythmic agent or a local anaesthetic; (iii) at least one of a citrate and a general anaesthetic; and (iv) magnesium ions, preferably an elevated source of magnesium ions to the subject.

In another aspect, the present invention is directed to a method of inducing a low pain or analgesic state in a subject comprising the administration of (i) a compound selected from at least one of a potassium channel opener, potassium channel agonist and an adenosine receptor agonist; (ii) an antiarrhythmic agent or a local anaesthetic; (iii) at least one of a citrate and a general anaesthetic; (iv) a general anaesthetic; and (v) magnesium ions, preferably an elevated source of magnesium ions to the subject.

The present invention is also directed to use of (i) a compound selected from at least one of a potassium channel opener, potassium channel agonist and an adenosine receptor agonist; (ii) an antiarrhythmic agent or a local anaesthetic; (iii) at least one of a citrate and a general anaesthetic; and (iv) magnesium ions, preferably an elevated source of magnesium ions in the manufacture of a medicament for inducing a hypotensive state or a low pain or analgesic state in a subject to the subject.

The present invention is also directed to use of (i) a compound selected from at least one of a potassium channel opener, potassium channel agonist and an adenosine receptor agonist; (ii) an antiarrhythmic agent or a local anaesthetic; (iii) at least one of a citrate and a general anaesthetic; and (iv) magnesium ions, preferably an elevated source of magnesium ions for inducing a hypotensive state or a low pain or analgesic state in a subject.

The present invention is also directed to (i) a compound selected from at least one of a potassium channel opener, potassium channel agonist and an adenosine receptor agonist; (ii) an antiarrhythmic agent or a local anaesthetic; (iii) at least one of a citrate and a general anaesthetic; and (iv)

magnesium ions, preferably an elevated source of magnesium ions for use in inducing a hypotensive state or a low pain or analgesic state in a subject.

In yet another preferred aspect, the administration occurs at a hypothermic temperature. In particular, below 10° C. More preferably, below 4° C.

In yet another aspect, the invention provides a composition which may be used in the methods described above, wherein the composition comprises (i) a compound selected from at least one of a potassium channel opener, potassium channel agonist and an adenosine receptor agonist; (ii) an antiarrhythmic agent or a local anaesthetic; and (iii) at least one of a citrate and a general anaesthetic.

In yet another aspect the invention provides a composition which may be used in the methods described above, wherein the composition comprises (i) a compound selected from at least one of a potassium channel opener, potassium channel agonist and an adenosine receptor agonist; (ii) an antiarrhythmic agent or a local anaesthetic; (iii) at least one of a citrate and a general anaesthetic; and (iv) magnesium ions, preferably an elevated source of magnesium ions.

In yet another aspect the invention provides a composition which may be used in the methods described above which comprises (i) a compound selected from at least one of a potassium channel opener, a potassium channel agonist and an adenosine receptor agonist; (ii) an antiarrhythmic agent or a local anaesthetic; (iii) at least one of a citrate and a general anaesthetic; and (iv) magnesium ions, preferably an elevated source of magnesium ions.

In one embodiment, the composition further comprises a pharmaceutically acceptable carrier.

In another embodiment, the composition is a pharmaceutical composition such as a cardioplegic or cardioprotectant composition.

In a further embodiment, the composition may be in the form of a kit in which each of the components (i), (ii) and (iii) are held separately. The kit may be adapted to ensure simultaneous, sequential or separate administration of components (i), (ii) and (iii) when used in the methods described above.

The present invention is directed to a method of reducing at least one of inflammation, coagulation, adhesions and scar formation in an injured subject.

In one aspect the present invention is directed to a method of reducing inflammation in an injured subject comprising the administration of (i) a compound selected from at least one of a potassium channel opener, a potassium channel agonist and an adenosine receptor agonist; and (ii) an antiarrhythmic agent or a local anaesthetic to the subject.

In one aspect the present invention is directed to a method of reducing coagulation in an injured subject comprising the administration of (i) a compound selected from at least one of a potassium channel opener, a potassium channel agonist and an adenosine receptor agonist; and (ii) an antiarrhythmic agent or a local anaesthetic to the subject.

In one aspect the present invention is directed to a method of reducing adhesions in an injured subject comprising the administration of (i) a compound selected from at least one of a potassium channel opener, a potassium channel agonist and an adenosine receptor agonist; and (ii) an antiarrhythmic agent or a local anaesthetic to the subject.

In one aspect the present invention is directed to a method of reducing scar formation in an injured subject comprising the administration of (i) a compound selected from at least one of a potassium channel opener, a potassium channel agonist and an adenosine receptor agonist; and (ii) an antiarrhythmic agent or a local anaesthetic to the subject.

Preferably, the methods also include administration of an elevated source of magnesium ions. Preferably, the methods also includes the administration of an anti-inflammatory agent and/or metabolic fuel to a subject in need thereof.

The present invention is also directed to use of (i) a compound selected from at least one of a potassium channel opener, a potassium channel agonist and an adenosine receptor agonist; and (ii) an antiarrhythmic agent or a local anaesthetic in the manufacture of a medicament for reducing at least one of inflammation, coagulation, adhesions and scar formation in an injured subject.

The present invention is also directed to use of (i) a compound selected from at least one of a potassium channel opener, a potassium channel agonist and an adenosine receptor agonist; and (ii) an antiarrhythmic agent or a local anaesthetic for reducing at least one of inflammation, coagulation, adhesions and scar formation in an injured subject.

The present invention is also directed to (i) a compound selected from at least one of a potassium channel opener, a potassium channel agonist and an adenosine receptor agonist; and (ii) an antiarrhythmic agent or a local anaesthetic for use in reducing at least one of inflammation, coagulation, adhesions and scar formation in an injured subject.

Preferably, the anti-inflammatory agent is BOH.
Preferably, the metabolic fuel is citrate.
Preferably, the antiarrhythmic agent is lidocaine.
Preferably, the potassium channel opener, a potassium channel agonist and adenosine receptor agonist is adenosine.

In another aspect, the present invention is directed to a composition for use in the methods defined above.

In one preferred aspect, the composition used in these methods comprises (i) adenosine (ii) lidocaine and (iii) a source of elevated magnesium ions.

In one aspect, the composition is administered by spray. Alternatively, the composition is suitable for topical application for example to reduce or prevent adhesions or scar formation after surgery.

In yet another aspect the present invention is directed to a method of inducing a hypotensive state in an injured subject suffering from at least one of inflammation, coagulation, adhesions and scar formation comprising the administration of (i) a compound selected from at least one of a potassium channel opener, a potassium channel agonist and an adenosine receptor agonist; and (ii) an antiarrhythmic agent or a local anaesthetic; and (iii) an elevated source of magnesium ions to the subject.

In yet another aspect the present invention is directed to a method of inducing a low pain or analgesic state in an injured subject suffering from at least one of inflammation, coagulation, adhesions and scar formation comprising the administration of (i) a compound selected from at least one of a potassium channel opener, a potassium channel agonist and an adenosine receptor agonist; (ii) an antiarrhythmic agent or a local anaesthetic; and (iii) an elevated source of magnesium ions to the subject.

The methods for inducing or assisting to induce controlled hypotensive anaesthesia or a low pain or analgesic state are useful for emergency transport, surgery or clinical interventions to reduce blood loss, inflammation and coagulopathy and further injury.

In yet another aspect the invention provides a composition which may be used in the methods described above which comprises (i) a compound selected from at least one of a potassium channel opener, a potassium channel agonist and an adenosine receptor agonist; and (ii) an antiarrhythmic agent or a local anaesthetic.

In one embodiment, the composition further comprises a pharmaceutically acceptable carrier.

In another embodiment, the composition is a pharmaceutical composition.

In a further embodiment, the composition may be in the form of a kit in which components (i) and (ii) are held separately. The kit may be adapted to ensure simultaneous, sequential or separate administration of components (i) and (ii) when used in the methods defined above. Further aspects of the present invention and further embodiments of the aspects described in the preceding paragraphs will become apparent from the following description, given by way of example and with reference to the accompanying drawings.

BRIEF DESCRIPTION OF THE DRAWINGS

FIG. 10 shows graphs showing bolus alone compared to one-two-step (bolus-infusion) for A: MAP and B: heart rate (Group 2)

FIG. 19 shows ECG traces A and B demonstrating the effect of hemodynamic stabilization with adenosine agonist plus lidocaine and magnesium after extreme blood loss.

FIG. 24 shows graphs A and B showing the effect of adenosine and lidocaine solution with sildenafil citrate over 2 hours warm arrest (29° C.) given every 20 minutes (2 min infusion) and 60 min reperfusion.

FIG. 25 shows graphs C and D showing the effect of adenosine and lidocaine solution with sildenafil citrate over 2 hours warm arrest (29° C.) given every 20 minutes (2 min infusion) and 60 min reperfusion.

FIG. 41 shows a table showing the effect of 0.9% NaCl ALM on hemodynamics and rectal temperature during 5 hours following CLP in a rat model of severe sepsis.

DETAILED DESCRIPTION OF THE EMBODIMENTS

Figure 1:
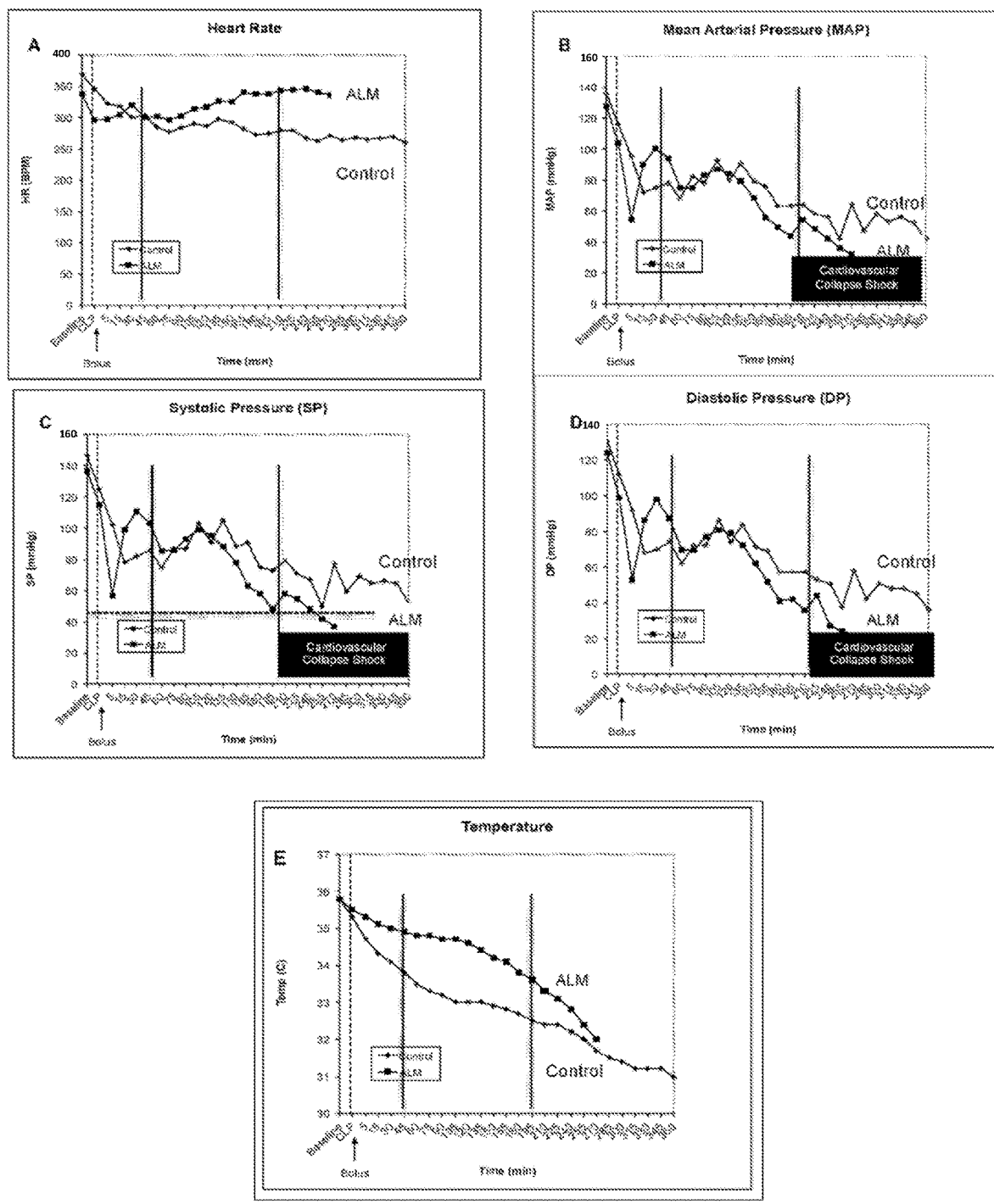
FIG. 1 shows graphs showing measurement of (A) Heart Rate; (B) MAP; (C) Systolic Pressure; (D) Diastolic Pressure; (E) Temperature against Time (min) in Rat Polymicrobial Bacterial Infection Model: Single Bolus Intravenous Treatment only for Rat ALM Bolus v's Control.

The invention relates to methods of increasing blood pressure to an optimal level in a subject that has suffered a life threatening hypotension or shock. The invention also relates to compositions for use in these methods and pharmaceutical preparations suitable for such treatments.

In one aspect the present invention provides a method of increasing blood pressure in a subject that has suffered a life threatening hypotension or shock comprising the administration of (i) a compound selected from at least one of a potassium channel opener, a potassium channel agonist and an adenosine receptor agonist; and (ii) an antiarrhythmic agent or a local anaesthetic. Preferably the method also includes administration of an elevated source of magnesium ions. The method may also include the administration of an anti-inflammatory agent and/or metabolic fuel.

It will be appreciated that the components of the composition may be administered simultaneously, sequentially or separately depending on the intended use. For convenience, this composition will be referred to in this specification as the "composition" or "composition useful in methods according to the invention", although there are a number of combinations of components embodying the invention which are compositions useful in the invention.

According to this aspect the composition is administered in two stages. First by bolus followed by iv drip. The present invention with the a bolus and drip therapy is designed to treat uncontrolled hemorrhage (life threatening hypotension) in patients with or without suspected TBI, and along with its whole body protection properties would also be applicable for widespread potential medical preparedness efforts and capabilities in mass casualty situations such as train accidents, plane crashes, natural disasters or from terrorist attacks. The new resuscitation fluid has the potential to fill a major capability gap for military and public purpose.

Separate from injury states with blood loss, there are injury states where blood loss has not occurred. These include brain injury whereby in the United States about 2 million cases are reported annually with approximately 500,000 people being hospitalized. A large proportion of nerve cell death is NMDA-receptor-mediated is linked to excessive stimulation of NMDA receptors coupled with other factors initiates a complex cascade of deleterious biochemical events. Ischemic cerebrovascular disease without blood loss is also a leading cause of mortality and the major cause of chronic disability in the adult population in the western world today. Ischemic heart disease (which includes myocardial infarction, angina pectoris and heart failure when preceded by myocardial infarction) also can all occur without blood loss is the leading cause death worldwide. The present invention with a bolus and drip therapy can also be used for injury states without blood loss.

The invention can treat any serious injury of a traumatic or non-traumatic origin that results in a life threatening shocked state that affects normal brain and whole body function. Conversely, it can treat the shocked state that is the result of brain injury or neural disease. The invention can treat both the shocked state, the brain and the whole body. In addition the invention can treat brain injury without hemorrhage or blood loss.

Another aspect of the invention is that the treatment can be used over a wide temperature range with or without extracorporeal life support device. Hypothermia is believed to be protective for the body, particularly the brain, and is used commonly in major surgery and coma-like states. Although the mode, timing and rate of cooling and rewarming remain controversial, mild therapeutic hypothermia has shown to beneficial but deep hypothermia may in some critically ill states be preferred, and extreme below 10° C. may be life-saving in other extreme forms of near-death or death.

Without being bound by any theory or mode of action of the present invention, a proposed mechanism of the invention includes a whole body improvement of circulation, improved local and CNS control of blood pressure, improved inflammatory and coagulation states and improved tissue oxygenation with multi-organ protection including the brain. Since the medulla in the brainstem is responsible for breathing, heart rate, blood pressure, arrhythmias and the sleep-wake cycle, part of the mechanism may reside in the composition's action in this region of the brain. The specific area may be the nucleus tractus solitaris (NTS), which is the first nucleus in the medulla that receives and integrates sensory information from cardiovascular and pulmonary signals in the body. The NTS receives afferent projections from the arterial baroreceptors, carotid chemoreceptors, volume receptors and cardiopulmonary receptors for processing and makes autonomic adjustments along with higher orders of the brain to maintain arterial blood pressure within a narrow range of variation.

Although the cardiovascular and pulmonary systems are primarily controlled by the brainstem, other 'higher' areas in the central autonomic network (e.g. in the forebrain) are known to be involved, and the invention is not limited to the brain stem but also to these higher control centers. This central autonomic network consists of three hierarchically ordered circuits or loops: 1) the short-term brainstem-spinal loops, 2) the limbic brain-hypothalamic-brainstem-spinal cord loops mediating anticipatory and stress responses, and 3) the intermediate length hypothalamic-brainstem-spinal cord loops mediating longer-term autonomic reflexes (e.g. involved in temperature regulation). The paraventricular nucleus (PVN) is one of the most important hypothalamic nucleus of the central autonomic network. The PVN comprises approximately 21,500 neurones is the "autonomic master controller" and a critical regulator of numerous endocrine and autonomic functions. Regulation of body temperature is also under hypothalamic control of brainstem and spinal autonomic nuclei related to longer-term autonomic reflexes. Activation of sympathetic nervous system is involved in the increase of heat generation and decrease of heat loss: control of thermoregulation muscle tone, shivering, skin blood flow and sweating may be affected. The parvocellular neurons of the PVN are known to be involved in the control of central autonomic outflow. Cholinergic activation of PVN decreases body temperature and cholinergic activation of SON increases body temperature.

Another aspect of the mechanism underpinning the invention is improved heart rate variability, which also indicates CNS protection and improved balance of electrical homeostasis. Improvement of heart rate variability during resuscitation from shock also supports the concept of improved CNS function. However, local control of the heart function and blood pressure cannot be ruled out. Acute brain injury results in decreased heart beat oscillations and baroreflex sensitivity indicative of uncoupling of the autonomic and cardiovascular systems. Brain vagal and sympathetic cardiac influences operate on the heart rate in different frequency bands. While vagal regulation has a relatively high cut-off frequency, modulating heart rate both at low and high frequencies, up to 1.0 Hz, sympathetic cardiac control operates only <0.15 Hz. The clinical relevance of the information on autonomic cardiac control provided by heart rate variability parameters is supported by the evidence that reduced heart rate variability and baroreflex control of heart rate is associated with increased mortality after myocardial infarction as well as in heart failure patients, and with increased risk of sudden arrhythmic death. Thus by the CNS mechanism of improved heart rate variability, the invention may act to bring balance to these intricate interactions between the periphery and brain and restore homeostasis.

Another aspect of the mechanism underpinning the invention is nitric oxide (NO) in the CNS and periphery as one example using a nitric oxide inhibitor shows that composition fails to allow the animal to recover after shock. Both nitric oxide (NO) and glutamate in the brainstem nuclei are involved in central cardiovascular regulation. Activation of the NO system in the lower brainstem modulates a variety of neuronal pathways; NO was shown to induce GABA and glutamate releases within the medulla. NO is involved in the modulation of the baroreflex within the nucleus tractus solitarius (NTS) and can be activated in the brain is activated in the states of homeostatic imbalances, including hypertension and stress. Further NO has been linked to vagal afferent input to the NTS in the medulla oblongat, which may help regulate inflammation and therefore coagulation.

The invention described in this specification largely relates to compositions, methods of treatment, and methods of manufacturing a medicament for treatment involving a composition which comprises (i) a compound selected from at least one of a potassium channel opener, a potassium channel agonist and an adenosine receptor agonist; and (ii) antiarrhythmic agent or a local anaesthetic. Preferably the composition includes an elevated source of magnesium ions. The composition may also include or be administered with an anti-inflammatory agent and/or metabolic fuel.

The invention is directed toward a method of inducing whole body arrest. In this specification, inducing whole body arrest refers to inducing a coma-like state in which an animal or person is in between life and death for an extended period prior to definitive medical care. Whole body arrest also refers to inducing a sleep state or brain arrest. It is believed that such methods of inducing whole-body arrest reduces the harmful effects of a life threatening condition to assist the body in preparation for definitive care or delayed resuscitation.

The present invention could be used in the treatment of a number of injury, trauma and disease states. For example, the body of a patient that is treated for injury or trauma may require to be arrested. Generally, the translation of new experimental therapies of whole body arrest into a clinically safe and effective pharmacology has had extremely limited success. The examples below represent a number of life-threatening situations that require urgent medical attention and rescuing. The current invention is not limited to the examples but extends to all critical illnesses and diseases requiring urgent life support in the hospital or out of hospital settings including military injury and trauma on the battlefield. Some of these illnesses and diseases are described in the definition section below.

The invention described in this specification largely relates to compositions, methods of treatment and uses involving a composition comprising (i) a compound selected from at least one of a potassium channel opener, a potassium channel agonist and an adenosine receptor agonist; (ii) an antiarrhythmic agent or a local anaesthetic; and (iii) at least one of a citrate and a general anaesthetic together with additional components where applicable. In a preferred form, the composition includes an elevated source of magnesium ions. It will be appreciated that the components of this composition may be administered simultaneously sequentially or separately depending on the intended use. For convenience, this composition will be referred to in this specification as the "composition" or "composition useful in methods according to the invention", although there are a number of combinations of components embodying the invention which are compositions useful in the invention.

Another aspect of the invention, the methods according to the invention can be used over a wide temperature range with or without extracorporeal life support device. Hypothermia is believed to be protective for the body, particularly the brain, and is used commonly in major surgery and coma-like states. Although the mode, timing and rate of cooling and rewarming remain controversial, mild therapeutic hypothermia has shown to beneficial but deep hypothermia may in some critically ill states be preferred, and extreme below 10° C. may be life-saving in other extreme forms of near-death or death.

In one aspect, the composition according to the invention is administered at a hypothermic temperature, in particular below 10° C., more particularly below 4° C.

Without being bound by any theory or mode of action of the present invention, one proposed mechanism may include a pharmacological-induced CNS-linked cardiovascular collapse of heart rate and blood pressure followed by a spontaneous recovery of physiological function after a period of time of partial or complete whole body standstill. Since the medulla in the brainstem is responsible for breathing, heart rate, blood pressure, arrhythmias and the sleep-wake cycle, part of the mechanism may reside in the composition's action in this region of the brain. The specific area may be the nucleus tractus solitaris (NTS), which is the first nucleus in the medulla that receives and integrates sensory information from cardiovascular and pulmonary signals in the body. The NTS receives afferent projections from the arterial baroreceptors, carotid chemoreceptors, volume receptors and cardiopulmonary receptors for processing and makes autonomic adjustments along with higher orders of the brain to maintain arterial blood pressure within a narrow range of variation. Improvement of heart rate variability during sepsis and trauma also supports the concept of improved CNS function. However, local control of the heart function and blood pressure cannot be ruled out.

Although the cardiovascular and pulmonary systems are primarily controlled by the brainstem, other 'higher' areas in the central autonomic network (e.g. in the forebrain) are known to be involved, and the invention is not limited to the brain stem but also to these higher control centers. This central autonomic network consists of three hierarchically ordered circuits or loops: 1) the short-term brainstem-spinal loops, 2) the limbic brain-hypothalamic-brainstem-spinal cord loops mediating anticipatory and stress responses, and 3) the intermediate length hypothalamic-brainstem-spinal cord loops mediating longer-term autonomic reflexes (e.g. involved in temperature regulation). The paraventricular nucleus (PVN) is one of the most important hypothalamic nucleus of the central autonomic network. The PVN comprises approximately 21,500 neurones is the "autonomic master controller" and a critical regulator of numerous endocrine and autonomic functions. Regulation of body temperature is also under hypothalamic control of brainstem and spinal autonomic nuclei related to longer-term autonomic reflexes. Activation of sympathetic nervous system is involved in the increase of heat generation and decrease of heat loss: control of thermoregulation muscle tone, shivering, skin blood flow and sweating may be affected. The parvocellular neurons of the PVN are known to be involved in the control of central autonomic outflow. Cholinergic activation of PVN decreases body temperature and cholinergic activation of SON increases body temp.

Another aspect of the invention in addition to inducing a coma state may also reduce infection, prevent an immunosuppressive state, reduce inflammation, correct coagulation disorders and prevent or decrease postoperative cognitive decline associated with brain injury or any surgery. Thus the invention by inflammation and coagulation may act to bring balance to these intricate interactions between the periphery and brain and restore homeostasis. Improved heart rate variability also indicates CNS protection and improved balance of electrical homeostasis.

Another aspect of the mechanism underpinning the invention is nitric oxide (NO) in the CNS and periphery as one example using a nitric oxide inhibitor shows that composition fails to allow the animal to recover after shock. Both nitric oxide (NO) and glutamate in the brainstem nuclei are involved in central cardiovascular regulation. Activation of the NO system in the lower brainstem modulates a variety of neuronal pathways; NO was shown to induce GABA and glutamate releases within the medulla. NO is involved in the modulation of the baroreflex within the nucleus tractus solitarius (NTS) and can be activated in the brain is activated in the states of homeostatic imbalances, including hypertension and stress. Further NO has been linked to vagal afferent input to the NTS in the medulla oblongata, which may help regulate inflammation and therefore coagulation.

The present invention relates to reducing at least one of inflammation, coagulation, adhesions and scar formation in the body of a subject following injury. The invention also relates to compositions for use in these methods and pharmaceutical preparations including topical preparation, suitable for such treatments.

In one aspect the present invention is directed to a method of reducing inflammation in a subject that has been injured comprising the administration of (i) a compound selected from at least one of a potassium channel opener, a potassium channel agonist and an adenosine receptor agonist; and (ii) an antiarrhythmic agent or a local anaesthetic to the subject. Preferably, the method includes the administration of an elevated source of magnesium ions. Preferably, the method also includes the administration of an anti-inflammatory agent and/or metabolic fuel to a subject in need thereof.

In one aspect the present invention is directed to a method of reducing coagulation in a subject that has been injured comprising the administration of (i) a compound selected from at least one of a potassium channel opener, a potassium channel agonist and an adenosine receptor agonist; and (ii) an antiarrhythmic agent or a local anaesthetic to the subject. Preferably, the method includes the administration of an elevated source of magnesium ions. Preferably, the method also includes the administration of an anti-inflammatory agent and/or metabolic fuel to a subject in need thereof.

In one aspect the present invention is directed to a method of reducing adhesions in a subject that has been injured comprising the administration of (i) a compound selected from at least one of a potassium channel opener, a potassium channel agonist and an adenosine receptor agonist; and (ii) an antiarrhythmic agent or a local anaesthetic to the subject. Preferably, the method includes the administration of an elevated source of magnesium ions. Preferably, the method also includes the administration of an anti-inflammatory agent and/or metabolic fuel to a subject in need thereof.

In one aspect the present invention is directed to a method of reducing scar formation in a subject that has been injured comprising the administration of (i) a compound selected from at least one of a potassium channel opener, a potassium channel agonist and an adenosine receptor agonist; and (ii) an antiarrhythmic agent or a local anaesthetic to the subject. Preferably, the method includes the administration of an elevated source of magnesium ions. Preferably, the method also includes the administration of an anti-inflammatory agent and/or metabolic fuel to a subject in need thereof.

Without being bound by any theory or mode of action of the present invention, one proposed mechanism of action to reduce or prevent adhesions in a patient's response to surgery includes the ability of the composition once administered to the blunt the inflammatory responses by reducing pro-inflammatory cytokines including IL-6 and TnF-alpha. Another proposed mechanism of action to reduce adhesions in a patient's response to surgery includes the ability of the composition once administered to blunt the coagulation responses and reduce fibrin degradation. Alternatively, another proposed mechanism of action to reduce adhesions in a patient's response to surgery includes the invention's ability to reduce the incidence of infection via it antiinflammatory and coagulative restorative properties.

Without being bound by any theory or mode of action of the present invention, one proposed mechanism include a pharmacological-induced CNS-linked improvement to whole body function to injury.

The invention described in this specification largely relates to compositions, methods of treatment, and methods of manufacturing a medicament for treatment involving a composition comprising (i) a compound selected from at least one of a potassium channel opener, a potassium channel agonist and an adenosine receptor agonist and (ii) an antiarrhythmic agent or a local anaesthetic together with additional components where applicable. Preferably, the composition includes a source of elevated magnesium ions.

It will be appreciated that the components of the composition may be administered simultaneously, sequentially or separately depending on the intended use.

For convenience, this composition will be referred to in this specification as the "composition" or "composition useful in methods according to the invention", although there are a number of combinations of components embodying the invention which are compositions useful in the invention.

Definitions

Traumatic Brain injury (TBI) is defined as damage to the brain resulting from an external physical or mechanical force, such as that caused by rapid acceleration or deceleration, blast waves, crush, an impact or penetration by a projectile. It can lead to temporary or permanent impairment of cognitive, physical and psychosocial function. In a traumatic injury, damage to nerve tissue is usually focused in one or more areas of the brain at first, although tearing can result in diffuse injury.

Non-traumatic Brain Injury is any injury to the brain that does not result from any cause that does not injure the brain using physical force, but rather occurs via infection, poisoning, tumor, or degenerative disease. Causes include lack of oxygen, glucose, or blood are considered non-traumatic. Infections can cause encephalitis (brain swelling), meningitis (meningeal swelling), or cell toxicity, as can tumors or poisons. These infections can occur through stroke, heart attack, near-drowning, strangulation or a diabetic coma, poisoning or other chemical causes such as alcohol abuse or drug overdose, infections or tumors and degenerative conditions such as Alzheimer's disease and Parkinson's disease. Non-traumatic injury, damage is usually spread throughout the brain and exceptions include tumors and an infection that may remain localised or spreads evenly from one starting point.

Injury from a Traumatic Event is cell, tissue, organ or whole body damage that can occur from a traumatic or non-traumatic event. Injury may appear as the primary injury from the initial traumatic event, and secondary injury which is a time-dependent process progressing from the primary event and may include, but not limited to, injuries from infection, ischemic injury, reperfusion injury with an inflammatory, coagulation and central nervous system regulatory dysfunction. Importantly, primary injuries (wounds and burns) for war are distinct from peacetime traumatic injuries because these higher velocity projectiles and/or blast devices cause a more severe injury and accompanying wounds are frequently contaminated by clothing, soil, and environmental debris. However, the secondary injuries share many similarities to the civilian setting with the exception of long evacuation times where complications can arise.

Injury from a Non-Traumatic Event: Injuries can also occur from a primary non-traumatic (not from a physical or mechanical force) and includes damage resulting from infection, poisoning, tumor, or degenerative disease. Lack of oxygen, glucose, or blood can be considered non-traumatic arising from these causes. Infections can cause encephalitis (brain swelling), meningitis (meningeal swelling), or cell toxicity, as can tumors or poisons. These infections can occur through stroke, heart attack, near-drowning, strangulation or a diabetic coma, poisoning or other chemical causes such as alcohol abuse or drug overdose, infections or tumors and degenerative conditions such as Alzheimer's disease and Parkinson's disease.

Haemorrhage: Bleeding from a break in the wall of one or more blood vessels from an injury or trauma, and it will continue as long as the vessel remains open and the pressure inside the vessel exceeds that pressure on the outside of the vessel wall.

Non-Compressible Hemorrhage: Hemorrhage that cannot be stopped with direct compression. Over 80% of hemorrhagic deaths on the battlefield are attributed to non-compressible internal hemorrhage that is not accessible to a tourniquet or direct compression. Non-compressible torso hemorrhage is the leading cause of potentially survivable trauma in the battlefield. Most deaths occur in first hour Uncontrolled Hemorrhage: Same as non-compressible bleeding from one or more blood vessels that cannot be controlled.

Hypertonic saline is defined as a saline concentration greater than normal isotonic saline which is 0.9% NaCl (0.154 M).

Shock is defined as a severe hypotensive state when the arterial blood pressure is too low to maintain an adequate supply of blood and oxygen to the body's cells, organs and tissues.

Shock is the result of "circulatory collapse" which can be causes from many internal and external sources. It can be caused by a heart attack or heart failure, stroke, cardiac arrest from heart or a respiratory origin (choking, drowning, hanging), internal or external bleeding (hypovolemic shock), infection (septic shock), dehydration, severe burns (burn shock), or severe vomiting and/or diarrhea, all of which involve the loss of large amounts of bodily fluids. Shock can be caused by severe allergic reaction or injury (traumatic or non-traumatic) such as brain injury and bleeding.

Systolic arterial blood pressure is the maximum amount of work or force exerted on the arterial wall by the blood (usually measured by a sphygmomanometer) during the contraction of the left ventricle of the heart. Systolic pressure is the highest reading of blood pressure measurement (systolic/diastolic). A palpable pulse refers to feeling the highest or systolic pressure at various arterial locations in the body (radial, carotid, femoral) (Lamia et al., 2005).

Diastolic arterial blood pressure is the minimum amount of work or force exerted by the blood on the arterial wall as the heart relaxes. It is the lower number of the blood pressure reading (systolic/diastolic).

Mean Arterial Pressure (MAP) is an index of perfusion pressure of the vital organs and tissues where MAP=(⅔× diastolic pressure)+(⅓×systolic pressure) or diastolic pressure plus ⅓ (systolic–diastolic pressure).

Normotensive Resuscitation: Conventional treatment of the shocked trauma patient involves intravenous fluid administration to bring the blood pressure back to "normal". The rational for normotensive resuscitation has been to maintain tissue perfusion and vital organ function while diagnostic and therapeutic procedures are being performed. Traditionally for every I L of estimated blood loss, 3 L of crystalloid has been recommended if complete fluid resuscitation is to be achieved. This method is controversial because it produces inflammatory and coagulopathy disturbances. The choice of resuscitation fluid to produce optimal outcome is also highly controversial.

Hypotensive resuscitation in the trauma setting is defined as a small volume of fluid(s) to resuscitate a patient's MAP from a shocked state (MAP<40 mmHg) to a higher value to support life until any active bleeding is controlled. Hypotensive refers to a range of pressures below the normal arterial blood pressure (130/80). Hypotensive resuscitation is different from "permissive" hypotensive resuscitation because it encompasses a wider pressure range of low-pressure resuscitation. The term "permissive" refers to the return of a palpable pulse.

Permissive hypotensive resuscitation is defined as a small volume of fluid(s) to resuscitate a patient's MAP from a shocked state (MAP<40 mmHg) to a systolic blood pressure of 60 to 80 mmHg required to establish a radial pulse. The Advanced Trauma Life Support (ATLS) guidelines teach that a carotid, femoral, and radial pulse correlates to a certain systolic blood pressure (SBP) in hypotensive trauma patients with the following values: Carotid pulse only=SBP 60-70 mmHg, Carotid & Femoral pulse only=SBP 70-80 mmHg; Radial pulse present=SBP >80 mmHg. Guidelines for Pediatric arterial pressures would be different. Without being bound by any particular theory or mode of action our invention may or may not have a palpable pulse but will have sufficient blood flow to the organs and tissues to sustain life after hemorrhagic shock with or without TBI.

Hypotensive anaesthesia is the controlled regulation of mean arterial pressures (MAP) that reduces blood loss during surgery or clinical interventions. Studies have shown that if MAP is reduced to 50 mmHg during surgery or interventions the blood loss can reduce by over 50%, which may reduce the need for fluid or blood products. The reduced blood loss also limits dilution and consumption of coagulation factors and subsequent postoperative rebound hypercoagulability. If MAP is maintained at 60 mmHg rather than 50 mmHg, blood loss is about 40% greater. Hypotensive anaesthesia can be induced using either general or regional anaesthesia and enhanced using vasodilators to improve cardiac output.

Therapeutic Hypothermia or "targeted hypothermia" is the active "controlled" cooling of a cell, organ or whole body to reduce injury. It has clinical applications for arrest, protection and preservation of the brain and heart during cardiac surgery, and has shown to be useful after cardiac arrest or treating an unconscious or coma patient in the out-of-hospital environment. The rate and degree of cooling and targeted body temperature is controversial. Deep Hypothermic Circulatory Arrest (DHCA) or hypothermic cardiac standstill is a surgical technique that involves cooling the body of the patient and stopping blood circulation. Mild hypothermia is a core body temperature of 33 to 36° C., moderate is 28 to 32° C., severe is 25 to 28 and deep hypothermia is 20 to 25° C. or below. Extreme therapeutic hypothermia would be below 10° C.

Infection: Hemorrhagic shock can lead to infection from ischemia of the bowel from translocation of enteric bacteria to cause infection. Hypertonic saline has been shown to reduce this bacterial translocation.

Injury can be broadly characterised as reversible and irreversible cell injury. For example, reversible cell injury can lead to heart dysfunction usually from arrhythmias and/or stunning. Stunning is normally characterised as loss of left pump function during restoration of blood flow following periods of ischemia. If severe, it can lead to the death of the heart, usually from arrhythmias, even though the heart cells themselves are not initially dead. Irreversible injury by definition arises from actual cell death which may be fatal depending upon the extent of the injury. The amount of cell death can be measured as infarct size. During recovery from cardioplegic arrest, if the conditions are adequate, the heart can be restored substantially to normal function of the tissue by reperfusion, with minimal infarct size. The most common ways to assess return of function of a heart are by measuring pressures that the heart can generate; heart pump flow; and the electrical activity of the heart. This data is then compared to data measured from pre-arrest conditions. In this specification the terms "injury" and "damage" may be used interchangeably.

Marine Stingers: There is an enormous diversity and complexity of venoms and poisons in marine animals. Fatalities have occurred from envenoming by sea snakes, venomous fish (stonefish), cone shells or snails, blue-ringed octopus and jellyfish. There are numerous venomous jellyfish around the pacific rim and Australia. *Chironex fleckeri*, the box jellyfish, is the most lethal causing rapid cardiorespiratory depression. *Carukia barnesi*, another small carybdeid leads to the so-called 'lrukandji' syndrome which includes delayed pain from severe pain, muscle cramping, vomiting, anxiety, restlessness, sweating and prostration, severe hypertension and acute cardiac failure. Other Australian carybdeid jellyfish that may be associated with the syndrome include *Carukia shinju, Carybdea xaymacana, Malo maxima, Malo kingi, Alatina mordens, Gerongia rifkinae*, and *Morbakka fenneri* ("*Morbakka*"). Other significant genera of jellyfish include *Tamoya, Pelagia, Cyanea, Aurelia* and *Chyrosaora*.

The syndromic illness, resulting from a characteristic relatively minor sting, develops after about 30 minutes. The mechanisms of actions of their toxins appear to include modulation of neuronal sodium channels leading to massive release of endogenous catecholamines (*C. barnesi, A. mordens* and *M. maxima*) and possibly stress-induced cardiomyopathy. In human cases of severe envenomation, systemic hypertension and myocardial dysfunction are associated with membrane leakage of troponin indicating heart cell death. Clinical management includes parenteral analgesia, antihypertensive therapy, oxygen and mechanical ventilation. The present invention may alleviate some of these symptoms.

Brain injury without blood loss includes traumatic brain injury and stroke. The goal of therapy in patients with severe head injury is to avoid secondary brain damage including reducing brain swelling.

Heart injury without blood loss: Goal would be to improve cardiovascular stabilization.

Hemmorhagic shock: Traumatic brain injury (TBI) from injury and trauma is often complicated by hemorrhagic shock (HS) and visa versa. Combination of TBI and HS is highly lethal, and the optimal resuscitation strategy for this combined insult remains unclear. Most studies of HS after experimental TBI have focused on intracranial pressure; few have explored the effect of HS on neuronal death after TBI. Valproic acid (VPA), a histone deacetylase inhibitor, can improve survival after hemorrhagic shock (HS), protect neurons from hypoxia-induced apoptosis, and attenuate the inflammatory response.

Sepsis and septic shock: Sepsis affects the brain, and the impairment of brain function resulting from sepsis is often associated with severe infectious disease. The effects of sepsis on the brain are detectable in previously healthy brains but are amplified in cases with concomitant brain injury, as after traumatic brain injury or subarachnoid haemorrhage. Previous injuries, in fact, increase brain vulnerability to the complex cascade of events summarized in the term "septic encephalopathy". Brain and sepsis remains a difficult and relatively unexplored topic with no treatments.

Cardiogenic Shock (CS) occurs in 5% to 8% of patients hospitalized with ST-elevation myocardial infarction. CS is a state of end-organ hypoperfusion including brain damage due to cardiac failure. The definition of CS includes hemodynamic parameters: persistent hypotension (systolic blood pressure <80 to 90 mm Hg or mean arterial pressure 30 mm Hg lower than baseline) with severe reduction in cardiac index and adequate or elevated filling pressure or right ventricular [RV] end-diastolic pressure >10 to 15 mm Hg. Mortality can range from 10% to 80% depending on demographic, clinical, and hemodynamic factors. These factors include age, clinical signs of peripheral hypoperfusion and anoxic brain damage.

Obstructive Shock is due to obstruction of blood flow outside of the heart. Pulmonary embolism and cardiac tamponade are examples of obstructive shock. Similar to cardiogenic shock.

Vasogenic Shock is shock resulting from peripheral vascular dilation produced by factors such as toxins that directly affect the blood pressure to fall; and include anaphylactic shock (allergic reaction) and septic shock (bacterial, viral or fungal).

Neurogenic shock is a hypotension that is attributed to the disruption of the autonomic pathways within the spinal cord. Hypotension can lead to brain injury or result from brain, spinal cord or cervical injury.

Spinal Cord Shock: This is not circulatory collapse and separate from neurogenic shock.

Burn Shock is defined as tissue damage caused by a variety of agents, such as heat, chemicals, electricity, sunlight, or nuclear radiation. The injury a β-dimensional mass of damaged tissue and can produce massive inflammatory response and coagulopathy and can lead to shock and organ failure including brain damage.

Dehydration, severe vomiting and/or diarrhea shock is shock is the result of loss of large amounts of bodily fluids.

Diabetic Shock: Diabetic coma is a reversible form of coma found in people with diabetes mellitus.

Alternate Fuels for Brain Function During Treatment

Maintaining normoglycemia of a casualty is of great importance during any medical treatment to reduce mortality and improve outcome whether on the battlefield, evacuation or in the prehospital, surgical and medical intensive care unit. Normally glucose is the primary fuel for the brain but in the critically ill from injury, infection, trauma and disease, glucose uptake and metabolism can be impaired. Hyperglycemia aggravates underlying brain damage and influences both morbidity and mortality in critically ill patients by inducing tissue acidosis oxidative stress, and cellular immunosuppression, which, in turn, promote the development of multiorgan failure.

Hypoglycemia impairs energy supply causing metabolic perturbation and inducing cortical spreading depolarizations. Consequently, both hyperglycemia and hypoglycemia need to be avoided to prevent aggravation of underlying brain damage. Both hyper- and hypoglycemia have been associated with poor outcome in traumatic brain injury (TBI). Stress insulin resistance (high blood glucose) is a marker for mortality in traumatic brain injury. The present invention with alternative fuels for metabolism in life threatening situations or in the critical ill such a diabetes may reduce tissue acidosis oxidative stress, and cellular immunosuppression.

Ketones and Citrate

Alternative energy sources that can bypass glucose as a fuel include ketones (acetone or acetoacetate) or carboxylic acids (D-beta-hydroxybutryate). Natural hibernating animals produce ketones (and carboxylic acids) during hibernation to replenish the energy currency of the cell (adenosine-5'-triphosphate, ATP) and humans do the same during starvation. D-beta-hydroxybutryate was reported to suppress lactic acidemia and hyperglycemia via alleviation of glycolysis during hemorrhagic shock in rats. D-beta-hydroxybutryate is converted to acetyl-CoA through pathways separate than glycolysis before entering the the Krebs Cycle and preferential utilization of D-beta-hydroxybutryate rather than glucose as an energy substrate might reduce the deleterious accumulation of rising glucose or maintain a normoglycemic state. Ketones have been successfully applied to both rapidly developing pathologies (seizures, glutamate excitotoxicity, hypoxia/ischemia) and neurodegenerative conditions (Parkinson's disease, Alzheimer's disease) and more recently TBI. The brain's ability to increase its reliance on ketone bodies appears to be a form of cerebral metabolic adaptation. Cerebral shifting to ketone metabolism requires (1) increasing the availability of ketones, (2) increasing cerebral uptake of ketones, and (3) potentially increasing the activity of the necessary enzymes for ketone metabolism.

In those specific life-threatening or critically ill states loss of the anabolic effect of insulin (insulin resistance) is a key component of the adverse metabolic consequences. The underlying mechanisms for the development of insulin resistance remain unclear. Even a moderate degree of hyperglycemia appears detrimental for the outcome of critically ill patients. The available literature suggests a causal link between hyperglycemia and adverse outcome in sepsis and a benefit of intensive insulin therapy in sepsis equal to the benefit found in critical illness without sepsis and critical illness in general. Prevention of cellular glucose toxicity by strict glycemic control appears to play a predominant role, but other metabolic and non-metabolic, anti-inflammatory effects of insulin seem to contribute to the clinical benefits realized.

In the critically ill, impairment to metabolism may occur from the inhibition of pyruvate dehydrogenase has been reported in sepsis, shock or traumatic brain injury. This may limit pyruvate conversion to acetyl-coenzyme A, the main substrate that fuels the Krebs cycle to replenish ATP in the cell's powerhouse, the mitochondria. A large part of Acetyl CoA comes from glucose metabolism (glycolysis) however Acetyl CoA can alternatively come from other pathways such as ketone metabolism, which forms acetyl CoA primes the cycle by forming citrate. Citrate administration may also bypass glucose requirement during insulin resistance and improve outcome. Ketones and citrate have the advantage of not needing insulin to enter the cell and generate ATP in the mitochondria, and thus may replenish the Krebs cycle if acetyl CoA is limiting or when Krebs cycle intermediates are limiting as a result of sepsis. Citrate can also act by lowering the cellular burden of non-esterified fatty acids that have been implicated in mitochondrial dysfunction during sepsis.

Improves heart rate variability: Another aspect of the invention is to improve neuroautonomic regulation of heart rate and blood pressure oscillations by reducing dangerous oscillations in the body's normal biorhythms such as in heart rate and blood pressure which implies improved whole body and brain function. Increasing HR variability, infection, inflammation and coagulation outside the brain may improve brain function including postoperative cognitive decline. Postoperative delirium, are a major cause of morbidity associated with surgery. POCD occurs in 7-26% of patients undergoing surgery. The possibility exists that elevations of TNF in the periphery lead to cognitive decline. Efferent nerve connections from the vagal nerve to the spleen can be modulated to block experimental septic shock and autoimmune immune models of rheumatoid arthritis.

Improves brain swelling and intra-cranial pressure: Another aspect of the invention may be to reduce on brain swelling, reduce intracranial pressure, improve blood flow to the brain, reduce brain inflammation, brain coagulopathy and secondary injury in the brain, and the benefit this has in the body's circulation and multiple organ function. The invention improves "Integration" on how nervous system can perform high level functions to improve whole body function.

Treatment and Method with Rescue Devices for the critically ill and life-threatening situations: In any critical illness when there is a profound myocardial depression and hemodynamic failure such as in the unconscious patient, severe sepsis, septic shock, hemorrhagic shock, cardiogenic shock, myocardial infarctions, cardiac arrest, brain injury, adult respiratory distress syndrome (ARDS) they may be rescued using venoarterial extracorporeal membrane oxygenation (ECMO), a portable life saving device similar to cardiopulmonary bypass. ECMO provides extracorporeal life support with artificial heart and lung for cardiopulmonary failure (Bartlett and Gattinoni, 2010). ECMO can provide partial or total support, is temporary (days to weeks but in children following heart surgery may be months), and requires systemic anticoagulation. ECMO controls gas exchange and perfusion, stabilizes the patient physiologically, decreases the risk of ongoing iatrogenic injury, and allows ample time for diagnosis, treatment, and recovery from the primary injury or disease. ECMO is used in a variety of clinical circumstances and the results depend on the primary indication. ECMO provides life support but is not a form of treatment (Bartlett and Gattinoni, 2010). Our invention could be used to rescue the critically ill or wounded prior to ECMO as a treatment and continued after ECMO has been connected for stabilization. A similar case would occur with cardiopulmonary bypass.

Coma is a reversible state of deep, often prolonged unconsciousness caused by a variety of problems—traumatic head injury, stroke, brain tumor, drug or alcohol intoxication, poisons, toxins, or even from an underlying illness, such as diabetes or an infection. Coma can also occur as a serious perioperative complication. Coma can also be medically induced which is different from natural hibernation, torpor or estivation as there are no profound falls in temperature and metabolism without further intervention. In medicine, a coma is usually induced for brain injury repair after trauma using a controlled dose of a barbiturate such as pentobaribital or thiopental general anaesthetics. Barbiturates reduce the metabolic rate of brain tissue, as well as the brain blood flow.

General anesthesia is the induction of a state of unconsciousness with the absence of pain sensation over the entire body, through the administration of anaesthetic drugs. It is used during certain medical and surgical procedures. Careful control of the amounts of anaesthetics administered prevent death.

Local anesthesia is any technique to induce the absence of sensation in part of the body, generally for the aim of inducing local analgesia, that is, local insensitivity to pain. It is distinguished from general anesthesia by being a local effect on the body not a general effect on the whole body. Local anesthesia, in a strict sense, is anesthesia of a small part of the body.

Regional anesthesia is aimed at anesthetizing a larger part of the body such as a leg or arm, and general anesthesia refers to the whole body.

Conduction anesthesia is a hybrid and encompasses a great variety of local and regional anaesthetic techniques for surgery or medical use.

The vegetative state and the minimally conscious state are disorders of consciousness that can be acute and reversible or chronic and irreversible. Diffuse lesions of the thalami, cortical neurons, or the white-matter tracts that connect them cause the vegetative state, which is wakefulness without awareness.

Brain Death is the final clinical expression of complete and irreversible brain damage and loss of brain function, as evidenced by cessation of breathing and other vital reflexes, unresponsiveness to stimuli, absence of muscle activity, and a flat electroencephalogram for a specific length of time.

Brain Arrest is a cessation of brain signaling activity without irreversible brain damage. Since there is no irreversible brain damage, it is separate from brain death. During arrest the brain is supported by 'pilot light' or maintenance metabolism and there could be degrees of metabolism depending on conditions of arrest. Shares much in common with a reversible coma-like state. This condition shares some features with a reversible coma-like state, but differs from it by also arresting the brainstem area which is the area of the brain that controls heart rate, blood pressure and breathing.

Suspended Animation is a state of inactivity with a profound fall in energy metabolism where all life's processes are slowed and in an apparent 'animate or lifeless' state.

Hibernation is a state of 'winter' sleep or inactivity characterized by profound metabolic and respiratory depression and lower body temperature. Hibernation is an adaptation of certain animals to survive the winter months with little or no food. It is an energy-conserving strategy.

Torpor is a short-term hibernation with a lower body temperature. Transitions into and out of torpor are more physiologically challenging than the extreme metabolic suppression and cold body temperatures of torpor per se.

Aestivation is a state of 'summer' sleep or inactivity characterized by profound metabolic and respiratory depression and lower body temperature in certain animals living in warm climates as an adaptation to survive drought conditions.

Hibernation States vs. Suspended Animation: Winter or Summer Hibernation differs from suspended animation because the animal in natural hibernation undergoes periods of sporadic euthermic 'wake-up' arousals wherein body temperature, metabolism and renal reperfusion is restored to typical values then the animal re-enters its deeper sleep. The hibernator has arousal cycles throughout the period of hibernation and during each arousal cycle the animal still remains in a "sleepy/drowsy state".

Pulseless electrical activity (PEA) is a clinical condition characterized by unresponsiveness and lack of palpable pulse in the presence of organized cardiac electrical activity. Pulseless electrical activity has previously been referred to as electromechanical dissociation (EMD). PEA occurs when a major cardiovascular, respiratory, or metabolic derangement results in the inability of cardiac muscle to generate sufficient force in response to electrical depolarization. PEA is always caused by a profound cardiovascular insult (eg, severe prolonged hypoxia or acidosis or extreme hypovolemia or flow-restricting pulmonary embolus). Hypoxia secondary to respiratory failure is probably the most common cause of PEA, with respiratory insufficiency accompanying 40-50% of PEA cases. Situations that cause sudden changes in preload, afterload, or contractility often result in PEA.

Traumatic Brain Injury (TBI): In the United States, about 2 million cases are reported every year with approximately 500,000 people being hospitalized. The goal of therapy in patients with severe head injury is to avoid secondary brain damage including reducing brain swelling. Analgesia and sedation are an essential part of the therapy and barbiturates bring about the most pronounced decrease of brain metabolic rate and intra-cranial pressure. In addition, osmotic agents to reduce brain swelling are important and include mannitol and hypertonic saline (3% to 30% NaCl). Glutamate is the main excitory and GABA the main inhibitory neurotransmitter in the brain. Glutamate excitotoxicity plays an important role in the development of secondary injuries that occur following TBI. Acute increases in extracellular glutamate levels have been detected in both experimental brain trauma models and in human patients, and can lead to over-stimulation of glutamate receptors, resulting in a cascade of excitotoxic-related mechanisms culminating in neuronal damage and death. Lack of clinical success with glutamate receptor antagonists suggests that process of injury is more complicated that simply a "glutamate storm". A common consequence of traumatic brain injury, is diffuse traumatic axonal injury (TAI) and the underlying pathology involves inflammatory processes and coagulopathy.

In acute brain injury physiological uncoupling can occur between the CNS (autonomic) and the cardiovascular systems on multiple levels involving the brain, the sinoatrial node, the peripheral vasculature, and arterial baroreceptors leading to decreased heart beat oscillations, abnormal baroreflex sensitivity and heart rate variability, particularly at low frequencies. The present invention may improve neuro-autonomic regulation of heart rate and blood pressure oscillations and this would lead to improved whole body homeostasis at the level of metabolic, inflammatory and coagulation systems. Neural mechanisms are known to regulate inflammation; for example, the vagus nerve activity inhibits macrophage activation and the synthesis of tumor necrosis factor in the reticuloendothelial system through the release of acetylcholine.

Lastly, the cell's mitochondria play a critical role in ischaemia/reperfusion injury and cell death in traumatic brain injury and other forms of trauma. Injury may arise from oxidative stress, opening of the mitochondrial permeability transition pore (MPTP) and calcium overload. Protection from injury to a tissue or organ, including traumatic brain injury, may be afforded by inhibiting mPTP opening, thereby maintaining mitochondrial homeostasis and inhibiting pro-apoptotic protein release. Examples of mPTP inhibitors include melatonin and cyclosporine A, Sanglifehrin A, $Ca^{2+}$ chelation, ATP and Magnesium.

Treatment for delirium, demential and postoperative cognitive dysfunction (POCD): Cognitive decline is associated with traumatic brain injury, cardiac arrest (see below) or any major surgery and is a major cause of morbidity. Delirium is an acute onset of transient disturbed mental function (attention and orientation). Delirium occurs in 7-26% of patients undergoing surgery. Dementia is a series of syndromes associated with global deterioration of cognitive ability lasting months to years. POCD is a deterioration in performance in a battery of subjective neuropsychological tests that would be expected in <3.5% of controls.

Cardiac arrest/sudden death: Cardiac arrest is the abrupt cessation of cardiac pump function, which may be reversible by a prompt first respondent intervention but will lead to death in its absence. Comatose victim's of out-of-hospital cardiac arrest (OHCA) have high mortality (>95%) due to a complex pathophysiology that includes cardiovascular dysfunction, inflammation, coagulopathy, brain injury and persistence of the precipitating pathology. Therapeutic hypothermia (TH) is the only intervention that has been shown to improve outcomes in this patient population. In the 1990s, the concept of suspended animation was reintroduced as a new method of resuscitation of cardiac arrest patients who could not be resuscitated using standard of care. The idea was to preserve the viability of brain and whole body during cardiac arrest, until restoration of stable spontaneous circulation or prolonged artificial circulation is possible. Experimentally it has also been shown in animals that cardiac arrest leads to altered CNS baroreflex transmission and death and was reminiscent of that seen in humans who have sustained central lesions. Sudden death in humans with central lesions correlates with loss of CNS baroreflex transmission, cardiac arrhythmias and possibly cardiac damage.

Stroke: Ischemic cerebrovascular disease is the third leading cause of mortality and the major cause of chronic disability in the adult population in the western world today. A large proportion of nerve cell death during ischemia/reperfusion is NMDA-receptor-mediated and is linked to excessive stimulation of NMDA receptors (excessive glutamate production, see TBI above) coupled with other factors initiates a complex cascade of deleterious biochemical events. Numerous clinical trials of glutamate receptor antagonists for the treatment of stroke have been unsuccessful. However, stroke is more complex than glutamate increase and involves CNS imbalances, which can affect whole body function. Neurohumoral and other factors may feed back to alter the regulation of the operating point and generate CNS-cardiovascular interactions affecting hemodynamic stability in critically ill patients suffering from stroke.

Refractory status epilepticus (RSE) is a common problem in intensive care units and emergency departments with high mortality. RSE is defined as status epilepticus that continues despite treatment with benzodiazepines and one antiepileptic drug. Although propofol is considered an alternative treatment to barbiturates for the management of RSE, only limited data are available.

Subarachnoid hemorrhage, Cerebral Aneurysms, Abdominal aneurysms: Subarachnoid hemorrhage (SAH) is characterized by bleeding into the subarachnoid space, often caused by ruptured aneurysm. Aneurysmal rupture occurs in 700,000 individuals per year worldwide, with 40,000 cases taking place in the United States. These are life-threatening situations requiring emergency treatment.

Treatment for Heart Attack and Cardiogenic shock: Ischaemic heart disease is a set of symptoms caused by reduced blood flow to the heart and includes myocardial infarction (heart attack), angina pectoris (chest pain) and is the leading cause death worldwide. A heart attack occurs if the flow of oxygen-rich blood to a section of heart muscle suddenly becomes blocked and is a serious medical emergency. Cardiogenic shock is based upon an inadequate circulation of blood due to primary failure of the ventricles of the heart to function effectively. The most common cause of cardiogenic shock is damage to the heart muscle from a severe heart attack. Both can lead to circulatory collapse.

Treatment for Acute respiratory distress syndrome (ARDS) for Adult and Infants: ARDS is life-threatening reaction to injuries or acute infection to the lung. If not attended to the patient will die without rescue support.

Treatment for Civilian Military Trauma: Blood Loss, Burns or Blast Injury

The wars in Afghanistan (2006-present) and Iraq (2003-09) have resulted in the highest rates of combat casualties for the US and coalition forces since the Vietnam conflict, and deaths from close proximity blast injury patterns are the most common. Burns can be associated with blast injury. Blast or non-blast catastrophic hemorrhage is responsible for up to 50% of trauma deaths on the battlefield, and up to 20% of these may be salvageable. In the civilian setting, hemorrhage is responsible for 30 to 40% of the 5.8 million trauma deaths each year globally, with one-third to one-half occurring in the pre-hospital environment. Hemorrhagic shock arises from insufficient cardiac output leading to systemic hypotension, widespread tissue hypoperfusion, ischemia and hypoxia, inflammation and coagulopathy. Its severity will depend upon the volume of blood lost, the duration of shock and on the ability of the heart and body to compensate with the blood remaining in the circulation. In a 1984 Col. Ronald Bellamy launched a global challenge to develop a new resuscitation fluid to decrease preventable combat death following severe to massive blood loss. Today, despite advances in blood control technologies such as tourniquets and hemostatic bandages, the 'Bellamy challenge' remains wide open. There is no therapy to rescue the body in these conditions. In those states where massive blood loss has occurred it remains possible to place the body in a coma-like state for a period of time until the casualty can be transported to hospital for definitive care.

Treatment for Infection and Sepsis: Worldwide 20 to 30 million people become septic each year and over 8 million die. Currently there is no method and drug therapy to treat severe sepsis. Every hour 1000 people die and 24,000 die each day. Sepsis in increasing at an alarming rate of 8% to 13% per year in developed countries. Sepsis affects all ages from neonatal through to the elderly and critically ill. Sepsis is often diagnosed too late for treatment to be effective. Late detection is due to delay in detecting high temperatures, increased heart rate and breathing rate and increased white cell count, all of which could be due to other diseases. Recognition and speed of delivery of care are key factors to the high incidence of sepsis. A patient with sepsis is five times more likely to die than a patient who suffered a heart attack or stroke. Most people are not aware that sepsis is a leading cause of death worldwide. War wound infections have long posed a major challenge for military medicine, and as the care of casualties continues to enhance survival rates, infectious complications will remain a major cause of morbidity. Despite improvement in medical care, severe sepsis and septic shock remain an unmet medical need requiring breakthrough treatments and technologies. In those patients with severe sepsis or septic shock it remains possible to place the body in a coma-like state for a period of time until the casualty can be transported to hospital for definitive care.

Treatment for Severe Burns: More than 2 million people in the United States require treatment for burns each year, and between 3,000 and 4,000 die of severe burns. Burns are injuries to tissue that result from heat, electricity, radiation, or chemicals and a major problem on the battlefield. When tissues are burned, fluid leaks into them from the blood vessels, causing swelling. Severe burns cause immediate nervous shock and severe infections. People with deep or extensive burns may require resuscitation, intravenous fluids, surgery, and rehabilitation.

Treatment for Circulatory collapse: Cardiovascular collapse is any conditions where there is a sudden loss of effective blood flow due to cardiac and/or peripheral vascular factors and may reverse spontaneously (e.g., neurocardiogenic syncope; vasovagal syncope) or only with interventions (e.g., cardiac arrest). The latter is distinguished from the transient forms of cardiovascular collapse in that it usually requires an intervention to achieve resuscitation. In contrast, vasodepressor syncope and many primary bradyarrhythmic syncopal events are transient and non-life-threatening, with spontaneous return of consciousness. Without being bound by any particular theory or mode of action, the treatment according to the invention may reduce the incidence of irreversible injury of the central nervous system by achieving greater hemodynamic stability. In those patients with circulatory collapse it remains possible to place the body in a coma-like state for a period of time and reduce the incidence of irreversible injury of the central nervous system by achieving greater hemodynamic stability.

Method for inducing Circulatory arrest for aortic reconstruction surgery. Surgery on the thoracic aorta using hypothermic circulatory arrest carries significant morbidity and mortality due to neurological (brain) complications. Hypothermic circulatory arrest temporarily suspends blood flow under very cold body temperatures so blood circulation can be stopped for up to 40 minutes without harm to the patient. This allows surgery to safely be performed on the aorta. During the last decades, different cerebral protection methods have been introduced to reduce the incidence of such brain complications. Our invention may assist in placing the whole body in a state for surgery with brain protection.

Treatment for Neurodegeneration diseases: The CNS and in particular the autonomic nervous system (ANS) plays a role in a wide range of somatic and mental diseases. The prevalence of neurodegenerative disorders is increasing, but effective treatments are lacking. Neurodegenerative diseases show remarkable fluctuations in neurological functions, which may not be caused by sudden loss or gain of nerve cells. Instead, it is likely that they reflect variations in the activity of neural networks and, perhaps, chronic intoxication by abnormal proteins that the brain is temporarily able to overcome. Glutamate excitotoxicity has also been linked to chronic neurodegenerative disorders such as amyotrophic lateral sclerosis, multiple sclerosis (MS), Parkinson's disease and others. Without being bound by any particular theory or mode of action the methods according to the invention may reduce the imbalances in GABA and NMDA receptors may help slow or arrest the progression of the neurodegenerative disorders and this along with improved CNS balance may improve outcomes including improved CNS regulation of heart-rate variability, inflammation and coagulation.

Treatment for Abnormal Biorhythms in Injury, Infection, Surgery, Trauma or Disease: Acute brain injury results in decreased heart beat oscillations and baroreflex sensitivity indicative of uncoupling of the autonomic and cardiovascular systems. Without being bound by any particular theory or mode of action the methods according to the invention may improve neuroautonomic regulation of heart rate and blood pressure oscillations by reducing dangerous oscillations in the body's normal biorhythms such as in heart rate and blood pressure which implies improved brain function. Alternations in biorhythms also affect inflammation and disease states. For example, efferent nerve connections from the vagal nerve to the spleen can be modulated to block experimental septic shock and autoimmune immune models of rheumatoid arthritis.

Treatment and Method with Rescue Devices for the critically ill and life-threatening situations: In any critical illness when there is a profound myocardial depression and hemodynamic failure such as in the unconscious patient, severe sepsis, septic shock, hemorrhagic shock, cardiogenic shock, myocardial infarctions, cardiac arrest, brain injury, adult respiratory distress syndrome (ARDS) they may be rescued using venoarterial extracorporeal membrane oxygenation (ECMO), a portable life saving device similar to cardiopulmonary bypass. ECMO provides extracorporeal life support with artificial heart and lung for cardiopulmonary failure. ECMO can provide partial or total support, is temporary (days to weeks but in children following heart surgery may be months), and requires systemic anticoagulation. ECMO controls gas exchange and perfusion, stabilizes the patient physiologically, decreases the risk of ongoing iatrogenic injury, and allows ample time for diagnosis, treatment, and recovery from the primary injury or disease. ECMO is used in a variety of clinical circumstances and the results depend on the primary indication. ECMO provides life support but is not a form of treatment. Without being bound by any particular theory or mode of action the methods according to the invention could be used to rescue the critically ill or wounded prior to ECMO as a treatment and continued after ECMO has been connected for stabilization. A similar case would occur with cardiopulmonary bypass.

Adhesion is scar tissue formation. An adhesion is a band or deposits of fibrous strands/scar tissue that joins two internal body surfaces that are not usually connected. Adhesions develop as the body attempts to repair itself after surgery, infection, injury (traumatic and non-traumatic) and radiation. It is part of reaction or response to injury, which encompasses a wide range of inflammation, coagulation, endocrinological, and haematological effects. Typically adhesions involve the peritoneal surface, or may develop between any two surfaces during the healing process. Adhesions may also develop between adjacent solid organs, the intestines, fallopian tubes, omentum, or the abdominal wall.

Adhesion formation is a direct result of surgical trauma, inflammation, blood coagulation and the formation of 'sticky' fibrin networks on or between the peritoneal surfaces and attaching to the internal organs causing pain and dysfunction such as bowel obstructions. Adhesions begin to occur as fibroblasts, which proliferate and move toward the site of injury, migrate into these fibrin networks where collagen and other components of extracellular matrix are deposited. This results in the formation of extensive, dense, cohesive and tenacious post-operative fibrous adhesions. Adhesions are a major source of post-operative morbidity and, in some instances, mortality in patients who have had internal surgery. Abdominal and pelvic surgical procedures, which are a form of controlled trauma, commonly result in the development of adhesions.

Postsurgical adhesions have four major negative impacts on health care outcomes. First, adhesions cause significant morbidity, including intestinal obstruction, infertility and pelvic pain. Second, adhesions are associated with multiple surgical complications. Third, these complications lead to greater surgical workload and utilization of hospital and other health care resources. Fourth, all these negative impacts result in significant economic burden to society.

The Peritoneum is the lining of the abdominal cavity. Histologically it consists of two layers: a mesothelium and a connective tissue layer. The mesothelial cell layer is supported by a basement membrane, which has an underlying sheet of connective tissue. The connective tissue consists of the extra-cellular matrix made up of glycoproteins, glycosaminoglycans, proteoglycans, bundles of fibres of different types of collagen, several types of cells (scattered fibroblasts, macrophages and mast cells) and a varying quantity of fat. In the sub-serous space vascular structures, lymphatics and nerves are present. The nerves in the parietal peritoneum feature specialized receptors (thermo, chemo, and mechano-receptors), whereas the nerves attached to the intra-abdominal organs of the visceral peritoneum do not possess such specialized receptors but instead form networks that essentially respond to tension. The peritoneum is an "organ" and has multiple protective functions including regulation of inflammation, fibrinolysis, angiogenesis, and tissue remodeling processes. It maintains homeostasis by allowing exchange of molecules and production of peritoneal fluid, thus providing an environment in which intra-abdominal organs can function properly. It takes part in the formation and degradation of postoperative adhesions. The sequence of changes during the adhesion formation is indispensable in the healing of peritoneal trauma. The surface lining of the peritoneum is the key site in adhesion formation and prevention.

Peritoneal cavity is the virtual space between the parietal and visceral peritoneum making up a closed sac in the male and an open sac in the female through the gynaecological tract. The parietal and visceral peritoneum forms the most extensive serous membrane in the body with a surface area globally equal to that of the skin.

Adhesion surgery is a procedure performed to remove adhesions around the joints, pelvic organs or other organs in the abdomen. Surgery may be open or minimally invasive including arthroscopic, laprosopic or robotic surgery (e.g. da Vinci Surgical System).

Open surgery is the traditional type of surgery where a long incision is normally made by the surgeon to insert the instruments, and visualize and perform the surgery through the incision. Alternatively, less-invasive surgical approaches are common and include arthroscopic and laproscopic procedures (see below). Any surgery, including robotic surgery, leads to tissue injury and increases the possibility of infection and adhesion formation.

Arthroscopic Surgery is a type of minimally invasive "keyhole" surgery that is used to diagnose and treat medical conditions associated with the joints and to repair damage to the joints. The procedure is most commonly used on knees, wrists, elbows, ankles, shoulders and hips. Arthroscopy can be used repair damaged cartilage, remove fragments of loose bone, treat frozen shoulder and reduce pain in the joints and hips. Arthroscopy is also used to diagnose and treat adhesions in all joints, as well as in the abdominal peritoneal cavity. Complications following hip arthroscopy are largely transient with incidences between 0.5% and 6.4%. A problem of arthroscopic surgery is persistent post-operative pain caused by intra-articular adhesions have been reported both after open and arthroscopic approaches to the shoulder, knee and hip. In general, arthroscopy is primarily for examination, diagnosis and treatment of joint diseases and injuries whereas laproscopy is for examination, diagnosis and treatment of the abdomen.

Hypotensive Anaesthesia: Hypotensive anaesthesia is the controlled regulation of mean arterial pressures (MAP) that reduces blood loss during surgery or clinical interventions. Studies have shown that if MAP is reduced to 50 mmHg during surgery or interventions the blood loss can reduce by over 50%, which may reduce the need for fluid or blood products. The reduced blood loss also limits dilution and consumption of coagulation factors and subsequent postoperative rebound hypercoagulability. If MAP is maintained at 60 mmHg rather than 50 mmHg, blood loss is about 40% greater. Hypotensive anaesthesia can be induced using either general or regional anaesthesia and enhanced using vasodilators to improve cardiac output. Hypotensive anaesthesia is commonly used in orthopaedic surgery such as knee surgery.

Laproscopic Surgery is a type of minimally invasive "keyhole" surgery because it uses a number of small incisions and a specialized tubular instruments and a special camera known as a laparoscope are passed and the operator performs the surgery from viewing high-resolution video monitors in the operating room. At the beginning of the procedure, the abdomen is inflated with carbon dioxide gas to provide a working and viewing space for the surgeon. It is common surgical practice as it has advantages over open surgery in reducing the rate of adhesion formation, shorter hospital stay and an earlier return to normal activities and work. Similar to open surgery, laparoscopic surgery affects both the integrity and biology of the peritoneum. One complication of surgery after previous laparotomy is inadvertent enterotomy during reopening of the abdomen or subsequent adhesion. Laparoscopic surgery is also used to treatment lysis of adhesions. The incidence can be as high as 20% in open surgery and between 1% and 100% in laparoscopy depending on the underlying disease. Clinical and experimental studies have demonstrated that laparoscopic surgery may preserve the systemic immune system better than open procedures; Both systemic C-reactive protein levels and IL-6 levels are lower in patients undergoing laparoscopy than in those undergoing laparotomy.

Surgery per se causes trauma or injury from the act of performing surgery and/or from the procedures used to support the surgery such as intubation, catheters, infusions, drugs, external assist machines such as cardio-pulmonary bypass, ECMO and others. Direct trauma can occur from an incision, diathermy, retraction, compression beneath sternal retractor blades, desiccation, wetting, local hypothermia, and direct trauma from instruments, cauterisers, sutures, staples, and organ, tissue or joint manipulation. These procedures can also cause infection. The body reacts to surgical procedures using a complex systemic "early-defense" system activated by trauma, infection, stress, neoplasia, and inflammation and coagulation disorders. Part of this early-defense system is called the acute phase or stress response (see definition below). Systemic inflammation also results in a systemic acute phase response. Ways to improve the patient's response to surgery such as blunting the early inflammatory and coagulation response may reduce secondary complications including infection and adhesions. The problem is massive as data from 56 countries showed that in 2004 the annual volume of major surgery was an estimated 187 million-281 million operations, or approximately one operation annually for every 25 human beings alive. The rate of major complications has been documented to occur in 3-16% of inpatient surgical procedures, and the death rate 0.4-0.8%. Nearly half the adverse events in these studies were determined to be preventable.

The acute phase response (APR) is a complex systemic early-defense of the body system activated by infection, injury, trauma, infection, stress, neoplasia, and inflammation. The term 'acute phase' was introduced in the 1930s when the first "acute phase" protein, C-reactive protein was discovered early during pneumococcal infection of monkeys and humans. Today, CRP remains an APP of primary interest in humans, where it is a major marker of infection, autoimmune disease, trauma, surgery, malignancy, and necrosis including myocardial infarction. Although nonspecific, acute phase response serves as a core of the innate immune response involving physical and molecular barriers and responses that serve to prevent infection, clear potential pathogens, initiate inflammatory processes, and contribute to resolution and the healing process. A prominent feature of this early response is the appearance of pro-inflammatory cytokines, particularly IL-6 and the induction of acute phase proteins in the liver and elsewhere such as C-reactive protein, fibrinogen, $\alpha_2$-macroglobulin and other anti-proteinases, which are involved in the restoration of homeostasis. In addition, cytokines and growth factors, such as transforming growth factor-beta (TGF-b) and TNFα, are secreted by polymorphonuclear leukocytes (PMN's or neutrophils). Systemic inflammation results in a systemic acute phase response. Acute phase proteins are blood proteins primarily synthesized by hepatocytes as part of the acute phase response. The goal of acute phase response is reestablishing homeostasis and promot healing. However, uncontrolled and prolonged action of cytokines is potentially harmful, therefore mechanisms exist which limit the activity of cytokines, to reduce inflammation and coagulation disorders is required. Acute phase proteins have been well recognized for their application to human diagnostic medicine and have been described to have value in the diagnosis and prognosis of cardiovascular disease, autoimmunity, organ transplant, and cancer treatment.

With respect to adhesion formation surgical trauma results in mesothelial damage and elicits an inflammatory response. Mesothelial cells balloon and detach from the basal membrane, thereby creating denuded areas. The inflammatory reaction is accompanied by the production and release of a broad spectrum of biologically active proteins and the exudation of protein-rich fluid. The peritoneal fibrinolytic response is rapidly disturbed leading to peritoneal hypofibrinolysis leading to clotting (see Inflammation and coagulation below). Besides surgical trauma, laproscopy can damage the peritoneal layer from increasing abdominal pressure with peritoneal distension, exposure to $CO_2$ inflation (see laproscopic surgery) and intense illumination and cooling of the peritoneal cavity. Surgical trauma and cardiopulmonary bypass also contribute to a major inflammatory response in the patient after cardiac surgery.

Postoperative adhesions are a natural consequence of surgical tissue trauma and healing. Adhesions that develop after an surgical operation or arthroscopic intervention to the body. Postoperative intra-abdominal and pelvic adhesions are the leading cause of infertility, chronic pelvic pain, and intestinal obstruction. Some surgical barriers have been demonstrated effective for reducing postoperative adhesions, but there is no substantial evidence that their use improves fertility, decreases pain, or reduces the incidence of postoperative bowel obstruction.

Arthroscopic procedures are, at best, semi-sterile, as the extremity has fluid extravasate throughout the duration of the procedure. Converting from an arthroscopic procedure to an open procedure may increase the potential for development of an infection from routine skin pathogens. The incidence of deep infection after standard open rotator cuff repair has been reported to range from 0.3% to 2%.

Mesenteric ischaemia is a condition characterized by high mortality and occurs when the blood flow to the small intestine is slowed or stopped. Due to the diminished blood flow, the cells in your gut fed by the mesenteric artery are starved for oxygen, and can become damaged and lead to Ileus, adhesions, infection and severe sepsis. Mesenteric venous thrombosis can occur when a blood clot develops in the vein that carries blood away from the intestines and may result from acute or chronic inflammation of the pancreas (pancreatitis), abdominal infection, bowel diseases, such as ulcerative colitis, Crohn's disease or diverticulitis, hypercoagulation disorders, injury (traumatic or non-traumatic) to the abdomen.

Intestinal ischaemia is defined as reduced blood flow to the entire intestine and can occur in clinical scenarios such as organ transplantation, trauma and cardio-pulmonary bypass, as well as in neonatal necrotizing enterocolitis or persistent ductus arteriosus. Ischemia can lead to inflammation, infection, multiple organ dysfunction and death.

Inflammatory bowel disease is an inflammatory disease of the bowel and the cause(s) are not fully known. Genetic, environmental, microbial, and immunologic factors are involved, but the precise mechanisms are obscure. Examples include ulcerative colitis and Crohn's disease. Immunosuppressive therapy can have potentially life-threatening consequences such as infections and reactivations of latent infections like tuberculosis or cytomegalovirus. Treatment often emphasizes a program rather than a drug therapy. Adhesions can also common after inflammation.

Ileus is a disruption of the normal movement of the gastrointestinal tract and more often as simply bowel obstruction. It is caused by decreased motor activity of the GI tract due to non-mechanical causes such as low blood supply to parts of intestine (mesenteric ischemia), inflammation (e.g. acute pancreatitis, peritonitis, diverticulitis) and infection (eg sepsis). Paralytic ileus is a common side effect of some types of surgery and called postsurgical ileus. Ileus may increase adhesion formation, because intestinal segments have more prolonged contact, allowing fibrous adhesions to form, and intestinal distention causes serosal injury and ischemia. Improved blood supply and correction of coagulopathy and reduced inflammation from the present invention would be expected to reduce the complications of ischemia and formation of sepsis.

Opening the peritoneal cavity during general abdominal, vascular, gynaecological, urological and orthopaedic surgery may lead to adhesion formation in up to 95% of Patients. Peritoneal adhesions are a consequence of peritoneal irritation by surgical injury, inflammation and infection.

Abdominal Surgery adhesions develop following trauma to the mesothelium, which is damaged often by surgical handling and instrument contact, foreign materials such as sutures and glove dusting powder, desiccation, and overheating. Adhesions occur in up to 95% of patients following lower abdominal abdominal surgical procedures, whether open or laparoscopic. The clinical consequences of postoperative adhesions are well documented and include small bowel obstruction, secondary infertility in women, and reduced quality of life. Intra-abdominal adhesions constitute between 49% and 74% of the causes of small bowel obstruction. Studies have shown that postsurgical adhesions are responsible for up to 40% of infertility cases. Post-operative adhesions are the leading cause of intestinal obstruction in the developed world accounting for 40% of all intestinal obstructions and 60-70% of small bowel obstructions.

Abdominal infections (complicated): Despite advances in diagnosis, surgery, and antimicrobial therapy, mortality rates associated with complicated intra-abdominal infections remain exceedingly high. They include a wide spectrum of pathological conditions, ranging from uncomplicated appendicitis to fecal peritonitis. In a recent study of 702 patients who underwent surgery or interventional drainage to address complicated intra-abdominal infections, generalized peritonitis was observed in 43.3% cases, and localized peritonitis or abscesses in 57.7% of patients. 87% were community acquired and 13% were hospital or healthcare-associated infections. The overall mortality rate was 10.1% (71/702). The final results of the CIAOW Study will be published following the conclusion of the study period in March 2013.

Adhesions occur in more than 90% of the patients following major abdominal surgery and in 55-100% of the women undergoing pelvic surgery.

Postoperative adhesions occur in 60% to 90% of patients undergoing major gynecologic surgery and represent one of the most common causes of intestinal obstruction. The incidence of adhesion-related intestinal obstruction after gynecologic surgery for benign conditions without hysterectomy is approximately 0.3%, increasing to 2% to 3% among patients who undergo hysterectomy, and is as high as 5% if a radical hysterectomy is performed. Postoperative adhesions are sequelae of impaired fibrinolysis of the fibrin and cellular exudate after peritoneal injury. Adequate blood supply is essential for normal fibrinolysis. Improved blood supply to areas of injury and ischemia may improve outcomes.

Adhesion formation after cardiac surgery is a well-documented and a significant complication encountered during secondary re-operative procedures. Redo's can account for up to 15 to 20% of all 350,000 operations performed each year in the USA, and a similar figure in Europe. Prevention of adhesions after the first cardiac surgery operation would reduce the risk during secondary redo procedures. After most if not all open-heart procedures, extensive adhesions form between the epicardial surface of the pericardium (see below Heart Pericardium) and the inner surface of the sternum (Sternal adhesions).

The pericardium is double-walled sac containing the heart and the roots of the great vessels. The pericardial cavity lies between the visceral pericardium and the parietal pericardium (the two layers). This cavity is filled with pericardial fluid which serves as a shock absorber by reducing friction between the pericardial membranes for heart movement. The opening of the pericardial cavity during cardiac surgery promotes the formation of adhesions, which are considered unavoidable. Post-operative intrapericardial adhesions may complicate the technical aspects of reoperations and they increase the risk of injury to the heart and great vessels as well as perioperative bleeding. In two large series of cardiac reoperations, the rate of inadvertent injury ranged from 7% to 9%.

Sternal adhesions occur after opening and closing the sternum (often called the zipper) after cardiovascular surgery. Sternal re-entry and dissection of post-operative cardiac adhesions expose the patient to risks, such as injury to the innominate vein and aorto-coronary bypass grafts. A 2% to 6% incidence of major vascular injury, often including the right ventricle, right atrium, or aorta has been reported as a direct result of sternal adhesions. These can lead to catastrophic injury during re-entry and possibly death. Deep sternal wound infection is a devastating complication of cardiac surgery, with a historical incidence of 0.4-5%. The prevailing approach for deep sternal wound infection of debridement and flap coverage without osseous closure makes subsequent reoperation difficult. A method of reducing sternal wound adhesions and infection would reduce cardiac surgery complications for recovery and redo-operations.

Inflammation is a local or systemic immune response of the body to injury (traumatic and non-traumatic), infection, surgery or radiation, and without being bound by any particular mode of action or theory has been linked to adhesions formation. In the condition of peritoneal adhesions, surgical trauma results in damage to the mesothelial layer of the peritoneum and elicits an inflammatory response. Mesothelial cells enlarge and detach from the basal membrane and create denuded areas. The inflammatory reaction is accompanied by the production and release of a broad spectrum of biologically active proteins and the exudation of protein-rich fluid. Accompanying this change to mesothelial dysfunction is a decreased peritoneal fibrinolysis which is a hypofibrinolysis or promotion of clotting (See Inflammation and Coagulation and Adhesions). This hypofibrinolytic state may be caused by both an increase in its inhibitors and a quick release of tPA from the visceral peritoneum during surgery.

In the condition of adhesive capsulitis it is thought to involve synovial inflammation. IL-1a, IL-1b, TNF-alpha, COX-1, and COX-2 were expressed at significantly high levels in the joint capsules of the frozen shoulder group compared with those of the control group. Post-operative intrapericardial adhesions is linked to (1) loss of mesothelial cells, (2) accumulation of fibrin in areas devoid of mesothelial cells, (3) loss of normal pericardial fibrinolysis, and (4) local inflammation. Early signs of local inflammation involves vascular congestion, tissue edema, and white blood cell margination.

Inflammation can promote coagulation (ability of the blood to clot) and visa versa. Abdominal surgery elicits an inflammatory response, which is accompanied by the formation of fibrin in the peritoneal cavity. During conventional surgery, the peritoneal fibrinolytic system is rapidly depressed, which eventually might lead to peritoneal adhesion formation. A hypofibrinolytic state is a procoagulant state (hypercoagulopathy) and may be caused by both an increase in its inhibitors and a quick release of tissue-type plasminogen activator (tPA) from the visceral peritoneum during surgery. tPA is the chief plasminogen activator in the blood, however its activity is restricted by plasminogen activating inhibitors type 1 (PAI-1) and type 2 (PAI-2). Inadequate peritoneal fibrinolysis may result from decreased tPA, increased PAI-1 and PAI-2, or both. Reduced fibrinolysis in human peritoneum associated with infection (peritonitis) and abdominal surgery correlates with increased adhesion formation and may thus be an important early biochemical event leading to adhesion formation. The regulation of plasmin-mediated fibrin degradation in the peritoneal cavity is poorly understood. However, new insights in the cellular distribution of fibrinolytic components in peritoneal tissue suggest that the mesothelium appears to have a principal role in fibrin regulation in the peritoneal cavity and in the early formation of adhesions.

Increased clotting is normally associated with increasing tissue factor (TF) expression, eliciting the expression of leukocyte adhesion molecules on the intravascular cell surfaces, and down regulating the fibrinolytic and protein C anticoagulant pathways. Thrombin, in turn, can promote inflammatory responses. This creates a cycle that logically progresses to vascular injury and the formation of adhesions. In the case of post-pericardial adhesions, a layer of neoconnective tissue is formed on the pericardial surfaces covered by fibrin accumulations and inflammatory cells and fibroblasts. Fibrin strands are the scaffolds for the growth of connective tissue that generates adhesions. Collagen fibers are deposed between the denuded pericardial surfaces and areas of inflammatory cell accumulation. Finally, the connective tissue promotes the fusion between the visceral and parietal pericardium. Early signs of angiogenesis are evident. In clinical practice, very dense and bleeding adhesions can be observed at reoperation during this period.

The primary role of TNF alpha is in the regulation of immune cells. TNF alpha is a cytokine involved in systemic and local inflammation, and along with other cytokines stimulates the acute phase reaction (see definition above) to stress including injury, infection and adhesions. TNF-alpha used as a biological marker for postoperative intra-abdominal adhesion formation and shoulder. Recent studies show that early blocking of the activity of TNF-alpha with infliximab after cecal abrasion resulted in lower rates of adhesion formation.

TNF alpha via the inflammatory response is linked to other clinical problems associated with autoimmune disorders. TNF-alpha also induces activation of coagulation. Activated protein C inhibits TNF-alpha production. Activated protein C (and antithrombin) may inhibit the endothelial perturbation induced by cytokines. Antithrombin regulates TNF-alpha induced tissue factor expression on endothelial cells by an unknown mechanism. Activated protein C and antithrombin, and their pathways of regulation, may be useful targets for treating coagulation abnormalities associated with sepsis or other inflammation diseases. These sites and pathways inhibit not only coagulation but also involved with the downregulation of anticoagulant activities of endothelial cells. These processes may play an important role in the injury hypothesis of adhesion formation. Any drug therapy that inhibits TNF alpha has many therapeutic targets including reducing injury, infections and adhesions.

Persistent pain from nerve endings as they become entrapped within developing adhesions can occur after surgery, infection, injury (trauma) and radiation. Pain can arise from a number of causes but injury and uncontrolled inflammation are central. Persistent pain can occur among arthroscopic joint surgery (knee, elbow, shoulder and hip). Inflammation and fibrosis of the joint capsule is a problem with shoulder reconstruction or surgery and can lead to pain and limited motion. Rotator cuff repair is one of the most painful arthroscopic procedures.

Adhesive capsulitis also known as frozen shoulder, is a common condition involving scapulohumeral pain and loss of motion and occurs in 2% to 5% of the general population. The disease is thought to be a combination of synovial and capsular tissue inflammation and capsular fibrosis. Conditions such as calcific tendonitis, bicipital tenosynovitis, glenohumeral and acromioclavicular arthritis, and tears of the rotator cuff can also lead to a stiff and painful shoulder.

Nearly half of all cancer patients receive radiation therapy. High-energy radiation can kill or control the spread of cancer cells along with chemotherapy and surgery. A possible late complication of abdominal or pelvic radiation therapy is abdominal adhesions, a type of fibrous scarring that can remain unrecognized until months or years later.

Tissue: The term "tissue" is used herein in its broadest sense and refers to any part of the body exercising a specific function including organs and cells or parts thereof, for example, cell lines or organelle preparations. Other examples include conduit vessels such as arteries or veins or circulatory organs such as the heart, respiratory organs such as the lungs, urinary organs such as the kidneys or bladder, digestive organs such as the stomach, liver, pancreas or spleen, reproductive organs such as the scrotum, testis, ovaries or uterus, neurological organs such as the brain, germ cells such as spermatozoa or ovum and somatic cells such as skin cells, heart cells (ie, myocytes), nerve cells, brain cells or kidney cells.

Organ: The term "organ" is used herein in its broadest sense and refers to any part of the body exercising a specific function including tissues and cells or parts thereof, for example, endothelium, epithelium, blood brain barrier, cell lines or organelle preparations. Other examples include circulatory organs such as the blood vessels, heart, respiratory organs such as the lungs, urinary organs such as the kidneys or bladder, digestive organs such as the stomach, liver, pancreas or spleen, reproductive organs such as the scrotum, testis, ovaries or uterus, neurological organs such as the brain, germ cells such as spermatozoa or ovum and somatic cells such as skin cells, heart cells i.e., myocytes, nerve cells, brain cells or kidney cells.

Donor Organs: In another aspect the present invention may allow for subjects in a coma-like state or having whole body arrest, to donate organs. The methods protect cells tissues, organs for use in transplantation.

Subject: The subject may be a human or an animal such as a livestock animal (eg, sheep, cow or horse), laboratory test animal (eg, mouse, rabbit or guinea pig) or a companion animal (eg, dog or cat), particularly an animal of economic importance. Preferably, the subject is human.

Body: The body is the body of a subject defined above.

Comprises: It will also be understood that the term "comprises" (or its grammatical variants) as used in this specification is equivalent to the term "includes" and should not be taken as excluding the presence of other elements or features.

Prior art: Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art. Pharmaceutical composition: The term "pharmaceutical composition" as used in this specification also includes "veterinary composition".

Reducing: The term "reducing" includes minimizing or preventing.

Derivative: The term derivative refers to variations in the structure of compounds. The derivatives are preferably "pharmaceutically acceptable derivative" which includes any pharmaceutically acceptable salt, hydrate, ester, ether, amide, active metabolite, analogue, residue or any other compound which is not biologically or otherwise undesirable and induces the desired pharmacological and/or physiological effect.

Salts: Salts of the compounds are preferably pharmaceutically acceptable, but it will be appreciated that non-pharmaceutically acceptable salts also fall within the scope of the specification, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

Magnesium Ions

In one embodiment, the methods and compositions according to the invention further include magnesium ions, preferably elevated magnesium ions i.e. over normal plasma concentrations. Preferably the magnesium is divalent and present at a concentration of 800 mM or less, 0.5 mM to 800 mM, 10 mM to 600 mM, 15 mM to 500 mM, 20 mM to 400 mM, 20 mM or 400 mM, more preferably 20 mM. Magnesium sulphate and magnesium chloride are suitable sources in particular magnesium sulphate.

The inventor has also found that the inclusion of the magnesium ions with (i) a compound selected from at least one of a potassium channel opener, a potassium channel agonist and an adenosine receptor agonist; and (ii) an antiarrhythmic agent or a local anaesthetic may also reduce injury. The effect of the particular amounts of magnesium ions is to control the amount of ions within the intracellular environment. Magnesium ions tend to be increased or otherwise restored to the levels typically found in a viable, functioning cell.

Thus in another aspect, the composition useful in the methods according to the invention may further include a source of magnesium in an amount for increasing the amount of magnesium in a cell in body tissue.

According to this aspect, there is provided a method of increasing blood pressure in a subject that has suffered a life threatening hypotension or shock, including the administration of a composition including (i) a compound selected from at least one of a potassium channel opener, a potassium channel agonist and an adenosine receptor agonist; and (ii) an antiarrhythmic agent or a local anaesthetic and an elevated source of magnesium ions. The composition may also include or be administered with an anti-inflammatory agent and/or metabolic fuel.

Potassium

If potassium is present in the composition it will typically be present in an amount at physiological levels to ensure that the blood concentration of the subject is less than 10 mM or 3 to 6 mM. This means that when the composition is administered, the cell membrane remains in a more physiological polarised state thereby minimising potential damage to the cell, tissue or organ. High concentrations or concentrations above physiological levels of potassium would result in a hyperkalemic composition. At these concentrations the heart would be arrested alone from the depolarisation of the cell membrane.

One advantage of using physiological concentrations of potassium is that it renders the present composition less injurious to the subject, in particular paediatric subjects such as neonates/infants. High potassium has been linked to an accumulation of calcium which may be associated with irregular heart beats during recovery, heart damage and cell swelling. Neonates/infants are even more susceptible than adults to high potassium damage during cardiac arrest. After surgery a neonate/infant's heart may not return to normal for many days, sometimes requiring intensive therapy or life support.

In one embodiment, there is no potassium present in the composition.

Adenosine Receptor Agonist

In the embodiments of the invention described above and below, component (i) of the composition may be an adenosine receptor agonist. While this obviously includes adenosine itself or derivatives thereof such as CCPA and the like described below, the "adenosine receptor agonist" may be replaced or supplemented by a compound that has the effect of raising endogenous adenosine levels. This may be particularly desirable where the compound raises endogenous adenosine levels in a local environment within a body. The effect of raising endogenous adenosine may be achieved by a compound that inhibits cellular transport of adenosine and therefore removal from circulation or otherwise slows its metabolism and effectively extends its half-life (for example, dipyridamole) and/or a compound that stimulates endogenous adenosine production such as purine nucleoside analogue Acadesine™ or AICA-riboside (5-amino-4-imidazole carboxamide ribonucleoside). Acadesine is also a competitive inhibitor of adenosine deaminase (Ki=362/vM in calf intestinal mucosa.) Acadesine™ is desirably administered to produce a plasma concentration of around 50 μM but may range from 1 μM to 1 mM or more preferably from 20 to 200 μM. Acadesine™ has shown to be safe in humans from doses given orally and/or intravenous administration at 10, 25, 50, and 100 mg/kg body weight doses.

Suitable adenosine receptor agonists may be selected from: $N^6$-cydopentyladenosine (CPA), N-ethylcarboxamido adenosine (NECA), 2-[p-(2-carboxyethyl)phenethyl-amino-5'-N-ethylcarboxamido adenosine (CGS-21680), 2-chloroadenosine, $N^6$-[2-(3,5-demethoxyphenyl)-2-(2-methoxyphenyl)ethyladenosine, 2-chloro-$N^6$-cyclopentyladenosine (CCPA), N-(4-aminobenzyl)-9-[5-(methylcarbonyl)-beta-D-robofuranosyl]-adenine (AB-MECA), ([IS-[1 a,2b,3b,4a (S*)]]-4-[7-[[2~(3-chloro-2-thienyl)-1-methyl-propyl]amino]-3H-imidazole[4,5-b]pyridyl-3-yl]cyclopentane carboxamide (AMP579), $N^6$-(R)-phenylisopropyladenosine (R-PLA), aminophenylethyladenosine (APNEA) and_cyclohexyladenosine (CHA). Others include full adenosine A1 receptor agonists such as N-[3-(R)-tetrahydrofuranyl]-6-aminopurine riboside (CVT-510), or partial agonists such as CVT-2759 and allosteric enhancers such as PD81723. Other agonists include N6-cyclopentyl-2-(3-phenylaminocarbonyltriazene-1-yl)adenosine (TCPA), a very selective agonist with high affinity for the human adenosine A1 receptor, and allosteric enhancers of A1 adenosine receptor includes the 2-amino-3-naphthoylthiophenes. Preferably, the A1 adenosine receptor agonist is CCPA.

The concentration of adenosine receptor agonist in the composition maybe 0.0000001 to 100 mM, preferably 0.001 mM to 50 mM and most preferably 0.1 mM to 25 mM. In one embodiment, the concentration of the adenosine receptor agonist in the composition is about 19 mM.

The contact concentration of adenosine receptor agonist may be the same or less than the composition concentration set out above It will be appreciated if the composition is diluted with a pharmaceutically acceptable carrier, including but not limited to blood, saline or a physiological ionic solution, the dosage of the composition may be adapted to achieve the most preferred contact concentrations.

Potassium Channel Openers or Agonists

In addition to the adenosine receptor agonist, or instead of the adenosine receptor agonist, component (i) of the composition may be a potassium channel opener.

Potassium channel openers are agents which act on potassium channels to open them through a gating mechanism. This results in efflux of potassium across the membrane along its electrochemical gradient which is usually from inside to outside of the cell.

Thus potassium channels are targets for the actions of transmitters, hormones, or drugs that modulate cellular function. It will be appreciated that the potassium channel openers include the potassium channel agonists which also stimulate the activity of the potassium channel with the same result. It will also be appreciated that there are diverse classes of compounds which open or modulate different potassium channels; for example, some channels are voltage dependent, some rectifier potassium channels are sensitive to ATP depletion, adenosine and opioids, others are activated by fatty acids, and other channels are modulated by ions such as sodium and calcium (ie. channels which respond to changes in cellular sodium and calcium). More recently, two pore potassium channels have been discovered and thought to function as background channels involved in the modulation of the resting membrane potential.

Potassium channel openers may be selected from the group consisting of: nicorandil, diazoxide, minoxidil, pinacidil, aprikalim, cromokulim and derivative U-89232, P-1075 (a selective plasma membrane KATP channel opener), emakalim, YM-934, (+)-7,8-dihydro-6,6-dimethyi-7-hydroxy-8-(2-oxo-1-piperidinyl)-6H-pyrano[2,3-1] benz-2,1, 3-oxadiazole (NIP-121), R0316930, RWJ29009, SDZPC0400, rimakalim, symakalim, YM099, 2-(7,8-dihydro-6,6-dimethyl-6H-[1,4]oxazino[2,3-f][2,1,3]benzoxadiazol-8-yl) pyridine N-oxide, 9-(3-cyanophenyl)-3,4,6,7, 9,10-hexahydro-1,8(2H,5H)-acridinedione (ZM244085), [(9R)-9-(4-fluoro-3-125iodophenyl)-2,3,5,9-tetrahydro-4H-pyrano[3,4-b]thieno[2,3-e]pyridin-8(7H)-one-1,1-dioxide] ([125I]A-312110), (−)-N-(2-ethoxyphenyl)-N'-(1,2,3-trimethyipropyl)-2-nitroethene-1,1-diamine (Bay X 9228), N-(4-benzoyl phenyl)-3,3,3-trifiuro-2-hydroxy-2-methylpropionamine (ZD6169), ZD6169 (KATP opener) and ZD0947 (KATP opener), WAY-133537 and a novel dihydropyridine potassium channel opener, A-278637. In addition, potassium channel openers may be selected from BK-activators (also called BK-openers or BK(Ca)-type potassium channel openers or large-conductance calcium-activated potassium channel openers) such as benzimidazolone derivatives NS004 (5-trifluoromethyl-1-(5-chloro-2-hydroxyphenyl)-1,3-dihydro-2H-benzimidazole-2-one), NS1619 (1,3-dihydro-1-[2-hydroxy-5-(trifluoromethyl)phenyl]-5-(trifluoromethyl)-2H-benzimidazol-2-one), NS1608 (N-(3~(trifluoromethyl)phenyl)-N'-(2-hydroxy-5-chlorophenyl)urea), BMS-204352, retigabine (also GABA agonist). There are also intermediate (eg. benzoxazoles, chlorzoxazone and zoxazolamine) and small-conductance calcium-activated potassium channel openers.

Diazoxide and nicorandil are particular examples of potassium channel openers or agonists.

Diazoxide is a potassium channel opener and in the present invention it is believed to preserve ion and volume regulation, oxidative phosphorylation and mitochondrial membrane integrity (appears concentration dependent). More recently, diazoxide has been shown to provide cardio-protection by reducing mitochondrial oxidant stress at reoxygenation. At present it is not known if the protective effects of potassium channel openers are associated with modulation of reactive oxygen species generation in mitochondria. Preferably the concentration of the diazoxide is between about 1 to 200 uM. Typically this is as an effective amount of diazoxide. More preferably, the contact concentration of diazoxide is about 10 μM.

Nicorandil is a potassium channel opener and nitric oxide donor which can protect tissues and the microvascular integrity including endothelium from ischemia and reperfusion damage. Thus it can exert benefits through the dual action of opening KATP channels and a nitrate-like effect. Nicorandil can also reduce hypertension by causing blood vessels to dilate which allows the heart to work more easily by reducing both preload and afterload. It is also believed to have anti-inflammatory and anti-proliferative properties which may further attenuate ischemia/reperfusion injury.

In addition, potassium channel openers may act as indirect calcium antagonists, ie they act to reduce calcium entry into the cell by shortening the cardiac action potential duration through the acceleration of phase 3 repolarisation, and thus shorten the plateau phase. Reduced calcium entry is thought to involve L-type calcium channels, but other calcium channels may also be involved.

Some embodiments of the invention utilise direct calcium antagonists, the principal action of which is to reduce calcium entry into the cell. These are selected from at least five major classes of calcium channel blockers as explained in more detail below. It will be appreciated that these calcium antagonists share some effects with potassium channel openers, particularly ATP-sensitive potassium channel openers, by inhibiting calcium entry into the cell.

Adenosine as well as functioning as an adenosine receptor agonist is also particularly preferred as the potassium channel opener or agonist. Adenosine is capable of opening the potassium channel, hyperpolarising the cell, depressing metabolic function, possibly protecting endothelial cells, enhancing preconditioning of tissue and protecting from ischaemia or damage. Adenosine is also an indirect calcium antagonist, vasodilator, antiarrhythmic, antiadrenergic, free radical scavenger, arresting agent, anti-inflammatory agent (attenuates neutrophil activation), analgesic, metabolic agent and possible nitric oxide donor. More recently, adenosine is known to inhibit several steps which can lead to slowing the blood clotting process. In addition, elevated levels of adenosine in the brain has been shown to cause sleep and may be involved in different forms or dormancy. An adenosine analogue, 2-chloro-adenosine, may be used.

The concentration of potassium channel opener or agonist in the composition may be 0.0000001 to 100 mM, preferably 0.001 mM to 50 mM and most preferably 0.1 mM to 25 mM. In one embodiment, the concentration of the potassium channel opener in the composition is about 19 mM.

The contact concentration of potassium channel opener or agonist may be the same or less than the composition concentration set out above It will be appreciated if the composition is diluted with a pharmaceutically acceptable carrier, including but not limited to blood, saline or a physiological ionic solution, the dosage of the composition may be adapted to achieve the most preferred contact concentrations.

In a preferred form, the potassium channel opener, potassium channel agonist and/or adenosine receptor agonist has a blood half-life of less than one minute, preferably less than 20 second.

Citrate

A citrate is used in the methods and compositions of the present invention. Examples of a citrate include citrate and derivatives thereof such as citric acid, salts of citrate, esters of citrate, polyatomic anions of citrate or other ionic or drug complexes of citrate. When citrate in its various forms is not included in the composition it can be administered separately in a blood, blood: crystalloid ratio or crystalloid solution and mixed to the preferred level in the composition prior to administration to the body, organ, tissue or cell.

Preferably, the form of citrate includes citrate phosphate dextrose (CPD) solution, magnesium citrate, sodium citrate, potassium citrate or sildenafil citrate, more preferably CPD.

In the critically ill, impairment to metabolism may occur from the inhibition of pyruvate dehydrogenase in sepsis, shock or traumatic brain injury. This may limit pyruvate conversion to acetyl-coenzyme A, the main substrate that fuels the Krebs cycle to replenish ATP in the cell's powerhouse, the mitochondria. A large part of Acetyl CoA comes from glucose metabolism (glycolysis) however Acetyl CoA can alternatively come from other pathways such as ketone metabolism, which forms acetyl CoA primes the cycle by forming citrate. Citrate administration may also bypass glucose requirement during insulin resistance and improve outcome. Citrate has the advantage of not needing insulin to enter the cell and generate ATP in the mitochondria, and thus may replenish the Krebs cycle if acetyl CoA is limiting or when Krebs cycle intermediates are limiting as a result of sepsis. Citrate can also act by lowering the cellular burden of non-esterified fatty acids that have been implicated in mitochondrial dysfunction during sepsis.

The concentration of a citrate in the composition may be 0.0000001 to 100 mM, preferably 0.001 mM to 50 mM and most preferably 0.1 mM to 10 mM. In one embodiment, the concentration of citrate in the composition is about 2.1 mM.

The contact concentration of a citrate may be the same or less than the composition concentration set out above.

It will be appreciated if the composition is diluted with a pharmaceutically acceptable carrier, including but not limited to blood, saline or a physiological ionic solution, the dosage of the composition may be adapted to achieve the most preferred contact concentrations.

Antiarrhythmic Agent or Local Anaesthetic

The composition useful in methods according to the invention also includes an antiarrhythmic agent. Antiarrhythmic agents are a group of pharmaceuticals that are used to suppress fast rhythms of the heart (cardiac arrhythmias). The following table indicates the classification of these agents.

| CLASS | Channel effects | Repolarisation Time | Drug Examples |
| --- | --- | --- | --- |
| IA | Sodium block | Prolongs | Quinidine, disopyramide, Procaine |
| IB | Sodium block | Shortens | Lidocaine, phenytoin, mexiletine, Tocainide |
| IC | Sodium block | Unchanged | Flecainide Propafenone, moricizine |
| II | Phase IV (depolarising current); Calcium channel | Unchanged | Beta-blockers including sotalol |
| III | Repolarising Potassium Currents | Markedly prolongs | Amiodarone, Sotalol, bretylium |
| IVA | AV nodal calcium block | Unchanged | Verapamil, diltiazem |
| IVB | Potassium channel openers | Unchanged | Adenosine, ATP |

It will also be appreciated that the antiarrhythmic agent may induce local anaesthesia (or otherwise be a local anaesthetic), for example, mexiletine, diphenylhydantoin, prilocaine, procaine, mepivocaine, quinidine, disopyramide and Class 1B antiarrhythmic agents.

Preferably, the antiarrhythmic agent is a class I or class III agent. Amiodarone is a preferred Class III antiarrhythmic agent. More preferably, the antiarrhythmic agent blocks sodium channels. More preferably, the antiarrhythmic agent is a class IB antiarrhythmic agent. Class 1B antiarrhythmic agents include lidocaine or derivatives thereof, for example, QX-314 is a quaternary lidocaine derivative (i.e., permanently charged) and has been shown to have longer-lasting local anaesthetic effects than lidocaine-HCl alone.

Preferably the class 1B antiarrhythmic agent is lidocaine. In this specification, the terms "lidocaine" and "lidocaine" are used interchangeably. Lidocaine is also known to be capable of acting as a local anaesthetic probably by blocking sodium fast channels, depressing metabolic function, lowering free cytosolic calcium, protecting against enzyme release from cells, possibly protecting endothelial cells and protecting against myofilament damage. At lower therapeutic concentrations lidocaine normally has little effect on atrial tissue, and therefore is ineffective in treating atrial fibrillation, atrial flutter, and supraventricular tachycardias. Lidocaine is also a free radical scavenger, an antiarrhythmic and has anti-inflammatory and anti-hypercoagulable properties. It must also be appreciated that at non-anaesthetic therapeutic concentrations, local anaesthetics like lidocaine would not completely block the voltage-dependent sodium fast channels, but would down-regulate channel activity and reduce sodium entry. As antiarrhythmic, lidocaine is believed to target small sodium currents that normally continue through phase 2 of the action potential and consequently shortens the action potential and the refractory period.

As lidocaine acts by primarily blocking sodium fast channels, it will be appreciated that other sodium channel blockers may be used instead of or in combination with the antiarrhythmic agent in the composition of the present invention. It will also be appreciated that sodium channel blockers include compounds that act to substantially block sodium channels or at least downregulate sodium channels. Examples of suitable sodium channel blockers include venoms such as tetrodotoxin and the drugs primaquine, QX, HNS-32 (CAS Registry #186086-10-2), NS-7, kappa-opioid receptor agonist U50 488, crobenetine, pilsicainide, phenytoin, tocainide, mexiletine, NW-1029 (a benzylamino propanamide derivative), RS100642, riluzole, carbamazepine, flecainide, propafenone, amiodarone, sotalol, imipramine and moricizine, or any of derivatives thereof. Other suitable sodium channel blockers include: Vinpocetine (ethyl apovincaminate); and Beta-carboline derivative, nootropic beta-carboline (ambocarb, AMB).

In one embodiment, the composition according to the invention comprises (i) a compound selected from at least one of a potassium channel opener, a potassium channel agonist and an adenosine receptor agonist; and (ii) an antiarrhythmic agent or local anaesthetic. Preferably the composition includes an elevated source of magnesium ions. Preferably, the antiarrhythmic agent is a local anaesthetic such as lidocaine.

The concentration of antiarrhythmic agent or local anaesthetic in the composition may be 0.0000001 to 100 mM, preferably 0.001 mM to 50 mM and most preferably 0.1 mM to 40 mM. In one embodiment, the concentration of antiarrythmic agent or local anaesthetic in the composition is about 37 mm.

The contact concentration of antiarrhythmic agent or local anaesthetic may be the same or less than the composition concentration set out above.

It will be appreciated if the composition is diluted with a pharmaceutically acceptable carrier, including but not limited to blood, saline or a physiological ionic solution, the dosage of the composition may be adapted to achieve the most preferred contact concentration.

General Anaesthetic

The compositions useful in the methods according to the invention may also include a general anaesthetic.

In one embodiment, the composition according to the invention comprises (i) a compound selected from at least one of a potassium channel opener, a potassium channel agonist and an adenosine receptor agonist; (ii) an antiarrhythmic agent or local anaesthetic; and (iii) a general anaesthetic. Preferably, this composition includes a citrate and/or an elevated source of magnesium ions.

Understanding coma requires an understanding of general anesthesia, which is separate from local, regional or conduction anesthesia. Placing a patient in a state of general anesthesia is crucial for safely and humanely performing most surgical and many nonsurgical procedures. General anaesthetics are administered by intravenous injection or inhalation and they alter neuronal activity, change the basal extracellular activity of neurotransmitters, alter receptor affinities, and transmitter-induced postsynaptic response.

All general anaesthetics are central nervous system (CNS) depressants. General anaesthetics act primarily by: 1) enhancing inhibitory signals, or 2) blocking excitatory signals in the brain or CNS. GABA (Gamma-aminobutyric acid) is the major inhibitory neurotransmitter in the adult mammalian CNS and the activation of its receptor, the $GABA_A$ receptor, inhibits GABA neurotransmission and leads to decreased excitability, neuronal sedation or unconsciousness. At least 40% of inhibitory synaptic processing in the mammalian brain uses GABA.

Preferably, the general anaesthetic is selected from propofol (dipravan), barbiturates sodium thiopental (pentothal) and methohexital (brevital), etomidate, benzodiazepines and neuroactive steroids (alphaxolone, aplhaldolone, hydroxydione and minaxolone). These are all $GABA_A$ receptor agonists and decrease brain excitability by hyperpolarizing the cell membrane and making it refractory to stimulation or depolarization. Propofol and etomidate not only decrease excitability from being $GABA_A$ agonists, but at higher concentrations they act on the $GABA_A$ receptor directly.

Preferably, the general anaesthetic is a $GABA_A$ receptor agonist, more preferably propofol.

A second major neurotransmitter in brain is excitatory glutamate and its voltage dependent NMDA (N-methyl-D-aspartate) receptor. The NMDA receptor is sometimes called the glutamate receptor. Other ligands include aspartate, d-serine and glycine. Aspartate does not stimulate the receptor as strong as glutamate. The NMDA receptor channel is normally blocked by extracellular $Mg^{2+}$ ions, which is removed during depolarization. General anaesthetics ketamine, amantadine, methoxetamine, nitrous oxide cyclopropane, act by antagonizing the NMDA receptor and reduce or block brain depolarization. Ketamine analgesia is used in the military for suspected TBI. Another NMDA receptor antagonist is xenon gas, which is also a $K_{ATP}$ channel opener and is involved in neuroprotective mechanisms.

Preferably, the general anaesthetic is a NMDA antagonist.

Although much is known about the individual anaesthetics themselves, there is no unifying theory of how general anaesthetics induction of a state of unconsciousness with the absence of pain sensation over the entire body. The bottom-up approach primarily considers anaesthetics as molecular compounds, which interact with ion channels or G-protein coupled receptors in the brain. One theory suggests loss of excitability is due to fast changes to membrane potentials, depolarization/hyperpolarization, changes in neuronal cell firing, as well as slow changes to second messenger cascades and protein synthesis. This idea implicitly assumes that neurochemical action of anaesthetics and is restricted to neurotransmitter systems in the CNS. EEG activity often serves as the explanatory mediator between modulatory projection systems and network activity. The second theory is the top-down approach and considers the behavioral endpoints of anaesthetics, such as loss of consciousness, amnesia, sedation, and a loss of nociception. They make references to mainly thalamic and cortical brain areas, their anatomical connection and functional connectivity, and again the EEG activity serves as a phenomenological explanation.

General anaesthetics can impair the immune system through their action on $GABA_A$ receptors. The anaesthetic drug, propofol, is a first line agent for sedation of critically ill patients on intensive care. It can have side effects and increase in the incidence of secondary pneumonia from 35% to 53%. $GABA_A$ receptors are present on monocytes with properties similar to CNS $GABA_A$ receptors. The functional data provide a possible explanation as to why chronic propofol and thiopental administration can increase the risk of infection in critically ill patients: their action on $GABA_A$ receptors inhibits normal monocyte behaviour. The data also suggest a potential solution: monocyte $GABA_A$ receptors are insensitive to diazepam, thus the use of benzodiazepines as an alternative anesthetising agent may be advantageous where infection is a life threatening problem.

Excitotoxicity is the pathological process by which nerve and other brain cells are damaged from neurotransmitter overload. Glutamate can be neurotoxic primarily through overactivation of the NMDA subtype receptors leading to intracellular calcium overload, production of free radicals, lipid peroxidation, and cell death. There are many NMDA receptors, which include $GABA_A$, $GABA_B$, and $GABA_C$. $GABA_A$ and $GABA_C$. Excitotoxicity has been implicated in neuronal degeneration and death cascade in acute conditions such as hypoxia-ischemia-reperfusion injury, traumatic brain injury, stroke, hypoglycemia, prolonged epileptic seizures, and chronic neurodegenerative diseases such as multiple sclerosis (MS), Alzheimer's disease, Huntington's disease, Parkinson's disease, amyotrophic lateral sclerosis, and AIDS dementia. Propofol and barbiturates are known to reduce glutamate excitoxicity. Other GABA/Glycine receptor site antagonists have also been investigated for acute diseases like stroke and head trauma as well as chronic ones like dementia and chronic pain. It is believed that neuronal damage spreads from the focus to the penumbral zone via the release of factors e.g. potassium, glutamate, aspartate, which cause protracted bouts of depolarization and further injury.

In another embodiment the composition may include one or more general anaesthetics, preferably GABA(A) receptor agonist and NMDA agonist. In one embodiment, the general anaesthetic is thiobarb.

It will be appreciated that the general anaesthetic may be administered as part of the composition according to the invention or as a different composition i.e. separately, sequentially or simultaneously.

Anti-Inflammatory Agent

In another embodiment of the invention, the composition according to the invention further includes an anti-inflammatory agent. Anti-inflammatory agents such as beta-hydroxybutyrate (BOH), niacin and GPR109A can act on the GPR109A receptor (also referred to as hydroxyl-carboxylic acid receptor 2 or HCA-2). This receptor is found on immune cells (monocytes, macrophages), adipocytes hepatocytes, the vascular endothelium, and neurones.

Valproic acid is also a suitable anti-inflammatory agent. VPA is a short-chain branched fatty acid with anti-inflammatory neuro-protective and exon-remodelling effects. Valproic acid (VPA) is a histone deacetylase inhibitor that may decrease cellular metabolic needs following traumatic injury. Valproic acid (VPA) has proven to be beneficial after traumatic injury and has been shown to improve survival in lethal models of hemorrhagic shock. VPA also is known to have cytoprotective effects from an increase acetylation of nuclear histones, promoting transcriptional activation of deregulated genes, which may confer multi-organ protection. It may also have beneficial effects in preventing or reducing the cellular and metabolic sequelae of ischemia-reperfusion injury and reduce injury to the endothelium through the TGF- and VEGF functional pathways.

Accordingly, in a further embodiment the composition according to the invention includes (i) a compound selected from at least one of a potassium channel opener, a potassium channel agonist and an adenosine receptor agonist; (ii) an antiarrhythmic agent or local anaesthetic; and (iii) an anti-inflammatory agent. Preferably the composition includes an elevated source of magnesium ions.

Preferably, the anti-inflammatory agent activates a HCA-2 receptor such as beta-hydroxybutyrate (BOH).

The processes of inflammation and thrombosis are linked through common mechanisms. Therefore, it is believed that understanding of the processes of inflammation will help with better management of thrombotic disorders including the treatment of acute and chronic ischaemic syndromes. In the clinical and surgical settings, a rapid response and early intervention to an organ or tissue damaged from ischemia can involve both anti-inflammatory and anti-clotting therapies. In addition to protease inhibitors which attenuate the inflammatory response, further anti-inflammatory therapies have included the administration of aspirin, normal heparin, low-molecular-weight heparin (LMWH), non-steroidal anti-inflammatory agents, anti-platelet drugs and glycoprotein (GP) IIb/IIIa receptor inhibitors, statins, angiotensin converting enzyme (ACE) inhibitor, angiotensin blockers and antagonists of substance P. Examples of protease inhibitors are indinavir, nelfinavir, ritonavir, lopinavir, amprenavir or the broad-spectrum protease inhibitor aprotinin, a low-molecular-weight heparin (LMWH) is enoxaparin, non-steroidal anti-inflammatory agent are indomethacin, ibuprofen, rofecoxib, naproxen or fluoxetine, an anti-platelet drug such as aspirin, a glycoprotein (GP) IIb/IIIa receptor inhibitor is abciximab, a statin is pravastatin, an angiotensin converting enzyme (ACE) inhibitor is captopril and an angiotensin blocker is valsartin.

Accordingly, in another embodiment of the invention, a selection of these agents is added to the composition useful in the methods according to the invention to deliver improved management of inflammation and clotting in order to reduce injury to cells, tissues or organs. Alternatively, the composition according to the invention may be administered together with any one or more of these agents.

In particular, protease inhibitors attenuate the systemic inflammatory response in patients undergoing cardiac surgery with cardiopulmonary bypass, and other patients where the inflammatory response has been heightened such as AIDS or in the treatment of chronic tendon injuries. Some broad spectrum protease inhibitors such as aprotinin are also reduce blood loss and need for blood transfusions in surgical operations such as coronary bypass.

Accordingly, in a further embodiment the composition according to the invention comprises (i) a compound selected from at least one of a potassium channel opener, a potassium channel agonist and an adenosine receptor agonist; (ii) an antiarrhythmic agent or a local anaesthetic; (iii) at least one of a citrate and a general anaesthetic; and (iv) an anti-inflammatory agent.

Preferably the composition includes an elevated source of magnesium.

Preferably, the anti-inflammatory agent activates a HCA-2 receptor such as beta-hydroxybutyrate (BOH).

Valproic acid is also a suitable anti-inflammatory agent. Valproic acid (VPA) is a histone deacetylase inhibitor that may decrease cellular metabolic needs following traumatic injury. Valproic acid (VPA) has proven to be beneficial after traumatic injury and has been shown to improve survival in lethal models of hemorrhagic shock. VPA also is known to have cytoprotective effects from an increase acetylation of nuclear histones, promoting transcriptional activation of deregulated genes, which may confer multi-organ protection. It may also have beneficial effects in preventing or reducing the cellular and metabolic sequelae of ischemia-reperfusion injury and reduce injury to the endothelium through the TGF-$\beta$ and VEGF functional pathways.

Sphingosine-1-phosphate (S1P) is also a suitable anti-inflammatory agent.

The concentration of anti-inflammatory agent in the composition may be 0.0000001 to 300 mM, preferably 0.001 mM to 50 mM and most preferably 0.1 mM to 10 mM.

The contact concentration of anti-inflammatory agent may be the same or less than the composition concentration as set out above.

It will be appreciated if the composition is diluted with a pharmaceutically acceptable carrier, including but not limited to blood, saline or a physiological ionic solution, the dosage of the composition may be adapted to achieve the most preferred contact concentrations.

Metabolic Fuel

In another embodiment of the invention, the composition according to the invention further includes a metabolic fuel. Preferably, the metabolic fuel is a citrate. Examples of a citrate include citrate and derivatives, thereof such as citric acid, salts of citrate, esters of citrate, polyatomic anions of citrate or other ionic or drug complexes of citrate. When citrate in its various forms is not included in the composition it can be administered separately in a blood, blood:crystalloid ratio or crystalloid solution and mixed to the preferred level in the composition prior to administration to the body, organ, tissue or cell.

Preferably, the form of citrate includes citrate phosphate detrose (CPD) solution, magnesium citrate, sodium citrate, potassium citrate or sildenafil citrate, more preferably CPD.

Accordingly, in a further embodiment the composition according to the invention includes (i) a compound selected from at least one of a potassium channel opener, a potassium channel agonist and an adenosine receptor agonist; (ii) an antiarrhythmic agent or a local anaesthetic; and (iii) a metabolic fuel. Preferably the composition includes an elevated source of magnesium ions.

Alternatively, in a further aspect, the composition according to the invention may include (i) a compound selected from at least one of a potassium channel opener, a potassium channel agonist and an adenosine receptor agonist; (ii) an antiarrhythmic agent or a local anaesthetic; (iii) a metabolic fuel; and (iv) an anti-inflammatory agent. Preferably the composition includes an elevated source of magnesium ions.

The concentration of metabolic fuel in the composition may be 0.0000001 to 100 mM, preferably 0.001 mM to 50 mM and most preferably 0.1 mM to 10 mM. In one embodiment, the concentration of citrate in the composition is about 2.1 mM.

The contact concentration of metabolic fuel may be the same or less than the composition concentration set out above.

It will be appreciated if the composition is diluted with a pharmaceutically acceptable carrier, including but not limited to blood, saline or a physiological ionic solution, the dosage of the composition may be adapted to achieve the most preferred contact concentrations.

Beta-Blockers

It will be appreciated that anti-adrenergics such as beta-blockers, for example, esmolol, atenolol, metoprolol and propranolol could be used in combination with the potassium channel opener, potassium channel agonist and/or adenosine receptor agonist to reduce calcium entry into the cell. Preferably, the beta-blocker is esmolol. Similarly, alpha (1)-adrenoceptor-antagonists such as prazosin, could be used instead in combination with the potassium channel opener, potassium channel agonist and/or adenosine receptor agonist to reduce calcium entry into the cell and therefore calcium loading. Preferably, the antiadrenergic is a beta-blocker. Preferably the beta-blocker is esmolol.

$Na^+/Ca^{2+}$ exchange inhibitors Adenosine is also known to indirectly inhibit the $Na^+/Ca^{2+}$ exchanger which would reduce cell sodium and calcium loading. It will be appreciated that inhibitors of the $Na^+/Ca^{2+}$ exchanger would lead to reduced calcium entry and magnify the effect of adenosine. $Na^+/Ca^{2+}$ exchange inhibitors may include benzamyl, KB-R7943 (2-[4-(4-Nitrobenzyloxy)phenyl]ethyl]isothiourea mesylate) or SEA0400 (2-[4-[(2,5-difluorophenyl) methoxy]phenoxy]-5-ethoxyaniline).

Calcium Channel Blockers

Some embodiments of the invention utilise calcium channel blockers which are direct calcium antagonists, the principal action of which is to reduce calcium entry into the cell. Such calcium channel blockers may be selected from three different classes: 1,4-dihydropyridines (eg. nitrendipine), phenylalkylamines (eg. verapamil), and the benzothiazepines (e.g. diltiazem, nifedipine). It will be appreciated that these calcium antagonists share some effects with potassium channel openers, particularly ATP-sensitive potassium channel openers, by inhibiting calcium entry into the cell.

Calcium channel blockers are also called calcium antagonists or calcium blockers. They are often used clinically to decrease heart rate and contractility and relax blood vessels. They may be used to treat high blood pressure, angina or discomfort caused by ischaemia and some arrhythmias, and they share many effects with beta-blockers (see discussion above).

Five major classes of calcium channel blockers are known with diverse chemical structures: 1. Benzothiazepines: eg Diltiazem, 2. Dihydropyridines: eg nifedipine, Nicardipine, nimodipine and many others, 3. Phenylalkylamines: eg Verapamil, Diarylaminopropylamine ethers: eg Bepridil, 5. Benzimidazole-substituted tetralines: eg Mibefradil.

The traditional calcium channel blockers bind to L-type calcium channels ("slow channels") which are abundant in cardiac and smooth muscle which helps explain why these drugs have selective effects on the cardiovascular system. Different classes of L-type calcium channel blockers bind to different sites on the alpha1-subunit, the major channel-forming subunit (alpha2, beta, gamma, delta subunits are also present). Different sub-classes of L-type channel are present which may contribute to tissue selectivity. More recently, novel calcium channel blockers with different specificities have also been developed for example, Bepridil, is a drug with $Na^+$ and $K+$ channel blocking activities in addition to L-type calcium channel blocking activities. Another example is Mibefradil, which has T-type calcium channel blocking activity as well as L-type calcium channel blocking activity.

Three common calcium channel blockers are diltiazem (Cardizem), verapamil (Calan) and Nifedipine (Procardia). Nifedipine and related dihydropyridines do not have significant direct effects on the atrioventricular conduction system or sinoatrial node at normal doses, and therefore do not have direct effects on conduction or automaticity. While other calcium channel blockers do have negative chronotropic/dromotropic effects (pacemaker activity/conduction velocity). For example, Verapamil (and to a lesser extent diltiazem) decreases the rate of recovery of the slow channel in AV conduction system and SA node, and therefore act directly to depress SA node pacemaker activity and slow conduction. These two drugs are frequency- and voltage-dependent, making them more effective in cells that are rapidly depolarizing. Verapamil is also contraindicated in combination with beta-blockers due to the possibility of AV block or severe depression of ventricular function. In addition, mibefradil has negative chronotropic and dromotropic effects. Calcium channel blockers (especially verapamil) may also be particularly effective in treating unstable angina if underlying mechanism involves vasospasm.

Omega conotoxin MVIIA (SNX-111) is an N type calcium channel blocker and is reported to be 100-1000 fold more potent than morphine as an analgesic but is not addictive. This conotoxin is being investigated to treat intractible pain. SNX-482 a further toxin from the venom of a carnivorous spider venom, blocks R-type calcium channels. The compound is isolated from the venom of the African tarantula, *Hysterocrates gigas*, and is the first R-type calcium channel blocker described. The R-type calcium channel is believed to play a role in the body's natural communication network where it contributes, to the regulation of brain function. Other Calcium channel blockers from animal kingdom include Kurtoxin from South African Scorpion, SNX-482 from African Tarantula, Taicatoxin from the Australian Taipan snake, Agatoxin from the Funnel Web Spider, Atracotoxin from the Blue Mountains Funnel Web Spider, Conotoxin from the Marine Snail, HWTX-I from the Chinese bird spider, Grammotoxin SIA from the South American Rose Tarantula. This list also includes derivatives of these toxins that have a calcium antagonistic effect.

Direct ATP-sensitive potassium channel openers (eg nicorandil, aprikalem) or indirect ATP-sensitive potassium channel openers (eg adenosine, opioids) are also indirect calcium antagonists and reduce calcium entry into the tissue. One mechanism believed for ATP-sensitive potassium channel openers also acting as calcium antagonists is shortening of the cardiac action potential duration by accelerating phase 3 repolarisation and thus shortening the plateau phase. During the plateau phase the net influx of calcium may be balanced by the efflux of potassium through potassium channels. The enhanced phase 3 repolarisation may inhibit calcium entry into the cell by blocking or inhibiting L-type calcium channels and prevent calcium (and sodium) overload in the tissue cell.

Calcium channel blockers can be selected from nifedipine, nicardipine, nimodipine, nisoldipine, lercanidipine, telodipine, angizem, altiazem, bepridil, amlodipine, felodipine, isradipine and cavero and other racemic variations. In addition, it will be appreciated that calcium entry could be inhibited by other calcium blockers which could be used instead of or in combination with adenosine and include a number of venoms from marine or terrestrial animals such as the omega-conotoxin GVIA (from the snail conus geographus) which selectively blocks the N-type calcium channel or omega-agatoxin IlA and IVA from the funnel web spider *Agelelnopsis aperta* which selectively blocks R- and P/Q-type calcium channels respectively. There are also mixed voltage-gated calcium and sodium channel blockers such as NS-7 to reduce calcium and sodium entry and thereby assist cardioprotection. Preferably the calcium channel blocker is nifedipine.

Opioid

In another embodiment of the invention, the methods and compositions according to the invention further include an opioid. The inventor also found the inclusion of an opioid in the composition, particularly D-Pen[2,5]enkephalin (DP-DPE), may also result in significantly less damage to the cell, tissue or organ.

Accordingly, in a further embodiment the composition according to the invention further includes an opioid.

Opioids, also known or referred to as opioid agonists, are a group of drugs that inhibit opium (Gropion, poppy juice) or morphine-like properties and are generally used clinically as moderate to strong analgesics, in particular, to manage pain, both peri- and post-operatively.

Other pharmacological effects of opioids include drowsiness, respiratory depression, changes in mood and mental clouding without loss of consciousness.

Opioids are also believed to be involved as part of the 'trigger' in the process of hibernation, a form of dormancy characterised by a fall in normal metabolic rate and normal core body temperature. In this hibernating state, tissues are better preserved against damage that may otherwise be caused by diminished oxygen or metabolic fuel supply, and also protected from ischemia reperfusion injury.

There are three types of opioid peptides: enkephalin, endorphin and dynorphin.

Opioids act as agonists, interacting with stereospecific and saturable binding sites, in the heart, brain and other tissues. Three main opioid receptors have been identified and cloned, namely mu, kappa, and delta receptors. All three receptors have consequently been classed in the G-protein coupled receptors family (which class includes adenosine and bradykinin receptors). Opioid receptors are further subtyped, for example, the delta receptor has two subtypes, delta-1 and delta-2. Examples of opioid agonists include for example TAN-67, BW373U86, SNC80 ([(+)-4-[alpha(R)-alpha-[(2S,5R)-4-allyl-2,5-dimethyl-1-piperazinyl]-(3-methoxybenzyl)-N,N-diethylbenzamide), (+)BW373U86, DA-DLE, ARD-353 [4-((2R5S)-4-(R)-4-diethylcarbamoylphenyl)(3-hydroxyphenyl)methyl)-2,5-dimethylpiperazin-1-yl-methyl) benzoic acid], a nonpeptide delta receptor agonist, DPI-221 [4-((alpha-S)~alpha-((2S,5R)-2,5-dimethyl-4-(3-fluorobenzyl)-1-piperazinyl)benzyl)-N,N-diethylbenzamide], Cardiovascular effects of opioids are directed within the intact body both centrally (ie, at the cardiovascular and respiratory centres of the hypothalamus and brainstem) and peripherally (ie, heart myocytes and both direct and indirect effects on the vasculature). For example, opioids have been shown to be involved in vasodilation. Some of the action of opioids on the heart and cardiovascular system may involve direct opioid receptor mediated actions or indirect, dose dependent non-opioid receptor mediated actions, such as ion channel blockade which has been observed with antiarrhythmic actions of opioids, such as arylacetamide drugs. It is also known that the heart is capable of synthesising or producing the three types of opioid peptides, namely, enkephalin, endorphin and dynorphin. However, only the delta and kappa opioid receptors have been identified on ventricular myocytes.

Without being bound by any mode of action, opioids are considered to provide cardioprotective effects, by limiting ischaemic damage and reducing the incidence of arrhythmias, which are produced to counter-act high levels of damaging agents or compounds naturally released during ischemia. This may be mediated via the activation of ATP sensitive potassium channels in the sarcolemma and in the mitochondrial membrane and involved in the opening potassium channels. Further, it is also believed that the cardioprotective effects of opioids are mediated via the activation of ATP sensitive potassium channels in the sarcolemma and in the mitochondrial membrane.

It will be appreciated that the opioids include compounds which act both directly and indirectly on opioid receptors. Opioids also include indirect dose dependent, non-opioid receptor mediated actions such as ion channel blockade which have been observed with the antiarrhythmic actions of opioids. Opioids and opioid agonists may be peptidic or non-peptidic. Preferably the opioid is selected from enkephalins, endorphins and dynorphins. Preferably, the opioid is an enkephalin which targets delta, kappa and/or mu receptors. More preferably the opioid is selected from delta-1-opioid receptor agonists and delta-2-opioid receptor agonists. D-Pen [2, 5]enkephaiin (DPDPE) is a particularly preferred Delta-1-Opioid receptor agonist. In one embodiment, the opioid is administered at 0.001 to 10 mg/kg body weight, preferably 0.01 to 5 mg/kg, or more preferably 0.1 to 1.0 mg/kg.

Compounds for Minimizing or Reducing Water Uptake

The methods and compositions according to the invention may further include the use of at least one compound for minimizing or reducing the uptake of water by a cell in the cell, tissue or organ.

A compound for minimizing or reducing the uptake of water by a cell in the tissue tends to control water shifts, ie, the shift of water between the extracellular and intracellular environments.

Accordingly, these compounds are involved in the control or regulation of osmosis. One consequence is that a compound for minimizing or reducing the uptake of water by a cell in the tissue reduces cell swelling that is associated with Oedema, such as Oedema that can occur during ischemic injury.

Compounds for minimizing or reducing the uptake of water by a cell in a tissue are typically impermeants or receptor antagonists or agonists. An impermeant according to the present invention may be selected from one or more of the group consisting of: sucrose, pentastarch, hydroxyethyl starch, raffinose, mannitol, gluconate, lactobionate, and colloids.

Suitable colloids include, but not limited to, Dextran-70, 40, 50 and 60, hydroxyethyl starch and a modified fluid gelatin. A colloid is a composition which has a continuous liquid phase in which a solid is suspended in a liquid. Colloids can be used clinically to help restore balance to water and ionic distribution between the intracellular, extracellular and blood compartments in the body after an severe injury. Colloids can also be used in solutions for organ preservation. Administration of crystalloids can also restore water and ionic balance to the body but generally require greater volumes of administration because they do not have solids suspended in a liquid. Thus volume expanders may be colloid-based or crystalloid-based.

Colloids include albumin, hetastarch, polyethylene glycol (PEG), Dextran 40 and Dextran 60. Other compounds that could be selected for osmotic purposes include those from the major classes of osmolytes found in the animal kingdom including polyhydric alcohols (polyols) and sugars, other amino acids and amino-acid derivatives, and methylated ammonium and sulfonium compounds.

Cell swelling can also result from an inflammatory response which may be important during organ retrieval, preservation and surgical grafting. Substance P, an important pro-inflammatory neuropeptide is known to lead to cell oedema and therefore antagonists of substance P may reduce cell swelling. Indeed antagonists of substance P, (-specific neurokinin-1) receptor (NK-1) have been shown to reduce inflammatory liver damage, i.e., oedema formation, neutrophil infiltration, hepatocyte apoptosis, and necrosis. Two such NK-1 antagonists include CP-96,345 or [(2S,3S)-cis-2-(diphenylmethyl)-N-((2-methoxyphenyl)-methyl)-1-azabicyclo(2.2.2.)-octan-3-amine (CP-96,345)] and L-733,060 or [(2S,3S)3-([3,5-bis(trifluoromethyl)phenyl]methoxy)-2-phenylpiperidine]. R116301 or [(2R-trans)-4-[1-[3,5-bis(trifluoromethyi)benzoyl]-2-(phenylmethyl)-4-piperidinyl]-N-(2,6-dimethylphenyl)-1-acetamide (S)-Hydroxybutanedioate] is another specific, active neurokinin-1 (NK(1)) receptor antagonist with subnanomolar affinity for the human NK(1) receptor (K(i): 0.45 nM) and over 200-fold selectivity toward NK(2) and NK(3) receptors. Antagonists of neurokinin receptors 2 (NK-2) that may also reduce cell swelling include SR48968 and NK-3 include SR142801 and SB-222200. Blockade of mitochondrial permeability transition and reducing the membrane potential of the inner mitochondrial membrane potential using cyclosporin A has also been shown to decrease ischemia-induced cell swelling in isolated brain slices. In addition glutamate-receptor antagonists (AP5/CNQX) and reactive oxygen species scavengers (ascorbate, Trolox®, dimethylthiourea, Tempol®) also showed reduction of cell swelling. Thus, the compound for minimizing or reducing the uptake of water by a cell in a tissue can also be selected from any one of these compounds.

It will also be appreciated that the following energy substrates can also act as impermeants. Suitable energy substrate can be selected from one or more from the group consisting of: glucose and other sugars, pyruvate, lactate, glutamate, glutamine, aspartate, arginine, ectoine, taurine, N-acetyl-beta-lysine, alanine, proline, beta-hydroxy butyrate and other amino acids and amino acid derivatives, trehalose, floridoside, glycerol and other polyhydric alcohols (polyols), sorbitol, myo-innositol, pinitol, insulin, alpha-keto glutarate, malate, succinate, triglycerides and derivatives, fatty acids and carnitine and derivatives. In one embodiment, the at least one compound for minimizing or reducing the uptake of water by the cells in the tissue is an energy substrate. The energy substrate helps with recovering metabolism. The energy substrate can be selected from one or more from the group consisting of: glucose and other sugars, pyruvate, lactate, glutamate, glutamine, aspartate, arginine, ectoine, taurine, N-acetyl-beta-lysine, alanine, proline and other amino acids and amino acid derivatives, trehalose, floridoside, glycerol and other polyhydric alcohols (polyols), sorbitol, myo-innositol, pinitol, insulin, alpha-keto glutarate, malate, succinate, triglycerides and derivatives, fatty acids and carnitine and derivatives. Given that energy substrates are sources of reducing equivalents for energy transformations and the production of ATP in a cell, tissue or organ of the body, it will be appreciated that a direct supply of the energy reducing equivalents could be used as substrates for energy production. For example, a supply of either one or more or different ratios of reduced and oxidized forms of nicotinamide adenine dinucleotide (e.g. NAD or NADP and NADH or NADPH) or flavin adenine dinucleotides (FADH or FAD) could be directly used to supply bond energy for sustaining ATP production in times of stress. Beta-hydroxy butyrate is a preferred energy substrate.

In addition to providing energy substrates to the whole body, organ, tissue or cell, improvements in metabolising these substrates may occur in the presence of hydrogen sulphide ($H_2S$) or H2S donors (eg NaHS). The presence of hydrogen sulphide ($H_2S$) or H2S donors (eg NaHS) may help metabolise these energy substrates by lowering energy demand during arrest, protect and preserve the whole body, organ, tissue or cell during periods of metabolic imbalance such ischemia, reperfusion and trauma. Concentrations of hydrogen sulfide above 1 microM (10-6 M) concentration can be a metabolic poison that inhibits respiration at Respiratory Complex IV, which is part of the mitochondrial respiratory chain that couples metabolising the high energy reducing equivalents from energy substrates to energy (ATP) generation and oxygen consumption. However, it has been observed at lower concentrations, below $10^{-6}$ M (eg $10^{-10}$ to $10^{-9}$M), hydrogen sulfide may reduce the energy demand of the whole body, organ, tissue or cell which may result in arrest, protection and preservation. In other words, very low levels of sulfide down-regulate mitochondria, reduce $O_2$ consumption and actually increase "Respiratory Control" whereby mitochondria consume less $O_2$ without collapsing the electrochemical gradient across the inner mitochondrial membrane. Thus there are observations that a small amount of sulfide, either directly or indirectly, may close proton leak channels and better couple mitochondrial respiration to ATP production more tightly, and this effect may improve the metabolism of high energy reducing equivalents from energy substrates. There is also the possibility that a sulphur cycle exists between the cell cytosol and mitochondria in mammals, including humans, providing the sulphur concentration is low. The presence of a vestige sulphur cycle would be consistent with current ideas on the evolutionary origin of mitochondria and their appearance in eukaryote cells from a symbiosis between a sulfide-producing host cell and a sulfide-oxidizing bacterial symbiont. Thus, hydrogen sulphide ($H_2S$) or $H_2S$ donors (eg NaHS) may be energy substrates themselves in addition to improving the metabolism of other energy substrates. Accordingly, in one form, the invention provides a composition as described above further including hydrogen sulphide or a hydrogen sulfide donor.

Preferably, the compound for minimizing or reducing the uptake of water by the cells in the tissue is PEG. PEG reduces water shifts as an impermeant but also may preserve cells from immune recognition and activation. Impermeant agents such as PEG, sodium gluconate, sucrose, lactobionate and raffinose, trehalose, are too large to enter the cells and hence remain in the extracellular spaces within the tissue and resulting osmotic forces prevent cell swelling that would otherwise damage the tissue, which would occur particularly during storage of the tissue.

Preferably, the concentration of the compound for minimizing or reducing the uptake of water by the cells in the tissue is between about 5 to 500 mM. Typically this is an effective amount for reducing the uptake of water by the cells in the tissue. More preferably, the concentration of the compound for reducing the uptake of water by the cells in the tissue is between about 20 and 200 mM. Even more preferably the concentration of the compound for reducing the uptake of water by the cells in the tissue is about 70 mM to 140 mM.

Typically, the contact concentration of the compound for minimizing or reducing the uptake of water by the cells in the tissue is the same or less than the composition concentration set out above.

It will be appreciated if the composition is diluted with a pharmaceutically acceptable carrier, including but not limited to blood, saline or a physiological ionic solution, the dosage of the composition may be adapted to achieve the most preferred contact concentrations.

In a further embodiment, the composition useful in the methods according to the invention may include more than one compound for minimizing or reducing the uptake of water by the cells in the tissue. For example, a combination of impermeants (raffinose, sucrose and pentastarch) may be included in the composition or even a combination of colloids, and fuel substrates may be included in the composition.

Surfactant

The methods and compositions according to the invention may further include a surfactant that has rheologic, antithrombotic, anti-inflammatory and cytoprotective properties. Examples of surfactants are HCO-60, sodium dodecyl sulfate (SDS), Tween 80, PEG 400, 0.1 to 1% Pluronic 68, F127 and poloxamer 188 (P188). P188 is a surface acting agent with cytoprotective effects of cells, tissues and organs and has been shown to be protective against trauma, electric shock, ischemia, radiation, osmotic stress, heart attack, stroke, burns and haemorrhagic shock. Poloxamer 188 was also associated with potentially beneficial changes in membrane protein expression, reduced capillary leakage, and less hemodilution in pediatric cardiac surgery. Other surfactant-protecting agents such as prostacyclin analog iloprost are also protective and has shown to improve preservation of surfactant function in transplanted lungs. Preferably, the non-ionic surfactant for minimizing or reducing cell damage for the present invention is P188.

Myofilament Inhibitor

The methods and compositions according to the invention may further include a reversible myofilament inhibitor such as 2,3-butanedione monoxime (BDM) to arrest, protect and preserve organ function. Myosin-actin interactions are present in nearly every cell for transport, trafficking, contraction, cytoskeleton viability. BDM has been shown to improve preservation in skeletal muscle, kidney and renal tubules, lung, and heart. Preferably, the myosin inhibitor BDM is the choice for reducing cellular demand and minimizing cell damage during injury or ischemia-reperfusion injury.

Compound for Inhibiting Transport of Sodium and Hydrogen Ions

The inventor has also found that the inclusion of a compound for inhibiting transport of sodium and hydrogen ions across a plasma membrane of a cell in the tissue with (i) a compound selected from at least one of a potassium channel opener, a potassium channel agonist and an adenosine receptor agonist; and (ii) an antiarrhythmic agent or local anaesthetic assists in reducing injury and damage.

Thus in another aspect, the composition useful in the methods according to the invention further includes a compound for inhibiting transport of sodium and hydrogen ions across a plasma membrane of a cell in the tissue.

The compound for inhibiting transport of sodium and hydrogen across the membrane of the cell in the tissue is also referred to as a sodium hydrogen exchange inhibitor. The sodium hydrogen exchange inhibitor reduces sodium and calcium entering the cell.

Preferably the compound for inhibiting transport of sodium and hydrogen across the membrane of the cell in the tissue may be selected from one or more of the group consisting of Amiloride, EIPA(5-(N-entyl-N-isopropyl)-amiloride), cariporide (HOE-642), eniporide, Triamterene (2,4,7-triamino-6-phenylteride), EMD 84021, EMD 94309, EMD 96785, EMD 85131 and HOE 694. B11 B-513 and T-162559 are other inhibitors of the isoform 1 of the Na+/H+ exchanger.

Preferably, the sodium hydrogen exchange inhibitor is Amiloride (N-amidino-3,5-diamino-6-chloropyrzine-2-carboximide hydrochloride dihydrate). Amiloride inhibits the sodium proton exchanger (Na+/H+ exchanger also often abbreviated NHE-1) and reduces calcium entering the cell. During ischemia excess cell protons (or hydrogen ions) are believed to be exchanged for sodium via the Na+/H+ exchanger.

Preferably, the concentration of the sodium hydrogen exchange inhibitor in the composition is between about 1.0 nM to 1.0 mM. More preferably, the concentration of the sodium hydrogen exchange inhibitor in the composition is about 20 µM.

Typically, the contact concentration of the sodium hydrogen exchange inhibitors is the same or less than the composition concentration set out above.

It will be appreciated if the composition is diluted with a pharmaceutically acceptable carrier, including but not limited to blood, saline or a physiological ionic solution, the dosage of the composition may be adapted to achieve the most preferred contact concentrations.

Antioxidants

The composition useful in the methods according to the invention may also include an antioxidant.

Antioxidants are commonly enzymes or other organic substances that are capable of counteracting the damaging effects of oxidation in the tissue. The antioxidant may be selected from one or more of the group consisting of: allopurinol, carnosine, histidine, Coenzyme Q 10, n-acetylcysteine, superoxide dismutase (SOD), glutathione reductase (GR), glutathione peroxidase (GP) modulators and regulators, catalase and the other metalloenzymes, NADPH and NAD(P)H oxidase inhibitors, glutathione, U-74006F, vitamin E, Trolox (soluble form of vitamin E), other tocopherols (gamma and alpha, beta, delta), tocotrienols, ascorbic acid, Vitamin C, Beta-Carotene (plant form of vitamin A), selenium, Gamma Linoleic Acid (GLA), alpha-lipoic acid, uric acid (urate), curcumin, bilirubin, proanthocyanidins, epigallocatechin gallate, Lutein, lycopene, bioflavonoids, polyphenols, Trolox®, dimethylthiourea, Tempol®, carotenoids, coenzyme Q, melatonin, flavonoids, polyphenols, aminoindoles, probucol and nitecapone, 21-aminosteroids or lazaroids, sulphydryl-containing compounds (thiazolidine, Ebselen, dithiolethiones), and N-acetylcysteine. Other antioxidants include the ACE inhibitors (captopril, enalapril, lisinopril) which are used for the treatment of arterial hypertension and cardiac failure on patients with myocardial infarction. ACE inhibitors exert their beneficial effects on the reoxygenated myocardium by scavenging reactive oxygen species. Other antioxidants that could also be used include beta-mercaptopropionylglycine, O-phenanthroline, dithiocarbamate, selegilize and desferrioxamine (Desferal), an iron chelator, has been used in experimental infarction models, where it exerted some level of antioxidant protection. Spin trapping agents such as 5'-5-dimethyl-1-pyrrolione-N-oxide (DMPO) and (a-4-pyridyl~1-oxide)-N-t-butylnitrone (POBN) also act as antioxidants. Other antioxidants include: nitrone radical scavenger alpha-phenyl-tert-N-butyl nitrone (PBN) and derivatives PBN (including disulphur derivatives); N-2-mercaptopropionyl glycine (MPG) a specific scavenger of the OH free radical; lipooxygenase inhibitor nordihydroguaretic acid (NDGA); Alpha Lipoic Acid; Chondroitin Sulfate; L-Cysteine; oxypurinol and Zinc.

Preferably, the antioxidant is allopurinol (1H-Pyrazolo[3,4-a]pyrimidine-4-ol). Allopurinol is a competitive inhibitor of the reactive oxygen species generating enzyme xanthine oxidase. Allopurinol's antioxidative properties may help preserve myocardial and endothelial functions by reducing oxidative stress, mitochondrial damage, apoptosis and cell death.

Cellular Transport Enzyme Inhibitor

In another embodiment, the methods and compositions according to the invention include a cellular transport enzyme inhibitor, such as a nucleoside transport inhibitor, for example, dipyridamole, to prevent metabolism or breakdown of components in the composition such as adenosine. The half life of adenosine in the blood is about 10 seconds so the presence of a medicament to substantially prevent its breakdown will maximise the effect of the composition of the present invention.

Dipyridamole is advantageously included in the composition a concentration from about 0.01 µM to about 10 mM, preferably 0.05 to 100 µM. Dipyridamole and has major advantages with respect to cardioprotection. Dipyridamole may supplement the actions of adenosine by inhibiting adenosine transport and breakdown leading to increased protection of cells, tissues and organs of the body during times of stress. Dipyridamole may also be administered separately for example by 400 mg daily tablets to produce a plasma level of about 0.4 µg/ml, or 0.8 µM concentration.

Composition Types

The composition may be suitable for administration to the tissue in liquid form for example, solutions, syrups or suspensions, or alternatively they may be administered as a dry product for constitution with water or other suitable vehicle before use. Alternatively, the composition may be presented as a dry product for constitution with water or other suitable vehicle. Such liquid preparations may be prepared by conventional means with pharmaceutically acceptable additives such as suspending agents, emulsifying agents, non-aqueous vehicles, preservatives and energy sources.

In another form, the invention comprises a composition in tablet form, including nutraceutical or supplement applications and in another form, the invention comprises an aerosol which could be administered via oral, skin or nasal routes.

The composition useful in the methods according to the invention may be suitable for topical administration to the tissue. Such preparation may be prepared by conventional means in the form of a cream, ointment, jelly, solution or suspension.

Aqueous suspensions contain the active materials in admixture with excipients suitable for the manufacture of aqueous suspensions. Such excipients are suspending agents, for example sodium carboxymethylcellulose, methylcellulose, hydropropyl methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Aqueous suspensions may also contain one or more preservatives, for example benzoates, such as ethyl, or n-propyl p-hydroxybenzoate, one or more colouring agents, one or more flavouring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

Syrups and elixirs may be formulated with sweetening agents, for example glycerol, propylene glycol, sorbitol or sucrose. Such formulations may also contain a demulcent, a preservative and flavouring and colouring agents.

The composition may also be formulated as depot preparations. Such long acting formulations may be administered by implantation (eg, subcutaneously or intramuscularly) or by intramuscular injection. Thus, for example, the composition according to the invention may be formulated with suitable polymeric or hydrophobic materials (eg, as an emulsion in an acceptable oil or ion exchange resins, or as sparingly soluble derivatives, for example, as a sparingly soluble salt.

The composition may also be in the form of a veterinary composition, which may be prepared, for example, by methods that are conventional in the art. Examples of such veterinary compositions include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intramammary injection where a suspension or solution is introduced in the udder via the teat;

(c) topical applications, e.g. as a cream, ointment or spray applied to the skin; or (d) intravaginally, e.g. as a pessary, cream or foam.

Pharmaceutically Acceptable Carriers

While it is possible for each component of the composition to contact the tissue alone, it is preferable that the components of the composition be provided together with one or more pharmaceutically acceptable carriers. Each carrier must be pharmaceutically acceptable such that they are compatible with the components of the composition and not harmful to the subject. Preferably, the pharmaceutical composition is prepared with liquid carriers, such as an ionic solution, for example NaCl or a buffer.

A preferred pharmaceutically acceptable carrier is a buffer having a pH of about 6 to about 9, preferably about 7, more preferably about 7.4 and/or low concentrations of potassium. For example, the composition has a total potassium concentration of up to about 10 mM, more preferably about 2 to about 8 mM, most preferably about 4 to about 6 mM. Suitable buffers include Krebs-Henseleit which generally contains 10 mM glucose, 117 mM NaCl, 5.9 mM KCl, 25 mM NaHCO$_3$, 1.2 mM NaH$_2$PC>4, 1.12 mMCaCb (free Ca$^{2+}$=1.07 mM) and 0.512 mM MgCl$_2$ (free Mg$^{2+}$=0.5 mM), Tyrodes solution which generally contains 10 mM glucose, 126 mM NaCl, 5.4 mM KCl, 1 mM CaCl$_2$, 1 mM MgCl$_2$, 0.33 mM NaH$_2$PO$_4$ and 10 mM HEPES (N-[2-hydroxyethyl]piperazine-N'-[2-ethane sulphonic acid], Fremes solution, Hartmanns solution which generally contains 129 NaCl, 5 mM KCl, 2 mM CaCl$_2$ and 29 mM lactate and Ringers-Lactate, Ringers acetate and saline (NaCl) such as 0.1 to 25% NaCl, preferably, 0.9% NaCl, plasma-lyte, normosol.

In another embodiment, the composition according to the invention is hypertonic. In particular, the composition has a saline concentration greater than normal isontic saline which is 0.9% NaCl (0.154M).

Other naturally occurring buffering compounds that exist in muscle that could be also used in a suitable ionic environment are carnosine, histidine, anserine, ophidine and balenene, or their derivatives.

It is also advantageous to use carriers having low concentrations of magnesium, such as, for example up to about 2.5 mM, but it will be appreciated that high concentrations of magnesium, for example up to about 20 mM, may be used for cell, tissue or organ contact concentrations if desired without substantially affecting the activity of the composition. If the composition is administered into the body fluids (e.g. blood or body cavity) it will appreciated that magnesium will undergo immediate dilution and substantially lower cell, tissue or organ contact concentrations. To avoid this dilution effect on reducing the activity of magnesium, the magnesium concentration in the composition may be as high as 2.0M (2000 mM) prior to administration into the body.

In addition, typical buffers or carriers (as discussed above) in which the composition of the invention is administered typically contain calcium at concentrations of around 1 mM as the total absence of calcium has been found to be detrimental to the cell, tissue or organ. In one form, the invention may also include using carriers with low calcium (such as for example less than 0.5 mM) so as to decrease the amount of calcium within a cell in body tissue, which may otherwise build up during injury/trauma/stunning. Preferably the calcium present is at a concentration of between 0.1 mM to 0.8 mM, more preferably about 0.3 mM. As described in the present invention, elevated magnesium and low calcium has been associated with protection during ischemia and reoxygenation of an organ. The action is believed to be due to decreased calcium loading.

In another embodiment, the pharmaceutically acceptable carrier is a bodily fluid such as blood or plasma. In another embodiment, the pharmaceutically acceptable carrier is crystalloid or blood substitute.

Preferred Compositions

In a further aspect, the composition useful in the methods according to the invention includes (i) a potassium channel opener or agonist and/or an adenosine receptor agonist; and (ii) an antiarrhythmic agent or a local anaesthetic and one or more of:

an anti-inflammatory agent;
a metabolic fuel;
opioid;
calcium channel blocker;
at least one compound for reducing uptake of water;
sodium hydrogen exchange inhibitor;
antioxidant;
a source of magnesium in an amount for increasing the amount of magnesium in a cell in body tissue; and
a pharmaceutically acceptable carrier such as an ionic solution for example NaCl or a buffer.

Preferably, this composition has two, three or four of the above components. Preferred additional components include one or more of an anti-inflammatory agent, a metabolic fuel such as a citrate, source of magnesium and a pharmaceutically acceptable carrier such as a buffer. It is also contemplated that this composition may include more than one of the same component, for example two different potassium channel openers may be present in the composition. It is also contemplated that one component may have more than one function. For example, some calcium antagonists share effects with potassium channel openers.

In another aspect there is also provided a composition useful in the methods according to the invention further including an effective amount of elevated magnesium.

In one embodiment, the composition useful in the methods according to the invention includes adenosine and lidocaine. This composition may optionally include a metabolic fuel such as a citrate for example CPD.

In one embodiment, the composition according to the invention, includes adenosine and lidocaine. This composition may optionally include an anti-inflammatory agent, such as beta-hydroxybutyrate.

One preferred form of the composition according to the invention is a combination of adenosine and lidocaine. In a preferred form, the composition may also include an anti-inflammatory agent, such as beta-hydroxybutyrate, and/or a metabolic fuel, such as a citrate for example CPD.

In one embodiment, the composition contains 0.1 to 40 mM of adenosine, 0.1 to 80 mM of lidocaine or a salt thereof such as a HCl salt, 0.1 to 2000 mM of a source of magnesium such as $MgSO_4$, 0.1 to 20 mM of a citrate such as CPD and 0.9 to 3% of an ionic solution, such as a buffer or NaCl.

When the composition is used to increase blood pressure in a subject that has suffered a life threatening hypotension or shock; or to induce a low pain or analgesic state or a hypotensive state in a subject that has suffered a life threatening hypotension or shock; or to reduce hypofusion in the whole body of a subject, lower concentrations of magnesium are used, such as 30 mM or less than 20 mM.

In a further aspect, the methods and compositions according to the invention comprise (i) a compound selected from at least one of a potassium channel opener, a potassium channel agonist and an adenosine receptor agonist; (ii) an antiarrhythmic agent or a local anaesthetic; (iii) at least one of a citrate and a general anaesthetic and one or more of:

an anti-inflammatory agent;
an opioid;
a calcium channel blocker;
at least one compound for reducing uptake of water;
a sodium hydrogen exchange inhibitor;
an antioxidant;

a source of magnesium in an amount for increasing the amount of magnesium in a cell in body tissue; and
a pharmaceutically acceptable carrier such as an ionic solution for example NaCl or a buffer.

Preferably, this composition has two, three or four of the above components. Preferred additional components include one or more of a general anaesthetic, an anti-inflammatory agent, a source of magnesium and a pharmaceutically acceptable carrier such as a buffer. It is also contemplated that this composition may include more than one of the same component, for example two different potassium channel openers may be present in the composition. It is also contemplated that one component may have more than one function. For example, some calcium antagonists share effects with potassium channel openers and the general anaesthetic may be an opioid.

In another aspect there is also provided a composition useful in the methods according to the invention further including an effective amount of elevated magnesium.

In one embodiment, the composition useful in the methods according to the invention includes adenosine, lidocaine, a citrate such as CPD and a pharmaceutically acceptable carrier. This composition may also include an effective amount of elevated magnesium.

In one embodiment, the composition according to the invention includes adenosine, lidocaine, a citrate, a general anaesthetic and pharmaceutically acceptable carrier. This composition may also include an effective amount of elevated magnesium. This composition may optionally include an anti-inflammatory agent, such as beta-hydroxybutyrate.

One preferred form of the composition according to the invention is a combination of adenosine, lidocaine, a citrate and a pharmaceutically acceptable carrier. In a preferred form, the composition may also include an anti-inflammatory agent, such as beta-hydroxybutyrate and/or a general anaesthetic, such as GABA(A) receptor agonist and/or NMDA antagonist.

In one embodiment, the composition contains 0.1 to 40 mM of adenosine, 0.1 to 80 mM of lidocaine or a salt thereof such as a HCl salt, 0.1 to 2000 mM of a source of magnesium such as $MgSO_4$, 0.1 to 20 mM of a citrate such as CPD and 0.9% to 3% of an ionic solution such as NaCl or a buffer.

In relation to whole body arrest, where the composition is functioning as a cardioplegic composition, higher concentrations of magnesium are used, such as 300 to 500 mM or 400 mM. When the composition is being used to induce a coma-like state or sleep state, a hypotensive state, or a low pain or analgesic state and is functioning as a cardioprotectant composition lower concentrations of magnesium are used, such as 30 mM or less than 20 mM.

When the composition is being used to reduce inflammation, coagulation, adhesions, scar tissue formation, or to induce a hypotensive stat in an injured subject, lower concentrations of magnesium may be used, such as 30 mM or less than 20 mM.

Modes of Administration

The method of the present invention involves contacting a tissue with the composition for a time and under conditions sufficient for reducing injury to the cell, tissue or organ. The composition may for example be infused or administered as a bolus intravenous, intracoronary or any other suitable delivery route as pre-treatment for protection during a cardiac intervention such as open heart surgery (on-pump and off-pump), angioplasty (balloon and with stents or other vessel devices) and as with clot-busters (anti-clotting drug or agents).

The composition may be administered intravenously or be administered both intravenously and intraperitoneally or directly accessing a major artery such as the femoral artery or aorta in patients who have no pulse from massive exsanguination, or in the carotid artery or another artery during aortic dissection to protect the brain from hypoxia or ischemia. In one embodiment, the composition may be administered intravenously and intraperitoneally simultaneously, the perineum acting as, in effect, a reservoir of composition for the bloodstream as well as acting on organs in the vicinity with which it comes into contact. Another rapid route of administration is intraosseously (into the bone). This is particularly suitable for a trauma victim, such as one suffering shock. Moreover, where the composition contains two or more components, these may be administered separately but simultaneously. Substantially simultaneous delivery of the component to the target site is desirable. This may be achieved by pre-mixing the components for administration as one composition, but that is not essential.

The invention is directed towards the simultaneous increase in local concentration (for example an organ such as the heart) of the components of the composition.

The invention may be practised by administering the composition using a perfusion pump, often associated with a procedure known as "miniplegia" or "microplegia", in which minimal amount of components are titrated by means of a finely adjustable pump directly via a catheter. In the invention, a protocol utilises miniplegia as described above, where micro amounts are titrated directly to the heart, using the patient's own oxygenated blood. The reference to a "setting" is a measure on the pump, such as a syringe pump, of the amount of substance being delivered directly to the organ, such as a heart.

Alternatively, the composition may be administered by aerosol.

The composition can also be infused or administered as a bolus intravenous, intracoronary or any other suitable delivery route for protection during cardiac intervention such as open heart surgery (on-pump and off-pump), angioplasty (balloon and with stents or other vessel devices) and as with clot-busters to protect and preserve the cells from injury.

Accordingly, the tissue may be contacted by delivering the composition intravenously to the tissue. This involves using blood as a vehicle for delivery to the tissue. In particular, the composition may be used for blood cardioplegia. Alternatively, the composition may be administered directly as a bolus by a puncture (eg, by syringe) directly to the tissue or organ, particularly useful when blood flow to a tissue or organ is limiting. The composition for arresting, protecting and preserving a tissue may also be administered as an aerosol, powder, solution or paste via oral, skin or nasal routes.

Alternatively, the composition may be administered directly to the tissue, organ or cell or to exposed parts of the internal body to reduce injury.

The composition according to the invention may be used with crystalloid cardioplegia to minimise injury to a tissue. In one application for a surgical or diagnostic procedure such a composition could be administered to provide localised arrest of the target tissue as well as protection during reperfusion and postconditioning.

The composition may be delivered according to one of or a combination of the following delivery protocols: intermittent, continuous and one-shot. Accordingly, in another aspect of the invention, the composition may be administered as a single dose of the composition.

In another aspect of the invention, the composition may be administered by intermittent administration. A suitable administration schedule is a 2 minute induction dose every 20 minutes throughout the arrest period. The actual time periods can be adjusted based on observations by one skilled in the art administering the composition, and the animal/human model selected. The invention also provides a method for intermittently administering a composition for reducing injury to the cell, tissue or organ.

The composition can of course also be used in continuous infusion with both normal and injured tissues or organs, such as heart tissue. Continuous infusion also includes static storage of the tissue, whereby the tissue is stored in a composition according to the invention, for example the tissue may be placed in a suitable container and immersed in a composition (or solution) for transporting donor tissues from a donor to recipient.

Preferably, the composition according to the invention is administered in two steps (referred to as "one-two step iv infusion"). The first administration is by bolus followed by drip infusion.

In one embodiment, the composition is administered in one shot as a bolus or in two steps as a bolus followed by infusion.

The dose and time intervals for each delivery protocol may be designed accordingly. The components of the composition according to the invention may be combined prior to administration or administered substantially simultaneously or co-administered.

The composition may be administered by intravenous, intraosseous, intra-cardiac, intraperitoneal, spinal or cervical epidural.

In another embodiment, the composition useful in the methods according to the invention may be administered with or contain blood or blood products or artificial blood or oxygen binding molecules or solutions to improve the body's oxygen transport ability and survival by helping to reduce hypoxic and ischemic damage from blood loss. The oxygen-containing molecules, compounds or solutions may be selected from natural or artificial products. For example, an artificial blood-based product is perfluorocarbon-based or other haemoglobin-based substitute. Some of the components may be added to mimic human blood's oxygen transport ability such Hemopure™, Gelenpol™, Oxygent™, and PolyHeme™. Hemopore is based on a chemically stabilized bovine hemoglobin. Gelenpol is a polymerized hemoglobin which comprises synthetic water-soluble polymers and modified heme proteins. Oxygent is a perflubron emulsion for use as an intravenous oxygen carrier to temporarily substitute for red blood cells during surgery. Polyheme is a human hemoglobin-based solution for the treatment of life-threatening blood loss.

It is believed that the oxygenation of the body from a variety of ways including but not limited to oxygen gas mixture, blood, blood products or artificial blood or oxygen binding solutions maintains mitochondrial oxidation and this helps preserve the myocyte and endothelium of the organ. Without being bound by any particular mode or theory, the inventor has found that gentle bubbling with 95% $O_2$/5% $CO_2$ helps maintains mitochondrial oxidation which helps preserve the myocyte and coronary vasculature.

In one preferred embodiment the composition useful in the methods according to the invention is aerated with a source of oxygen before and/or during administration. The source of oxygen may be an oxygen gas mixture where oxygen is the predominant component.

In another aspect the method according to the invention includes:

providing in a suitable container a composition as described above;

providing one or more nutrient molecules selected from the group consisting of blood, blood products, artificial blood and a source of oxygen;

optionally aerating the composition with the oxygen (for example, in the case of isolated organs) or combining the nutrient molecules with the composition, or both; and placing the tissue, cell or organ in contact with the combined composition under conditions sufficient to reduce injury.

This method may include the further step of postconditioning the cell, tissue or organ.

Preferably the oxygen source is an oxygen gas mixture. Preferably oxygen is the predominant component. The oxygen may be mixed with, for example $CO_2$. More preferably, the oxygen gas mixture is 95% $O_2$ and 5% $CO_2$.

The composition useful in the methods of the invention is highly beneficial at about 10° C. but can also be used to prevent injury over a wider temperature range up to about 37° C. Accordingly, the composition may be administered to the cell, tissues or organs at a temperature range selected from one of the following: from about 0° C. to about 5° C., from about 5° C. to about 20° C., from about 20° C. to about 32° C. and from about 32° C. to about 38° C. It is understood that "profound hypothermia" is used to describe a tissue at a temperature from about 0° C. to about 5° C. "Moderate hypothermia" is used to describe a tissue at a temperature from about 5° C. to about 20° C. "Mild hypothermia" is used to describe a tissue at a temperature from about 20° C. to about 32° C. "Normothermia" is used to describe a tissue at a temperature from about 32° C. to about 38° C., though the normal body temperature is around 37 to 38° C.

The compositions would also find use as a topical spray or soaked in a gauze soaked and applied to an organ, tissue or cell of the body and has application for surgery and clinical interventions. This application may include a topical aerosol for spraying on surgical incisions or wounds, and around the area of these wounds. For example, the composition could be used for applying to a median sternotomy (sternal incision) in cardiac surgery, and applied during and after the operation to reduce or prevent adhesions from occurring between the underside of sternum area to the underlying heart and other tissues after the operation. In cardiac surgeries that require redoing major complications can occur from tissues and organs adhering to the underside of the sternum. In abdominal surgery, the composition could be applied to the internal organs during and prior to closing the incision to reduce or prevent adhesions from occurring in the abdominal cavity after surgery. The composition could also be used for incisions made for artery or venous catheterizations. For example, during a cut down and cannulation of the femoral artery or vein the area could be sprayed or soaked and the surgical well with the composition to prevent adhesions from occurring after the incision is closed. Another application would be for harvesting veins or arteries to be used for cardiac surgery as conduits to replace the blocked arteries on the heart in a coronary artery bypass operation. For example, the saphenous vein is exposed from a long incision in the leg and harvested for cardiac surgery, and the area could be sprayed or topically applied on a gauze. The composition would also have an application for less invasive endoscopic harvesting of blood vessels. Topical applications of the composition would also find applications on areas of the heart itself particularly where potential cell fibrosis or injury may occur locally around the region of the heart responsible for arrhythmias or other heart dysfunctions. The whole heart could also be sprayed topically to protect it from any adhesions or dysfunction.

In another embodiment, the composition according to the invention is hypertonic. In particular, the composition has a saline concentration greater than normal isontic saline which is 0.9% NaCl (0.154M).

Dosages

It will be appreciated that the amount of active ingredients present in the composition will depend on the nature of the subject (whole body, isolated organ circuit in the body or isolated cell, organ or tissue ex vivo) and the proposed method of treatment or use. The amount should be effective for the end use, for example, one or more of the components should be present "in an amount sufficient to increase blood pressure".

Below contains the preferred and most preferred ranges of active ingredients in the composition for medical and veterinary use. Abbreviations: IV intravenous; IA intra-arterial; IO intra-osseous; IC intracardiac; A Adenosine; L lidocaine-HCl; M Magnesium Sulphate; BHB beta-hydroxy butyrate; P propofol; NaCl sodium chloride (%)

| Admin | Indication | A mg/kg | L mg/kg | M mg/kg | Propofol (P) mg/kg | BHB | Citrate | Saline (%) |
|---|---|---|---|---|---|---|---|---|
| BOLUS | | | | | | | | |
| 1) Bolus IV, IA, IO or IC | Brain Arrest; Whole body Arrest | 0.01 to 20 preferred 0.1 to 10 More preferred | 0.02 to 40 preferred 0.1 to 10 More preferred | 0 to 2000 preferred 25 to 500 More preferred | 0.1 to 50 | 2 g/5 L blood = 4 mM (Range 0.02 to 10 g/5 L | 1.5 g/5 L blood = 1 mM (Range 0.10 to 5 g/5 L | 0.9% 3% 5% or 7.5% |
| | Most Preferred composition: Rat (0.4 kg): 0.5 ml bolus 0.5 mg A, 1 mg L, 50 mg M, 1 mg/kg P in 0.9% NaCl Pig (40 kg): 1.25 mg A/kg, 2.5 mg L/kg, 250 mg M/kg 1 to 5 mg/kg P (in 0.9% NaCl) | | | | | | | |
| 2) Bolus IV, IA, IO or IC | Whole body protection | 0.001 to 5.0 preferred 0.01 to 5 More preferred | 0.005 to 10.0 preferred 0.1 to 5 More preferred | 0.003 to 30 preferred 0.1 to 5 More preferred | 0.005 to 10.0 | 0.01 to 0.05 g/kg preferred | 0.005- 0.03 g/kg preferred | 0.9% 3% 5% 7.5% |
| | Most Preferred composition: Rat: 0.3 ml 0.9% NaCl containing A 0.025 mg/kg; L 0.075 mg/kg; M 0.3 mg/kg Pig and human: 10 ml bolus 0.9% NaCl with the above or 0.8 mg A/kg; 1.6 mg L/kg and 1 mg M/kg | | | | | | | |
| 3) Bolus IV, IA, IO or IC | Whole body Hypo-tensive Resuscit-ation | 0.001 to 5.0 | 0.005 to 10.0 | 0.003 to 30 | 0.005 to 10.0 | 0.01 to 0.05 g/kg preferred | 0.005-0.03 g/kg preferred | 0.9% 3% 5% or 7.5% |
| | Most Preferred composition: Same as above but with 3% NaCl not 0.9% NaCl | | | | | | | |
| Bolus Deliverytimes | Range of bolus administration times 1 sec to 15 min Most Preferred: 10 sec Rat 1-5 min Pig 1-5 min Human BOLUS- INFUSION/DRIP TREATMENT METHOD FOR . . . | | | | | | | |
| Bolus | As Above (2) or (3) 3% saline if required and brain injury suspected | | | | | | | |
| Infusion or Drip | | | | | | | | |
| | Surgery, Injury Infection, Sepsis, Burns Stabilization, Haemorrhage Shock, Brain Injury, Stroke Heart attack, Pain, circulatory arrest, dialysis. Childbirth, Seizures | 0.01 to 20 | 0.5 to 100 | 0.1 to 100 | 0.01 to 5 mg/kg/min. Can top up with 25 mg bolus (may not require P for some targets) | 2 g/5 L blood = 4 mM Range 0.02 to 10 g/5 L (may not require BHB) | 1.5 g/5 L blood = 1 mM (Range0.1 0 to 5 g/5 L (may not always require) | 0.9% 3% 5% or 7.5% 23.5% |
| | Most Preferred: 0.9% or 3% NaCl Rat: 1 ml/kg/hr A: 3 mg/kg; L: 6 mg/kg; 3.36 mg/kg Pig/Human 10 ml/kg/hr with the above ALM or higher A: 12 mg/kg; L: 24 mg/kg; 12 mg/kg | | | | | | | |
| Flow rates | For the above Rat: (eg. IV IO) 0.1 to 10 ml/kg/hr Pig:Human: (eg. IV IO) 1.0 to 50 ml/kg/hr Isolated human brain circuit perfusion (via a cerebral artery such as carotid) for aortic, endarterectomy or other brain protection surgery and interventions: 1 to 100 ml/kg/min Whole body bypass flow 1 to 500 ml/min/kg for aortic pressure of 80 mmHg or lower in case of hypotensive anaesthesia (see below). Cardiac perfusion: 1 to 500 ml/min (0.01to 10 ml/min/kg human) Most Preferred Whole body Rat 1 ml/kg/hr Pig/human 10 ml/kg/hr Brain Circuit: 10-30 ml/kg/min Heart Circuit 2 to 10 ml/kg/min Arrest: flow 4-7 ml/kg/min (A; 1.4 mg/kg; L: 2.9 mg/kg; M: 0.06 g/kg) Non-arrest 1 ml/kg/min of the above BOLUS-INFUSION/DRIP PREVENTATIVE METHOD FOR . . . | | | | | | | |

-continued

| Admin | Indication | A mg/kg | L mg/kg | M mg/kg | Propofol (P) mg/kg | BHB | Citrate | Saline (%) |
|---|---|---|---|---|---|---|---|---|
| Bolus | As Above | | | | | | | |
| Infusion or Drip | | | | | | | | |
| | Surgery, Pain | 0.01 to 20 preferred | 0.5 to 100 preferred | 0.1 to 100 preferred | 0.01 to 5 mg/kg/min. | 2 g/5 L blood = 4 mM | 1.5 g/5 L blood = 1 mM | 0.9% |
| | Infection | 0.1 to 20 More preferred | 0.2 to 40 More preferred | 1 to 30 More preferred | Can top up with 25 mg bolus (may not require P for some targets) | (Range 0.02 to 10 g/5 L (may not require BHB) | (Range 0.1 0 to 5 g/5 L (may not require) | 3% |
| | Inflammation | | | | | | | 5% or |
| | Coagulopathy | | | | | | | 7.5% |
| | Adhesions | | | | | | | 23.5% |
| | Cardiac injury | | | | | | | |
| | Renal injury | | | | | | | |
| | Brain injury | | | | | | | |
| | Lung injury | | | | | | | |
| | Gut Injury | | | | | | | |
| | Immuno-suppresion | | | | | | | |
| | dialysis | | | | | | | |

Most Preferred composition:
0.9% or 3% NaCl
Rat: 1 ml/kg/hr
A: 3 mg/kg; L: 6 mg/kg; 3.36 M mg/kg
Pig/Human
10 ml/kg/hr with the above or higher A: 12 mg/kg; L: 24 mg/kg; M 12 mg/kg INDUCTION OF HYPOTENSIVE STATE AND/OR HYPOTENSIVE ANAESTHESIA (without arresting the brainstem)

| Bolus | | 0.1 to 10.0 | 0.1 to 20.0 | 0.1 to 20 | 0.005 to 10.0 | | | 0.9% |
|---|---|---|---|---|---|---|---|---|
| | | | | | | | | 3% |
| | | | | | | | | 5% or |
| | | | | | | | | 7.5% |

Most Preferred composition:
10 or 20 ml bolus
0.9% NaCl
0.8 mg A/kg; 1.6 mg L/kg and 1 mg M/kg. 3% NaCl may be used if brain injury suspected

| Infusion-Drip | | 1 to 40 preferred | 1 to 80 preferred | 1 to 50 preferred | 0.01 to 5 mg/kg/min | | | |

Most Preferred composition:
10 ml/kg/hr with A: 12 mg/kg; L: 24 mg/kg; M: 12 mg/kg or more hypotension A: 18 mg/kg; L: 36 mg/kg; M: 20 mg/kg
1) Specialized surgery (e.g. shoulder, hip, knee or circulatory arrest. Placement of heart valves via transluminal catheter technique without thoracotomy or extracorporal circulation. 2) whole body protection (reduce injury infection, inflammation, coagulopathy as above) 3) to reduce blood loss during Damage Control Surgery
P: 0.1 to 0.2 mg P/kg/min (may not require P for some indications)

Similarly, it will be appreciated that the concentrations of each component in the composition may be diluted by body fluids or other fluids that may be administered together with the composition. Typically, the composition will be administered such that the concentration of each component in the composition contacts the tissue about 100-fold less. For example, containers such as vials that house the composition may be diluted 1 to 100 parts of blood, plasma, crystalloid or blood substitute for administration.

It will be understood that the invention disclosed and defined in this specification extends to all alternative combinations of two or more of the individual features mentioned or evident from the text or drawings. All of these different combinations constitute various alternative aspects of the invention.

EXAMPLES

Embodiments of the invention will now be described with reference to the following non-limiting examples.

Example 1: One-Two IV Injection Administration Protocol of ALM

The cecal ligation and puncture model is considered the gold standard for sepsis research. In contrast to toll receptor agonists such as lipopolysaccharide (LPS) toxin model which is only detectable in only a minority of patients with sepsis, the cecal ligation model mimics the human disease of ruptured appendicitis or perforated diverticulitis. The cecal model also reproduces the dynamic changes in the cardiovascular system seen in humans with sepsis. In addition, the model recreates the progressive release of pro-inflammatory mediators.

The gastrointestinal tract often can be damaged directly from penetrating or blunt trauma, but also from ischemic injury from any kind of major surgery, cardiac arrest, burns, haemorrhage and shock. Ischemic injury poses a significant risk of infection and sepsis because the gut wall becomes leaky and bacteria translocates into the peritoneal cavity resulting in a medical emergency. Reducing the impact of infection from GI injury would also reduce adhesions as infection is one cause of adhesions as the body attempts to repair itself. Adhesions may appear as thin sheets of tissue similar to plastic wrap, or as thick fibrous bands. Up to 93 percent of people who have abdominal surgery go on to develop adhesions.

Rat Model of Cecal Polymicrobial Sepsis

Male Sprague Dawley rats (300-450 g) were fed ad libitum with free access to water and housed in a 12-hr light-dark cycle. Animals were not heparinized and anesthetized with an intraperitoneal injection of 100 mg/kg sodium thiopentone (Thiobarb). Anesthetized animals were positioned in the supine position on a custom designed cradle. A tracheotomy was performed and animals were artificially ventilated (95-100 strokes min$^{-1}$) on humidified room air using a Harvard Small Animal Ventilator (Harvard Apparatus, Mass., USA). A rectal probe was inserted 5.0 cm and the temperature ranged between 37 and 34° C. The caecum was isolated through midline laparotomy and ligated below ileocaecal valve. It was punctured with 18G needle four times through-and-through (8 holes). The abdominal cavity was surgically closed in 2 layers. Rats were randomly assigned into either control or groups for Example 1 (bolus only) and Example 2 (bolus plus drip infusion).

Example 1a: One-Bolus of ALM is Insufficient to Support Hemodynamics

Example 1a

Control animals receive intravenous 0.3 ml bolus 0.9% NaCl and treatment groups was 0.3 ml bolus 0.9% NaCl with 1 mM Adenosine (0.24 mg/kg), 3 mM Lidocaine (0.73 mg/kg), and 2.5 mM $MgSO_4$ (0.27 mg/kg), in 0.9% NaCl.

Results are shown in FIG. 1 (A-E) FIG. 1 (A-E) show that ALM IV bolus ONLY strategy stabilized the cardiovascular system for about 1 hour and preserved body temperature at around 34 C for 3 hours. However One-Bolus ALM failed to Sustain Stabilization over 5 hours of polymicrobial infection (sepsis).

ALM bolus stabilized the cardiovascular system for about 60 min then failed to protect against collapse and SEPTIC SHOCK over 5 hours of polymicrobial infection.

Rat Polymicrobial Bacterial Infection Model: Single Bolus Intravenous Treatment Only Example 1b: One Bolus Plus Drip Infusion (One-Two IV Injection Strategy) Showed Hemodynamic Support and Avoidance of Septic Shock Control animals receive intravenous 0.3 ml bolus 0.9% NaCl and drip infusion (0.4 ml/hr) 0.9% NaCl. Treatment animals received 0.3 ml bolus 0.9% NaCl with 1 mM Adenosine (0.24 mg/kg), 3 mM Lidocaine (0.73 mg/kg, and 2.5 mM $MgSO_4$ (0.27 mg/kg), and a different composition for drip infusion (0.4 ml/hr) comprising 12 mg/kg/hr Adenosine, 34 mg/kg/hr Lidocaine, and 13.44 mg/kg/hr $MgSO_4$ in 0.9% NaCl The control and treatment was withdrawn after 4 hr and animals monitored for further 60 min.

Figure 2:
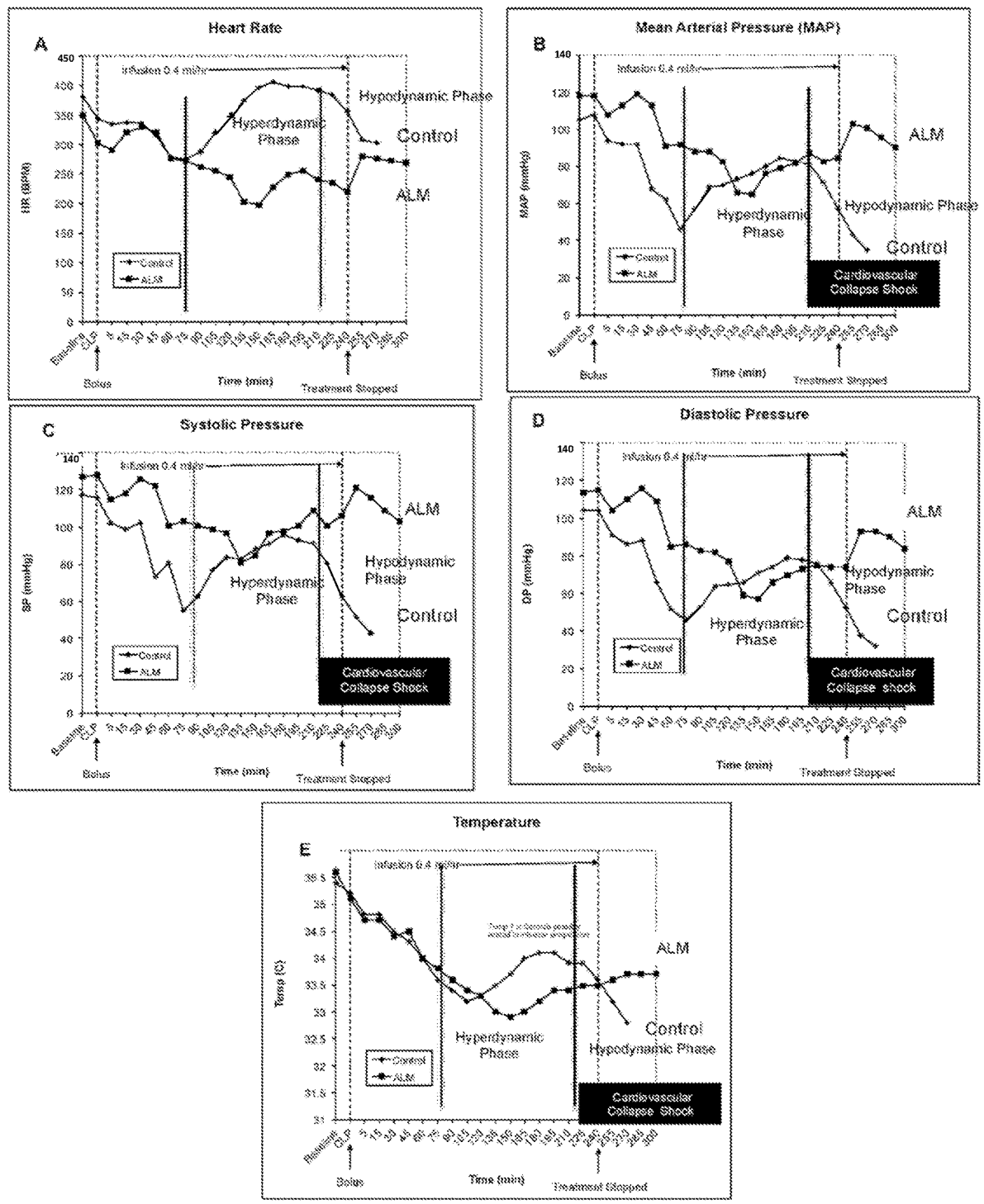
FIG. 2 shows graphs showing measurement of (A) Heart Rate; (B) MAP; (C) Systolic Pressure; (D) Diastolic Pressure; (E) Temperature against Time (min) in Rat Polymicrobial Bacterial Infection Model: One-Two Intravenous Treatment Delivery over 5 hours for Rat ALM Bolus v's Control. (see example 1)

Results are shown in FIG. 2 (A-E) FIG. 2 (A-E) show that ALM IV bolus infusion one-two treatment strategy stabilizes the cardiovascular system and preserves body temperature regulation during 5 hours of polymicrobial infection (sepsis).

Heart rate increases in saline controls in increases after 90 min then sharply decreased after 225 min in direct contrast to ALM treatments which show reduction in HR and more stabilization and increases after 150 min. This hyperdynamic phase (90-225 min) in controls is well known and due to increased sympathetic activity and stress as a result of the infection. ALM stability implies improved heart rate variability improved central nervous system control of heart rate.

Most surprisingly are the differences in mean arterial pressure, systolic arterial pressure and diastolic arterial pressures (FIGS. 2 A-D). Control animals increase developed pressures during the hyperdynamic phase (90-225 min) consistent with increased heart rate then dramatically decrease pressures and enter into Septic shock from cardiovascular collapse. In direct contrast, the ALM treated groups stabilize hemodynamics over the 5 hour period (FIGS. 2 A-D) and protect against shock.

In contrast to saline controls, ALM treatment also improves body temperature control and begin to increase body temperature after 150 min. This is significant as it implies improved central nervous function during 5 hour of infection compared to controls which went into septic shock ALM bolus and intravenous infusion prevented animal from cardiovascular collapse and avoided SEPTIC SHOCK over 5 hours of polymicrobial infection.

Example 2: Effect of Dose Response of ALM Infusion to Reduce Inflammation (Tumor Necrosis Factor-Alpha, TNF-Alpha) During Endotoxemia in the Pig Background:

The primary role of TNF alpha is in the regulation of immune cells. TNF alpha is a cytokine involved in systemic inflammation, and along with other cytokines stimulates the acute phase reaction to stress and infection. TNF-alpha also induces activation of coagulation in different pathological states including sepsis. Activated protein C inhibits TNF-alpha production. Activated protein C (and antithrombin) may inhibit the endothelial perturbation induced by cytokines. Antithrombin regulates TNF-alpha induced tissue factor expression on endothelial cells by an unknown mechanism. Activated protein C and antithrombin, and their pathways of regulation, may be useful targets for treating coagulation abnormalities associated with sepsis or other inflammation diseases. These sites and pathways inhibit not only coagulation but also involved with the downregulation of anticoagulant activities of endothelial cells.

Methods:

A dose response of ALM infusion on inflammation was studied in the swine model of lipopolysaccharide (LPS, an obligatory component of Gram-negative bacterial cell walls) endotoxemia at 90 min infusion (Infusion of LPS for 5 hours 1 µg/kg/min) into 40 kg female pigs.

Pigs were fasted overnight, but allowed free access to water. Anesthesia was induced with midazolam (20 mg) and s-ketamin (250 mg) and maintained with a continuous infusion of fentanyl (60 µg/kg/h) and midazolam (6 mg/kg/h). The animals were intubated and volume-controlled ventilated (S/5 Avance, Datex Ohmeda, Wis., USA) with a positive end-expiratory pressure of 5 cm $H_2O$, FiO2 of 0.35, and a tidal volume of 10 ml/kg. Ventilation rate was adjusted to maintain $PaCO_2$ between 41-45 mmHg. The body temperature was maintained around 38° C. during the entire study. All animals received normal saline (NS) at a maintenance rate of 10 ml/kg/h during surgery and the baseline period and was increased to 15 ml/kg/h during LPS infusion.

Figure 3:
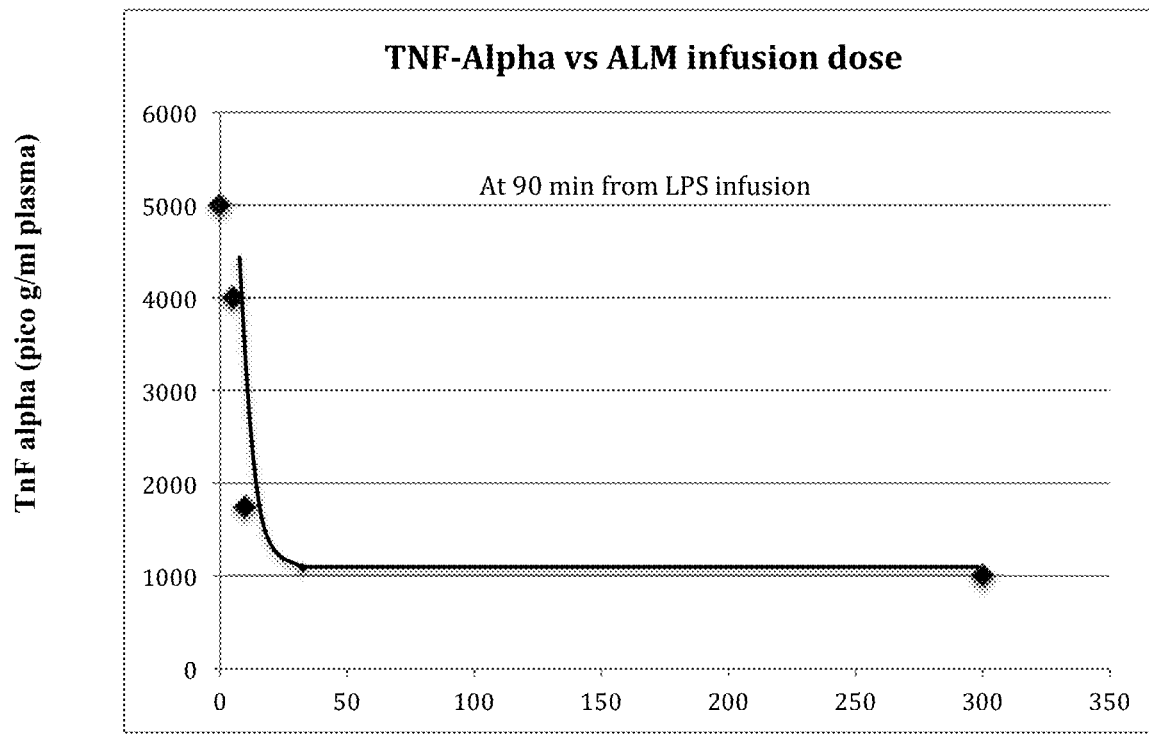
FIG. 3 shows a graph comparing TNF-Alpha versus ALM infusion dose. The X-axis refers to the dose of adenosine (A) in the ALM dose with the following combinations being tested: 1) Control animal TNF-alpha with LPS alone infusion; 2) 5 µg A/10 µg Lidocaine/5.6 µg $MgSO_4$/kg/min; 3) 10 µg A/20 µg Lidocaine/5.6 µg $MgSO_4$/kg/min; 4) 300 µg A/600 µg Lidocaine/336 µg $MgSO_4$/kg/min. (see example 2)

The results are shown in FIG. 3. The Y-axis is TnF-alpha in plasma produced at 90 min in response to the LPS infusion and the X-axis refers to the dose of adenosine (A) in the different ALM doses with the following combinations being tested:

1) Control animal with LPS alone infusion.
2) 5 µg Adenosine/10 µg Lidocaine-HCl/5.6 µg $MgSO_4$/kg/min over a 4 hour period or 0.3 mg Adenosine per kg/hour, 0.6 mg/kg/hour lidocaine and 0.34 mg $MgSO_4$/kg/hr. The stock composition for infusion (in mM) was 0.075 mM Adenosine, 0.148 mM lidocaine and 0.187 mM $MgSO_4$
3) 10 µg A/20 µg Lidocaine/5.6 µg $MgSO_4$/kg/min over a 4 hour period or 0.6 mg Adenosine per kg/hour, 1.2 mg/kg/ hour lidocaine and 0.34 mg MgSO$_4$/kg/hr. The stock composition for infusion (in mM) was 0.15 mM Adenosine, 0.296 mM lidocaine and 0.187 mM MgSO$_4$ 4) 300 μg A/600 μg Lidocaine/336 μg MgSO$_4$/kg/min over a 4 hour period or 18 mg Adenosine per kg/hour, 36 mg/kg/hour lidocaine and 20 mg MgSO$_4$/kg/hr. The stock composition for infusion (in mM) was 4.5 mM Adenosine, 8.88 mM lidocaine and 11 mM MgSO$_4$.

Interpretation:

1. Increasing the dose of ALM dramatically inhibits TNF alpha after 90 min of infusion of LPS toxin in the swine model in vivo.

2. Inhibition appears to begin at low concentrations above 10 μg A/20 μg Lidocaine/5.6 μg MgSO$_4$/kg/min The example shows that ALM reduces TnF alpha in a dose dependent manner. Since the primary role of TNF alpha is in the regulation of immune cells and early inflammation, the present invention shows that it can reduce the appearance of TNF alpha in the blood. TNF alpha is a cytokine involved in systemic inflammation, and along with other cytokines stimulates the acute phase reaction to stress and infection. TNF-alpha also induces activation of coagulation in different pathological states including sepsis. The present invention by inhibiting TnF alpha may reduce inflammation and reduce the impact inflammation has on coagulation during infection, sepsis and septic shock. Since adhesions can be caused by infection, the present invention also may reduce the incidence of adhesions. Since inflammation is part of any injury process (traumatic or non-traumatic) particularly as a result of traumatic brain injury, the present invention also may reduce the secondary complications of brain injury. Since inflammation is a result of disease (heart attack, stroke, cardiac arrest, auto-immune diseases, hemorrhagic shock), the present invention also may reduce the complications of disease due to local or systemic inflammation. There is a major unmet need to reduce the impact of infection in health and disease, and to modulate the immune function of the host to reduce the impact of infection or prevent it from progressing into septic shock.

Significance

Sepsis is a very common complication of almost any infectious disease. There are >1.5 million people develop severe sepsis and septic shock annually in the United States and another 1.5 million people in Europe. Sepsis often develops in the field of co-morbidities like type 2 diabetes mellitus, chronic obstructive pulmonary disease, chronic heart failure and chronic renal disease, trauma, burns and surgery. Despite improvement in medical care, severe sepsis and septic shock remain an unmet medical need. There is a need for new drugs that modulate the immune function of the host to reduce the impact of infection or prevent it from progressing into septic shock. Drugs can be divided into three categories according to their mechanism of action: i) agents that block bacterial products and inflammatory mediators, ii) modulators of immune function, and iii) immunostimulation (reduce immunosuppression). Drug development could also have an impact on many pathologies involving low levels of inflammatory markets and immune imbalances. For example, recent studies suggest that acute and chronic cardiovascular disease is associated with a chronic low-grade inflammation that promotes adverse ventricular remodeling and correlates with disease progression. Several inflammatory mediators, including TNF-α, IL-1β, and IL-6, are involved in cardiac injury subsequent to myocardial ischemia and reperfusion, sepsis, viral myocarditis, and transplant rejection.

Several clinical trials of agents aimed at modulating the immune response of the host, such as anti-endotoxin antibodies, anti-tumour necrosis factor (TNF) antibodies and soluble TNF receptors, have failed to disclose any definite clinical benefit. The same applies to the administration of low-dose hydrocortisone as well as intense glucose control by continuous insulin infusion. Also biomodulators to block or inhibit inflammation have generally failed to improve the outcomes in patients with severe sepsis, septic shock, and MODS. The role of counter-inflammatory signaling and the newer concept of the cholinergic anti-inflammatory pathway are being investigated, and newer hypotheses are focusing upon the balancing of proinflammatory and counter-inflammatory mechanisms. Failure to define novel and effective treatments reflects fundamental gaps in our understanding of inflammation and its regulation.

Example 3: Coagulopathy Changes in the Rat Polymicrobial Bacterial Infection Model During One-Two Intravenous ALM Treatment Delivery Over 5 Hours Background: Severe sepsis, defined as sepsis associated with acute organ failure, is a serious disease with a mortality rate of 30-50%. Sepsis always leads to deranged coagulation, ranging from mild alterations up to severe disseminated intravascular coagulation (DIC) (hypercoagulopathy). Septic patients with severe DIC have microvascular fibrin deposition, which often leads to multiple organ failure and death. Alternatively, in sepsis severe bleeding might be the leading symptom (hypocoagulopathy), or even coexisting bleeding and thrombosis. There are no approved drugs for sepsis and currently constitutes a major unmet medical need requiring breakthrough technologies. The deranged coagulation, particularly DIC, is an important and independent predictor of mortality in patients with severe sepsis. The rat model used as an example below is a gold standard to mimic the pathophysiology of severe sepsis in humans.

Rat Model of Cecal Polymicrobial Sepsis

Male Sprague Dawley rats (300-450 g) were fed ad libitum with free access to water and housed in a 12-hr light-dark cycle. Animals were not heparinized and anesthetized with an intraperitoneal injection of 100 mg/kg sodium thiopentone (Thiobarb). Anesthetized animals were positioned in the supine position on a custom designed cradle. A tracheotomy was performed and animals were artificially ventilated (95-100 strokes min-1) on humidified room air using a Harvard Small Animal Ventilator (Harvard Apparatus, Mass., USA). A rectal probe was inserted 5.0 cm and the temperature ranged between 37 and 34° C. The caecum was isolated through midline laparotomy and ligated below ileocaecal valve. It was punctured with 18G needle four times through-and-through (8 holes). The abdominal cavity was surgically closed in 2 layers. Rats were randomly assigned into either control or groups for ALM Bolus and Infusion.

Control animals receive intravenous 0.3 ml bolus 0.9% NaCl and drip infusion (0.4 ml/hr) 0.9% NaCl. Treatment animals received 0.3 ml bolus 0.9% NaCl with 1 mM Adenosine (0.24 mg/kg), 3 mM Lidocaine-HCl (0.73 mg/kg, and 2.5 mM MgSO$_4$ (0.27 mg/kg, and a different composition for drip infusion (0.4 ml/hr) comprising 12 mg/kg/hr Adenosine, 34 mg/kg/hr Lidocaine, and 13.44 mg/kg/hr MgSO$_4$ in 0.9% NaCl The control and treatment was withdrawn after 4 hr and animals monitored for further 60 min.

Results are shown in Table 1.

TABLE 1

| One-two bolus infusion treatment One-Two Bolus-Infusion Treatment | | | | | |
|---|---|---|---|---|---|
| Saline Control 0.3 ml 0.9% NaCl bolus + 0.9% NaCl drip (4 hr) | | | ALM Bolus and Infusion 0.3 ml 0.9% NaCl ALM bolus + 0.9% NaCl ALM drip (4 hr) | | |
| Time | PT (sec) | aPTT | | PT (sec) | aPTT |
| * Baseline | 28 | 17 | *Baseline | 28 | 17 |
| 60 min | 71.9 | 300 | 60 min | 68.9 | 146.9 |
| 120 min | 85.3 | 193.5 | 120 min | 39.4 | 74.0 |
| 240 min | 22.3 | 131.5 | 300 min | 39.6 | 63.5 |

* Baseline: PT Normal = 28 sec; aPTT Normal = 17 sec
Definitions:
PT = prothrombin times (extrinsic clotting pathway begins with tissue factor and believed to be the initiator of clotting in vivo)
aPTT = activated partial thromboplastin time in contrast to the PT, measures the activity of the intrinsic and common pathways of coagulation. The term 'thromboplastin' in this test refers to the formation of a complex formed from various plasma clotting factors which converts prothrombin to thrombin and the subsequent formation of the fibrin clot.

Interpretation of Coagulopathy Data During 5 Hours of Polymicrobial Infection:

After 60 min:

Both Control and ALM treated animals showed initial hypocoagulopathy based on increases in both PT (extrinsic) and aPTT (intrinsic) clotting times relative to baseline values, however, less so for aPTT in ALM treated animals (50% lower). PT increased 2.5 times and aPTT increased over 17 times in controls and only 8.5 times in ALM treated rats compared to baseline aPTT. This may imply ALM treated animals resisting blood thinning at 60 min from the effect of infection.

After 120 min:

At 2 hours controls remain hypocoagulable (thinner blood). ALM corrected PT and aPTT towards baseline during infection.

After 240 min:

At 4 hours control rats became hypercoagulable (blood clots faster) which is common during sepsis and note this is the time when controls failed to maintain hemodynamics and suffered septic shock (see Example 1, FIGS. 1 A-E). Of special note, the ALM treated animals maintain clotting balance even after 60 min after treatment was turned off.

Summary:

What is surprising about this example was the blood in controls as a result of infection became thinner (hypocoagulable) then became thicker (hypercoagulable) and that ALM corrected both and moved the clotting properties of the blood toward normal homeostatic balance (baseline). This is surprising as there is no drug that has been reported to shift clotting properties in both directions, and simultaneously rescue the cardiovascular system from collapse and avoiding septic shock (FIGS. 2 A-E). This example demonstrates usefulness of the composition according to the invention to treat coagulopathy and potential for use in reducing brain injury, inflammation, adhesions and whole body arrest.

Example 4: AL Relaxation of the Mesenteric Artery and Increase Blood Flow to the GI Tract to Reduce Injury or Damage to the Gut, Reduce Infection and Reduce Adhesions Effect of a composition according to the invention to relax the mesenteric artery and potentially increase blood flow to the gastrointestinal tract.

Figure 4:
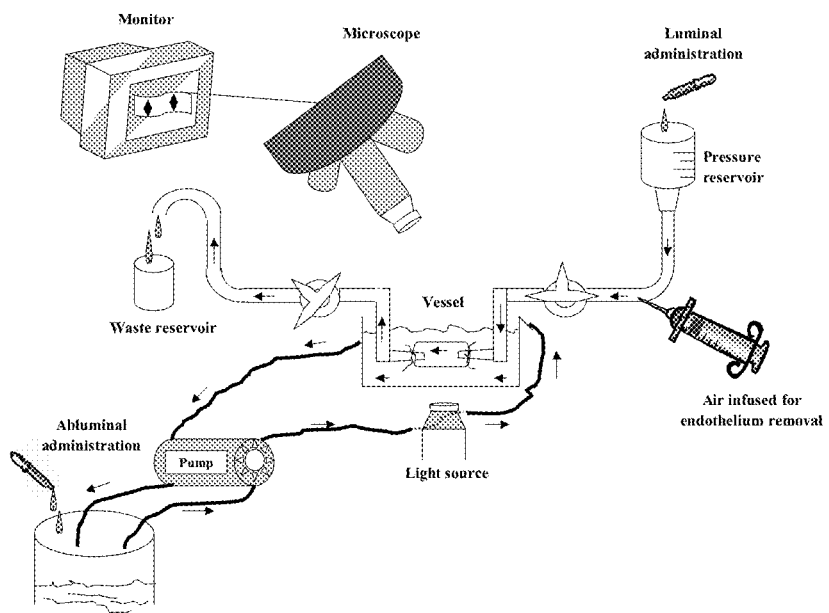
FIG. 4 shows a flow diagram of videomicroscopy procedure described in Example 4.

Method:

Male guinea pigs (250-300 g) were anesthetised and placed in a cradle and the abdomen opened. Second order mesenteric artery branches were isolated and mounted in a pressure myograph (see FIG. 4) under constant pressure of 60 mmHg and perfusion (luminal flow) of 100 uL/min with Krebs-Henseleit buffer (37° C.). Artery diameter was continuously measured using videomicroscopy (see FIG. 4). For the relaxation/vasodilation experiments arteries were equilibrated and then constricted with $10^{-8}$ M arginine vasopressin (AVP). Adenosine, lidocaine or adenosine-lidocaine together were administered 2) luminally and 2) abluminally and concentration curves were obtained. Stock solutions of adenosine and lidocaine alone or adenosine-lidocaine combined were made in deionized water to 20 mM. A range of volumes were pipetted to provide contact concentrations with the vessel lumen or outer wall that ranged from 0.001 to 1 mM. At the end of experiments, arteries were dilated using calcium-free solution to obtain 100% relaxation. A number of arteries were denuded by introducing 5 ml air into the lumen with flow rate 1000 μl/min. The air outflow was then clamped until the intraluminal pressure reached 70 mmHg, flow rate was reduced to 2 μl/min and the vessel remained pressurized for 10 minutes Example 4a: Effect of Adenosine (A), Lidocaine (L) and Adenosine and Lidocaine (AL) on Relaxation of Isolated Guinea-Pig Mesenteric Artery when Added in the Lumen (Luminal) or in the Bathing Solution (Abluminal)

Figure 5:
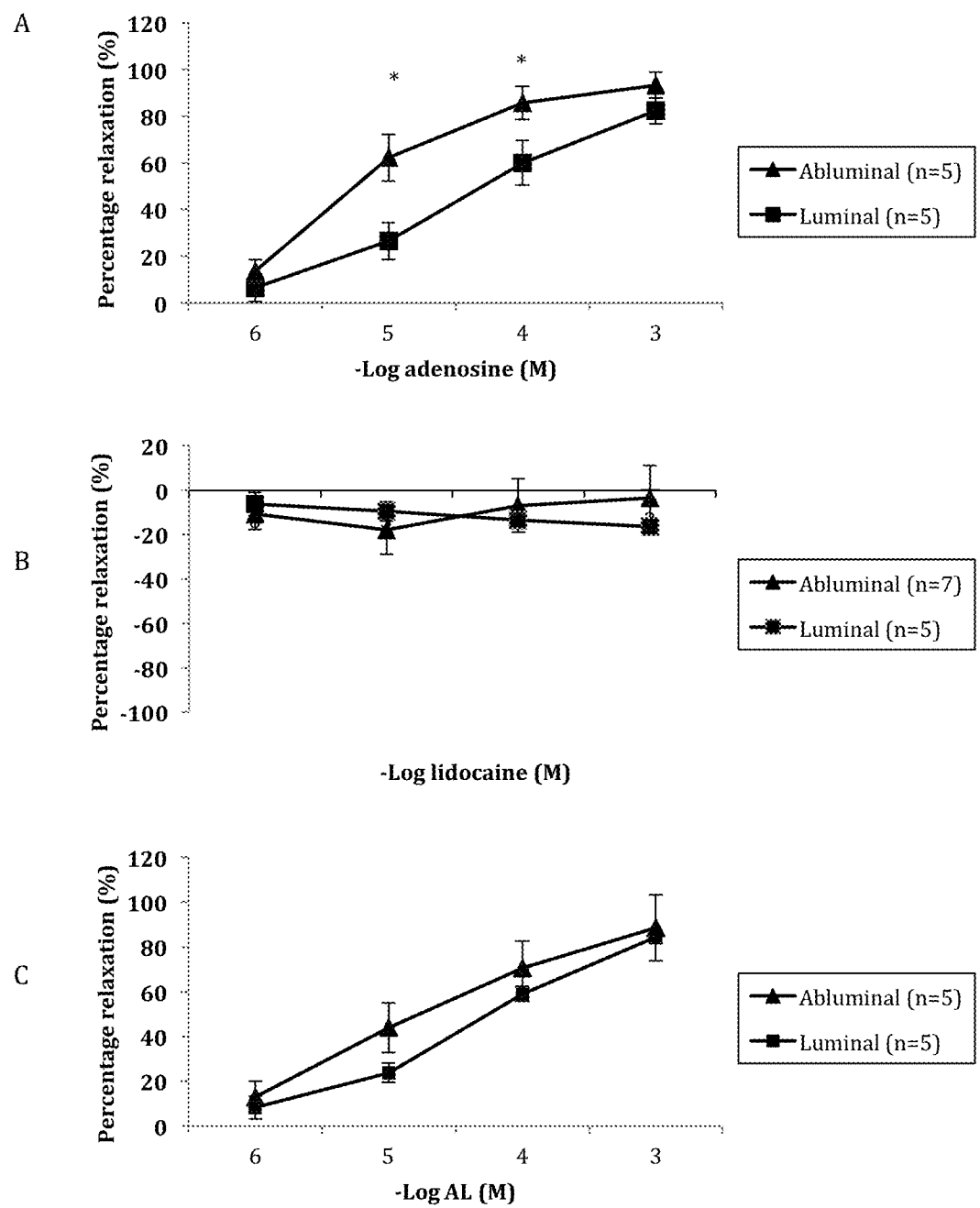
FIG. 5 shows graphs measuring the effect of Adenosine (A), lidocaine (L) and adenosine and lidocaine (AL) on % relaxation (Y axis) of isolated guinea-pig mesenteric artery when added in the lumen (luminal—square) or in the bathing solution (abluminal—diamond).

The results are shown in FIG. 5.

FIG. 5A shows that adenosine increased relaxation of the isolated intact mesenteric artery in a dose dependent manner, and that at 10 μM and 100 μM the effect of adenosine added to the bathing solution surrounding the vessel (abluminal administration) produced significantly more relaxation than if the solution was perfused through the lumen (inside the vessel). FIG. 5B. Shows that lidocaine failed to produce relaxation in the isolated intact mesenteric artery and there was no significant difference if the lidocaine was in the lumen or on the outside bathing solution. FIG. 5C: shows that adenosine-lidocaine together increased relaxation of the isolated intact mesenteric artery in a dose dependent manner. In contrast to adenosine alone (FIG. 5A) the greater relaxation from abluminal administration was not significantly different over the range of AL studied.

Interpretation:

The data support the notion that AL could relax the mesenteric artery and increase blood flow to the GI tract to reduce injury or damage to the gut, reduce infection and reduce adhesions (for sepsis, hypotensive TBI, adhesions and coma).

Figure 6:
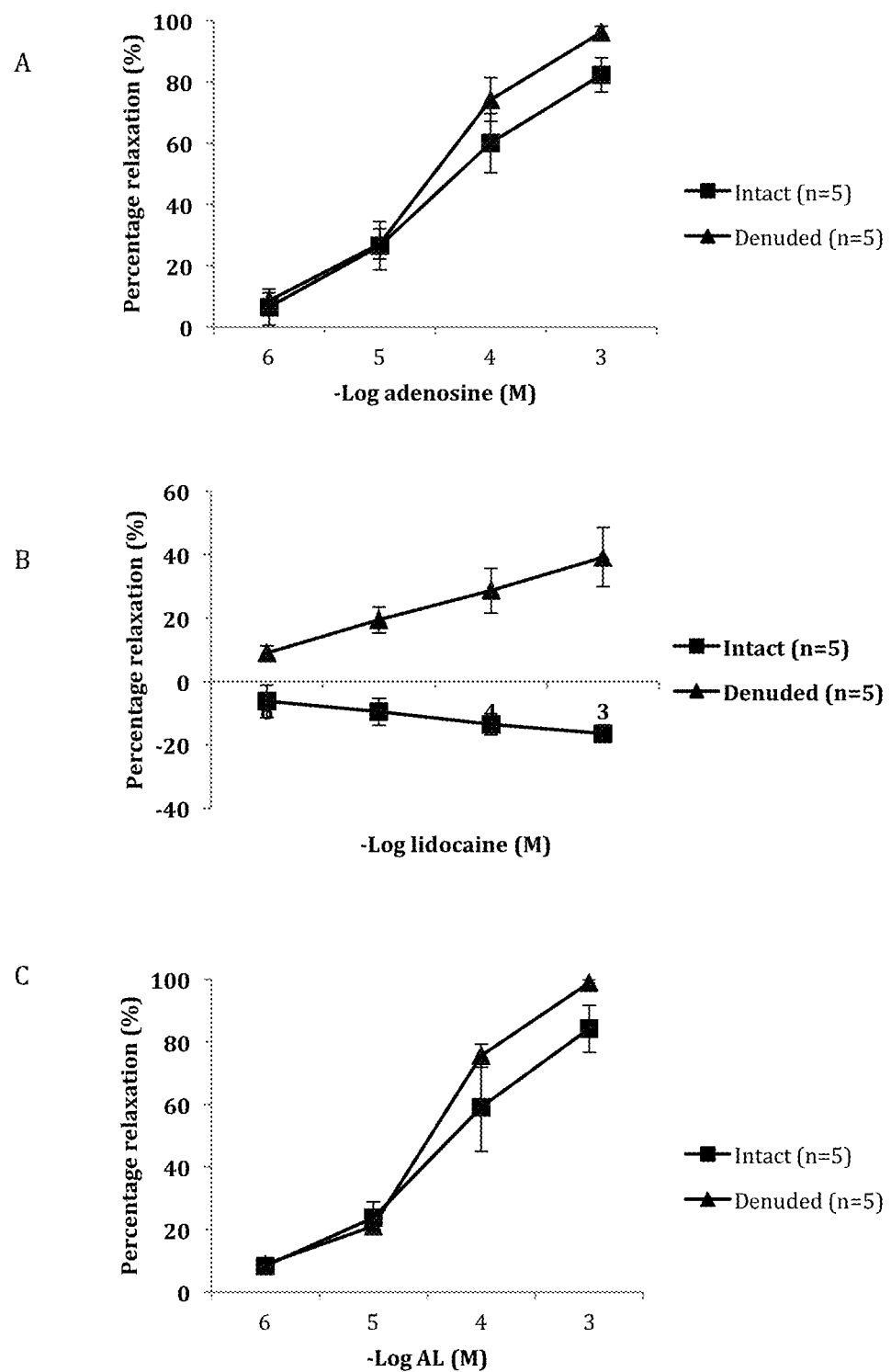
FIG. 6 shows graphs measuring the effect of Adenosine (A), lidocaine (L) and adenosine and lidocaine (AL) on % relaxation (Y axis) of isolated guinea-pig mesenteric artery when intact (square) or denuded (endothelium removed) (diamond)

Example 4b: The Effect of Adenosine, Lidocaine and Adenosine and Lidocaine on Relaxation of the Mesenteric Artery with or without an Intact Endothelium The results are shown in FIG. 6. It is shown here that Adenosine relaxed the mesenteric artery in a dose dependent manner in the presence and absence of endothelium and the relaxations were not significantly different between the two. Surprisingly, lidocaine did not significantly change mesenteric artery diameter in the presence of endothelium, but relaxed the artery when endothelium was absent. AL relaxed mesenteric artery in a dose dependent manner with or without an intact endothelium, and the relaxations were not significantly different.

Interpretation:

The data support the notion that AL could relax the mesenteric artery with or without an intact endothelium and increase blood flow to the GI tract to reduce injury or damage to the gut, reduce infection and reduce adhesions.

Example 5: Coagulopathy after Asphyxial-Hypoxia Induced Cardiac Arrest with Sepsis-Like Syndrome This example tests the effect of 0.9% NaCl ALM on correcting hypocoagulopathy (or reducing bleeding) and reducing blood clot retraction (strengthening the clot from breaking down) after asphyxial cardiac arrest with "sepsis-like" cardiac syndrome.

Background: Sepsis-Like Changes to Inflammation and Coagulation

The incidence of respiratory asphyxial-induced unconsciousness from cardiac failure occurs in 34% of all cardiac arrests cases, and up 90% of cases in the pediatric population. The other major cause of unconsciousness from cardiac arrest is from a cardiac origin, not a respiratory origin. Other pediatric and adult non-cardiac causes of asphyxial arrest include trauma, hanging, drug abuse, surgery, sepsis and/or a terminal disease. Poor outcomes from cardiac arrest arises from an inability of first responders to adequately rescue the heart (and brain) and treat the inflammatory and coagulation imbalances, which can lead to a post-cardiac arrest 'sepsis-like syndrome' and death within 72 hours. Post-cardiac arrest recovery is characterized by high levels of circulating cytokines and adhesion molecules, the presence of plasma endotoxin, and dysregulated leukocyte production of cytokines: a profile similar to that seen in severe sepsis. Coagulation abnormalities occur consistently after successful resuscitation, and their severity is associated with mortality.

Methodology:

Nonheparinized male Sprague Dawley rats (400-500 g, n=39) were randomly assigned to 0.9% saline (n=12) and 0.9% saline ALM (n=10) groups. A 0.5 mL bolus ALM contained 1.8 mM Adenosine, 3.7 mM Lidocaine-HCl and 4.0 mM $MgSO_4$. In the 0.5 ml there were 0.48 mg adenosine, 1.0 mg lidocaine-HCl and 2.4 mg $MgSO_4$. This was also equivalent to a bolus of 1.44 mg/kg adenosine, 3.0 mg/kg lidocaine-HCl and 7.2 mg/kg $MgSO_4$. After baseline data were acquired, the animal was surface cooled (33-34° C.) and the ventilator line clamped for 8 min inducing cardiac arrest (MAP <10 mmHg). After 8 min the respirator tubing clamp was released and 0.5 ml of solution was injected IV followed by 60 sec chest compressions (300 $min^{-1}$). Return of spontaneous circulation (ROSC), mean arterial pressure (MAP), heart rate (HR), and rectal temperature (RT) were recorded for 2 hr. Additional rats were randomized for ROTEM measurements (n=17).

Assessment of Coagulopathy Using Rotational Thromboelastometry (ROTEM):

ROTEM (Tem International, Munich, Germany) provides a real-time evaluation of the viscoelastic properties of whole blood in health and disease. Parameters include time to initiation of the clot, early clot formation kinetics, clot firmness and prolongation, clot fibrin-platelet interactions and clot lysis. Venous whole blood was obtained at baseline, following cardiac arrest, and at 120 min following ROSC or in those animals that failed to attain ROSC in the first 2 to 5 min of attempts. A volume of 1.8 ml blood was drawn into a 2.0 ml BD vacutainer containing citrate-phosphate-dextrose solution. After warming the blood at 37° C. for 5-10 min, EXTEM, INTEM and FIBTEM viscoelastic analysis was performed within 30 minute of blood withdrawal. The EXTEM test is extrinsically activated by thromboplastin (tissue factor) whereas INTEM test is activated by the contact phase (as in aPTT). FIBTEM is activated as in EXTEM with the addition of cytochalasin D, which inhibits platelet glycoprotein (GP) IIb/IIIa receptors. The FIBTEM test thus provides information about the effect of fibrin polymerization on clot strength and is independent of platelet involvement. The following parameters were measured in EXTEM, INTEM and FIBTEM. Clotting time (CT) or the time from start of measurement until a clot amplitude of 2 mm; clot formation time (CFT) which is the time from end of CT until a clot firmness of 20 mm; and maximum clot firmness (MCF) which is the final strength of the clot in mm arising from the interaction of fibrin and activated by platelets and factor XIII. The alpha angle (α) was also measured and represents the angle between baseline and a tangent at the maximum clot slope and clot amplitude (amplitude at 5 to 30 min) in mm over a 30 min period. The lysis index (LI, %) was estimated as the ratio of clot firmness (amplitude at 30 or 60 min) divided by MCF times 100. LI is an estimate of fibrinolysis, and hyperfibrinolysis was defined as estimated percent lysis ≥15%. Maximum clot elasticity (MCE) was calculated from MCE=(MCF×100)/(100−MCF). $MCE_{platelet}$ or the "platelet component" of clot strength was calculated as the difference in clot strength between EXTEM and FIBTEM where $MCE_{platelet}=MCE_{EXTEM}-MCE_{FIBTEM}$.

Prothrombin Time (PT) and Activated Partial Thromboplastin Time (aPTT):

The blood remaining from ROTEM analysis was centrifuged at room temperature and the plasma removed, snap frozen in liquid nitrogen, and stored at −80° C. until use. PT and aPTT were measured using a coagulometer (Trinity Biotech, Ireland) as described by Letson and colleague. These standard plasma coagulation tests reflect the kinetics of first fibrin formation with no information from platelet contributions. The PT is a measure of the integrity of the extrinsic and final common pathways analogous to EXTEM CT (CFT). The aPTT is a measure of the integrity of the intrinsic and final common pathways analogous to INTEM CT (CFT)

Table 2 below provides a summary of the Major Coagulation Changes over 2 hours of sustained return of spontaneous circulation (ROSC) in the rat model of 8 min asphyxial cardiac hypoxia and arrest.

TABLE 2

Major Coagulation Changes over 2 hours of sustained return of spontaneous circulation (ROSC) in the rat model of 8 min asphyxial cardiac hypoxia and arrest.

| Group | n | Condition | Observation (Relative to Baseline) | Interpretation |
|---|---|---|---|---|
| Intra-Cardiac Arrest | 7 | 8 min asphyxial hypoxia (33-34° C.) | No change in clotting times (EXTEM & INTEM)<br>↓ Clot Firmness (EXTEM)<br>↓ EXTEM and FIBTEM Lysis Index | Time to initiate clot unchanged (EXTEM, PT)<br>Time to elongate clot unchanged (INTEM, aPTT)<br>↑ Hyperfibrinolysis |
| 0.9% NaCl | 4 | Failed to Achieve ROSC | No change in EXTEM, PT clotting times<br>↑ Clotting times (INTEM, aPTT)<br>↓ Clot Firmness (INTEM)<br>↓ EXTEM and FIBTEM Lysis Index | Time to initiate clot unchanged (EXTEM, PT)<br>↑ Time to elongate clot (INTEM, aPTT)<br>↑ Hyperfibrinolysis |
| 0.9% NaCl | 8 | After 2 hours of sustained ROSC | ↑ Clotting times (EXTEM, PT & INTEM, aPTT)<br>↑ Clot formation time and angle<br>↓ Clot Firmness (EXTEM and INTEM)<br>↓ Clot Amplitude (A5-A30, EXTEM, INTEM)<br>↓ Elasticity (40% reduction)<br>No change in Lysis Index (FIBTEM) | ↑ Time to initiate clot (EXTEM, PT)<br>↑ Time to elongate clot (INTEM, aPTT)<br>Acute Hypocoagulopathy<br>Clot Retraction (amplitude ↓)<br>No Apparent Hyperfibrinolysis |
| 0.9% NaCl ALM | 10 | After 2 hours of sustained ROSC | No change in EXTEM clotting time (and PT), formation time, angle, max clot firmness.<br>↑ INTEM clot time (aPTT) and formation time<br>No change Clot Firmness (EXTEM and INTEM)<br>No change in Clot Amplitude (A5-A30)<br>No change in Lysis Index (EXTEM, INTEM FIBTEM).<br>No change in Elasticity | Time to initiate clot corrected (EXTEM, PT)<br>Clot elongation time not corrected (INTEM, aPTT)<br>Partial correction of clot formation time (50% lower than saline controls)<br>Clot Retraction corrected (EXTEM/INTEM)<br>No Apparent Hyperfibrinolysis<br>Stronger, Denser Fibrin network with Higher Elastic Modulus |

Interpretation:

The example shows that in all rats, ROTEM lysis index decreased during cardiac arrest, implying hyperfibrinolysis. Control ROSC survivors displayed hypocoagulopathy (prolonged EXTEM/INTEM CT, CFT, PT, aPTT), decreased maximal clot firmness (MCF), lowered elasticity and lowered clot amplitudes but no change in lysis index. ALM corrected these coagulation abnormalities at 120 min post-ROSC. Small bolus of 0.9% NaCl ALM improved survival and hemodynamics and corrected prolonged clot times and clot retraction compared to controls. In contrast to NaCl controls at 120 min, resuscitation with ALM fully corrected: 1) EXTEM hypocoagulopathy (CT, PT), 2) abnormal clot formation (CFT, alpha angle, MCF, elasticity), and 3) clot retraction (Table 2, Fig.). On the basis of ROTEM analysis ALM appears to correst the sepsis-like changes in clot abnormalities that occur after asphyxial cardiac hypoxia and arrest.

Figure 7:
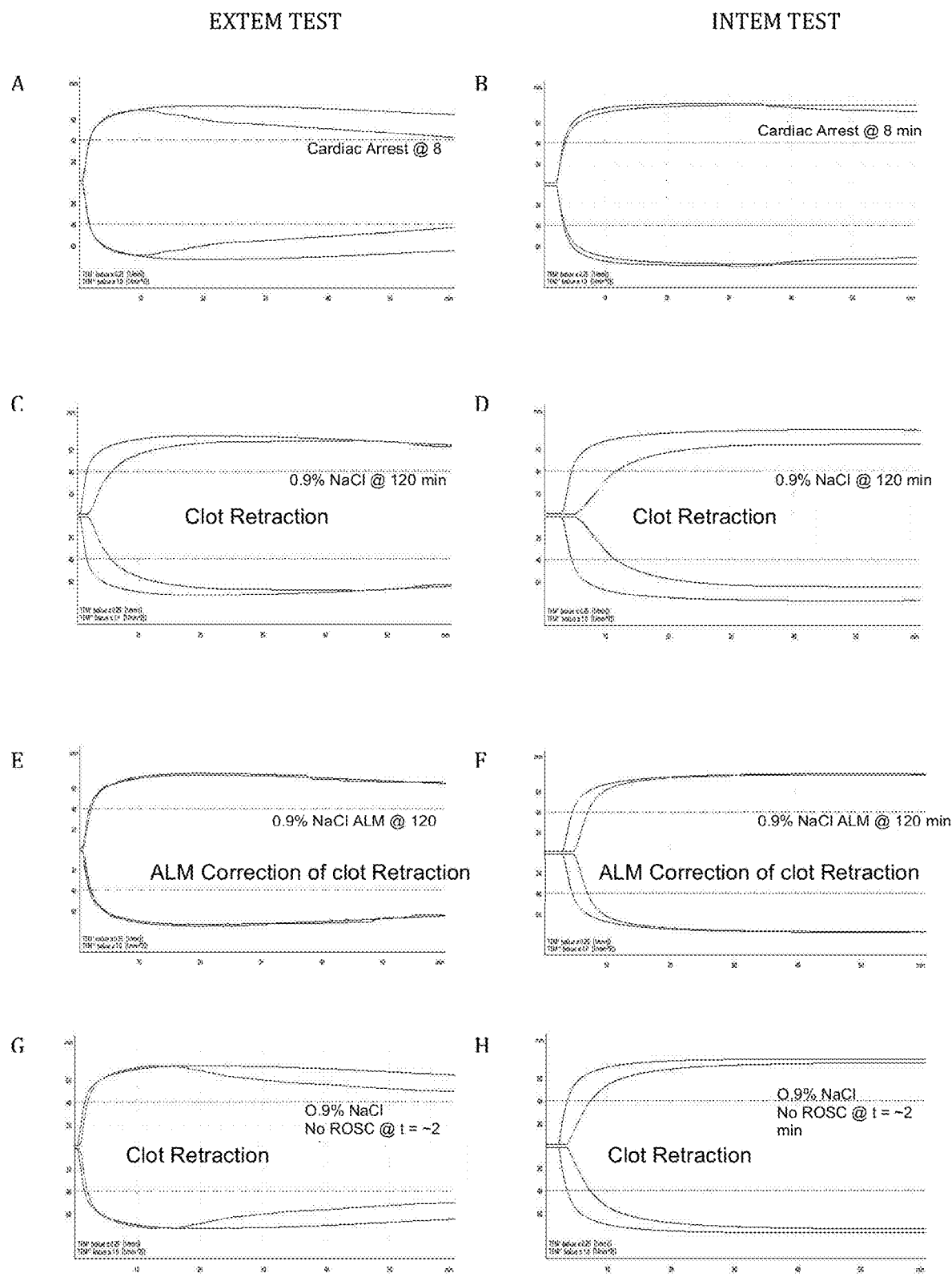
FIG. 7 shows ROTEM traces for the different groups asphyxial cardiac hypoxia and arrest (AB), 0.9% NaCl at 120 min (CD), 0.9% NaCl ALM at 120 min (EF), and in four controls that failed to achieve return of spontaneous circulation (ROSC) (GH). (See example 5)

FIG. 7 shows representative ROTEM traces for the different groups asphyxial cardiac hypoxia and arrest (AB), 0.9% NaCl at 120 min (CD), 0.9% NaCl ALM at 120 min (EF), and in four controls that failed to achieve ROSC (GH).

Interpretation:

The example shows that ALM administration prevents clot retraction (prevents a decrease in clot amplitude) thus making it a stronger clot to reduce bleeding. ALM's ability to correct clot strength (amplitudes) may be significant because point-of-care low clot strength is an independent predictor of massive transfusion, and coagulation-related mortality within 15 min following the resuscitation of trauma patients. Similarly, reduced or weak clot strength before hospital admission has been shown to be independently associated with increased 30-day mortality in trauma patients. That ALM fully corrected clot strength, maximum clot elasticity (MCE) and $MCE_{platelet}$ ($P<0.05$) (Table 2) compared to saline controls implies that ALM provides more favorable conditions for a stronger, denser fibrin network with higher elastic modulus (Table 1) and possibly higher thrombin concentrations compared with saline control. A clot with a lower elastic component, as we showed in saline controls at 120 min (Table 1), would incur more permanent deformation in response to flowing blood than a clot with a greater elastic component, which would return to its original shape when the stress is relieved. In conclusion, on the basis of ROTEM analysis ALM appears to alleviate the sepsis-like changes in clot abnormalities after asphyxial cardiac hypoxia and arrest.

Example 6a: ALM with General Anesthetic Whole Body Arrest (from NORMAL STATE)

Methods:

Male Sprague Dawley rat (650 g) were fed ad libitum with free access to water and housed in a 12-hr light-dark cycle. Animals were anesthetized with an intraperitoneal (IP) injection of 100 mg/kg sodium thiopentone (Thiobarb). After Thiobarb anesthesia, rats were positioned in the supine position on a custom designed cradle. A tracheotomy was performed and the animals artificially ventilated at 90-100 strokes per min on humidified room air using a Harvard Small Animal Ventilator (Harvard Apparatus, Mass., USA) to maintain blood $pO_2$, $pCO_2$ and pH in the normal physiological range. The left femoral vein and artery was cannulated using PE-50 tubing for drug infusions and blood pressure monitoring (UFI 1050 BP coupled to a MacLab) and the right femoral artery was cannulated for bleeding. Lead II electrocardiogram (ECG) leads were implanted subcutaneously on the left and right front legs and grounded to the back leg. The chest was opened and the heart was exposed to observe the effect the treatment in addition to the hemodynamic and ECG measurements. Rats were stabilized for 10 minutes prior to whole body arrest.

Estimated blood volume of 650 g rat is ~39.47 ml. The animal was not bled or in shock.

Baseline period before chest was opened: HR 425.5 bpm, BP 147/120 mmHg, MAP 133 mmHg, Temp 36.5° C. There was a drop in arterial blood pressures during stabilization period when chest opened to visualise heart. Prior to arrest bolus HR 334 bpm, BP 73/56 mmHg, MAP 62 mmHg, Temp 36.1° C.

Rat received 0.5 ml bolus containing 0.5 mg adenosine, 1 mg lidocaine-HCl and 0.05 g $MgSO_4$+1 mg/kg propofol in 0.9% NaCl. In the 0.5 ml bolus the concentrations of the actives in mM are 3.75 mM Adenosine, 7.38 mM lidocaine-HCl, 833 mM $MgSO_4$ and 3.71 mM propofol. When expressed in mg/kg animal the composition includes 1.5 mg/kg adenosine, 3 mg/kg lidocaine-HCl and 125 mg/kg $MgSO_4$ and 1 mg/kg propofol.

Results and Interpretation for Pharmacological Whole Body Arrest:

After an intravenous bolus of ALM/propofol the rat underwent circulatory collapse within 10 sec. The blood pressure fell to zero and the heart rate fell to zero. The heart rate returned after ~4 min. Began chest compressions at 6 min for 2 min only then again at 15 min and pressure increased. Within 10 min the hemodynamics returned to normal. The animal was monitored for 2 hours and hemodynamics were stable and following the experiment an autopsy showed no signs of ischemia to the heart, lungs, kidneys or gastrointestinal tract.

At 39 sec, 48 sec, 57 sec, 1 min 3 sec there were electrical 'flutter' signals in the ECG and this was associated with a small BP 'blip'. In between these ECG 'flutters' the HR returned to zero and BP returned to zero. This example shows that the heart retained the ability to be electromechanical coupled during these intermittent 'flutters'. After 1 min 40 sec the ECG flutters became more regular. Without being bound by any theory or mode of action of the present invention, one proposed mechanism of these intermittent 'flutters' is that these signals to the heart may be of CNS origin and possible from the brainstem nucleus tractus solitaris (NTS). After 4 min 24 sec the signals to the heart became more regular even though no blood pressure was generated. This state of electromechanical decoupling between heart rate and blood pressure, was most likely due to the insufficient blood in stretch the heart chamber dimensions and thereby stretch the myofilaments required for contraction and the generation of forward flow.

Two min of chest compressions at 6 min after the bolus injection increased blood pressure to 25 mmHg with extremely low pulse pressure, a state normally characterized as severe life-threatening shock. The heart rate was 115 bpm. This example demonstrates that the treatment can arrest the whole body and may include the brain with unexpected and surprising near-full hemodynamic recovery after 15 min.

Figure 12:
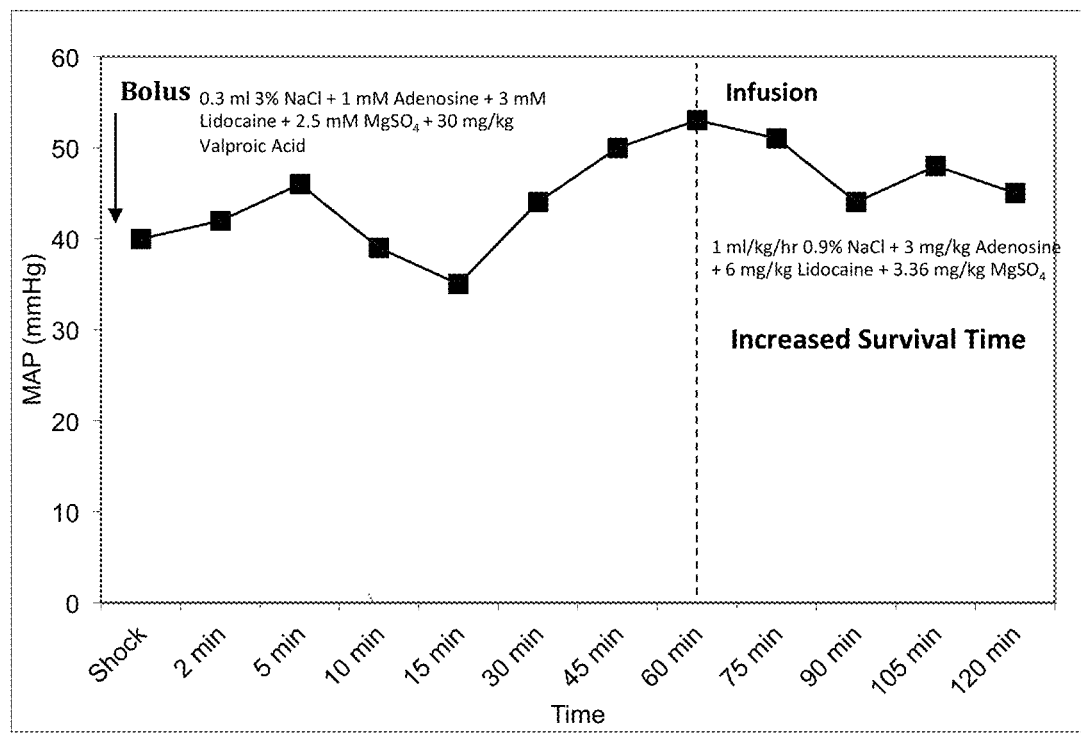
FIG. 12 shows a graph showing the effect of addition of valproic acid

This is also shown in FIGS. 12A-Q.

After an intravenous bolus of ALM/propofol the rat underwent circulatory collapse within 10 sec. The blood pressure fell to zero (not shown) and the heart rate fell to zero (see FIG. 12A). ECG Flutter at 39 sec, 48 sec, 57 sec, 1 min 3 sec (HR Zero with intermittent flutter/tiny BP spike (see FIG. 12B)—implying still electromechanically coupled).

ECG acceleratory 'blips' (see FIGS. 12C and 12D). More regular pattern started at 1 min 40 sec (HR ~35 bpm). Still coordinated transient pressure increase (trace not shown). During this time period noticed paws twitching and twitching in abdominal region Between 2-4 min ECG looked as shown in FIG. 12E):

4 min 24 sec HR formed more regular pattern on ECG (see FIG. 12F) (HR 143 bpm; lasted ~20 sec)

No pressure associated with this HR; flat-line BP measuring 6 mmHg for first 6 minutes At 6 min, started 2 min of heart compressions (fingertip directly on heart surface). Pressure trace is shown in FIG. 12G and heart rate is shown in FIG. 12H.

Small response to heart compressions. BP reading ~25 mmHg, HR ~115 bpm.

25 sec after ceased compressions (8 min 25 sec post arrest bolus), 1 single beat which then led to HR ~95 bpm @ 9 min (HR trace shown in FIG. 12I) No pressure associated with this HR (pressure still <10 mmHg PEA)

At 10 min HR ~100 bpm (no intervention since compressions stopped at 8 min) ECG trace shown in FIG. 12J.

At 12 min started to see some activity on pressure curve (BP 10 mmHg) Pressure trace shown in FIG. 12K.

At 15 min performed 60 sec heart compressions and pressure came back during chest compressions (Blood pressure trace shown in FIG. 12L, ECG is shown in FIG. 12M.

At 18 min HR 146 bpm BP 31/22 mmHg, MAP, 25 mmHg (Trace shown in FIGS. 12N and O), Temp 34.4° C.: 30 min BP 111/80 mmHg, MAP 92 mmHg (trace shown in FIG. 12P) HR 323 bpm (trace shown in FIG. 12Q) Temp 33.3° C.

Animal was monitored for 2 hr after blood pressure, heart rate ECG returned at 15 min post-arrest after single bolus. Total experimental time was 2 hours 15 min.

45 min: HR 323 bpm, BP 109/76 mmHg, MAP 87 mmHg, Temp 33.0° C.

60 min: HR 341 bpm, BP 95/65 mmHg, MAP 77 mmHg, Temp 32.8° C.

75 min: HR 343 bpm, BP 91/64 mmHg, MAP 75 mmHg, Temp 32.8° C.

90 min: HR 335 bpm, BP 92/68 mmHg, MAP 77 mmHg, Temp 32.7° C.

105 min: HR 321 bpm, BP 95/68 mmHg, MAP 78 mmHg, Temp 32.4° C.

120 min: HR 315 bpm, BP 102/70 mmHg, MAP 80 mmHg, Temp 32.2° C.

135 min: HR 295 bpm, BP 98/65 mmHg, MAP 75 mmHg, Temp 32.0° C.

After 2 hr there were no visual signs of ischemia on heart, lungs, liver or kidney.

Example 6b: Effect of Whole Body Arrest with ALM and Thiobarb

Inducing a pulseless electrical activity (PEA) State and Whole body arrest following 60 min Severe Shock in the Rat (~40% blood loss): HR=heart rate. MAP=mean arterial pressure Methods:

Male Sprague Dawley rats (300-400 g) were fed ad libitum with free access to water and housed in a 12-hr light-dark cycle. Animals were anesthetized with an intraperitoneal (IP) injection of 100 mg/kg sodium thiopentone (Thiobarb). After Thiobarb anesthesia, rats were positioned in the supine position on a custom designed cradle. A tracheotomy was performed and the animals artificially ventilated at 90-100 strokes per min on humidified room air using a Harvard Small Animal Ventilator (Harvard Apparatus, Mass., USA) to maintain blood $pO_2$, $pCO_2$ and pH in the normal physiological range. Rectal temperature was monitored using a rectal probe inserted 5 cm from the rectal orifice before, during and following shock and resuscitation, and previous experiments show the temperature ranges between 37 to 34° C. The left femoral vein and artery was cannulated using PE-50 tubing for drug infusions and blood pressure monitoring (UFI 1050 BP coupled to a MacLab) and the right femoral artery was cannulated for bleeding. Lead II electrocardiogram (ECG) leads were implanted subcutaneously on the left and right front legs and grounded to the back leg. Rats were stabilized for 10 minutes prior to blood withdrawal. Hemorrhagic shock was induced by withdrawing blood from the femoral artery at an initial rate of ~1 ml/min then decreasing to ~0.4 ml/min over 20 min. Initially blood was withdrawn slowly into a 10 ml heparinized syringe (0.2 ml of 1000 U/ml heparin) to reduce MAP to between 35 and 40 mmHg. If MAP increased, more blood was withdrawn to maintain its low value, and the process was continued over a 20 min period. The Thiobarb animal was left in shock for 60 min with frequent checking to ensure the MAP remains between 35 to 40 mmHg. After 60 min shock the animal was injected with an IV 0.5 ml bolus of hypertonic saline with ALM.

The rats received 0.5 ml ALM with 7.5% NaCl containing 0.2 ml of 0.2 mg adenosine, 0.2 mg lidocaine-HCl and 0.02 g magnesium sulphate (total volume injected IV was 0.5 ml made up to 7.5% NaCl). Thus in the 0.5 ml bolus there was 0.2 mg adenosine, 0.2 mg lidocaine-HCl and 0.02 g $MgSO_4$ and 0.038 g NaCl. The concentrations in mM in 0.5 ml bolus were 1.5 mM adenosine, 1.48 mM lidocaine-HCl and 333 mM $MgSO_4$, and 1270 mM NaCl. The composition actives in mg/kg are 0.6 mg/kg adenosine, 0.6 mg/kg lidocaine-HCl, 60 mg/kg $MgSO_4$ and 114 mg/kg NaCl and Thiobarb was 100 mg/kg.

Figure 8:
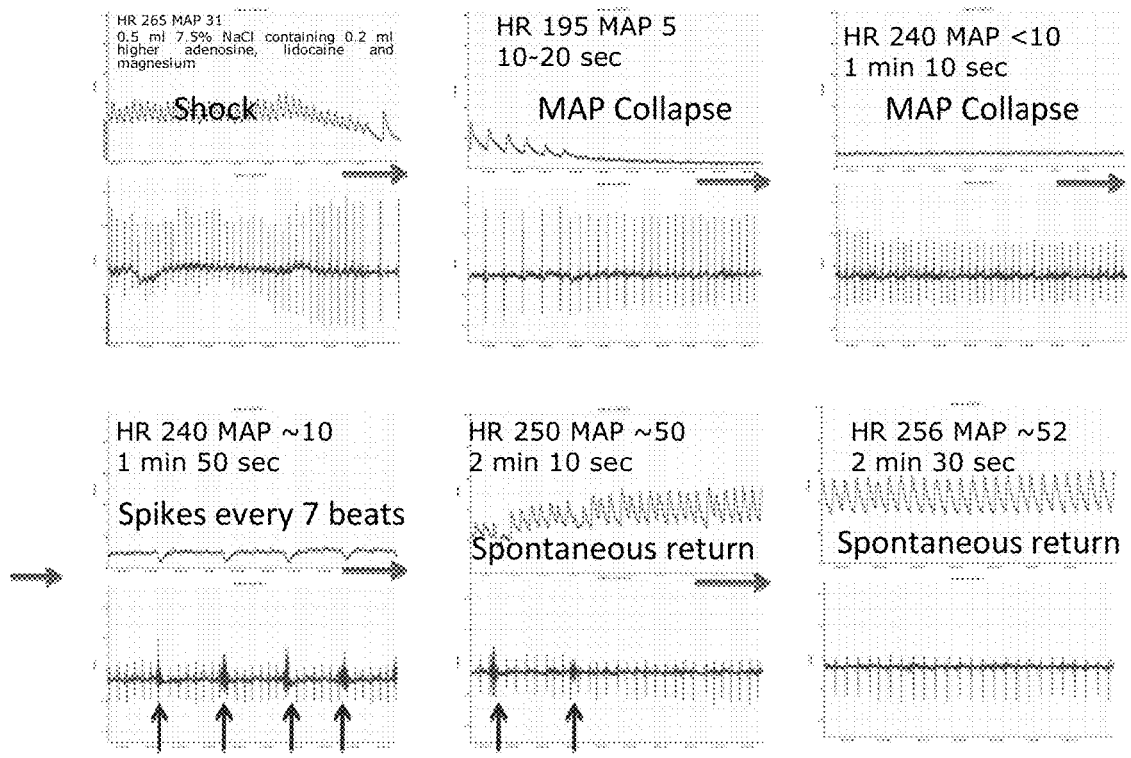
FIG. 8 shows graphs showing HR=heart rate. MAP=mean arterial pressure on rats following shock and drug induced MAP collapse and spontaneous return (see example 6b)

The results are shown in FIG. 8.

Interpretation:

A single 0.5 ml bolus resulted in a collapse in blood pressure but not heart rate. Having a heart rate and no pressure development is termed pulseless electrical activity (PEA) or electromechanical dissociation. After 1 min 50 sec, there were electrical amplitude spikes in voltage and these occurred after every 7 seconds, and within 20 seconds the blood pressure rose and after 2 min 30 sec the pressure was surprisingly 1.7 times higher than when the treatment was first administered. As with example 6a, without being bound by any theory or mode of action of the present invention, one proposed mechanism of these intermittent 'flutters' is that these signals to the heart may be of CNS origin and possible from the brainstem nucleus tractus solitaris (NTS). Example 6b differs from Example 6a because in heart rate fell to zero after treatment in Example 6a.

Example 7: Hypotensive Resuscitation

Background:

Heart rate variability is the physiological phenomenon of variation in the time interval between heartbeats. Heart rate and rhythm are largely under the control of the autonomic nervous system whereby the baroreflex continually adjusts heart rate to blood pressure via changes in vagal (parasympathetic) activity. In this way the arterial baroreflex also affects arrhythmogenesis and whole body hemodynamic stability. Thus sympathetic activation can trigger malignant arrhythmias, whereas vagal activity may exert a protective effect. Baroreflex sensitivity is quantified in ms of RR interval prolongation for each mmHg of arterial pressure increase. In the analysis of HR variability, there is a time domain and a frequency domain of analysis.

Time Domain:

The time domain measures of HR variability as calculated by statistical analyses (means and variance) from the lengths of successive R-R intervals in the ECG and considered reliable indices of cardiac parasympathetic activity. The time domain indices include SDNN, SADNN, NN50, pNN50, RMSSD, SDSD. The most commonly used are the average heart rate and the standard deviation of the average R-R intervals (SDNN) calculated over a 24-hour period or 5 min R-R period (SADNN). The SDNN mostly reflects the very-low-frequency fluctuation in heart rate behavior). NN50 is the number of pairs of successive beat to beat (NN) that differ by more than 50 ms or when expressed as a percentage (pNN50). The RMSSD is the square root of the mean squared differences of successive R-R intervals, and the SDSD is the standard deviation of successive differences of R-R intervals. These time domain measures are recognized to be strongly dependent on the vagal (parasympathetic) modulation with a low value indicating lower vagal tone. In contrast to SDNN, RMSSD is a short-term variation of heart rate and correlates with high frequency domain of heart rate variability reflecting fluctuations in HR associated with breathing.

Frequency Domain:

Frequency domain analysis is traditionally understood to indicate the direction and magnitude of sympatho-vagal balance of heart rate variability. It is obtained by dividing the heart rate signal into its low and high frequency bands and analyze the bands in terms of their relative intensities (power). The LF or low frequency band (0.04 to 0.15 Hz) is involved with oscillations related to regulation of blood pressure and vasomotor tone. The HF or high frequency band (0.15 to 0.4 Hz) reflects the effects of respiration on heart rate (i.e. in respiratory frequency range). Traditionally, the LF band reflects primarily sympathetic tone, the HF band reflects parasympathetic tone, and the ratio LF/HF is viewed as an index of sympatho-vagal balance. This traditional predictive interpretation has recently been challenged, and a consensus is growing that the LF does not represent sympathetic tone but mostly parasympathetic tone (90%), and that the LF/HF ratio does not represent an index of sympatho-vagal balance (Billman, 2013). Broad evidence still supports the idea that the HF reflects mostly parasympathetic tone.

The LF/HF ratio is much more complex than originally thought and it appears to be restricted to the estimation of parasympathetic influences on heart rate. An increase or decrease in the LF/HF ratio appears to reflect more on the different dominating parasympathetic oscillation inputs that determine blood pressure and vagal tone relative to those inputs involved in regulating fluctuations in HR associated with breathing (respiratory sinus arrhythmia). Sympathetic inputs would undoubtedly contribute to in vivo sympatho-vagal balance, however, it cannot be directly interpreted from the indices that are currently used to examine the time and frequency domains of heart rate variability. Direct analysis of baroreflex sensitivity may be more informative combined with HR variability analysis.

Methods:

Male Sprague Dawley rats (300-400 g) were fed ad libitum with free access to water and housed in a 12-hr light-dark cycle. Animals were anesthetized with an intraperitoneal (IP) injection of 100 mg/kg sodium thiopentone (Thiobarb). After Thiobarb anesthesia, rats were positioned in the supine position on a custom designed cradle. A tracheotomy was performed and the animals artificially ventilated at 90-100 strokes per min on humidified room air using a Harvard Small Animal Ventilator (Harvard Apparatus, Mass., USA) to maintain blood $pO_2$, $pCO_2$ and pH in the normal physiological range. Rectal temperature was monitored using a rectal probe inserted 5 cm from the rectal orifice before, during and following shock and resuscitation, and previous experiments show the temperature ranges between 37 to 34° C. The left femoral vein and artery was cannulated using PE-50 tubing for drug infusions and blood pressure monitoring (UFI 1050 BP coupled to a MacLab) and the right femoral artery was cannulated for bleeding. Lead II electrocardiogram (ECG) leads were implanted subcutaneously on the left and right front legs and grounded to the back leg. Rats were stabilized for 10 minutes prior to blood withdrawal. Hemorrhagic shock was induced by withdrawing blood from the femoral artery at an initial rate of ~1 ml/min then decreasing to ~0.4 ml/min over 20 min (40-50% blood loss). Initially blood was withdrawn slowly into a 10 ml heparinized syringe (0.2 ml of 1000 U/ml heparin) to reduce MAP to between 35 and 40 mmHg. If MAP increased, more blood was withdrawn to maintain its low value, and the process was continued over a 20 min period. The animal was left in shock for 60 min with frequent checking to ensure the MAP remains between 35 to 40 mmHg.

The ability of the invention to be employed for hypotensive resuscitation was examined in number of experiments, and it was found that survival for delayed retrieval times could only be achieved by an intravenous bolus followed by an intravenous infusion (one-two treatment strategy). A single intravenous bolus or a bolus followed by a bolus was not sufficient to prevent circulatory collapse and death after haemorrhagic shock.

Figure 9:
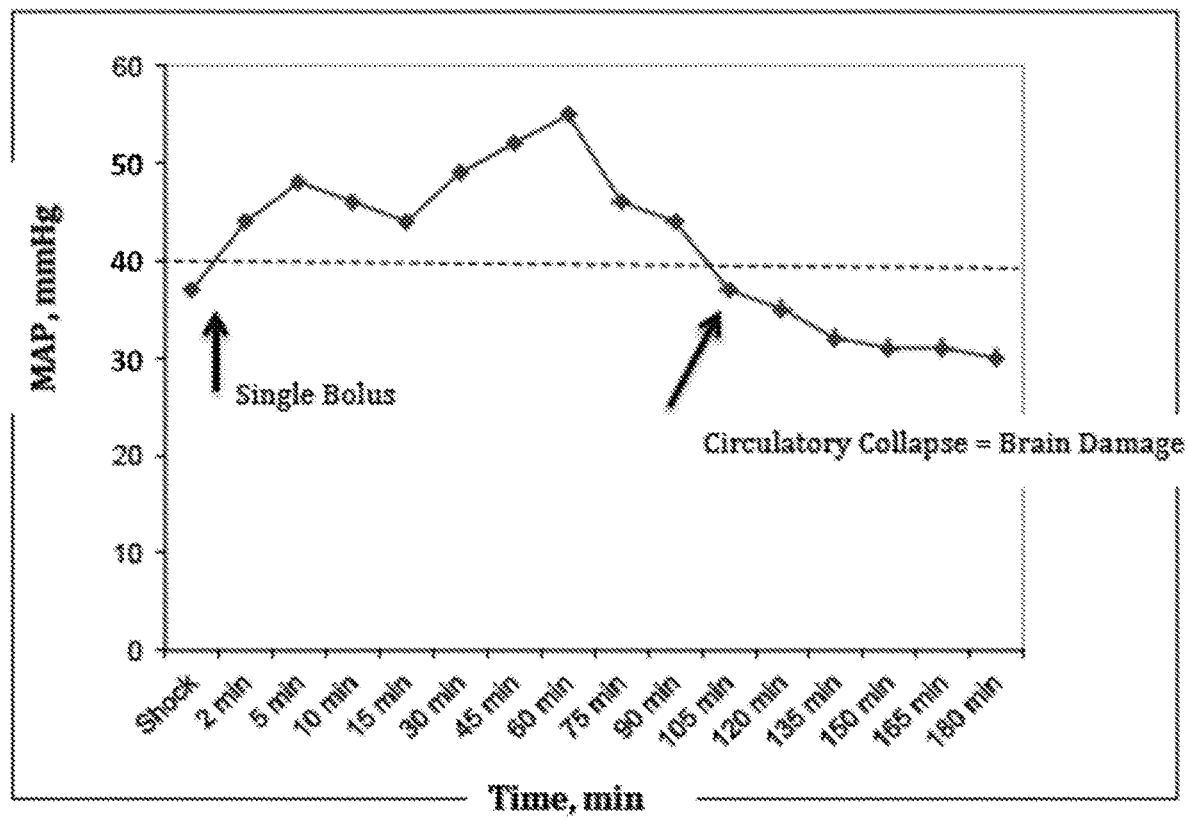
FIG. 9 shows a Graph showing MAP resuscitation following single 3% NaCl ALM single bolus (Group 1)
Figure 11:
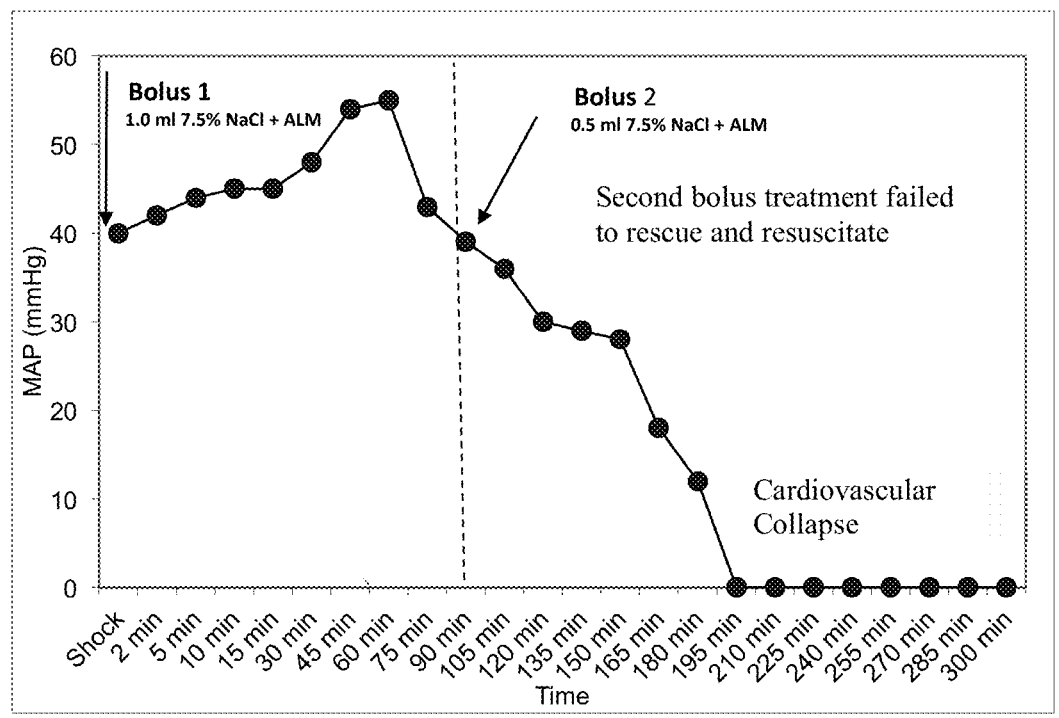
FIG. 11 shows graphs showing bolus-bolus for MAP (Group 3). (See example 7)

The results are shown in FIGS. 9 to 11.

FIG. 9. Group 1: Bolus Alone:

ALM treatment animal received intravenous 0.3 ml bolus 3.0% NaCl (508 mM, 0.045 g/kg) with 1 mM Adenosine (0.24 mg/kg), 3 mM Lidocaine (0.73 mg/kg), and 2.5 mM $MgSO_4$ (0.27 mg/kg).

Interpretation:

A single bolus raised mean arterial blood pressure initially into the hypotensive range but MAP could not be sustained and the fall in low pressure below shock values demonstrates circulatory collapse and this would cause brain damage from reduced blood flow to the brain. Pulseless activity and death occurred at around 3 hours. These results indicate that an infusion is required to improve long-term survival particularly during delayed retrieval and arrival at a definitive care facility in the prehospital or military setting.

FIG. 10: Group 2 Bolus Alone Vs Bolus and Infusion:

ALM treatment animal received intravenous 0.3 ml bolus 3.0% % NaCl with 1 mM Adenosine (0.24 mg/kg), 3 mM Lidocaine (0.73 mg/kg), and 2.5 mM $MgSO_4$ (0.27 mg/kg) and after 60 min and an infusion of 1 ml/kg/hr 0.9% NaCl+3 mg/kg Adenosine+6 mg/kg Lidocaine+3.36 mg/kg $MgSO_4$. In 1.0 ml of composition administered per kg body weight per hour comprised 11.23 mM adenosine, 22 mM lidocaine-HCl and 28 mM $MgSO_4$.

Interpretation:

Similar to Group 1 (FIG. 10), a single bolus raised MAP for 60 min after hemorrhagic shock but failed to maintain and MAP after this time (Single Bolus Graph A) and decreased resulting in circulatory collapse at 190 min. Upon the administration of an intravenous infusion (analogous to a drip) at 60 min, the MAP was maintained and the second treatment strategy protected the animal from cardiovascular system (Single Bolus with infusion Graph A). The one-two treatment method also with protected the heart rate compared to the single bolus (Graph B). These results provide evidence that a bolus followed by an infusion or drip delivering at the same flow rate into the vein is required to improve long-term survival particularly during delayed retrieval and arrival at a definitive care medical facility in the prehospital or military setting.

Group 3 Bolus-Bolus Treatment:

This example shows that an ALM treatment animal that received an intravenous 1 ml bolus of 7.5% NaCl ALM (1 mM Adenosine, 3 mM Lidocaine HCl; 2.5 mM $MgSO_4$) followed by a second 0.5 ml bolus of 7.5% NaCl ALM (1 mM Adenosine (0.24 mg/kg), 3 mM Lidocaine HCl (0.73 mg/kg); 2.5 mM $MgSO_4$ (0.27 mg/kg)) at 90 min did not improve survival. The first bolus led to increased MAP and then after 60 minutes MAP began to fall as the heart could no longer generate pressure, and a second bolus was administered at 90 min but failed to resuscitate and the animal died from cardiovascular or circulatory collapse. This example shows that a bolus-bolus treatment is not sufficient to prolong life.

Summary of the Data in FIGS. 9 to 11 Groups 1-3.

The examples provide evidence that a intravenous single bolus of 3% or 7.5% hypertonic saline with ALM treatment or a bolus-bolus administration are not adequate for sustained hypotensive resuscitation following a period of shock induced by bleeding. Survival requires the administration of a bolus followed by an intravenous infusion, which is equivalent to a bolus then a drip. This example is clinically (or venterinarily) relevant because long delays can occur to reach the patient or subject in prehospital or military settings. Long delays can also occur in Rural and Remote Medical hospitals or environments. The results also pertain to the battlefield environment where small expeditionary teams routinely operate in austere and hostile environments and have access to limited medical supplies and where evacuation times may be many hours to days depending upon location.

Interpretation of Heart Rate Variability Analysis (Table 3).

TABLE 3

Heart Rate Variability (HRV) Analysis During Hypotensive Resuscitation

| Parameter | Control | Treatment | Effect of Treatment |
|---|---|---|---|
| Hemodynamic Status | (7.5% NaCl) | 7.5% NaCl ALM | |
| Arterial MAP | | | |
| Shock before Resuscitation | 38 ± 1 (n = 8) | 38 ± 0.5 (n = 8) | No Change |
| At 30 min Resuscitation | 42 ± 2 (n = 8) | 54 ± 3 (n = 8)* | 1.3 times higher |
| At 60 min Resuscitation | 36 ± 5 (n = 8) | 60 ± 3 (n = 8)* | 1.7 times higher |
| Coagulopathy at 60 min Resus. | Hypocoagulable Not corrected | Normal ALM Corrected | Clotting times Corrected |

TABLE 3-continued

Heart Rate Variability (HRV) Analysis
During Hypotensive Resuscitation

| Parameter | Control | Treatment | Effect of Treatment |
|---|---|---|---|
| Heart Rate at 60 min | 283 ± 12 | 297 ± 11 | No difference |
| Rate Pressure Product (RPP) at 60 min | 13,911 ± 1753 | 22,563 ± 1785 | 1.6 times higher |
| Arrhythmias over 60 min | Ventricular (50% of animals) | None | No arrhythmias |
| Heart Rate Variability Time Domain Parameters (n = 4) | | | |
| SDNN (ms) | 11.4 ± 2.1 | 5.67 ± 1.2* | 50% of Control |
| NN50 | 21.0 ± 12.23 | 2.75 ± 0.48* | 13% of Control |
| Frequency Domain Parameters (n = 4) | | | |
| LF (ms$^2$) | 16.33 ± 5.88 | 7.45 ± 3.52 | 46% of Control |
| HF (ms$^2$) | 7.57 ± 3.81 | 5.21 ± 2.51 | 69% of Control |
| LF/HF | 2.52 ± 1.04 | 1.69 ± 0.82 | 67% of Control |

*Significantly higher in ALM treatment vs. Controls (P < 0.05)
MAP = mean arterial pressure
RPP = peak arterial systolic pressure times heart rate (index of myocardial O2 consumption)
SDNN indicates standard deviation of normal to normal R-R intervals, where R is the peak of a QRS complex (heartbeat)
NN50 is the number of pairs of successive beat to beat (NN) that differ by more than 50 ms.

The most striking result from heart rate variability in rats during hypotensive resuscitation following hemorrhagic shock is the effect of treatment to lower time and frequency domain parameters of heart rate variability analysis. In the time domain analysis, the effect of ALM treatment was to reduce the standard deviation of the average R-R intervals (SDNN) calculated over a 5 min R-R period (SADNN) by 50% (Table 3), and the number of pairs of successive beat to beat (NN) that differ by more than 50 ms (NN50) by 87% (Table 3). These data indicate that ALM treatment leads to greater stability in the ECG (lower fluctuations in heart rate behaviour) compared to 7.5% NaCl saline controls, and that this increased stability appears to be linked to a lower parasympathetic activity. In the frequency domain, ALM also reduced LF by 54% and HF by 31% relative to 7.5% NaCl controls, again implying a reduced parasympathetic input to heart rate variability at both low and high frequencies. The 33% lower LF/HF ratio in the ALM treated animals than controls would suggest either the drug 1) decreased parasympathetic control of MAP and vagal tone or 2) increased the regulating the effect of respiration on heart rate, or both compared to 7.5% NaCl alone. Since the animals were actively ventilated at ~90 strokes per min and heart rate was not different between groups, it appears the fall in LF/HF ratio is due to the drugs action to decrease the parasympathetic input on MAP and vagal tone to increase stability in heart rate. That the MAP during hypotensive resuscitation is significantly higher with ALM treatment, and that there were no arrhythmias compared to controls imply improved sympatho-vagal balance and possibly improved baroreflex gain in the ALM animals. Despite maintaining heart rate, control animals with their higher fluctuations in heart rate behaviour also had reduced ability to maintain MAP which was slowly returning to shock values after 30 min hypotensive resuscitation (Table 3).

Example 8: Effect of Beta Hydroxy Butyrate (BHB) and Valproic Acid on Hypotensive Resuscitation Hemodynamics Methods:

Male Sprague Dawley rats (300-400 g) were fed ad libitum with free access to water and housed in a 12-hr light-dark cycle. Animals were anesthetized with an intraperitoneal (IP) injection of 100 mg/kg sodium thiopentone (Thiobarb). After Thiobarb anesthesia, rats were positioned in the supine position on a custom designed cradle. A tracheotomy was performed and the animals artificially ventilated at 90-100 strokes per min on humidified room air using a Harvard Small Animal Ventilator (Harvard Apparatus, Mass., USA) to maintain blood $pO_2$, $pCO_2$ and pH in the normal physiological range. Rectal temperature was monitored using a rectal probe inserted 5 cm from the rectal orifice before, during and following shock and resuscitation, and previous experiments show the temperature ranges between 37 to 34° C. The left femoral vein and artery was cannulated using PE-50 tubing for drug infusions and blood pressure monitoring (UFI 1050 BP coupled to a MacLab) and the right femoral artery was cannulated for bleeding. Lead II electrocardiogram (ECG) leads were implanted subcutaneously on the left and right front legs and grounded to the back leg. Rats were stabilized for 10 minutes prior to blood withdrawal. Hemorrhagic shock was induced by withdrawing blood from the femoral artery at an initial rate of ~1 ml/min then decreasing to ~0.4 ml/min over 20 min. Initially blood was withdrawn slowly into a 10 ml heparinized syringe (0.2 ml of 1000 U/ml heparin) to reduce MAP to between 35 and 40 mmHg. If MAP increased, more blood was withdrawn to maintain its low value, and the process was continued over a 20 min period. The animal was left in shock for 60 min with frequent checking to ensure the MAP remains between 35 to 40 mmHg.

Group 1:

ALM treatment animal received intravenous 0.3 ml bolus 3.0% NaCl with 1 mM Adenosine (0.24 mg/kg), 3 mM Lidocaine (0.73 mg/kg), and 2.5 mM $MgSO_4$ (0.27 mg/kg) with 50 mM beta-hydroxy butyrate (D-isomer, 4.7 mg/kg).

Results are summarised in Table 4.

TABLE 4

| Time | HR (bpm) | BP (mmHg) | MAP (mmHg) | Temp (° C.) |
|---|---|---|---|---|
| Baseline | 350 | 156/101 | 119 | 36.1 |
| 20 min Bleed | 321 | 59/38 | 44 | 33.9 |
| 60 min Shock | 284 | 56/34 | 40 | 33.3 |
| 2 min Resus | 374 | 57/33 | 40 | 33.3 |
| 5 min Resus | 269 | 59/33 | 42 | 33.2 |
| 10 min Resus | 290 | 59/31 | 40 | 33.2 |
| 15 min Resus | 297 | 65/32 | 43 | 33.2 |
| 30 min Resus | 295 | 71/39 | 48 | 33.0 |
| 45 min Resus | 289 | 75/38 | 52 | 32.5 |
| 60 min Resus | 283 | 78/39 | 52 | 32.6 |

Total blood loss = 13.9 ml (~38% TBV)

Administration: 3.0% NaCl+1 mM Adenosine+3 mM Lidocaine+2.5 mM $MgSO_4$+50 mM D-β-Hydroxybutyrate (0.3 ml bolus); DL-β-Hydroxybutyrate (Sigma H6501) MW=126.09; Estimate [blood]=(0.3 ml/10 ml)×50 mM=1.5 mM [Estimated Plasma concentration]

Animal struggled in second 30 min of shock and required reinfusion of ~12 ml blood to maintain pressure Bolus injection resulted in typical bradycardia and MAP decrease seen with ALM.

MAP recovered quite quickly.

ALM with BHB "kick" started around 15 min and continued through 60 min resuscitation.

Interpretation:

A single bolus raised mean arterial blood pressure initially into the hypotensive range and sustained MAP for 60 min. Beta-hydroxy butyrate was added to the hypotensive resuscitation fluid because it is known to bind to the GPR109A receptor on immune cells (monocytes and macrophages) and the vascular endothelium to have a direct anti-inflammatory effect. This example shows that Beta-hydroxy butyrate did not compromise hemodynamic support of hypotensive resuscitation.

Group 2 (See FIG. 12):

Addition of histone deacetylase inhibitor valproic acid to ALM hypotensive resuscitation. This example shows that a single 0.3 ml bolus of 3% NaCl with 1 mM Adenosine (0.24 mg/kg), 3 mM Lidocaine (0.73 mg/kg), and 2.5 mM $MgSO_4$ (0.27 mg/kg). with administration of valproic acid (VPA) (231 mM in 0.3 ml or 30 mg/kg body weight) raised MAP in the hypotensive range from 40 to 55 mmHg over 60 min after hemorrhagic shock. The example further demonstrates that administering an intravenous infusion of 0.9% NaCl ALM protected the animal from suffering circulatory collapse. This provides evidence that the addition of valproic acid in a bolus followed by an infusion or drip maintained hemodynamics, and that histone deacetylase inhibitors may be useful for protecting the brain and other organs of the body during delayed retrieval from the prehospital or military setting to definitive care. VPA also is known to have cytoprotective effects from an increase acetylation of nuclear histones, promoting transcriptional activation of deregulated genes, which may confer multi-organ protection.

Example 9: Effect of Hemodynamic Stabilization with Adenosine Agonist Plus Lidocaine and Magnesium after Extreme 50% Blood Loss Methods:

Male Sprague Dawley rats (300-400 g) were fed ad libitum with free access to water and housed in a 12-hr light-dark cycle. Animals were anesthetized with an intraperitoneal (IP) injection of 100 mg/kg sodium thiopentone (Thiobarb). After Thiobarb anesthesia, rats were positioned in the supine position on a custom designed cradle. A tracheotomy was performed and the animals artificially ventilated at 90-100 strokes per min on humidified room air using a Harvard Small Animal Ventilator (Harvard Apparatus, Mass., USA) to maintain blood $pO_2$, $pCO_2$ and pH in the normal physiological range. Rectal temperature was monitored using a rectal probe inserted 5 cm from the rectal orifice before, during and following shock and resuscitation, and previous experiments show the temperature ranges between 37 to 34° C. The left femoral vein and artery was cannulated using PE-50 tubing for drug infusions and blood pressure monitoring (UFI 1050 BP coupled to a MacLab) and the right femoral artery was cannulated for bleeding. Lead II electrocardiogram (ECG) leads were implanted subcutaneously on the left and right front legs and grounded to the back leg. Rats were stabilized for 10 minutes prior to blood withdrawal. Hemorrhagic shock was induced by withdrawing blood from the femoral artery at an initial rate of ~1 ml/min then decreasing to ~0.4 ml/min over 20 min. Initially blood was withdrawn slowly into a 10 ml heparinized syringe (0.2 ml of 1000 U/ml heparin) to reduce MAP to between 35 and 40 mmHg. If MAP increased, more blood was withdrawn to maintain its low value, and the process was continued over a 20 min period. The animal was left in shock for 60 min with frequent checking to ensure the MAP remains between 35 to 40 mmHg.

Anaesthetized, ventilated male Sprague-Dawley Rat 336 g (estimated blood volume 20.93 ml)

Baseline HR 320 bpm, BP 117/77 mmHg, MAP 90 mmHg, Temp 36.4° C.

Total blood loss=10.2 ml (49% TBV)

Rat received 0.3 ml intravenous bolus 3% NaCl+75 µg/kg CCPA (2-Chloro-$N^6$ cyclopentyladenosine) (0.0225 mg in 0.3 ml), 3 mM Lidocaine-HCl (0.73 mg/kg), 2.5 mM $MgSO_4$ (0.27 mg/kg) Results are summarised in Table 5 and in FIGS. 19A and B.

TABLE 5

| Time (min) | HR | BP | MAP | Temp |
|---|---|---|---|---|
| 2 | 69 | 60/16 | 32 | 31.8 |
| 5 | 69.5 | 61/17 | 31 | 31.7 |
| 10 | 70.5 | 51/17 | 28 | 31.6 |
| 15 | 72.5 | 48/18 | 28 | 31.4 |
| 30 | 79.5 | 54/16 | 29 | 30.7 |
| 45 | 81 | 47/15 | 26 | 30.3 |
| 60 | 86 | 39/14 | 23 | 29.9 |
| 75 | 101 | 31/13 | 19 | 29.3 |
| 90 | 119 | 24/11 | 17 | 29.0 |

At end of 60 min shock HR 237 bpm, BP 56/33 mmHg, MAP 40 mmHg, Temp 32.0° C.

Blood Pressure (see FIG. 19) decreased & extreme bradycardia (more so than Adenosine)

Interpretation:

A single 0.3 ml bolus of the treatment after catastrophic blood loss surprisingly maintained mean arterial pressure (MAP) in a very stable state. The large pulse pressure (difference between systolic and diastolic arterial pressure) indicates a high heart stroke volume despite the body's circulation being maintained at these low arterial pressures. There were no visible signs of hypoxia to any organs or tissues. There were no markings/mottling/infarcts/ischemic damage seen on heart, lung, liver or kidney indicating protection. Without being limited to mechanism is appears that the addition of the adenosine agonist placed the animal in a deep sleep with protection. The Example suggests lowering the level of [CCPA] for and provide a bolus and further treatment in form of continuous infusion.

Example 10: Nitric Oxide Mechanisms of the Invention for Hypotensive Resuscitation and Other Injury States Including Whole Body Arrest (Data in FIG. 13)

Methods:

Male Sprague Dawley rats (300-400 g) were fed ad libitum with free access to water and housed in a 12-hr light-dark cycle. Animals were anesthetized with an intraperitoneal (IP) injection of 100 mg/kg sodium thiopentone (Thiobarb). After Thiobarb anesthesia, rats were positioned in the supine position on a custom designed cradle. A tracheotomy was performed and the animals artificially ventilated at 90-100 strokes per min on humidified room air using a Harvard Small Animal Ventilator (Harvard Apparatus, Mass., USA) to maintain blood $pO_2$, $pCO_2$ and pH in the normal physiological range. Rectal temperature was monitored using a rectal probe inserted 5 cm from the rectal orifice before, during and following shock and resuscitation, and previous experiments show the temperature ranges between 37 to 34° C. The left femoral vein and artery was cannulated using PE-50 tubing for drug infusions and blood pressure monitoring (UFI 1050 BP coupled to a MacLab) and the right femoral artery was cannulated for bleeding. Lead II electrocardiogram (ECG) leads were implanted subcutaneously on the left and right front legs and grounded to the back leg. Rats were stabilized for 10 minutes prior to blood withdrawal.

Hemorrhagic shock was induced by withdrawing blood from the femoral artery at an initial rate of ~1 ml/min then decreasing to ~0.4 ml/min over 20 min. Initially blood was withdrawn slowly into a 10 ml heparinized syringe (0.2 ml of 1000 U/ml heparin) to reduce MAP to between 35 and 40 mmHg. If MAP increased, more blood was withdrawn to maintain its low value, and the process was continued over a 20 min period. The animal was left in shock for 60 min with frequent checking to ensure the MAP remains between 35 to 40 mmHg. If MAP deviated from this range either shed blood was re-infused or further blood was withdrawn. Animals were resuscitated with intravenous 0.3 ml of 7.5% NaCl ALM (1 mM Adenosine (0.24 mg/kg), 3 mM Lidocaine (0.73 mg/kg), and 2.5 mM $MgSO_4$ (0.27 mg/kg)) with and without 30 mg/kg L-NAME. L-NAME (N,-nitro-L-arginine methyl ester hydrochloride) is a non-specific inhibitor of nitric oxide (NO) synthase activity (constitutive and inducible forms of nitric oxide synthase).

Interpretation of the Example with 7.5% NaCl ALM with and without L-NAME.

Figure 13:
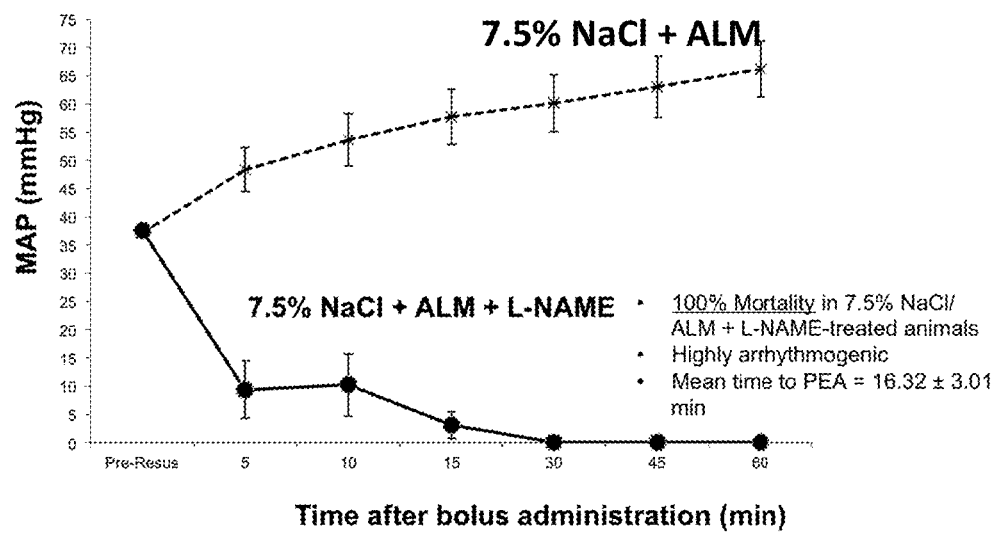
FIG. 13 shows a graph showing MAP resuscitation following single NaCl ALM bolus in the presence of L-NAME.

FIG. 13 shows that the addition of 30 mg/kg L-NAME to 7.5% NaCl/ALM totally abolished MAP resuscitation during the hypotensive period. There was 100% mortality in rats treated with 7.5% NaCl/ALM+30 mg/kg L-NAME with a reduction in mean arterial pressure below 20 mmHg at an average of 9 min after administration of the resuscitation bolus followed by pulseless electrical activity at 16 min. The addition of L-NAME led to ventricular dysrhythmia with each animal experiencing an average of 65.5±1.5 arrhythmic episodes. ALM cannot resuscitate in the presence of the NOS inhibitor L-NAME indicating the involvement of NOS & or NO in some way. The other interesting outcome of this experiment is that ALM blunted L-NAME's ability to vasoconstrict as it is well known that L-NAME induces endothelial-dependent vasoconstriction thereby increasing blood pressure and was investigated many years ago as a potential resuscitation agent.

This data supports our working hypothesis that ALM operates as a NO-dependent, 'pharmacological switch' which releases a natural "handbrake" on the shocked heart to gently raise MAP and improve whole body protection and stabilization, including brain. On the effect of ALM on the central nervous system, it is known that NO through site-specific and differential modulation of neuronal activity affects cardiac function. The nucleus tractus solitari (NTS) receives input from baroreceptors that is processed in this and other regions of the brain and eventually expressed with altered cardiac and whole body functions. Thus ALM may modulate CNS function to improve heart and multi-organ protection from hemodynamic, anti-inflammatory and coagulation correction mechanisms during shock states, and other forms or injury (traumatic and non-traumatic), burns, sepsis, infection and stress and disease states. This may be one of the underlying mechanisms of action of the invention.

Example 11: Brain and Whole Body Protection During Aortic Repair Surgery on Cardiopulmonary Bypass Background:

Despite recent advances in surgical techniques and cerebral protection, brain injury in the form of temporary or permanent neurological dysfunction remains a major cause of morbidity and mortality following aortic arch surgery or large intracranial aneurysm surgeries.

Three established techniques and perfusion strategies for aortic arch replacement and brain protection include: 1) hypothermic whole body circulatory arrest, 2) antegrade cerebral perfusion, and 3) retrograde cerebral perfusion. Only 15%-20% of surgeons continue to practice retrograde cerebral perfusion under certain conditions, as it offers little perfusion of the brain capillaries and appears to derive most of its benefits from hypothermia per se. Brain damage occurs from the use of cardiopulmonary bypass (CPB) and hypothermic circulatory arrest, temporary interruption of brain circulation, transient cerebral hypoperfusion, and manipulations on the frequently atheromatic aorta. A combination of antegrade and retrograde cerebral perfusion has also been shown to be useful for brain protection during aortic reconstruction.

Hypothermic circulatory arrest occurs when the systemic body temperature is around 20° C. for up to 30 min. It is during this time the surgeon performs the aortic repair and the brain must be protected. The brain is normally perfused with cold oxygenated whole blood or blood:fluid dilutions (e.g. 4 parts blood:1 part fluid) at temperatures 20 to 25° C. and as low as 6 to 15° C. Despite these standard-of-care procedures, this is a high-risk operation and there is an unmet need for improved pharmacological protection of the brain and body. The operative mortality for aortic arch replacement ranges from 6% to 23%, the incidence of permanent neurological dysfunction from 2% to 16%, and the incidence of temporary neurological dysfunction from 5.6% to 37.9%. Thus there is an unmet need to protect the brain and body during aortic arch procedures, and other types of circulatory arrest operations, in adults, pediatric patients and neonates.

Study Aim and Hypothesis:

The aim of the study is to test the protective effect of ALM and a general anesthetic on the brain, with and without an inflammatory such as beta-hydroxybutyrate (BHB) and brain fuel citrate. The vehicle can be whole blood, whole blood; crystalloid dilutions or crystalloid alone and isotonic or hypertonic with respect to saline. The hypothesis that will be tested is selective cerebral perfusion with blood containing a bolus of 10 ml ALM Propofol (1 mg adenosine; 2 mg Lidocaine-HCl and 0.3 g $MgSO_4$, 1 mg/kg propofol) administered via the innominate and left common carotid arteries (Di Eusanio, M., et al, 2003, J. Thorac Cardiovasc Surg 125, 849-854) followed by infusion 10 ml/kg/min containing (Adenosine; 0.2 mg/kg/min. Lidocaine-HCl; 0.4 mg/kg/min and $MgSO_4$; 0.224 g/kg/min), citrate (2 mM) and BHB (4 mM) with or without propofol (1 mg/kg) or thiopental (5 mg/kg), will protect the brain, reduce temporary and permanent neurological damage and reduce mortality in patients underdoing aortic arch repair. Treatment below is defined as the bolus plus infusion with propofol.

Study Plan:

There will be four arms to the the study 1) whole blood alone (no treatment), 2) whole blood alone with 3% saline, 3) whole blood with 3% saline and treatment, 4) whole blood with 3% saline and treatment (replace propofol with thiopental. The bolus followed by the infusion will be administered 5 min before the operation and continued during the circulatory arrest and rewarming after surgery. Data will be compared with blood or fluid vehicle alone with no additives.

Surgical Methods and Cerebral Perfusion:

60 patients (15 per group) will be recruited after obtaining the hospital's internal review board protocol approval and patient consent for the study. The methods for aortic arch surgery and dissection are described by Kruger et al., (Kruger, T., et al, 2011, Circulation 124, 434-443) and Misfield and others (Misfeld, M., et al, 2012, Ann Thorac Surg. 93, 1502-1508.), and references therein. Cerebral perfusion aims for a flow of 10 ml/kg body wt/min which is normally adjusted to maintain a radial arterial pressure of between 40 to 70 mm Hg. Cerebral monitoring is achieved by means of a right radial arterial pressure line, electroencephalography, regional oxygen saturation in the bilateral frontal lobes with near-infrared spectroscopy, and transcranial Doppler ultrasonographic measurement of the blood velocity of the middle cerebral arteries Primary and Secondary Endpoints:

Primary end points will include brain damage biomarkers such as neurofilament (NF), S10013, glial fibrillary acidic protein (GFAP), and ubiquitin carboxyl terminal hydrolase-L1 (UCH-L1) neuron-specific enolase (NSE)). Brain ischemia will be assessed using blood lactate levels and pH. Inflammation will be assessed using select markers (e.g. IL-1, IL-6, IL-12, tumor necrosis factor-alpha), and coagulopathy using coagulometry (aPTT, PT) and visco-elastic ROTEM analysis. Temporary neurological deficit, 30-day mortality and mortality-corrected permanent neurological dysfunction will be assessed. The 30-day mortality will include any death that occurred from the intraoperative period until the $30^{th}$ postoperative day. Secondary end points will be perioperative complications and perioperative and postoperative times, intubation times. This example will demonstrate one aspect of the invention, which is to protect the brain using non-arrest levels of the composition in bolus and constant infusion. An arm may be included where the doses are raised to examine another aspect of the invention to arrest the brainstem (and higher centres) during circulatory arrest for aortic reconstructions or large intracranial aneurysm surgeries. This example would also be applicable for pediatric and neonatal circulatory arrest interventions and surgeries.

Example 12: Brain and Whole Body Protection for Abdominal Aortic Aneurysm

Background:

Abdominal aortic rupture is a highly lethal event, claiming about 15,000 lives each year. Traditionally, open surgical repair with thoracotomy has been the mainstay of treatment, yet this surgery is associated with up to 50% perioperative mortality. Minimally invasive endovascular stent grafts has become popular and while still remaining a high-risk procedure with high mortality, it has been used with great success in the elective repair of aortic aneurysms. Thus there is an unmet need for improved pharmacological protection of the brain and body before, during and following the operation. Hypotensive anaesthesia may also be protective to reduce blood loss, however, the brain must be protected.

Study Aim and Hypothesis:

Thirty patients will be recruited after obtaining the hospital's internal review board protocol approval and patient consent for the study. The aim of the study is to test the protective effect of intravenous infusion of ALM with and without an inflammatory such as beta-hydroxybutyrate (BHB) and brain fuel citrate 5 min before and during minimally invasive endovascular stent grafts in the elective repair of aortic aneurysms. The hypothesis that will be tested is that intravenous bolus and infusion of 3% NaCl ALM with citrate (1 mM) and BHB (4 mM) will result in 1) targeted systemic hypotension to reduce bleeding, and 2) protect the body and organs (e.g. heart, brain, kidney and lung) in patients undergoing elective repair of aortic aneurysms. The bolus-infusion may reduce mortality from this high-risk operation. Controls will be infused with the vehicle only and the results compared. This example differs from example 11 as there is no special perfusion circuit isolating and protecting the brain.

Methods and Intravenous Infusion Rates:

60 patients (15 per group) will be recruited after obtaining the hospital's internal review board protocol approval and patient consent for the study. The minimally invasive endovascular non-surgical method is described by Smith and Ramirez and references therein (Smith and Ramirez, 2013). There will be four arms to the study: 1) 0.9% NaCl bolus and infusion, 2) 3% NaCl bolus and 3% infusion; 3) 0.9% NaCl with bolus-infusion treatment, and 4) 3% NaCl with bolus-infusion treatment. Treatment is ALM bolus (0.3 mg/kg adenosine; 0.6 mg/kg Lidocaine-HCl and 0.03 g/kg $MgSO_4$) followed by intravenous infusion of ALM (Adenosine; 0.2 mg/kg/min. Lidocaine-HCl; 0.4 mg/kg/min and $MgSO_4$; 0.224 g/kg/min), citrate (1 mM), BHB (4 mM). The bolus and infusion will commence 5 min before percutaneous endovascular repair. Infusion rate will begin at 10 ml/min/kg and increased to produce hypotensive anaesthetized state to reduce blood loss.

Primary and Secondary Endpoints:

The primary end points will be biomarkers for the clinical diagnosis of brain injury, inflammatory markers, coagulopathy, temporary neurological deficit, 30-day mortality and mortality-corrected permanent neurological dysfunction. The 30-day mortality included any death that occurred from the intraoperative period until the $30^{th}$ postoperative day. Secondary end points will be perioperative complications and perioperative and postoperative times, intubation times.

The data will demonstrate one aspect of the invention to protect the brain and organs of the body using non-arrest levels of the composition administered as bolus and infusion.

Example 13: Reducing Post-Partum Hemorrhage, Coagulopathy and Infection

Background:

Postpartum hemorrhage (PPH) is the leading cause of maternal mortality and disability, particularly in under-resourced areas. PPH is defined as bleeding from the genital tract (500 ml or more) after childbirth. The first line therapy for severe PPH includes transfusion of packed cells and fresh-frozen plasma in addition to uterotonic medical management and surgical interventions. Obstetric haemorrhage is associated with hemodynamic instability, inflammatory activation and coagulopathy and these women patients have a higher incidence of infection. Postpartum uterine sepsis is believed to arise from an ascending infection caused by colonizing vaginal flora. The incidence of infection (postpartum endometritis or infection of the decidua) after vaginal delivery is 0.9 and 3.9% and as high as 12-51% after Caesarean section.

Secondary coagulopathy is often underestimated in women during post-partum haemorrhage and if it is not untreated the condition can become severe PPH. Longer blood clotting times means that the blood gets thinner making the problem of bleeding becomes worse. In most cases, medical and transfusion therapy is not based on the actual coagulation state because conventional laboratory test results are usually not available for 45 to 60 minutes.

Study Aim and Hypothesis:

The aim of the study is to provide a bolus and infusion of ALM immediately following parturition and haemorrhage. An intravenous ALM bolus (0.3 mg/kg adenosine; 0.6 mg/kg Lidocaine-HCl and 0.03 g/kg $MgSO_4$) followed by intravenous infusion of ALM (Adenosine; 0.2 mg/kg/min. Lidocaine-HCl; 0.4 mg/kg/min and $MgSO_4$; 0.224 g/kg/min) at a flow rate of 10 ml/kg/min would be investigated.

The hypothesis to be tested that is that ALM therapy will correct coagulopathy, reduce bleeding and improve whole body function following childbirth such as improved hemodynamics, inflammation and reduce the incidence of infection.

Methods: Forty patients will be recruited after obtaining the hospital's internal review board protocol approval and patient consent for the study. Twenty patients will have no treatment and twenty patients will receive the bolus-infusion treatment. Cardiac function, hemodynamics, inflammatory markers and ROTEM coagulation indices including C-reactive protein will be measured. The study will show that ALM therapy compared to no treatment will correct coagulopathy and reduce post-partum complications and treatment for hemorrhage. A second study will be performed investigating the ALM therapy administered before parturition for complicated pregnancy/delivery cases to protect both the mother and baby. The data will demonstrate one aspect of the invention to protect the mother and organs of the body using non-arrest levels of the composition administered as bolus and infusion.

Example 14: Brain and Whole Body Protection for Neonatal or Pediatric Aortic Arch Reconstruction Background:

Each year, thousands of children undergo complex cardiac surgeries for the repair of congenital heart defects. Children are at high risk for brain (CNS) injury perioperatively in both the operating room, and the cardiac intensive care unit. Recent studies show that brain damage such as periventricular leukomalacia (PVL) and other MRI detected hypoxic-ischemic lesions can be as high as 50% to 70% incidence at the time of surgery in pediatric patients. PVL is a form of white-matter brain injury in infants and characterized by necrosis (more often coagulation) of white matter located around the fluid-filled ventricles. There is no treatment for PVL and it may lead to nervous system and developmental problems. In addition, in adult cardiac surgery cognitive deficits are present in over 50% of patients at the time of hospital discharge. Operative factors that contribute to brain injury in both pediatric and adult cardiac surgery include poor perfusion, anesthetic-induced brain toxicity, cardiopulmonary bypass-mediated inflammation, ischemia-reperfusion injury, thromboembolic events, and glucose, electrolyte and acid-based disturbances.

In addition to brain and organ injury occurring during cardiac surgery, the early postoperative period is also a highly vulnerable time for injury because of poor perfusion, free radical and oxidant damage, cyanosis, inflammation, coagulopathy, abnormal vascular reactivity, hyperthermia, endocrine abnormalities and poor glycemic control and insulin-resistance including pyruvate dehydrogenase inhibition. Postoperative variables such as cyanosis, low systolic and diastolic blood pressures, low cardiac output, and prolonged periods of poor cerebral $O_2$ saturation.

As with adult aortic repair and reconstruction, attempts to protect the neonatal or pediatric brain during corrective surgery are via antegrade cerebral perfusion. This can occur by direct or indirect cannulation of the innominate artery. Indirect cannulation is achieved by a graft sutured to the innominate artery or advancement of a cannula through the ascending aorta into the innominate artery, whereas direct cannulation is performed by directly cannulating the innominate artery. Since cardiopulmonary bypass and/or deep hypothermic circulatory arrest is a planned period of regional and whole body ischemia, it provides an optimal opportunity for pharmacologic strategies aimed to reduce brain and organ whole body injury.

Study Aim and Hypothesis.

The aim of the study is twofold: 1) to investigate the effect of intra-arterial ALM bolus and infusion 5 to 15 min and brain protection before beginning and continued throughout the surgical procedure, and 2) a second intravenous bolus and infusion 5 to 15 min and during circulatory arrest throughout the whole body where appropriate. The hypothesis is that the ALM therapy improves 1) brain and 2) whole body function compared to vehicle controls, including cardiac, renal and lung functional improvement. The therapy will reduce inflammation, reduce coagulation disturbances and lead to less whole body ischemia.

Methods:

Forty patients will be recruited after obtaining the hospital's internal review board protocol approval and patient consent for the study. The surgical method for neonatal aortic arch reconstruction is described by Malhotra and Hanley and references therein (Malhotra and Hanley, 2008). The intravenous whole body bolus-infusion will commence before cardiopulmonary bypass and cooling. Cardiopulmonary bypass will be initiated and once adequate venous drainage confirmed, the patient will be cooled to 22° C. to 24° C. for a minimum.

The arch vessels will then be prepared for cerebral perfusion. The innominate artery, the left carotid artery, and the left subclavian artery are each individually clamped with atraumatic neurovascular clips to ensure uniform cooling of the central nervous system. At this point, direct perfusion is isolated to the head and right arm, and the ALM bolus and infusion will commence at least 5 min before the operation at a flow rate of 30 ml/kg/min to generate sufficient cerebral pressures for optimal protection. After the surgical procedure the whole body ALM bolus-intravenous infusion can be lowered and continued for further stabilization in the intensive care unit. Thus there are two separate administrations: 1) intravenous bolus and infusion to whole body; and 2) intra-arterial bolus and infusion to brain circuit. The whole body infusion may have to be stopped as circulation is stopped and re-started. The doses would include ALM bolus (0.3 mg/kg adenosine; 0.6 mg/kg Lidocaine-HCl and 0.03 g/kg $MgSO_4$) followed by intravenous infusion of ALM (Adenosine; 0.2 mg/kg/min. Lidocaine-HCl; 0.4 mg/kg/min and $MgSO_4$; 0.224 g/kg/min) at 10 ml/min/kg (whole body), and arterial flow to the brain adjusted to meet the flow requirements according to surgeon preference.

Brain protection in neonates will include near infrared spectroscopy (NIRS), transcranial Doppler (TCD), electroencephalography (EEG), and serum measurement of S100B protein. Whole body protection will be assessed using routine haemodynamic measurements, cardiac output, ultrasound volume relaxation parameters of left ventricular function, troponins, inflammatory markers and coagulopathy. 30-day mortality and infection rates will be recorded. The data will demonstrate one aspect of the invention to protect the brain, heart, kidney and lungs using non-arrest levels of the composition.

Example 15: Reducing Inflammation, Coagulation Dysfunction, Infection and Adhesions During Neonatal or Pediatric Congenital Corrective Heart Surgery A recent study involving 28 centres and 32,856 patients reported that the percentage of patients having postoperative infection as 3.7%. Post-operative infections include sepsis, wound infection, mediastinitis, endocarditis, and pneumonia and any of these conditions contributes to prolonged LOS and increased hospital costs. Increased risk factors for major infections were age, reoperation, preoperative length of stay longer than 1 day, preoperative respiratory support or tracheostomy, genetic abnormality, and medium or high complexity score.

In addition, neonates and pediatric patients undergoing heart surgery have a significant incidence of neurologic, cardiac and acute renal problems. It has been reported that the prevalence of perioperative seizures can be 5 to 10%. Inflammation and coagulation dysfunction can occur as result of the trauma response to the surgery itself, and from exposure to cardiopulmonary bypass (CPB), which elicits a systemic inflammatory response.

The prevention of the pericardial adhesions is also an unmet need because many corrective surgeries require reoperations in the child's life and resternotomy continues to gain in importance with the increasing frequency of reoperations. Cardiac adhesions present a major problem to surgeons upon sternal re-entry to carry out staged cardiac repair. Estimates of the incidence of injury to cardiac structures upon resternotomy in patients with adhesions on the large vessels range from 1 to 10% of operations.

Aim and Hypothesis:

An intravenous bolus of ALM and infusion/drip will begin prior to placing the patient on CPB the cardiac surgery and continued throughout the surgery. The hypothesis is that the one-two ALM treatment will induce whole body protection from reducing inflammation and coagulopathy and improve cardiac function (lower troponin and lactate) and reduce infection. The bolus and drip will also improve brain and renal function following surgery and reduce hospital length of stay. The results will be compared with historical controls and with vehicle infusion.

Methods;

Twenty patients will be recruited after obtaining the hospital's internal review board protocol approval and patient consent for the study. Inflammation status will be evaluated from blood samples collected, and serum levels of interleukin (IL)-6, IL-8, tumor necrosis factor alpha, polymorphonuclear elastase (PMN-E), C-reactive protein (CRP), as well as the white blood cell (WBC) count, platelet count, and neutrophil count (NC) were measured. IL6 has recently been associated with acute kidney injury within the first 24 hours after pediatric cardiac surgery. Coagulation status will be assessed using ROTEM. Cardiac troponins will be measured during and following surgery including 12 hours and 24 hours post-operative times. Brain function will be assessed using blood markers and cerebral oximetry and transcranial Doppler ultrasonographic measurement of the blood velocity of the middle cerebral arteries.

The data will demonstrate that the intravenous bolus and drip or infusion will confer perioperative protection including improved whole body post-operative cardiac, renal and neural function and blunting of the inflammatory response and restoring coagulation leading to lower intensive care and hospital room stays. In those complicated cases where extracorporeal membrane oxygenation (ECMO) support is required in the specialized paediatric cardiac intensive care, the ALM therapy can be continued at a lower dose for whole body stabilization. The therapy will be shown to be a central component in the management neonatal, paediatric and adult patients, and the critically ill suffering a traumatic and non-traumatic injury.

Example 16: Brain Protection for Carotid Endarterectomy

Carotid endarterectomy is a procedure used to prevent stroke by correcting blockage in the common carotid artery, which delivers blood to the brain. Endarterectomy is the removal of material from the inside of the vessel causing the blockage. In endarterectomy, the surgeon opens the artery and removes the blockage. Many surgeons lay a temporary bypass or shunt to ensure blood supply to the brain during the procedure. The procedure may be performed under general or local anaesthetic. The shunts may take 2.5 minutes and ischemic cerebral signals (flat wave) in electroencephalographic can occur soon after insertion of the shunt. The mean shunting time can be around 1 hour for the operation to take place. Damage the brain and other organs can occur during the procedure. New ischemic lesions on diffusion-weighted magnetic resonance imaging are detected in 7.5% of patients after carotid endarterectomy. Twenty patients will be recruited after obtaining the hospital's internal review board protocol approval and patient consent for the study. The aim of the present study is to provide an arterial ALM bolus and infusion with and without propofol prior to placing the shunt, and continued for 60 min or as long as the operation takes. Diffusion-weighted magnetic resonance imaging will be conducted to examine if there are reduced lesions compared to saline or blood controls. The data will demonstrate one aspect of the invention to protect the brain, heart, kidney and lungs of the body using non-arrest levels of the composition involving a bolus and infusion. This is one aspect of the invention showing the clinical advantage of the bolus and drip (infusion) ALM treatment therapy on brain and whole body protection.

Example 17: Reduced Inflammation, Coagulation, Adhesions and Blood Loss Following Shoulder Surgery Modern arthroscopy has contributed significantly to greater flexibility and efficacy in addressing shoulder pathology. The procedure has the advantage of being less invasive, improved visualization, decreased risk of many postoperative complications, and faster recovery. Common shoulder conditions that can be managed arthroscopically include rotator cuff tears, shoulder instability, and labral pathology. Arthroscopic rotator cuff repair has a good clinical outcome but shoulder stiffness after surgery due to subacromial adhesion is a common and clinically important complication. Following rotor cuff repair, around 5% of patients will develop postoperative stiffness and require capsular release and lysis of adhesions. Risk factors for postoperative stiffness are calcific tendinitis, adhesive capsulitis, single-tendon cuff repair.

One of the further challenges of the arthroscopic procedures is the need for controlled hypotension during anaesthesia to lessen intra-articular haemorrhage and thereby provide adequate visualisation to the surgeon, and reduced local and systemic inflammation coagulopathy for the patient. Bones bleed at normal blood pressure and the shoulder is highly vascularized and this area is difficult if not impossible to use a tourniquet. Achievement of optimal conditions necessitates several interventions and manipulations by the anaesthesiologist and the surgeon, most of which directly or indirectly involve maintaining intra-operative blood pressure (BP) control.

Aim of the Study:

The aim of our study is: 1) to examine the effect of ALM injectable applications or topical sprays at select times within the joint to reduction of local adhesions, reduce local inflammation and reduce local coagulopathy and pain following surgical or arthroscopic repair of the rotator cuff. 2) to examine the effect of intravenous whole body ALM dose and infusion, with and without proprofol, to induce a hypotensive state to reduce bleeding during the surgery, and to protect the whole body from the trauma of surgery with reduced inflammation and coagulation and reduced pain.

Methods:

Thirty patients will be recruited after obtaining the hospital's internal review board protocol approval and patient consent for the study. The methods of rotor cuff repair are found in Paxton (Paxton, E. S., et al, 2013, J Am Acad Orthop Surg. 21, 332-342.) and Tantry (Tantry, T. P., et al, 2013, Indian J Anaesth. 57, 35-40). Hemodynamic, and blood inflammatory and coagulation markers will be assessed perioperatively, and cuff healing and adhesions will be monitored using CT arthrography or ultrasonography at 6 or 12 months after surgery. All patients will also be evaluated using the visual analog scale (VAS) for post-operative pain, passive range of motion at 2, 6 weeks, and 3, 6, 12 months after surgery.

The results will show that a subacromial injection of ALM will reduce inflammation and post operative shoulder stiffness and associated adhesion complications at 6 and 12 months, and the intravenous ALM bolus and infusion will lead to per-operative reduced whole body inflammation, coagulation disturbances and less blood lost during the procedure from the coagulopathy correction and inducing a reproducible hypotensive state. Importantly, the study will show that ALM bolus-infusion therapy will assist in inducing a whole body hypotensive anaesthesia to reduce bleeding, which would also be applicable for other types of interventions and surgery including knee surgery and the intravenous bolus-infusion will protect distal areas once a tourniquet at the knee is applied and released every 30 min. Thus the results of the study will demonstrate one aspect of the invention to protect the joint from stiffness and the whole body using non-arrest levels of the composition involving a bolus and infusion, and another aspect of the invention to facilitate hypotensive state for anesthesia with reduced blood loss.

Example 18: Reducing Infection and Post-Surgical Pericardial Adhesions

Background:

Opening of the pericardial cavity during cardio-thoracic surgical operations promotes inflammation, coagulopathy, injury and adhesions. Postsurgical intrapericardial adhesions may complicate the technical aspects of reoperations from injury to the heart and great vessels as well as perioperative bleeding. In two large series of cardiac reoperations, the rate of inadvertent injury ranged from 7% to 9%. Closing the chest (sternum) also has a risk of infection and adhesions. Sternal wound infections are a life-threatening complication after cardiac surgery associated with high morbidity and mortality. Deep sternal wound infection is also termed mediastinitis after median sternotomy occurs in 1 to 5% of patients and the associated mortality rate in the literature ranges from 10 to 47%.

Aim and Hypothesis:

The present invention will show that intravenous ALM bolus and infusion during the operation during or following the surgery will lower infection rate and incidence of adhesions following surgery. The second aim is to show that ALM in a syringe applied topically or by spray or other means of delivery to the area during, prior to closure of the wound, or following closure of the wound will reduce adhesions, promote healing and reduce infection following cardiac surgery.

Methods:

Sixty patients will be recruited after obtaining the hospital's internal review board protocol approval and patient consent for the study. Twenty patients will have no treatment.

Twenty patients will have only the topical treatment; and twenty patients will have both the intravenous bolus and infusion and topical combined. The methods for cardiac surgery are well described in the literature. Adhesions will be assessed using imaging modalities at 30 day, 60 day, 6 months and 12 months. Infections will be monitored and recorded post-operatively according to Singh and colleagues (Singh, K., et al, 2011, Semin Plast Surg. 25, 25-33). Type I infections are those that occur within the first week after sternotomy and typically have serosanguineous drainage but no cellulitis, osteomyelitis, or costochondritis. They are typically treated with antibiotics and a single-stage operation. However, the majority of cases are type II infections that normally occur during the second to fourth weeks after sternotomy and usually involve purulent drainage, cellulitis, and mediastinal suppuration. While it is understood that patients undergoing a median sternotomy for coronary artery bypass grafting have the highest rate of sternal wound infections compared with those for other surgeries, the above example for one aspect of the present invention would also apply to other surgeries and the problem of surgical wound infections.

Example 19: Treating and Reducing Pain Following Marine Envenomation

Background:

The Box Jellyfish (also known as the sea wasp or sea stinger) is the only known coelenterate that is lethal to humans. The venom has cardiotoxic, neurotoxic and dermatonecrotic components. It is injected by hundreds of thousands of microscopic stings over a wide area of the body and on the trunk. Absorption into the circulation is rapid. Each sting arises from the discharge of a nematocyst. The central rod of the microbasic mastigphore carries the venom, and is like a microscopic spear, which is impaled, on contact, into the victim by a springy protein. Other jellyfish may cause a similar syndrome such as Irukandji. When stung, the pain is absolutely excruciating and can lead to shock and death. Systemic magnesium, in slow boluses of 10-20 mMol, may attenuate pain and hypotension.

Aim and Hypothesis:

To bring pain relief and hemodynamic and pulmonary support to victims of Marine stingers. The hypothesis to be tested is that ALM will produce greater pain relief and whole body physiological support by reducing the devastating effect of the catecholamine storm compared with magnesium alone.

Methods:

Sixty patients who have been stung by box jellyfish will be recruited after obtaining the hospital's internal review board protocol approval and patient consent for the study. Twenty patients will have intravenous slow bolus or bolus and infusion of 10-20 mM magnesium sulphate alone. Twenty patients will receive intravenous slow bolus or bolus and infusion of adenosine, lignocaine with 10-20 mM magnesium sulphate (ALM), and twenty patients will have only the topical ALM treatment. The present invention with ALM will reduce pain, protect the organs including heart and lung, and reduce inflammation and coagulopathy. The present invention will also work by reducing the effect of the catecholamine cascade which can lead to a hypertensive state with associated cardiac and respiratory complications. The same study will be repeated in patients stung by Irukandji. The invention may apply to other marine and terrestrial envenomations.

It will be understood that the invention is not limited by the experiments described in Examples 11 to 19 and that any composition of the invention could be used in these experiments.

Figure 20:
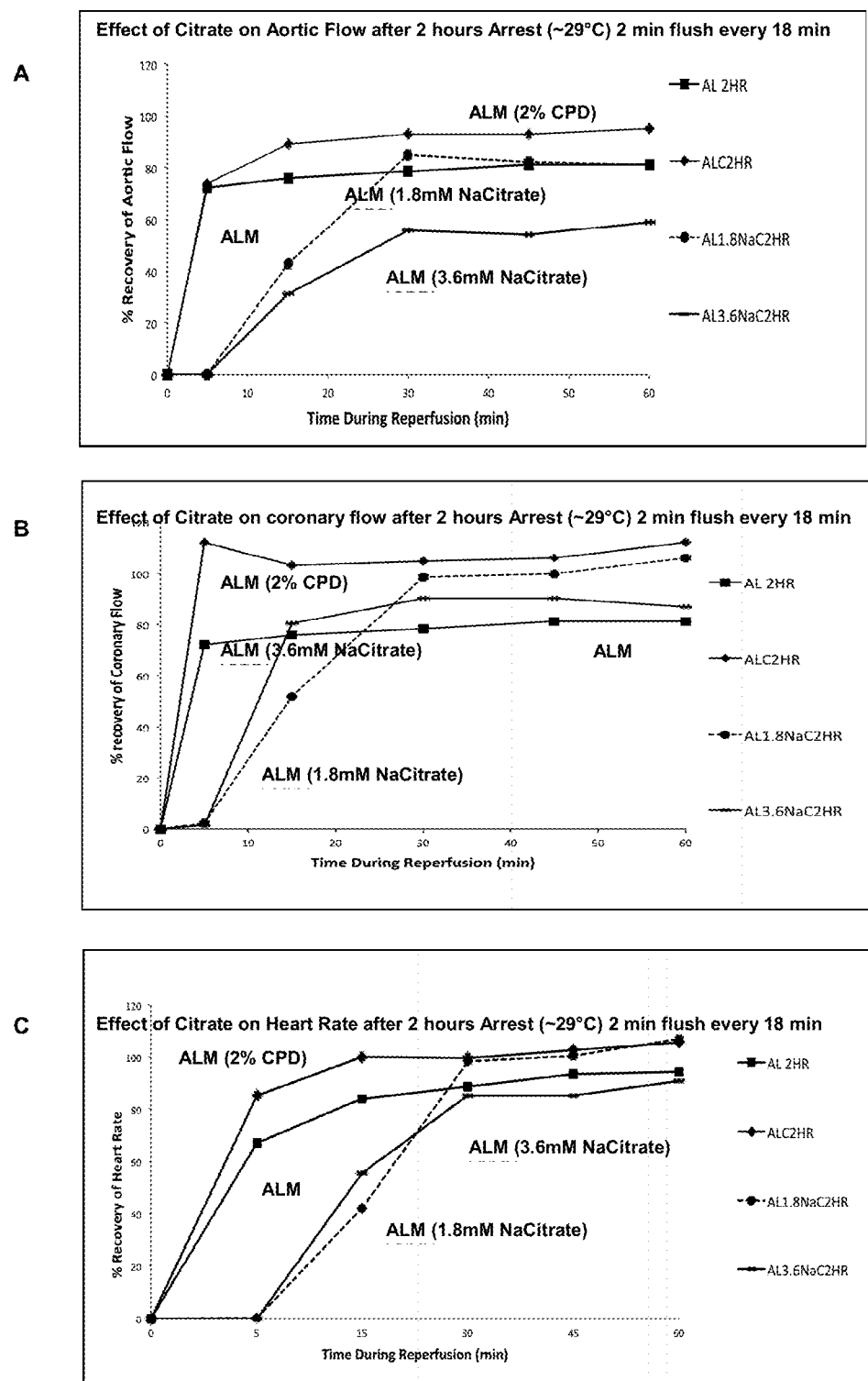
FIG. 20 shows graphs showing the effect of adenosine and lidocaine solution with different forms of citrate (citrate phosphate dextrose CPD and sodium citrate) and elevated magnesium. Graphs showing measurement of (A) heart aortic flow; (B) heart coronary flow; and (C) heart rate against 60 min of reperfusion time after 2 hours tepid arrest (heart temperature ~29° C.) in the isolated working rat heart. Hearts were flushed with normothermic cardioplegia every 18 min for 2 minutes (n=8 each group) (see example 1)

Example 20a: (FIG. 20A-C): Effect Adenosine and Lignocaine Solution with Two Forms of Citrate and Elevated Magnesium on Aortic Flow, Coronary Flow and Heart Rate after 2 Hours of Warm (Tepid) Heart Arrest in the Working Rat Heart. Function Monitored for 60 Min Reperfusion Background:

The working rat heart is considered the gold standard model for translation research in cardioplegia and preservation solutions for cardiac surgery or heart storage for transplantation. In 2004, we introduced into the literature a new concept of polarized arrest and protection for surgical cardioplegia employing a composition of adenosine and lidocaine in a physiological Krebs-Henseleit ionic solution (Dobson, 2004, 2010). This was also the subject of application WO 00/56145. In 2004 we showed that adenosine and lidocaine in a normokalemic solution arrested the heart by 'clamping' the myocyte's diastolic membrane potential at around −80 mV and was accompanied by a fall in oxygen consumption of over 95% (Dobson, 2004).

Methods:

Male Sprague-Dawley rats (350-450 g) were obtained from James Cook University's breeding colony. Animals were fed ad libitum and housed in a 12-hour light/dark cycle. On the day of experiment, rats were anaesthetised with an intraperitoneal injection of Thiobarb (Thiopentone Sodium; 60 mg/kg body wt) and the hearts were rapidly excised as described in Dobson and Jones (Dobson, 2004). Rats were handled in compliance with James Cook University Guidelines (Ethics approval number A1084), and with the 'Guide for Care and use of Laboratory Animals' from the National Institutes of Health (NIH Publication No. 85-23, revised 1985, and PHS Publication 1996). Adenosine (A9251 >99% purity) and all other chemicals were obtained from Sigma Chemical Company (Castle Hill, NSW). Lidocaine hydrochloride was purchased as a 2% solution (ilium) from the local Pharmaceutical Supplies (Lyppard, Queensland). Hearts were rapidly removed from anaesthetised rats and placed in ice-cold heparinised modified KH buffer.

Figure 14:
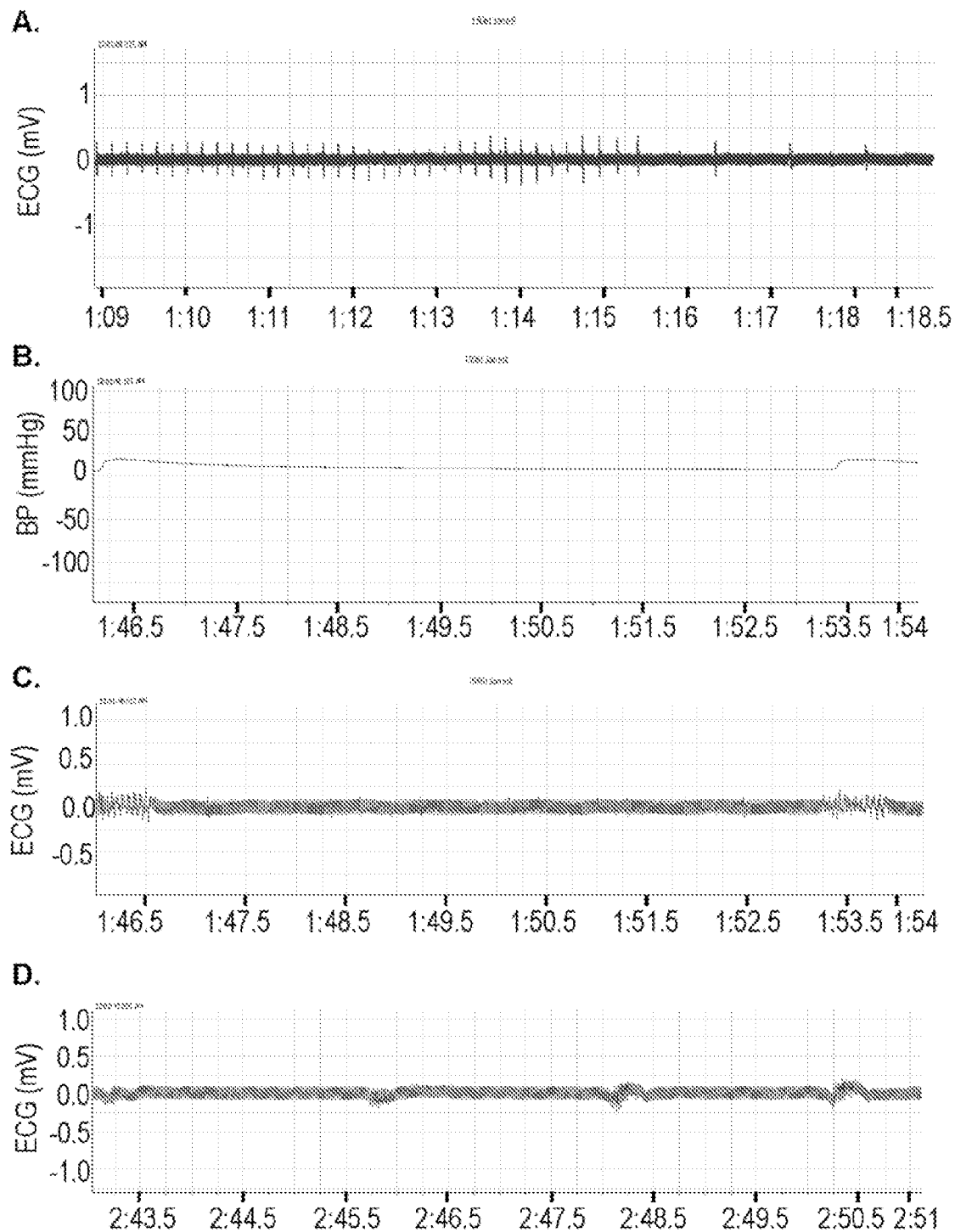
FIG. 14 shows ECG traces (A, C and D) and a blood pressure trace (B) showing the effect of ALM with a general anaesthetic from a normal state to whole body arrest.
Figure 15:
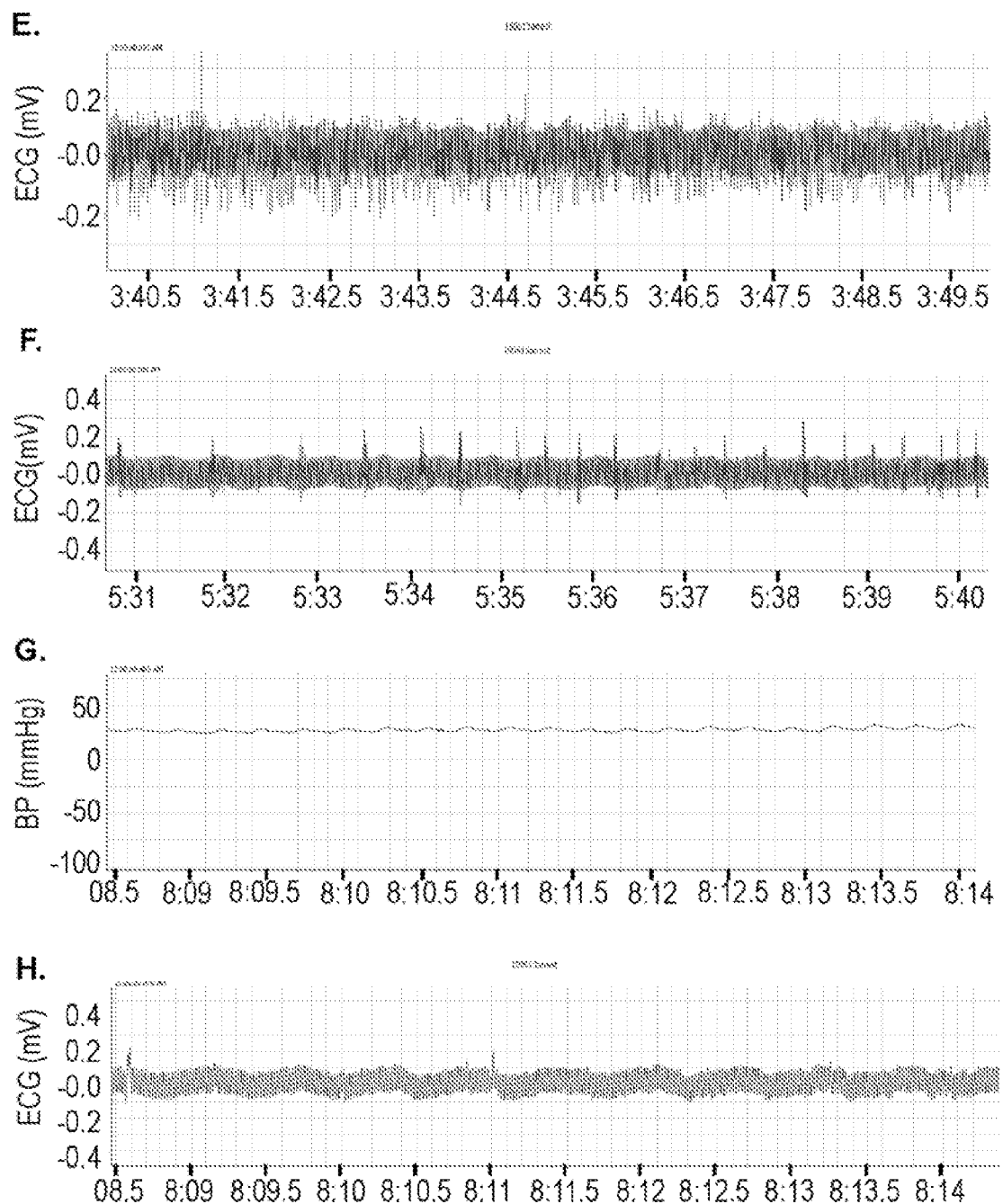
FIG. 15 shows ECG traces (E, F and H) and a blood pressure trace (G) showing the effect of ALM with a general anaesthetic from a normal state to whole body arrest.
Figure 16:
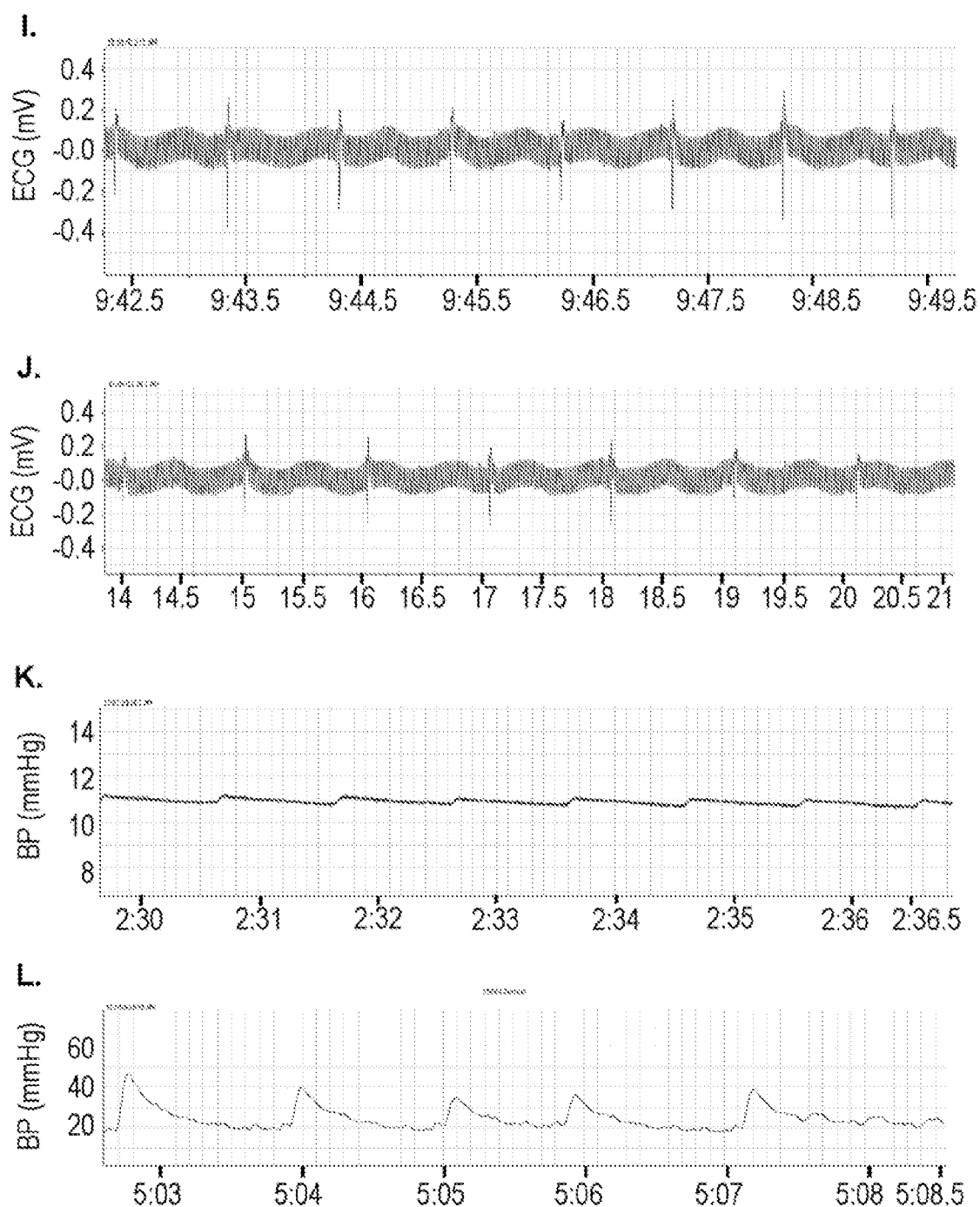
FIG. 16 shows ECG traces (I and J) and blood pressure traces (K and L) showing the effect of ALM with a general anaesthetic from a normal state to whole body arrest.
Figure 17:
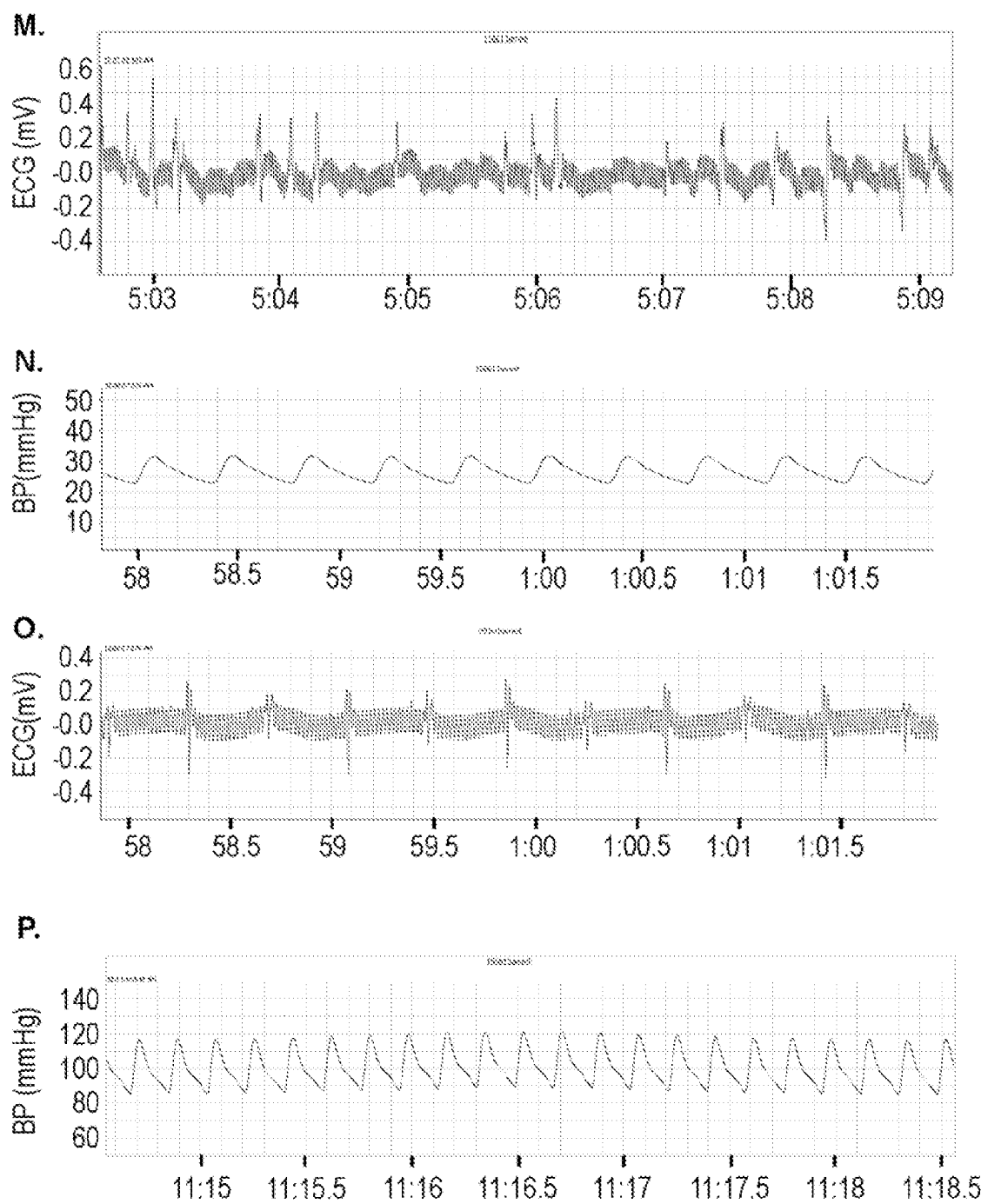
FIG. 17 shows ECG traces (M and O) and blood pressure traces (N and P) showing the effect of ALM with a general anaesthetic from a normal state to whole body arrest.
Figure 18:
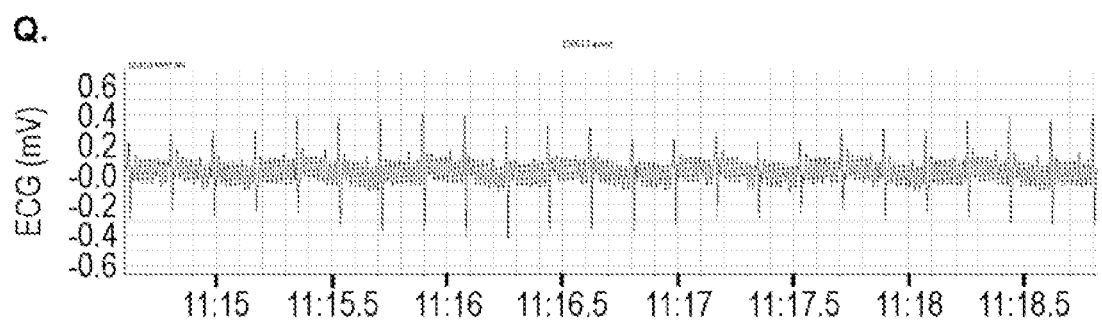
FIG. 18 shows ECG trace (Q) showing the effect of ALM with a general anaesthetic from a normal state to whole body arrest.

Details of heart preparation, attachment and perfusion are described in by Dobson and Jones (Dobson, 2004) and Rudd and Dobson (Rudd and Dobson, 2009). Briefly, hearts were attached to a Langendorff apparatus and perfused at a pressure head of 90 cm $H_2O$ (68 mmHg). The pulmonary artery was cannulated for collection of coronary venous effluent and $O_2$ consumption measurements. For working mode operation, a small incision was made in the left atrial appendage and a cannula inserted and sutured. The heart was then switched from Langendorff to the working mode by switching the supply of perfusate from the aorta to the left atrial cannula at a hydrostatic pressure of 10 cm $H_2O$ (pre-load) and an afterload of 100 cm $H_2O$ (76 mmHg). Hearts were stabilized for 15 minutes and pre-arrest data recorded before converting back to Langendorff mode prior to inducing normothermic arrest. Heart rate, aortic pressure, coronary flow and aortic flow were measured prior to and following 6 hour arrest and cold static storage (see FIG. 14). Aortic pressure was measured continuously using a pressure transducer (ADI Instruments, Sydney, Australia) coupled to a MacLab 2e (ADI Instruments). Systolic and diastolic pressures and heart rate were calculated from the pressure trace using the MacLab software.

Figure 21:
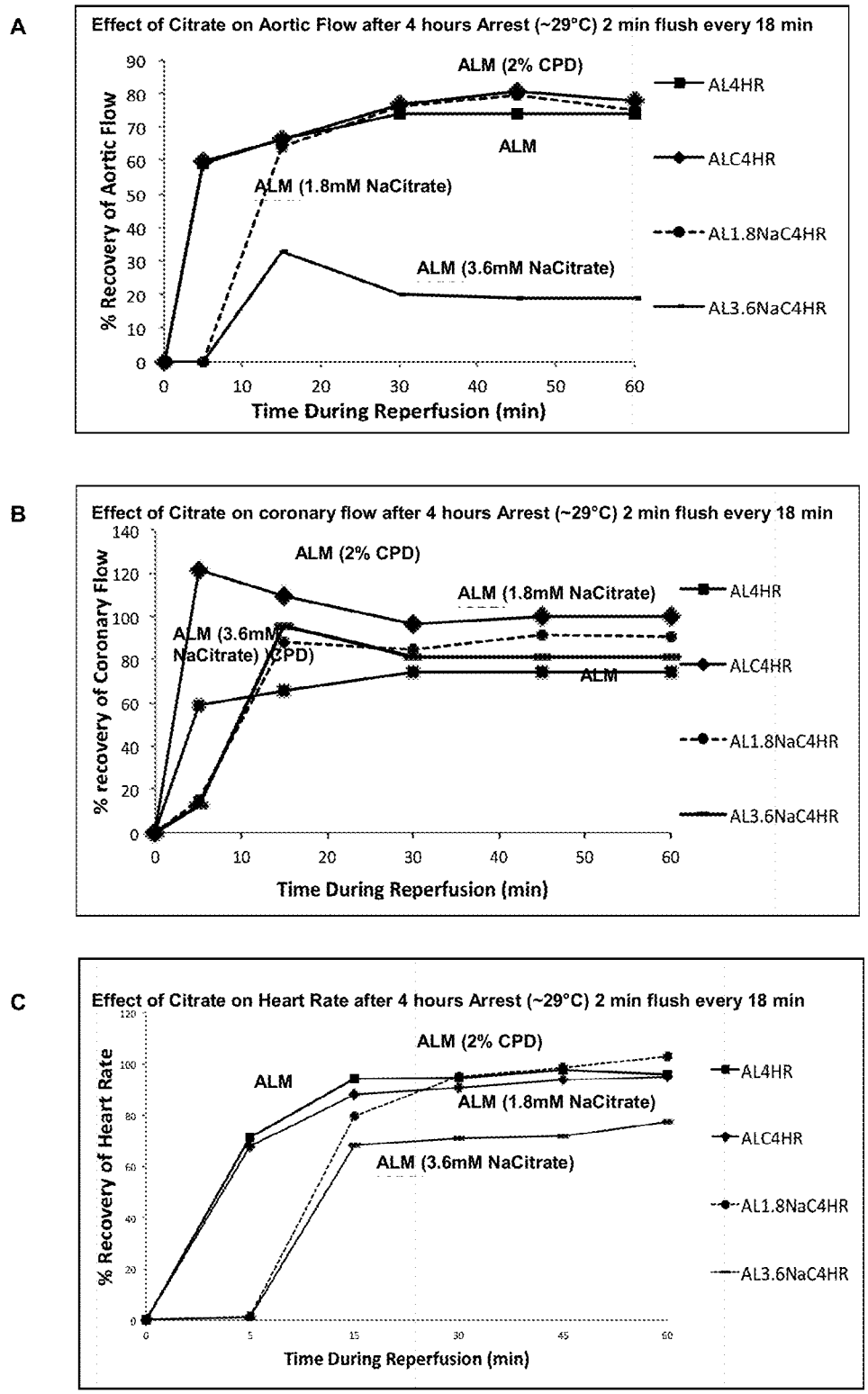
FIG. 21 shows graphs showing the effect of adenosine and lidocaine solution with different forms of citrate (citrate phosphate dextrose CPD and sodium citrate) and elevated magnesium. Graphs showing measurement of (A) heart aortic flow; (B) heart coronary flow; and (C) heart rate against 60 min of reperfusion time after 4 hours tepid arrest (heart temperature 29° C.) in the isolated working rat heart. Hearts were flushed with normothermic cardioplegia every 18 min for 2 minutes (n=8 each group) (see example 2)

Compositions:

Krebs buffer: Hearts were perfused in the Langendorff and working modes with a modified Krebs-Henseleit crystalloid buffer containing 10-mmol/L glucose, 117 mmol/L sodium chloride, 5.9-mmol/L potassium chloride, 25-mmol/L sodium hydrogen carbonate, 1.2-mmol/L sodium dihydrogenphosphate, 1.12-mmol/L calcium chloride (1.07-mmol/L free calcium ion), and 0.512-mmol/L magnesium chloride (0.5-mmol/L free magnesium ion), pH 7.4, at 37_C. The perfusion buffer was filtered with a 1-mm membrane and then bubbled vigorously with 95% oxygen and 5% carbon dioxide to achieve a P02 greater than 600 mm Hg. The perfusion buffer was not recirculated. The AL solution was made fresh daily and contained 200 μM (0.2 mM or 53.4 mg/L) adenosine plus 500 μM (0.5 mM or 136 mg/L) lidocaine-HCl in 10-mmol/L glucose-containing Krebs-Henseleit buffer (pH 7.7 at 37° C.), as described by Dobson and Jones with the following modifications: 16 mM $MgSO_4$ was used instead of 0.512 mM $MgCl_2$ in the arrest solution and two forms of citrate 1) citrate, phosphate and dextrose (CPD) commercially available solution, and 2) sodium citrate. The following groups were tested (n=8 per group):

Adenosine lidocaine magnesium (ALM) with 2% CPD (20 ml/L cardioplegia)
ALM with no citrate
ALM with 1.8 mM Na-citrate
ALM with 3.6 mM Na-citrate Intermittent Delivery:

The heart is arrested for a total time of 2 or 4 hours and arrest is ensured by a flush of cardioplegia every 18 min. The method of intermittent cardioplegic delivery has been previously described by Dobson and Jones (Dobson, 2004). Arrest in the Langendorff mode was induced by a 5-minute infusion of cardioplegic solution (50-100 mL) comprising 200 μM (0.2 mM or 53.4 mg/L) adenosine plus 500 μM (0.5 mM or 136 mg/L) lidocaine-HCL. The amount of A and L in mg in 100 ml over a 5 min period would be 5.34 mg adenosine and 13.6 mg Lidocaine-HCl or 1.07 mg adenosine per min and 2.72 mg/min lidocaine-HCl. Since the heart weighs around 1 gm in mg/min/kg this would be equivalent to 13.6 g/min/kg heart adenosine and 2.72 kg/min/kg heart lidocaine-HCl. through the aorta at 37° C. and a constant pressure of 68 mm Hg. After arrest, the aorta was cross-clamped at the completion of infusion with a plastic atraumatic aortic clip. Cardioplegia was replenished every 18 minutes with a 2-min infusion comprising 200 μM (0.2 mM or 53.4 mg/L) adenosine plus 500 μM (0.5 mM or 136 mg/L) lidocaine-HCL, after which the crossclamp was reapplied. After 2 hours (FIG. 20) or 4 hours (FIG. 21) of arrest with intermittent cardioplegic delivery, the heart was switched immediately to the working mode and reperfused with oxygenated, glucose-containing Krebs-Henseleit buffer at 37° C. The heart temperature during intermittent arrest ranged from 35° C. during delivery to about 25° C. before the next delivery (average 28°–30° C.), as directly measured and discussed by Dobson and Jones (Dobson, 2004).

Result and Explanation (FIG. 20A-C):

Surprisingly, at 60 min reperfusion, hearts arrested with ALM with citrate (2% CPD) cardioplegia returned 20% higher aortic flow (AF) than ALM alone after 2 hours warm intermittent arrest (FIG. 20A), and a 44% higher coronary flow (CF) (FIG. 20B). Since cardiac output (CO)=AF+CF in the working rat heart model, hearts arrested with ALM with citrate (2% CPD) had a 64% higher cardiac output than ALM alone. The second surprising finding was that hearts arrested with ALM and 1.8 mM Na-citrate cardioplegia generated 80% return of aortic flow, and equivalent to hearts arrested with ALM alone cardioplegia (FIG. 20A), but the addition of citrate led to a 38% higher coronary flow at 60 min reperfusion (FIG. 20B). This result demonstrates that at 60 min reperfusion the ALM 1.8 mM Na-Citrate hearts generated a 38% higher CO compared with hearts arrested with ALM cardioplegia alone for 2 hours. In addition, hearts arrested with ALM 2% CPD or 1.8 mM Na-citrate returned 105% of their baseline heart rate compared with 90% for ALM alone at 60 min reperfusion after 2 hours intermittent warm arrest, which represents a 17% higher return. Higher citrate levels (3.6 mM) generated 37.5% less aortic flow than ALM cardioplegia alone but similar coronary flow for a lower cardiac output. Thus it can be concluded that the addition of citrate in either CPD or 1.8 mM Na-citrate to ALM cardioplegia increased cardiac output by 67% and 38% respectively compared with hearts arrested in ALM cardioplegia alone.

Example 20b: (FIG. 21A-C)

This example is the same as Example 20a but differs by arresting the heart for 4 hours not 2 hours. After 4 hours arrest ALM (2% CPD)

Result and Explanation (FIG. 21A-C):

At 60 min reperfusion, hearts arrested with ALM citrate (2% CPD) or with ALM 1.8 mM Na-citrate cardioplegia returned similar aortic flow as ALM alone after 4 hours warm intermittent arrest (FIG. 21A), and a 20% and 10% higher coronary flow respectively than ALM alone (FIG. 21B). Thus ALM with citrate (2% CPD) or 1.8 mM Na-citrate had a 20% and 10% higher cardiac output than ALM alone. In addition, hearts arrested with ALM 2% CPD had 10% higher heart rate at 60 min reperfusion than ALM 1.8 mM Na-citrate or ALM cardioplegia alone. Higher citrate levels (3.6 mM) returned only 40% of baseline aortic flow and 80% coronary flow and heart rate. Thus it can be concluded that the addition of citrate as 2% CPD increased cardiac output by 20% and ALM (1.8 mM Na-citrate) over ALM alone after 4 hours of warm intermittent arrest compared with ALM cardioplegia alone. Heart rate was also nearly 100% return in ALM 1.8 mM Na-citrate compared with ALM alone at 60 min reperfusion.

Example 21(a): (FIG. 22A-D) the Effect of 8 Hours of Cold (4° C.) Continuous Perfusion of Adenosine and Lidocaine Solution with and without Gentle Bubbling (95% O2/5% $CO_2$) on Functional Recovery in the Isolated Working Rat Heart Background:

The adenosine and lidocaine solution is also versatile as a preservation solution at both cold static storage (4° C.) and warmer intermittent perfusion (28-30° C.) compared with FDA approved solution Celsior. The inventor published this information in the Journal of Thoracic and Cardiovascular Surgery in 2009 (Rudd and Dobson, 2009). In 2010, the inventor also showed that reperfusing the heart for 5 min with warm, oxygenated polarizing adenosine and lidocaine arrest following 6 hours cold static storage led to significantly higher recoveries in cold adenosine and lidocaine and Celsior hearts and it was proposed that this new reperfusion strategy may find utility during cold-to-warm 'wash' transitions and implantation of donor hearts.

In 2010 the inventor further reported that the adenosine and lidocaine cardioplegia could preserve the heart over 8 hours in cold static storage with a 78% return of cardiac output using normokalemic, polarizing adenosine and lidocaine at twice their concentrations (0.4 and 1 mM respectively) in glucose-Krebs-Henseleit solution with melatonin and insulin as ancillary or additional agents. This new adenosine and lidocaine preservation solution with ancillary agents returned 78% of cardiac output (CO) was significantly higher than 55% CO for AL cardioplegia, 25% CO for Celsior and 4% CO for Custodiol (HTK) preservation solutions after 8 hours cold static storage (4° C.). Thus adenosine and lidocaine alone (without ancillary agents) was not optimal for extended cold static storage times.

Over the past decade machine constant perfusion boxes or systems for organ preservation are becoming popular to prolong storage time and increase the donor pool. Perfusion with warm blood or oxygenated hypothermic preservation solutions may extend the ischemic interval and reduce reperfusion injury. These machines have a calibrated roller pump and membrane oxygenator to enable precise control of flow rate, oxygenation, and fluid temperature passing through the organ. Perfusing the heart with an oxygenated solution mimics the body's natural blood. If the tissue is able to maintain aerobic metabolism during machine perfused transport, the likelihood of myocardial damage is reduced. Another potential benefit to this method would be to increase the donor pool through the inclusion of marginal and non-heart beating donors. Continuous hypothermic perfusion of donor hearts may provide extra protection for long ischemic times and suboptimal donors. Thus transport of high-risk hearts using hypothermic machine perfusion provides continuous support of aerobic metabolism and ongoing washout of metabolic wastes.

Aim:

To examine the effect of gentle oxygenating the AL solution for 8 hour constant infusion preservation at 4° C. for possible use in machine boxes Compositions: Gentle Bubbling Adenosine and Lidocaine Solution and 5 min Rewarm: The modified Krebs Henseleit buffer contained 10 mmol/L glucose; 117 mmol/L NaCl, 5.9 mmol/L KCl, 25 mmol/L $NaHCO_3$, 1.2 mmol/L $NaH_2PO_4$, 0.225 mmol/L $CaCl_2$ (free $Ca^{2+}$=0.21 mmol/L), 2.56 mmol/L $MgCl_2$ (free $Mg^{2+}$=2.5 mmol/L), pH 7.4 at 37° C.

The buffer was filtered using a one micron (1 µM) membrane and was not recirculated. The concentration of adenosine in the solution was 0.4 mM. The concentration of lidocaine in the solution was 1 mM. This solution of modified Krebs Henseleit buffer, adenosine and lidocaine is referred to below as the cardioplegia preservation solution.

The 2.5 L glass bottle with the cardioplegia preservation solution was not actively bubbled itself. When gentle bubbling was required occurred in the vertical 30 cm long glass oxygenation chamber which delivered the cardioplegia to the isolated heart via the aorta and coronary artery ostia: ie retrograde Langendorff perfusion. The temperature-controlled chamber was filled with cardioplegia preservation solution and single gas tubing with a special stainless steel aerator at the end sitting at the bottom of the chamber prior to being delivered to the heart. Gentle bubbling was defined as a gas flow adjusted to deliver a few bubbles per sec in the chamber with 95% $O_2$/5% $CO_2$. In those cases were no bubbling was required the tubing was clamped off.

No Gentle Bubbling Adenosine and Lidocaine Solution and 5 min Rewarm:

The same composition as above but the solution was not bubbled with 95%$O2$/5% $CO_2$ to achieve a $pO_2$ around 140 mmHg and $pCO_2$ of around 5-10 mmHg and not recirculated.

Composition of Modified Krebs Henseleit (KH) Crystalloid Buffer for Baseline Data Before Arrest and 60 min Reperfusion in Working Mode The modified Krebs Henseleit buffer contained 10 mmol/L glucose; 117 mmol/L NaCl, 5.9 mmol/L KCl, 25 mmol/L NaHCO$_3$, 1.2 mmol/L NaH$_2$PO$_4$, 1.12 mmol/L CaCl$_2$ (free Ca$^{2+}$=1.07 mmol/L), 0.512 mmol/L MgCl$_2$ (free Mg$^{2+}$=0.5 mmol/L), pH 7.4 at 37° C. The perfusion buffer was filtered using a one micron (1 µM) membrane and then bubbled vigorously 95% $O_2$/5% $CO_2$ to achieve a $pO_2$ greater than 600 mmHg. The perfusion buffer was not recirculated.

Figure 22:
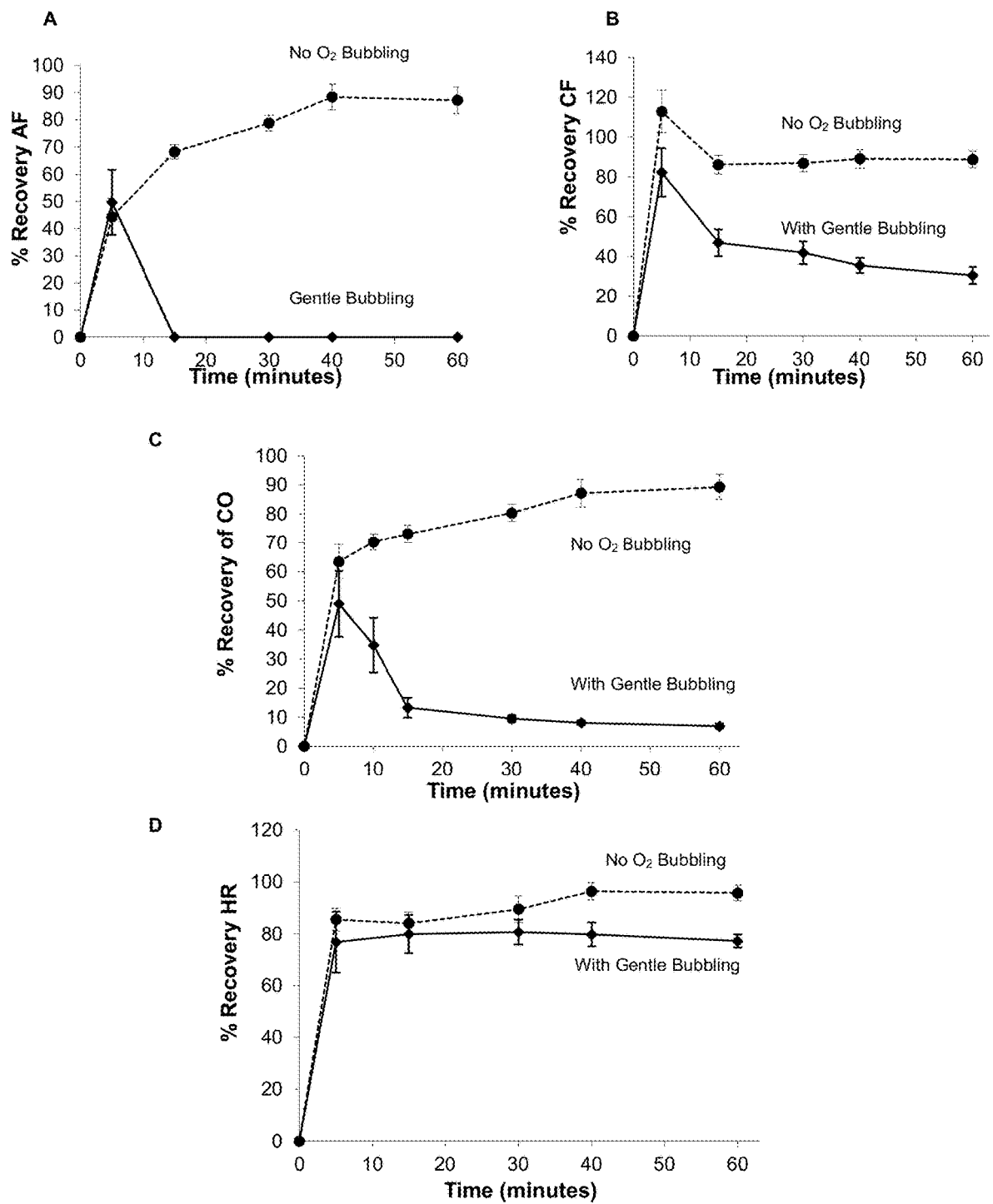
FIG. 22 shows graphs showing the effect of 8 hours of cold (4° C.) continuous perfusion of adenosine and lidocaine solution with and without gentle bubbling (95% $O_2$/5% $CO_2$) on functional recovery in the isolated working rat heart
Figure 23:
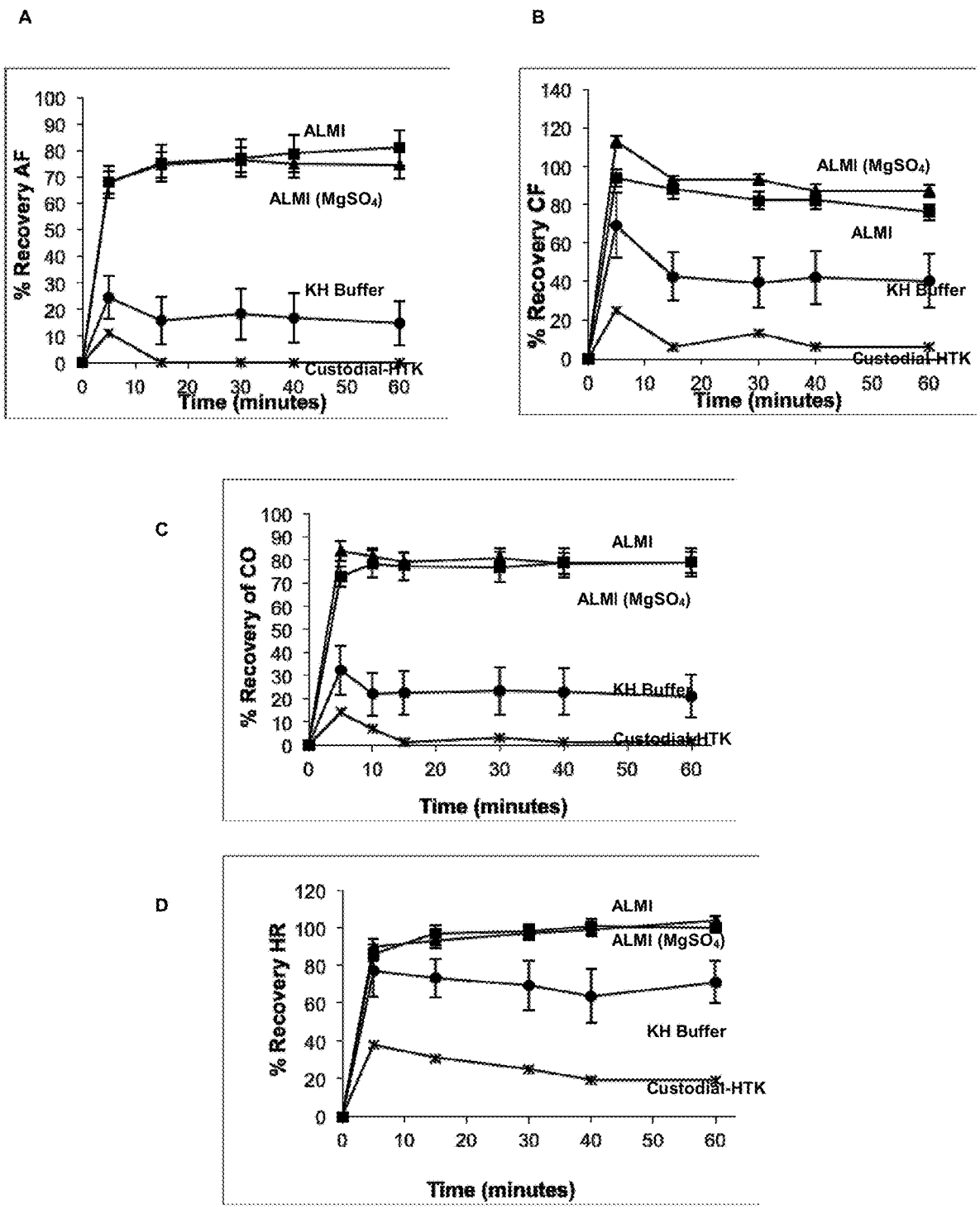
FIG. 23 shows graphs showing the effect of adding insulin and melatonin with high and low $MgSO_4$ to bubbled adenosine and lidocaine solution during 8 hours of constant perfusion at 4° C. in the isolated working rat heart.

Result and Explanation:

The following result was most surprising. Contrary to what was expected from the scientific and medical literature stating the advantages of gentle bubbling and oxygenation of long term preservation solutions for continual bathing of an organ or tissue, FIG. 22 shows that this was not the case. FIG. 22 shows that gently bubbling of the adenosine and lidocaine (lignocaine) preservation cold cardioplegia over the 8 hour cold perfusion period led to no aortic flow after 15 min reperfusion (FIG. 22A). Even more surprising, and in direct contrast, no active bubbling led to nearly 90% return of aortic flow or pump function. This result shows that gentle bubbling severely damages the heart to pump fluid from the left ventricle. In addition, gentle bubbling reduces coronary flow to 40% recovery of baseline compared to 90% for no-bubbling. This result indicates that gentle bubbling may damage the coronary vasculature that leads to a reduced recovery of flow from vasoconstriction. In summary, gentle bubbling led to a cardiac output (AF+CF) of less than 10% baseline indicating major damage to the heart's ability to function as a pump, whereas no bubbling of the adenosine and lidocaine preservation cardioplegia led to around 90% full recovery after 8 hours of constant perfusion at 4° C. (FIG. 22C). This unexpected effect of not-bubbling on ventricular function occurred despite 80% return in heart rate with gentle oxygenation, again showing that the effect of bubbling was on the ventricular muscle and coronary vasculature and not an inhibition of the pacemaker or the heart's conduction system (FIG. 22D).

Example 22(b): (FIG. 23A-D) the Effect of Adding Melatonin and Insulin with Low and High MgSO$_4$ to Bubbled Adenosine and Lidocaine Solution During 8 Hours of Constant Perfusion at 4° C. in the Isolated Working Rat Heart Methods:
Same as Example 21(a)
Compositions:
Same as Example 21(a) but with the following additions:
All solutions were gently bubbled during 8 hours of continuous perfusion. Gentle bubbling was defined as a gas flow adjusted to deliver a few bubbles per sec in the chamber with 95% $O_2$/5% $CO_2$. (see explanation in Example 21(a) Methods)

Adenosine and Lidocaine Cardioplegia Solution with Melatonin and Insulin (ALMI):

Same adenosine and lidocaine preservation cardioplegia above but with 100 µM melatonin and 0.01 IU/ml insulin (ALMI).

ALMI Mg2+ Solution:
Same as ALMI solution with the addition of 16 mmol/L MgSO$_4$.

Rewarm Solutions Before 60 min Reperfusion:
The rewarm solutions were the same solutions as the continuous infusion solutions but hearts were slowly rewarmed for 20 min in Langendorff mode by slowly heating the solutions to 37° C. and vigorously bubbled with 95% $O_2$/5% $CO_2$ to achieve a $pO_2$ greater than 600 mmHg and the solutions were not recirculated. This vigorous bubbling is in direct contrast to the gentle bubbling during 8 hours of perfusion (few bubbles per sec).

Reperfusion Solution:
After rewarm 60 min reperfusion solution following 8 hours constant perfusion as in Example 20(a)

Custodiol or Histidine-Tryptophan-Ketoglutarate Solution.

The Custodiol-HTK solution contained 15 mmol/L NaCl, 9 mmol/L, KCl, 4.0 mmol/L MgCl$_2$, 0.015 mmol/L CaCl$_2$, 1.0 mmol/L alpha-ketoglutarate, 180 mmol/L histidine, 18 mmol/L histidine-HCl, 30 mmol/L mannitol, and 2 mmol/L tryptophan.

Results and Explanation:

Equally surprising as Example 21(a) was the finding that adding melatonin and insulin to constant perfusion adenosine and lidocaine preservation cardioplegia largely abolished the damaging effects of gentle bubbling on aortic flow. Recall in Example 21(a) FIG. 22A), perfusing the heart with a solution of adenosine and lidocaine that had gentle bubbling resulted in zero aortic flow. The addition of melatonin and insulin with gentle bubbling led to 80% return of aortic flow (FIG. 22A) compared to 90% with adenosine and lidocaine without bubbling (FIG. 21A) implying that melatonin and insulin did not fully correct the damage but surprisingly reversed much of it after 8 hours of cold constant infusion and 60 min normothermic reperfusion (FIG. 22A). The addition of 16 mM MgSO$_4$ along to melatonin and insulin did not add further improvement with a 70% return of aortic flow compared to 80% with melatonin and insulin. Krebs Henseleit (KH) buffer alone only returned around 20% of aortic flow and FDA-approved preservation cardioplegia—custodial-HTK could not generate aortic flow (FIG. 22A). The same trends were seen in the functional recovery of coronary flow (CF) (FIG. 22B), heart rate (HR) (FIG. 22C) and cardiac output (CO) (FIG. 22D).

In conclusion, from Examples 21(a) and 21(b), adenosine and lidocaine preservation cardioplegia alone without gentle bubbling gave the highest return of aortic flow and cardiac output which implies superior left ventricular pump function than any cardioplegia group with different additives. Left ventricular pump function is a key parameter in assessing the success of donor heart storage and the success of cardiac function after heart transplantation or implantation.

Example 23: Effect of Adenosine and Lidocaine Solution with Low $Ca^{2+}$ (0.22 mM) and High $Mg^2$ (2.6 mM) (ALM) with 100 µM Cyclosporine A (ALM CyA) During 6 Hours Cold Static Storage (4° C.) in the Isolated Rat Heart Methods:

Hearts were rapidly removed from anaesthetised rats and placed in ice-cold heparinised modified KH buffer. Details of anesthesia, ethics approvals, heart preparation, attachment and perfusion are described in Rudd and Dobson (2009).

Krebs-Henseleit Perfusion Buffer (K-H):

The buffer contained 10 mmol/L glucose; 117 mmol/L NaCl, 5.9 mmol/L KCl, 25 mmol/L $NaHCO_3$, 1.2 mmol/L $NaH_2PO_4$, 1.12 mmol/L $CaCl_2$ (free $Ca^{2+}$=1.07 mmol/L), 0.512 mmol/L $MgCl_2$ (free $Mg^{2+}$=0.5 mmol/L), pH 7.4 at 37° C. The perfusion buffer was filtered using a one micron (1 µM) membrane and then bubbled vigorously with 95%02/5% $CO_2$ to achieve a $pO_2$ greater than 600 mmHg. The perfusion buffer was not recirculated.

Cold Static Storage Krebs-Henseleit Perfusion Buffer with Low Calcium High Magnesium:

The modified cold storage buffer (K-H ($LowCa^{2+}$:$HighMg^{2+}$)) contained 10 mmol/L glucose; 117 mmol/L NaCl, 5.9 mmol/L KCl, 25 mmol/L $NaHCO_3$, 1.2 mmol/L $NaH_2PO_4$, 0.22 mmol/L $CaCl_2$ (free $Ca^{2+}$=0.21 mmol/L), 2.6 mmol/L $MgCl_2$ (free $Mg^{2+}$=2.5 mmol/L), pH 7.4 at 37° C. The perfusion buffer was filtered using a one micron (1 µM) membrane and then bubbled vigorously with 95% $O_2$/5% $CO_2$ to achieve a $pO_2$ greater than 600 mmHg. The perfusion buffer was not recirculated.

Storage Adenosine-Lidocaine Solution with Low Calcium and High Magnesium:

The adenosine and lidocaine with low calcium and high magnesium (AL (Low $Ca^{2+}$:High $Mg^{2+}$)) solution contained (0.2 mM) adenosine plus 0.5 mM lidocaine in 10 mmol/L glucose containing Modified Krebs Henseleit ($LowCa^{2+}$:$HighMg^{2+}$) buffer (pH 7.7 at 37° C.) The solution was filtered using 0.2 µM filters and maintained at 37° C. The arrest solution was not actively bubbled with 95% $O_2$/5% $CO_2$ hence the higher pH. The average $pO_2$ of the AL solution was 140 mmHg and the $pCO_2$ was 5-10 mmHg.

Rats were randomly assigned to one of 2 groups (n=8 each group): 1) AL ($LowCa^{2+}$:$HighMg^{2+}$) cold (4° C.) static storage plus 5 min rewarming KH 2) AL ($LowCa^{2+}$:$HighMg^{2+}$)+100 uM Cyclosporine A. After 5 min rewarm, hearts were switched to working mode and reperfused with modified KH buffer for 60 min.

Results:

TABLE 6

| 6 hours cold arrest (n = 8) | Aortic Flow (ml/min) | Coronary Flow (ml/min) | Cardiac Output (ml/min) | Heart Rate Beats/min |
|---|---|---|---|---|
| Pre-Arrest 15 min | | | | |
| ALM | 68 ± 2 | 22 ± 2 | 90 ± 3 | 296 ± 11 |
| ALM CyA | 61 ± 4 | 18 ± 4 | 79 ± 4 | 269 ± 9 |
| SIX HOURS COLD STATIC STORAGE (4° C.) | | | | |
| Reperfusion 15 min | | | | |
| ALM | 30 ± 3 | 14 ± 1 | 44 ± 4 | 259 ± 14 |
| ALM CyA | 36 ± 7 | 18 ± 2 | 54 ± 9 | 235 ± 28 |
| 30 min | | | | |
| ALM | 37 ± 4 | 14 ± 1 | 51 ± 5 | 269 ± 12 |
| ALM CyA | 42 ± 4 | 17 ± 1 | 59 ± 6 | 286 ± 13 |
| 60 min | | | | |
| ALM | 33 ± 4 (49%) | 15 ± 1 (68%) | 48 ± 4 (53%) | 263 ± 10 |
| ALM CyA | 44 ± 4 (72%) | 19 ± 2 (106%)* | 63 ± 5 (80%) | 313 ± 9 |

Conclusions:

The addition of cyclosporine A improves cardiac output by 1.5 times following 6 hours cold static storage. Cyclosporine A may be a possible additive to the ALM cardioplegia/preservation solution for the arrest, protection and preservation of organs, cells and tissues.

Example 24: (FIG. 24) the Effect of Adenosine and Lidocaine Solution with 0.3 mg/L Sildenafil Citrate Over 2 Hours Warm Arrest (29° C.) Given Every 20 Minutes (2 Min Infusion) and 60 min Reperfusion in the Working Rat Heart Methods:

Rat Hearts were rapidly removed from anaesthetised rats and placed in ice-cold heparinised modified KH buffer. Details of anesthesia, ethics approvals, heart preparation, attachment and perfusion methods are described in Dobson and Jones (Dobson, 2004). The adenosine and lidocaine solution was made fresh daily and contained 200 µM (0.2 mM or 53.4 mg/L) adenosine plus 500 µM (0.5 mM or 136 mg/L) lidocaine-HCL (arrest and 2 min infusion every 20 min is the same as example 20) The concentration of sildenafil citrate 3 mg/L (6.3 micromolar).

Results:

During 60 min reperfusion, AL sildenafil citrate returned 86% of aortic flow, and 84% coronary flow for 85% cardiac output compared to baseline. In 2004 we published AL alone returned 74% as reported in Dobson and Jones. Heart rate returned 100% of baseline compared to 95% in 2004.

Conclusions:

AL sildenafil produces 85% cardiac output and 100% heart rate after 2 hours warm arrest.

Example 25: Effect of Adenosine and Lidocaine Solution with Normal $Ca^{2+}$ (1.12 mM) and Normal $Mg^{2+}$ (0.5 mM) with 10 mM 2,3-Butanedione Monoxime (BDM) a During 2 Hours of Warm Arrest (29° C.) in the Isolated Rat Heart (Intermittent Delivery Every 20 Min)

Rat Hearts were rapidly removed from anaesthetised rats and placed in ice-cold heparinised modified KH buffer. Details of anesthesia, ethics approvals, heart preparation, attachment and perfusion methods are described in Dobson and Jones (Dobson, 2004). The adenosine and lidocaine solution was made fresh daily and contained 200 µM (0.2 mM or 53.4 mg/L) adenosine plus 500 µM (0.5 mM or 136 mg/L) lidocaine-HCL (arrest and 2 min infusion every 20 min is the same as example 20)

Results:

TABLE 7

| 2 hrs warm arrest (n = 8) | Aortic Flow (ml/min) | Coronary Flow (ml/min) | Cardiac Output (ml/min) | Heart Rate Beats/min |
|---|---|---|---|---|
| Pre-Arrest 5 min | | | | |
| ALM BDM | 64 | 23 | 87 | 250 |
| 2 hours warm arrest using intermittent delivery (29° C.) | | | | |
| Reperfusion 15 min | | | | |
| ALM BDM 30 min | 8 | 15 | 26 | 156 |
| ALM BDM 45 min | 22 | 17 | 39 | 241 |
| ALM BDM | 27 | 17 | 44 | 262 |

Conclusions:

AL BDM recovers 105% heart rate after 2 hours warm arrest and 51% cardiac output.

Example 26: Effect of Adenosine and Lidocaine Solution with Normal $Ca^{2+}$ (1.12 mM) and Normal $Mg^{2+}$ (0.5 mM) with 54 µM Propofol (P) (1 mg/L) During 2 Hours of Warm Arrest (29° C.) in the Isolated Rat Heart (Intermittent Delivery Every 20 Min)

Methods:

Rat Hearts were rapidly removed from anaesthetised rats and placed in ice-cold heparinised modified KH buffer. Details of anesthesia, ethics approvals, heart preparation, attachment and perfusion methods are described in Dobson and Jones (Dobson, 2004). The adenosine and lidocaine solution was made fresh daily and contained 200 µM (0.2 mM or 53.4 mg/L) adenosine plus 500 µM (0.5 mM or 136 mg/L) lidocaine-HCL (arrest and 2 min infusion every 20 min is the same as example 20)

Results:

TABLE 8

| 2 hrs warm arrest (n = 8) | Aortic Flow (ml/min) | Coronary Flow (ml/min) | Cardiac Output (ml/min) | Heart Rate Beats/min |
|---|---|---|---|---|
| Pre-Arrest 5 min | | | | |
| ALM P | 62 | 20 | 82 | 257 |
| 2 hours warm arrest using intermittent delivery (29° C.) | | | | |
| Reperfusion 30 min | | | | |
| ALM P 45 min | 26 | 28 | 45 | 226 |
| ALM P 45 min | 48 | 21 | 53 | 250 |
| ALM P | 45 | 20 | 60 | 250 |

Conclusions:

AL propofol recovers 98% heart rate after 2 hours warm arrest and 73% cardiac output.

Example 27: Effects of Polarizing ALM with Insulin Microplegia Vs Buckberg 1:4 High Potassium Depolarizing Cardioplegia on Intracellular Metabolism in Human Cardiac Surgery. Pro-Survival Kinase, and Apoptosis in Humans This study compared the ALM with insulin cardioplegia (normal potassium) with high potassium cardioplegia in humans conducted at Division of Cardiac Surgery, University Of Verona Medical School, Italy.

Methods:

Sixty consecutive patients undergoing isolated aortic valve replacement were randomly allocated to adenosine-lidocaine-magnesium with insulin in the concentrations and dosages described in Example 28 (30 patients) or standard 4:1 blood DA (30 patients) according to "Buckberg-protocol". Coronary sinus blood was sampled for lactate release preoperatively (T0) and after reperfusion (T1). Myocardial specimens from right atrium were analyzed for high-energy phosphate content, energy charge, activation of pro-survival kinases Akt and ERK1/2, and cardiomyocyte apoptosis (TUNEL-assay) at T0 vs T1. Spontaneous recovery of sinus rhythm (SRSR) at aortic declamping was also recorded.

Results:

Data are presented in Table 9. Blood lactate from coronary sinus was lower at T1 after PA (2.04±0.03 mmol/L vs 2.57±0.02 after DA; p=0.03), whereas SRSR was higher (64% vs 32% in DA-patients; p=0.02). Plasma K+ did not significantly changed at T1 in PA patients (p=NS vs T0). PA, not DA, preserved myocardial high-energy phosphate content and energy charge (0.79±0.02 vs 0.73±0.02; p<0.001). Activation of pro-survival kinases Akt and ERK1/2 at T1 was higher after PA, not after DA (ΔpAkt/Akt −0.26 vs 0.85; ΔpERK1/ERK1-0.18 vs 0.77; ΔpERK2/ERK2-0.28 vs 0.65; p<0.001 after PA, p=N.S. after DA). Cardiomyocyte apoptotic index was lower after PA (0.13±0.10 vs 0.35±0.12; p=0.01).

TABLE 9

Effect of polarizing ALM with Insulin blood microplegia vs High Potassium Depolarizing 4:1 cardioplegia in humans. SRSR = spontaneous return of spontaneous rhythm

| Parameter | Polarized ALM with Insulin arrest | Depolarizing 4:1 arrest | Significant |
|---|---|---|---|
| Blood Lactate at reperfusion | 2.04 ± 0.03 | 2.57 ± 0.02 | Yes P = 0.03 |
| SRSR | 64% | 32 | Yes P = 0.02 |
| Plasma K+ | Not different | Not different | Not Significant |
| Energy Charge | 0.79 ± 0.02 | 0.73 ± 0.02 | Yes P < 0.001 |
| Pro-survival kinases (Akt and ERK1/2) | Activation was higher | Lower | Yes p < 0.001 |
| Myocyte apoptotic index | 0.13 ± 0.1 (60% less) | 0.35 ± 0.12 | Yes p = 0.01 |

Conclusion:

Polarising arrest with ALM and insulin preserves myocardial high-energy phosphates and energy charge, and activates pro-survival kinases Akt and ERK resulting in attenuated apoptosis. PA is superior to DA at the myocellular level.

Example 28: Effect of Polarizing Adenosine-Lidocaine-Magnesium (ALM) with Insulin Microplegia (MAPAS) Vs High Potassium Depolarizing 4:1 Cardioplegia in Higher Risk Diabetics Undergoing Revascularization Cardiac Surgery for Unstable Angina Diabetes mellitus affects 230 million people worldwide. Diabetes is a well-recognized independent risk factor for mortality and morbidity due to coronary artery disease. When diabetic patients need cardiac surgery, either CABG or valve operations, the presence of diabetes represents an additional risk factor for these major surgical procedures. Diabetic patients undergoing CABP have, on the basis of the relative risk evaluation, a 5-fold risk for renal complications, a 3.5-fold risk for neurological dysfunction, a double risk of being hemotransfused, reoperated or being kept 3 or more days in the ICU in comparison with non-diabetic patients. Moreover, diabetic patients undergoing valve operations have a 5-fold risk of being affected by major lung complications. Current hyperkalemic techniques of cardioplegic arrest result in increased myocardial apoptosis and necrosis in diabetics, especially during unstable angina (UA) and ischemia/reperfusion injury. No study has investigated the effects of microplegia addition with polarizing-arresting substrates with adenosine and lidocaine and magnesium (ALM) with insulin (MAPAS) in this setting.

This study compared the ALM-Insulin cardioplegia with high potassium cardioplegia in high-risk diabetic humans conducted at Division of Cardiac Surgery, University Of Verona Medical School, Italy.

Methods:

Sixty UA-diabetics undergoing CABG were randomized to adenosine/lidocaine with insulin (MAPAS) (30 patients) or 4:1-Buckberg cardioplegia (30 patients; Buck-Group). MAPAS composition was 10.4 mg Adenosine, 43 mg Lidocaine-HCl and 3.5 g MgSO$_4$ in 40 ml w1 mM Adenosine, 4 mM Lidocaine-HCl and 350 mM MgSO$_4$ in 40 ml) with insulin.

Induction of Arrest:

30 mM K$^+$ ALM(I)* vs 20 mM K$^+$ Buckberg (Additive 8 ml/L of blood cardiopleqia) Contact concentrations therefore for ALM are 8 µM A, 32 µM L and 2.8 mM MgSO$_4$ Maintenance:

8 mM K$^+$ ALM(I) vs 7 mM Buckberg (Additive 8 ml/L of blood cardioplegia) Contact concentrations therefore for ALM are 8 µM A, 32 µM L and 2.8 mM MgSO$_4$ Reperfusion (Reanimation):

HOT SHOT: No K$^+$ in ALM(I) vs 9 mM K$^+$ in Buckberg (Additive 50 ml/L of blood cardiopleqia) Contact concentrations therefore for ALM are 15 µM A, 60 µM L and 5.25 mM MgSO$_4$ Troponin-I and lactate were sampled from coronary sinus at reperfusion (T1), and from peripheral blood preoperatively (T0), at 6 (T2), 12 (T3) and 48 (T4) hours. Hemodynamic monitoring derived cardiac index (CI), left ventricular dP/dt, cardiac-cycle efficiency (CCE), indexed systemic vascular resistances (ISVR) and central venous pressure (CVP) preoperatively (T0), at ICU-arrival (T1), after 6 (T2) and 24 (T3) hours. Echocardiographic wall motion score index (WMSI) investigated the systolic function, E-wave (E), A-wave (A), E/A, peak early-diastolic TDI-mitral annular-velocity (Ea), E/Ea the perioperative diastolic function preoperatively (T0) and at 96 hours (T1).

Results:

Data are presented in Table 2. MAPAS with Insulin attenuated troponin-I and lactate release at T1 (p<0.001); postoperative troponin-I values were lessened by MAPAS (between-groups p=0.001), with an improved overall hemodynamic profile (between-groups p=0.0001, p=0.002, 0.0001, 0.0001 for CI, CCE, dP/dt and peripheral lactate) at similar preload and afterload values (between-groups p=N.S. for ISVR and CVP). Systolic and diastolic function improved only in MAPAS-Group (T0 vs T1-p≤0.01 for WMSI, E, A, E/A and Ea; p=NS in Buck-Group). Transfusions of red-packed cells and fresh-frozen plasma, ICU-stay and hospital-stay were all reduced by MAPAS (p≤0.0001).

TABLE 10

Effect of modified polarizing ALM with Insulin microplegia vs High Potassium Depolarizing 4:1 cardioplegia in higher risk diabetics undergoing revascularization cardiac surgery for unstable angina. ISVR = Indexed systemic vascular resistance

| Parameter | Polarized ALM arrest with INSULIN (MAPAS) | Depolarizing 4:1 arrest | Significant |
|---|---|---|---|
| Blood Lactate at reperfusion | Lower | Higher | Yes P < 0.001 |
| Troponin-1 | Lower | Higher | Yes P < 0.001 |
| Cardiac index | Higher | Lower | Yes P < 0.001 |
| Left dp/dT | Higher | Lower | Yes P < 0.001 |
| Cardiac cycle efficiency | Improved | | Yes p < 0.001 |
| ISVR | Not different | Not different | Not Significant |
| Central venous pressure | Not different | Not different | Not Significant |
| systolic function | Higher | Lower | Yes p < 0.001 |
| Hemodynamic profile | Higher | Lower | Yes p < 0.001 |
| Transfusions of red-packed cells | Lower | Higher | Significant p < 0.001 |
| Transfusions of fresh-frozen plasma, | Lower | Higher | Significant p < 0.001 |
| ICU-stay and hospital-stay | Lower | Higher | Significant p < 0.001 |

Conclusions:

Modified microplegia ALM with Insulin cardioplegia improved myocardial protection in high-risk diabetic patients referred to CABG surgery for unstable angina.

Example 29: The Effect of Microplegia ALM and Insulin Solution with a Form of Citrate (CPD or Sildenafiil Citrate) on Cardiac Function and Inflammation, Coagulation, and Brain Function During and Following Cardiac Surgery Background:

The use of cardiopulmonary bypass for surgical cardiac procedures is characterized by a whole-body inflammatory reaction and coagulation imbalances due to the trauma of surgery, contact of blood through nonendothelialized surfaces which can activate specific (immune) and nonspecific (inflammatory) and coagulative responses ( ). These responses are then related with postoperative injury to many body systems, like pulmonary, renal or brain injury, excessive bleeding and postoperative sepsis.

Methods:

Repeat the above clinical trial in Example 27 but with a form of citrate present with the ALM with insulin cardioplegia. With groups with ALM insulin with CPD and a separate group with ALMI and sildenafil citrate.

Expected Results:

This example will show that ALM cardioplegia with a form of citrate (CPD or sildenafil citrate) will improve cardiac function, reduce inflammation and reduce coagulation disturbances with less brain and renal injury.

Example 30: The Effect of ALM Solution with a Form of Citrate (CPD or Sildenafiil Citrate) on Cardiac Function and the Presence of Microparticles (MPs) in the Blood During and Following Cardiac Surgery Background:

The use of cardiopulmonary bypass for surgical cardiac procedures is characterized by a whole-body inflammatory reaction and coagulation imbalances due to the trauma of surgery, contact of blood through nonendothelialized surfaces which can activate specific (immune) and nonspecific (inflammatory) and coagulative responses. These responses are then related with postoperative injury to many body systems, like pulmonary, renal or brain injury, excessive bleeding and postoperative sepsis. Microparticles are known to contribute to activation of the complement system in patients undergoing cardiac surgery and may be linked to brain and organ injury.

Methods:

Repeat the above clinical trial as described in Example 27 but contain a form of citrate in the ALM cardioplegia with insulin.

Expected Results:

This example will show that ALM insulin cardioplegia with a form of citrate (CPD or sildenafil citrate) will improve cardiac function and reduce microparticles, reduce inflammation and reduce coagulation disturbances with less brain and renal injury.

Example 31: Lung Preservation with ALM with Sildenafil Citrate, ALM Citrate Phosphate Dextrose (CPD), ALM Citrate with Cyclosporine A or ALM with Erythropoietin, Glyceryl Trinitrate and Zoniporide in the Pig after 12 and 24 Hour Cold Ischaemia Background:

Pulmonary preservation for transplantation is associated with inflammation, endothelial cell injury and surfactant dysfunction. Inflammation and the induction of the primary immune response are important in arresting an organ and in lung preservation and can be assessed by measuring tumor necrosis factor alpha (TNFα), interleukin-6 (IL-6) and receptor for advanced glycation endproducts (RAGE) in bronchoalveolar lavage fluid.

Aim:

The study's goal is to assess the effect of ALM cardioplegia/preservation solutions on lung function following 12 and 24 hour cold storage and compare with Celsior and low phosphate dextran solution (e.g. Perfadex, Vitrolife) and Lifor (LifeBlood Medical Inc, NJ).

Methods:

The methods used for this porcine study are similar to Sommer and colleagues (Sommer et al., 2004) with the following modifications. Lungs will removed and perfused with ALM solutions (five ALM solutions) groups: ALM citrate phosphate dextrose (CPD (n=10), ALM CPD (n=10), ALM sildenafil citrate (n=10) and ALM citrate-cyclosporine A (n=10) or ALM with erythropoietin, glyceryl trinitrate and zoniporide (n=10) and these will be compared with Celsior (n=10) and low phosphate dextran solutions (n=10) and lifor (n=10). After 12 hr (80 hearts) and 24 hr (80 hearts) cold storage, the lungs will be transplanted into recipient animals. After reperfusion of the left lung, the right pulmonary artery and bronchus will be clamped. Bronchoalveolar lavage fluid (BALF) will be obtained before the surgical procedure and 2 hr after reperfusion. Surfactant activity will be measured from BALF using a pulsating bubble surfactometer. Hemodynamic and respiratory parameters will be assessed in 30-min intervals for 10 post-operative hours. Mortality will also be examined.

Expected Results:

The ALM preservation solutions will lead to no deaths after storage and implantation compared to Celsior or low potassium dextran, and Lifor storage solutions after both 12 and 24 hours. A second finding will be that ALM groups will have significantly less pulmonary vascular resistance index, and less sequestration of neutrophils compared to Celsior or low potassium dextran, and Lifor storage solutions after both 12 and 24 hours. Improvement in surfactant activity will also be evident in the ALM solutions and improved haemodynamics over 5 hours post storage and transplant.

Conclusions:

ALM cardioplegia preservation with sildenafil citrate or CPD will be superior to standard of care solutions and FDA approved Celsior and Perfadex (or Vitrolife), or Lifor for cold lung storage and implantation.

Example 32: Effect of ALM with Sildenafil Citrate, ALM Citrate, ALM Citrate with Cyclosporine A, ALM Erythropoietin or ALM with Erythropoietin, Glyceryl Trinitrate and Zoniporide in the Ex-Vivo Lung Perfusion (EVLP) Organ Care System (OCS)

Background:

Normothermic ex-vivo lung perfusion (EVLP) has advantages that include ongoing cellular metabolism with reduced injury and continuous functional evaluation of potential lungs post-retrieval. The disadvantages include cost and the expertise needed for its use.

Aim:

The aim of this study was to assess the feasibility of transplanting high-risk donor lungs using ALM solutions and comparing with Celsior and low potassium dextran solutions (Perfadex, Vitrolife) or Lifor (LifeBlood Medical) at 29-30° C. for lung preservation.

Method:

The method is that described in detail by Cypel and colleagues (Cypel et al., 2011). Ninety patients (10 per group) will be recruited after obtaining the hospital's internal review board protocol approval and patient or family consent for the study. Patients will be randomly assigned to ALM citrate, ALM sildenafil, ALM CPD, ALM CPD cyclosporine A, ALM Erythropoietin, and ALM with erythropoietin, glyceryl trinitrate and zoniporide or to Celsior and low K dextran or LIFOR solutions. Lungs will be perfused for 4 hours in the ex-vivo lung perfusion (EVLP) Organ Care System (OCS). Lungs will be considered suitable for transplantation if 1) during EVLP the PO2:FiO2 ratio (ie. the partial pressure of oxygen ex vivo (P02) to the fraction of inspired oxygen (FiO2) of 350 mm Hg or more) and 2) if deterioration from baseline levels of all three physiological measurements (pulmonary vascular resistance, dynamic compliance, and peak inspiratory pressure) was less than 15% while the lungs were ventilated with the use of a tidal volume of 7 ml per kilogram of donor body weight and a rate of 7 breaths per minute during the perfusion period. The primary end point will be graft dysfunction 72 hours after transplantation. Secondary end points will be 30-day mortality, bronchial complications, duration of mechanical ventilation, and length of stay in the intensive care unit and hospital.

Expected Results and Conclusions:

We will show that ALM solution with a form of citrate will have an improved functional after recovery in ex vivo perfused lungs for 4 hours at tepid temperatures from high-risk donors at tepid temperatures compared to Celsior, Perfadex, Vitrolife or Lifor solutions.

Example 33: Effect of ALM with Sildenafil Citrate, ALM Citrate, ALM Citrate Cyclosporine A, ALM Erythropoietin or ALM with Erythropoietin, Glyceryl Trinitrate and Zoniporide for the Ex-Vivo Lung Perfusion with and without Nanoparticles Containing Oxygen with the Capacity to Release $O_2$ to the Cells Mitochondria Background:

Long-term continuous perfusion preservation is hampered by the need for gas bottles to supply oxygen and carbon dioxide to meet the demands of the donor organ, tissue or cell. Oxygen is required to sustain life in amounts and partial pressures that can range from small to high-energy demand states. Nanobubbles can be prepared with gas "storage" core. Perfluoropentan gas can favor oxygen entrapment. On a volume basis, Van Liew has previously shown that gaseous perfluorocarbon compounds may deliver more oxygen than liquid perfluorocarbons. Oxygen loaded lipid-coated perfluorocarbon microbubbles have been prepared for oxygen delivery; these oxygen-enriched microbubbles have been tested in a rat model of anemia and the results showed that it maintained the rat's survival at very low hematocrit levels. The oxygen release kinetics could be enhanced after nanobubble insonation with ultrasound at 2.5 MHz. It has previously been shown that oxygen-filled nanobubbles were prepared using perfluoropentan as core and dextran sulphate, a polysaccharide polymer, as shell the dextran nanobubbles were able to release oxygen in hypoxic condition.

Aim:

The study is the same design as Example 31 differing only in the ALM groups with a form of citrate and oxygen loaded nanoparticle and solutions perfused lungs at normothermic (tepid) temperatures for 4 hours.

Methods:

Oxygen-filled nanobubbles were prepared using perfluoropentan as core and dextran sulphate, a polysaccharide polymer, as shell (Cavalli et al., 2009). Polyvinylpyrrolidone (PVP) was added to the shell as a stabilizing agent. Methods same as Example 31 and 5 ALM groups (50 lungs).

Expected Results and Conclusions:

We will show that ALM with a form of citrate with oxygen-loaded nanoparticles ex vivo perfused lungs for 4 hours from high-risk donors at tepid temperatures have equivalent or improved functional after recovery of lungs compared with ALM solutions without nanoparticles.

Example 34: Effect of ALM with Sildenafil Citrate, ALM with Citrate, ALM Citrate Cyclosporine A or ALM Erythropoietin (and a Separate Group ALM with Erythropoietin, Glyceryl Trinitrate and Zoniporide) to Treat the Donor Patient 5 to 15 Min Before Organ Harvest and Improve Donor Organ Viability and Function Background:

Transplanted lungs are subjected to injuries including the event causing death of the donor, the inflammatory cascade in brain death, resuscitation of the donor and management in the intensive-care unit and on ventilation. In addition there is injury related to organ harvest, preservation (storage or perfusion), transport, and implantation injury. Once implanted from donor to recipient, ischaemia-reperfusion injury is followed by immunological attack of the foreign organ by the recipient host. For optimum short-term and long-term results, a composition and method is needed to prevent injury at all these stages. Organ preservation thus begins in the donor. Cerebral injury and brain death also is associated with apparent hypercoagulation and poor organ outcome.

Aim:

The aim of this study is to examine the effect of ALM citrate infusions in the validated pig model of intracranial hemorrhage and brain death.

Methods:

Pigs will be divided into 8 groups of 10 pigs per group and the solutions will be infused 5 min before organ harvest after pronounced brain death and the catecholamine storm. The groups will include: ALM citrate (n=10), ALM CPD (n=10) ALM sildenafil (n=10), ALM citrate cyclosporine A (n=10), ALM Erythropoietin (n=10) or ALM with erythropoietin, glyceryl trinitrate and zoniporide (n=10) and these will be compared with Celsior (n=10) and low phosphate dextran solutions (n=10) and lifor (LifeBlood Inc) (n=10). The following metrics will include inflammatory markers TnF alpha, IL6, epinephrine, lactate, pH, hemodynamics, cardiac function prior to harvest and coagulopathy. Immediately following harvest; tissues will be prepared for histology and tissue fluorescence studies examining tissue injury.

Expected Results and Conclusions:

We will show that ALM citrate treated body after brain death will lead to less damage to tissues reduce coagulopathy and better prepare the organ, tissue or cell for cold storage, cold perfusion or warm perfusion than Celsior or low Potassium dextran and Lifor solutions prior to implantation into a recipient animal.

Example 35: Reducing Memory Loss, Blood Loss, Coagulopathy and Protecting the Kidney and Organs During Cardiac Surgery Including Aortic Repair Surgery: ALM Citrate Solution and Drug Loaded Solid Lipid Nanoparticles for Brain Protection Background:

Depending upon the type of cardiac surgery 10 to 40% of adult patients will experience transient cognitive dysfunction or delirium, which can last for up to 5 years, and 2%-13% patients will have a stroke. Four to 40% of patients will have some form of renal dysfunction and perioperative bleeding is a common complication of cardiac surgery with excessive bleeding occurring in 20% of patients, and 5-7% will lose in excess of 2 L within the first 24 h postoperatively.

It has been estimated that about 50% of blood loss is due to identifiable surgical bleeding, and the other 50% is due to a complex hypocoagulopathy associated with surgical trauma and cardiopulmonary bypass. Similarly, in pediatric patients undergoing complex congenital corrective operations, many will have acute post-operative complications such as tissue edema with postoperative weight gain, systemic coagulation disorders, surgical complications and low output syndrome (up to 25%), arrhythmias (27-48%), renal dysfunction (up to 30%), and cerebral dysfunction and stroke (5 to 10%). Brain injury in the form of temporary or permanent neurological dysfunction also remains a major cause of morbidity and mortality following aortic arch surgery or large intracranial aneurysm surgeries in both adults and pediatric and neonate patients.

Study Aim:

The aim of the study is to test the protective effect of ALM with sildenafil citrate, ALM citrate beta-hydroxy butyrate and ALM citrate-propofol loaded into nanospheres and without nanospheres on brain function. The vehicle will include whole blood.

Study Plan:

There will be four arms to the study 1) whole blood alone (no treatment), 2) whole blood alone with nanoparticles, 3) whole blood with ALM alone, 4) ALM with sildenafil citrate, 5) ALM citrate with beta-hydroxy butyrate and 6) ALM citrate-propofol in whole blood and the three treatment groups loaded in nanoparticles. Total number of 9 groups n=8 per group is 72 subjects. ALM bolus will be (1 mg adenosine; 2 mg Lidocaine-HCl and 0.3 g $MgSO_4$,) and ALM infusion Adenosine; 0.2 mg/kg/min. Lidocaine-HCl; 0.4 mg/kg/min and $MgSO_4$; 0.224 g/kg/min. Sildenafil=1 mg/L, propofol 1 mg/kg; BHB (4 mM blood concentration). 10 ml Bolus administered via the innominate and left common carotid arteries (Di Eusanio et al., 2003) followed by infusion 10 ml/kg/min in whole blood.

Surgical Methods and Cerebral Perfusion:

72 patients (8 per group) will be recruited after obtaining the hospital's internal review board protocol approval and patient consent for the study. The methods for aortic arch surgery and dissection are described by Kruger et al., (Kruger et al., 2011) and Misfield and others (Misfeld et al., 2012), and references therein. Cerebral perfusion aims for a flow of 10 ml/kg body wt/min which is normally adjusted to maintain a radial arterial pressure of between 40 to 70 mm Hg (Di Eusanio et al., 2003). Cerebral monitoring is achieved by a right radial arterial pressure line, electroencephalography, regional oxygen saturation in the bilateral frontal lobes with near-infrared spectroscopy, and transcranial Doppler ultrasonographic measurement of the blood velocity of the middle cerebral arteries.

Primary and Secondary Endpoints:

Primary end points will include brain damage biomarkers such as neurofilament (NF), S100β, glial fibrillary acidic protein (GFAP), and ubiquitin carboxyl terminal hydrolase-L1 (UCH-L1) neuron-specific enolase (NSE)) (Yokobori et al., 2013). Brain ischemia will be assessed using blood lactate levels and pH. Inflammation will be assessed using select markers (e.g. IL-1, IL-6, IL-12, tumor necrosis factor-alpha), and coagulopathy using coagulometry (aPTT, PT) and visco-elastic ROTEM analysis. Temporary neurological deficit, 30-day mortality and mortality-corrected permanent neurological dysfunction will be assessed. The 30-day mortality will include any death that occurred from the intraoperative period until the $30^{th}$ postoperative day. Secondary end points will be perioperative complications and perioperative and postoperative times, intubation times. This example will demonstrate one aspect of the invention, which is to protect the brain using non-arrest levels of the composition in bolus and constant infusion with and without nanoparticles. An arm may be included where the doses are raised to examine another aspect of the invention to arrest the brainstem (and higher centres) during circulatory arrest for aortic reconstructions or large intracranial aneurysm surgeries. This example would also be applicable for pediatric and neonatal circulatory arrest interventions and surgeries.

Example 36: Effect of AL or ALM Solution with Polyethylene Glycol

3-Butanedione Monoxime (BDM); polyethylene glycol, dextran-40; P188; Lactobionate; bovine serum albumin (BSA) to flush and preserve porcine kidneys for 10 hours.

Background:

Cold static cold storage remains the mainstay of preservation for kidney allografts worldwide but machine perfusion is becoming increasingly popular. The key to kidney preservation is to reduce damage to the kidney from pre-harvest to implantation, and of particular interest is the time for the kidney to provide adequate renal function, reducing the need for dialysis, the primary purpose of the transplant. One key factor is effective graft washout of blood remnants before ischemia cold storage. The presence of blood remnants and cellular debris may contribute to impaired blood flow and injury upon reperfusion. An effective washout of the kidney by the preservation solution prevents cell swelling, formation of interstitial edema, and excessive cellular acidosis, injury and potentially graft failure. Numerous preservation solutions have been developed for harvest and washout, storage, rewarming and reperfusion but none are optimal. In a recent review there was no clinical difference in the incidence of delayed graft function between Custodial (HTK), Celsior or University of Wisconsin (UW) solution. Eurocollins was associated with a higher risk of DGF than UW solution.

Aim:

To examine the effect of a variety of AL(M) solutions in kidney washout (flush) and 12 hours cold static preservation compared to FDA approved Custodial (HTK) in adult pigs. The amounts of A and L are as set out in the tables below (A=4 mM and L=10 mM, with the extra components as marked in the table in Krebs Henseleit buffer.

Methods:

Kidneys were harvested from Australian Yorkshire pigs (35-40 Kg) from a local abattoir in Charters Towers. Animals were sacrificed using a captive bolt stunner as per the Humane Slaughter Act and then exsanguinated. Kidneys were removed surgically and placed in a dish for approximately 15 minutes of warm ischaemia for preparation. The renal artery, vein and ureter were identified and clipped to avoid accidental damage, while excess peri-renal connective tissue and the renal capsule were removed. Kidneys were then flushed with 700-800 mls of preservation solution held at a 1 m pressure head. Once flushed, kidneys were weighed and placed in a zip-lock plastic bag containing 200-250 mls of the same preservation solution then stored at 4° C. for 12 hours in an ice-filled polystyrene retrieval box. Kidney weights were recorded 1) prior to, 2) following flushing and again 3) following the 12 hour cold static storage (CSS). For quantitative evaluation of the washout, the remaining red blood cells were counted in specimens of the corticomedullary junction. In a blinded manner, counting of RBCs was performed in ten randomly selected fields of hematoxylin and eosin (H&E)-stained sections Results

TABLE 11

| GROUP (n = 8) | % Weight Gain After Initial Flush relative to harvest weight | % Weight Gain After 12 Hrs COLD Storage | Number of red cells remaining after 12 hr storage under high power field (indicates ischaemic damage) |
| --- | --- | --- | --- |
| Custodial (HTK) | 33.7 ± 4 | 23.5 ± 3.5 | 185 ± 15 |
| AL (4/5) (4 mM Adenosine 5 mM lidocaine-HCl) with the following additions | | | |
| +PEG + 4% BSA | 14.5 ± 1 | 14.5 ± 1 | 45 ± 5 |
| +PEG + 10 mM BDM | 17 ± 1 | 18.5 ± 1 | 130 ± 10 |
| +PEG Alone | 20 ± 0.7 | 20 ± 1.8 | 130 ± 10 |
| +BSA Alone | 36.5 ± 1 | 31.5 ± 1.2 | 90 ± 30 |
| +PEG + 0.5% Dextran-40 | 24 ± 1 | 28.5 ± 2 | 75 ± 15 |
| 4% BSA + 0.5% Dextran-40 | 34 ± 1.2 | 29 ± 1.2 | 15 ± 3 |
| AL (4/10) (4 mM Adenosine 10 mM lidocaine-HCl) with the following additions | | | |
| +PEG + 10 mM BDM | 12.5 ± 0.7 | 17 ± 1 | 150 ± 8 |
| +PEG + 0.5% Dextran-40 | 23 ± 2 | 25.1 ± 1 | 15 ± 3 |
| 4% BSA + 0.5% Dextran-40 | 24.3 ± 1 | 22 ± 2 | 190 ± 12 |
| 4% BSA | 36 ± 1.5 | 31 ± 1.5 | 30 ± 10 |
| 4 mM A and 8 mM L + 4% BSA + 0.5% dextran | 2.5 ± 5 | 15 ± 2 | Not Determined |

Conclusions:

During the initial flush the AL (4/5) with PEG and BSA; or AL (4/5) with BDM alone or AL (4/5) with PEG alone had significantly lower kidney weight gains relative to gold standard HTK. AL (4/10) with BDM had 27% lower kidney weight after 12 hours cold storage, and AL (4/10) with PEG and BDM or AL (4/10) with PEG and 0.5% Dextran-40 were equivalent. Adenosine at 4 mM and Lidocaine at 8 mM with 4% BSA and 0.5% Dextran had significantly lower weight gains than HTK before and after 12 hours storage. The addition of 8 mM and 80 mM lactobionate to AL (4/8) with gave equivalent weight changes to HTK solution after 12 hours cold with 35±8 (n=8) and 38±10 (n=8) respectively (not in Table). The amount of remaining RBCs washed out from kidneys after 12 hours storage was significantly lower using AL (4/5) PEG+4% BSA, AL (4/5) 4% BSA+dextran and AL (4/10) PEG+dextran compared with HTK solution. This may suggest more protection and less ischemia.

Example 37: Arresting, Protecting and Preserving Stem Cells with ALM Sildenafil Citrate, ALM Citrate Phosphate Dextrose (CPD), ALM with CPD and Cyclosporine A or ALM with Erythropoietin, Glyceryl Trinitrate and Zoniporide Background:

Stem cells are pluripotent, self-renewing cells found in all multicellular organisms. In adult mammals, stem cells and progenitor cells act as a repair system for the body, replenishing tissues. The key is that stem cells have the potential to develop into many different kinds of human tissue cells. They remain 'quiescent' as undifferentiated cells within tissues or organs as long as tissue homeostasis does not require generation of new cells. Here, they can renew themselves or differentiate into some or all major specialized cell types that make up the tissue or organ. This 'quiescent' state, one reversible cell cycle withdrawal, has long been viewed as a dormant state with minimal basal activity. However, increasingly there is evidence that suggests that quiescent cells have specific transcriptional, post-transcriptional and metabolic programs that serve at least two functions. The first function is to actively maintain the quiescent state, indicating that this is not simply a state of dormancy but in fact under active regulation. The second is to prime the cells for activation, a process that is characterized by the upregulation of multiple cellular processes necessary for cells to enter the cell cycle and begin the process of differentiation. Neural stem cells (NSC) are not only a valuable tool for the study of neural development and function, but an integral component in the development of transplantation strategies for neural disease. Regardless of the source material, similar techniques are used to maintain NSC in culture and to differentiate NSC toward mature neural lineages. In addition, distinct cell membrane voltage controls are found in many precursor cell systems and cancer cells, which are known for their proliferative and differentiation capacities, respectively.

Aim:

To examine stem cell 'quiescence' in different solutions after 12 and 24 hours of warm 25° C.) and cold (4° C.) temperature storage and characterize the fate of defined populations of neural precursor cells following transplantation. Differentiated cells will exhibit typical morphological changes and expressed neuronal (nestin, mitogen-activated protein-2, synaptophysin), glial (S100, glial fibrillary acid protein).

Methods:

Methods for for isolating multipotent NSC and neural precursor cells (NPC) from embryonic rat CNS tissue (mostly spinal cord) are described in Bonner et al.,. In particular, neural precursor cells can be separated into neuronal and glial restricted precursors and used to reliably produce neurons or glial cells both in vitro and following transplantation into the adult CNS. Cells will be preserved in different culture solutions with and without ALM sildenafil citrate, ALM citrate phosphate dextrose (CPD), ALM with CPD and cyclosporine A or ALM with erythropoietin, glyceryl trinitrate and zoniporide and quiescent and differentiation will be examined after 12 and 24 hours. Membrane potentials will be performed using the methods described in Sundelacruz et al. (Sundelacruz et al., 2009).

Results and Expected Conclusions:

We expect that the ALM will maintain the membrane potential at its resting level and prevent hyperpolarization and differentiation compared to the culture media alone. The study will have significance in maintaining stem cells in a quiescent stage for longer times and improve viability and reduce loss of cells after transplantation and differentiation into tissues. The study also has the ability to control the voltage and growth and differentiation of cancer cells.

Example 38: Rat Model of Hypotensive Anesthesia and Whole Body Arrest

Male Sprague Dawley rats (300-450 g) were fed ad libitum with free access to water and housed in a 12-hr light-dark cycle. Animals were not heparinized and anesthetized with an intraperitoneal injection of 100 mg/kg sodium thiopentone (Thiobarb). Anesthetized animals were positioned in the supine position on a custom designed cradle. A tracheotomy was performed and animals were artificially ventilated (95-100 strokes $min^{-1}$) on humidified room air using a Harvard Small Animal Ventilator (Harvard Apparatus, Mass., USA). Femoral artery and vein cannulations were performed on the left leg for drug pressure monitoring and drug infusions. A lead II ECG was attached via ECG wires. A rectal probe was inserted 5.0 cm and the temperature ranged between 37 and 34° C.

Example A) Hypotensive Anesthesia

ALM+0.1% CPD. (0.2 ml Bolus)

A 0.2 ml bolus intravenous injection of a composition comprising 0.2 mg adenosine, 0.4 mg lidocaine-HCl and 200 mg $MgSO_4$ in 0.9% saline and 0.1% citrate phosphate dextrose (CPD) was administered to a rat. No propofol was in this composition. The concentration of each of the components in the composition was as follows, adenosine 3.75 mM, lidocaine-HCl 7.38 mM, $MgSO_4$ 833 mM, and citrate 3.4 mM. The dosage of each of the components administered to the animal was as follows, adenosine 0.6 mg/kg, lidocaine-HCl 1.2 mg/kg, $MgSO_4$ 600 mg/kg, and citrate 0.6 mg/kg.

Figure 26:
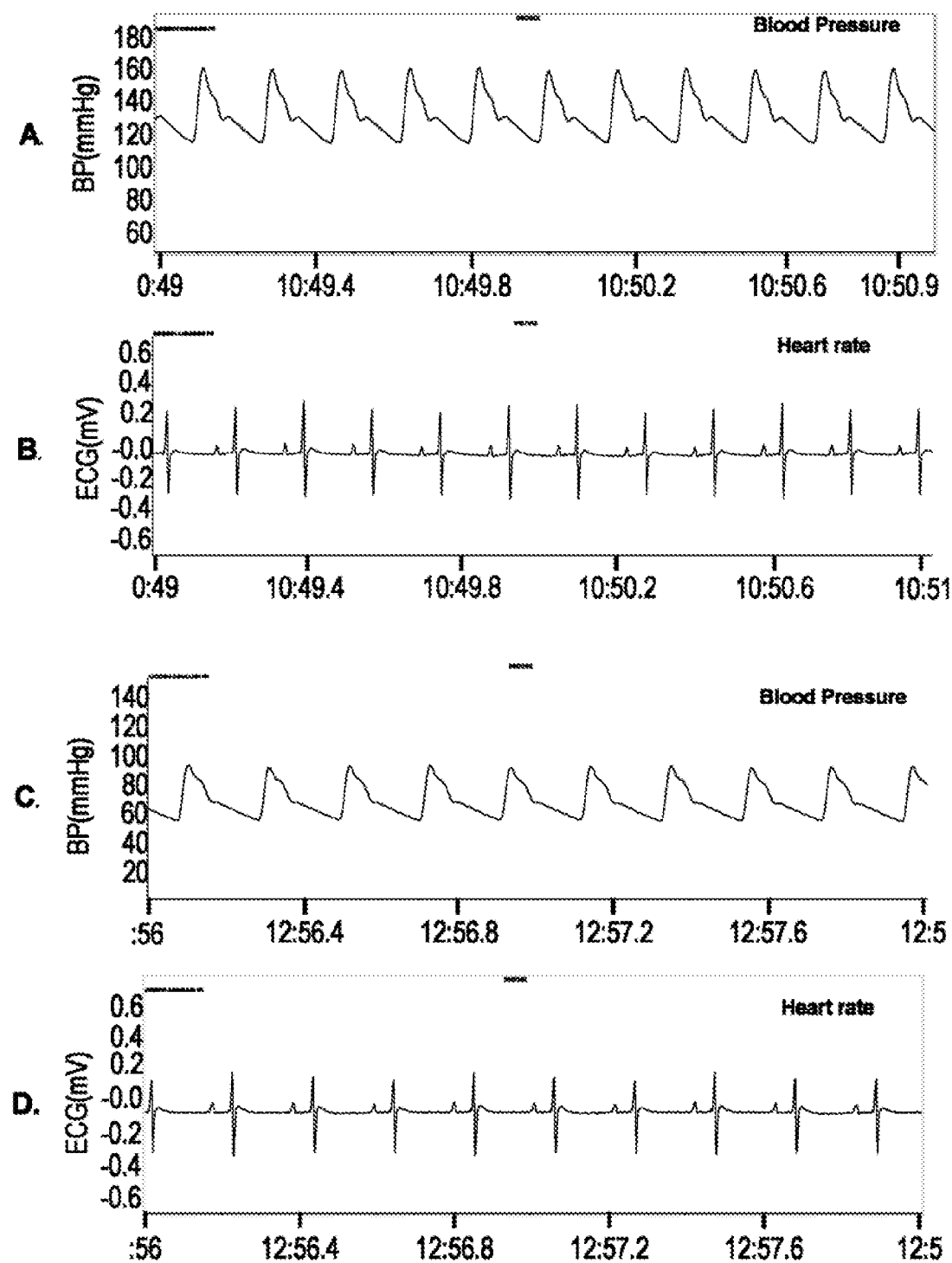
FIG. 26 shows ECG and blood pressure traces before and after inducing hypotensive anesthesia using ALM-CPD (A and B before, C and D after)

Results:

Initially, the baseline heart rate, blood pressure and mean arterial blood pressure (MAP) of the animal was HR 339 bpm, BP 159/113 mmHg, MAP 129 mmHg, Temp 36.7° C. (see FIGS. 26A and B). Two minutes after the bolus administration of the composition there was a fall in mean arterial pressure (MAP) from 129 mmHg to 67 mmHg and a MAP (a fall of 48% from baseline) and a heart rate fell from 339 to 288 beats per min (a 15% fall in heart rate from baseline) (see FIGS. 26C and D). Hypotension is often defined as either: mean arterial blood pressure (MAP) decrease of >40% and MAP <70 mm Hg. This hypotensive state was maintained for over 10 min.

Example B) Whole Body Arrest

ALM+0.1% CPD+1 mg/kg Propofol (0.1 ml Bolus)

In the same animal as Example 1, after 10 min, a 0.1 ml bolus intravenous injection of the composition comprising 0.1 mg adenosine, 0.2 mg lidocaine-HCl 200 mg $MgSO_4$, and propofol in 0.9% saline and 0.1% citrate phosphate dextrose (CPD) was administered. The concentration of each of the components in the composition was as follows, adenosine 3.75 mM, lidocaine-HCl 7.38 mM, $MgSO_4$ 1666 mM, citrate 3.40 mM and propofol 18.5 mM. The dosage of each of the components administered to the animal in this step was as follows, adenosine 0.6 mg/kg, lidocaine-HCl 1.2 mg/kg, $MgSO_4$ 600 mg/kg, citrate 0.3 mg/kg and propofol 1 mg/kg.

Figure 27:
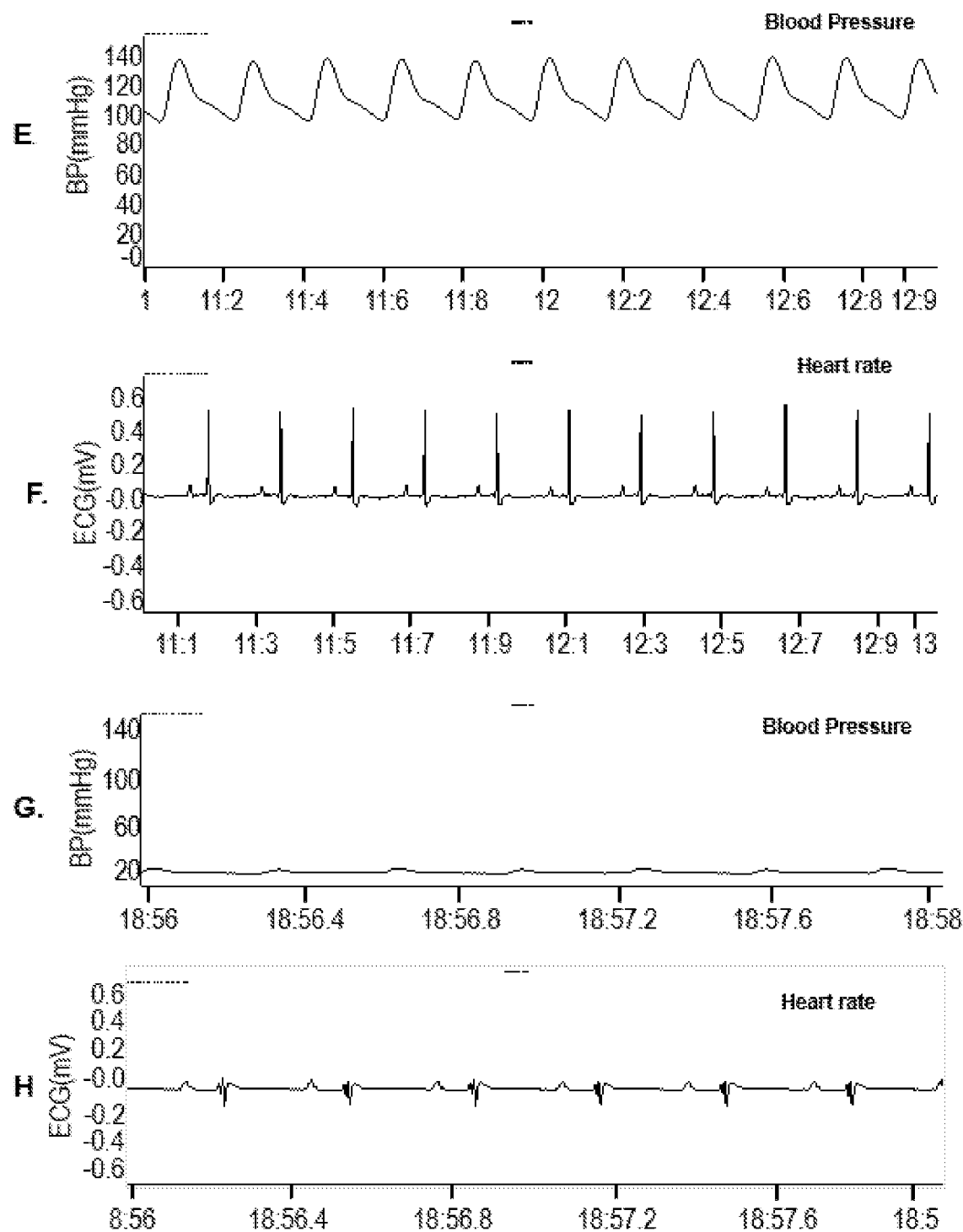
FIG. 27 shows ECG and blood pressure traces before and after inducing whole body arrest using ALM-CPD (E and F before, G and H after).
Figure 28:
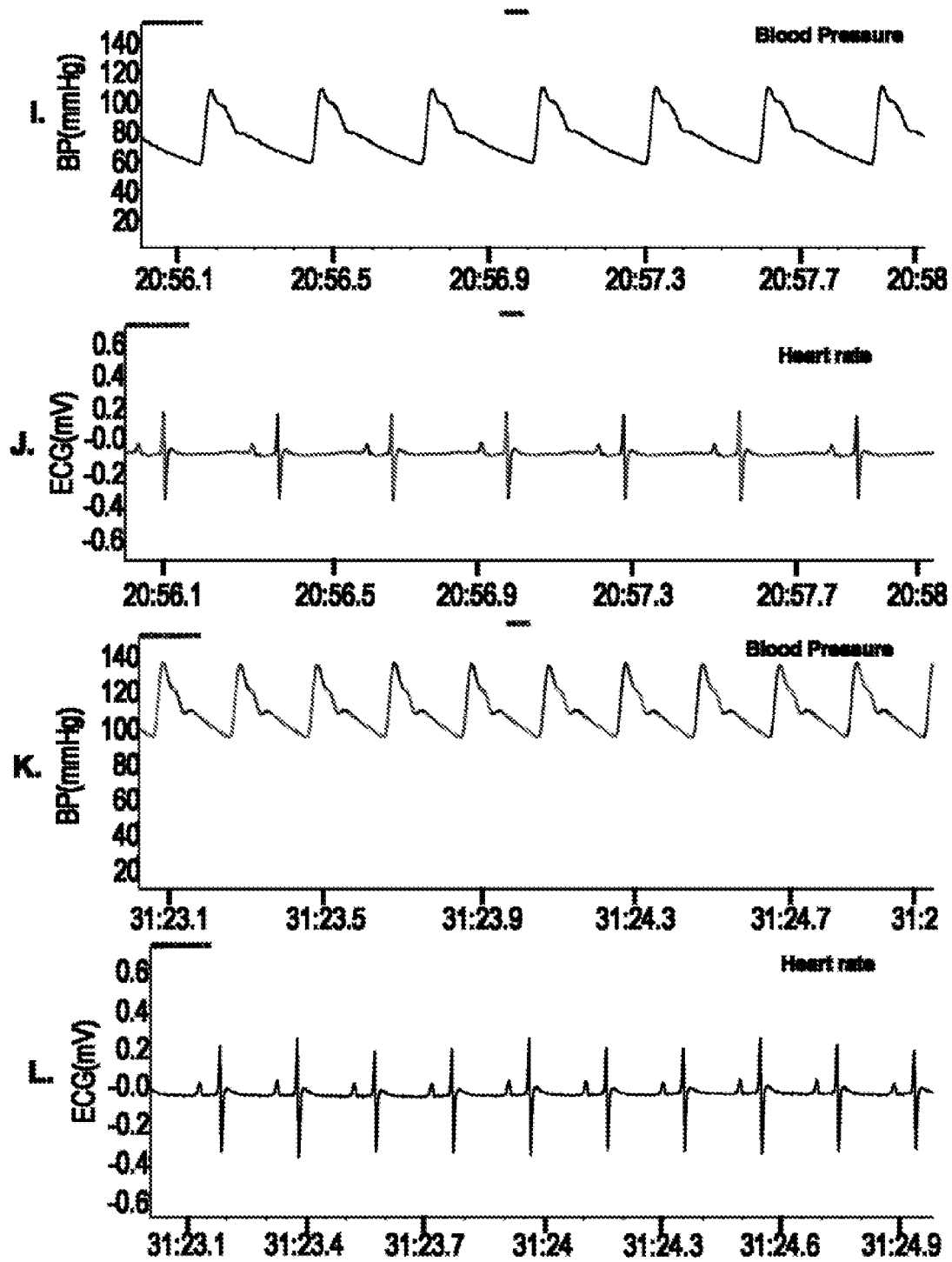
FIG. 28 shows ECG and blood pressure traces before and after inducing whole body arrest using ALM-CPD (I and J before, K and L after).

Results:

Initially, the baseline heart rate, blood pressure and mean arterial blood pressure (MAP) of the animal was HR 320 bpm, BP 137/95 mmHg, MAP 108 mmHg, Temp 37.0° C. (See FIGS. 27E and F). After administration of the composition, the blood pressure and heart rate immediately dropped to near zero (not shown) and after 3 min the MAP was 12 and heart rate 191 beats per min (3 min post-bolus: HR 191 bpm, BP 15/11 mmHg, MAP 12 mmHg, Temp 36.6° C., see FIGS. 27G and H)). After 5 minutes, MAP increased over 6 times and heart rate was 208 beats per min (HR 208 bpm, BP 109/57 mmHg, MAP 75 mmHg, Temp 36.4° C., see FIGS. 28I and J). After 15 minutes there was nearly full recovery of blood pressure and heart rate (HR 308 bpm, BP 135/92 mmHg, MAP 106 mmHg, Temp 36.1° C., see FIGS. 28K and L). The animal spontaneously returned hemodynamics without any chest compressions or other interventions.

Example 39: ALM-CPD Solution 1

39a: The Concentration of the Components in the Composition

A composition comprising 1.25 g Adenosine, 2.5 g Lidocaine HCl, 1.25 g $MgSO_4$ 2% CPD in 250 ml of 0.9% NaCl is provided. The concentration of each of the components in the composition was as follows, adenosine 18.71 mM, lidocaine-HCl 36.92 mM, $MgSO_4$ 20 mM, and citrate 2.1 mM.

39b: Preparation of ALM-CPD Solution 1

Typically, in preparing this solution the following method was followed:

Amounts of components of the composition:
Adenosine powder 1.25 g
Lidocaine Hydrochloride 2.5 g
Magnesium sulfate 50% solution (w/w)—2.5 ml
Sodium citrate dihydrate 0.1315 g
Citric acid monohydrate 0.01635 g
Sodium phosphate monobasic anhydrous 0.00965 g
Dextrose anhydrous powder 0.116 g
Sodium chloride 0.9% solution for total final volume of 250 ml Method:
Approximately 125 mL (50% of the volume) of the NaCl solution was placed into a vessel with stirring.

1. The adenosine base powder was added with stirring until dissolved.
2. The lidocaine HCl was added with stirring until dissolved.
3. The magnesium sulfate solution was added with stirring.
4. The sodium citrate dihydrate, citric acid monohydrate, sodium phosphate monobasic anhydrous powder and dextrose anhydrous powder were added with stirring until dissolved.

5. The pH of the solution was checked and adjusted if necessary to between 7.2 and 7.5 (preferably 7.4).
6. When the solids were completely dissolved, the solution was made up to 250 ml with 0.9% NaCl solution and filtered through a 0.22 micron filter into a sterile bag.

39c: Use of ALM-CPD Solution 1

The composition may be administered by IV infusion at the following rates:

IV Infusion Rates:

Bolus 0.1 ml/kg then 0.1-0.5 ml/kg/min during operation administered following anesthesia and maintain or change to 0.1 ml/kg/min during sternal closure for 2 hours at ICU. The IV administration could increase to 1 ml/kg/hr or higher, or lower than 0.1 ml/kg/hr.

The dosage amounts of each of the components of the composition administered during the operation and during sternal closure for 2 hours at ICU (recovery) is as follows:

During Operation: Infusion Rate: 0.1-0.5 ml/kg/Hr

Adenosine=when 0.5 ml/kg/hr is administered, 0.5 mL/250 mL×1.25 g=2.5 mg/kg/hr or;

when 0.1 ml/kg/hr is administered, 0.5 mg/kg/hr.

Lidocaine-HCl=when 0.5 ml/kg/hr is administered, 0.5/250×2.50=5.0 mg/hr/kg (which is equivalent to 350 mg/hr for a 70 kg human; and 35 mg for 7 kg pediatric patient); or when 0.1 ml/kg/hr is administered, 1 mg/kg/hr.

$MgSO_4$=when 0.5 ml/kg/hr is administered, 0.5 mL/250 mL×1.25 g=2.5 mg/hr/kg or;

when 0.1 ml/kg/hr is administered, 0.5 mg/kg/hr.

During Recovery: Infusion Rate: 0.1 ml/kg/Hr (Reduced from 0.5 to 0.1 During Sternal Closure and Continued for 2 Hours into ICU Adenosine=0.1/250×1.25 g=0.5 mg/hr/kg.

Lidocaine-HCl=0.1/250×2.50=1.0 mg/hr/kg (which is equivalent to 70 mg/hr for a 70 kg human; and 7 mg/hr for 7 kg pediatric patient).

$MgSO_4$=0.1/250×1.25 g=0.5 mg/hr/kg.

The methods and dosages mentioned above provide several advantages relative to published clinical doses for adenosine, lidocaine and magnesium combined in cardiac surgery, major surgery and following severe traumatic brain injury: The above mentioned dosages of adenosine used during the infusion are substantially reduced compared to the dosages of adenosine typically used during major surgery, such as when adenosine is used as an analgesic.

The above mentioned dosages of magnesium used during the infusion are substantially reduced compared to the dosages of magnesium typically used during major surgery, such as when magnesium is used during cardiac surgery.

Example 40: ALM-CPD Solution 2

40a: The Concentration of the Components in the Composition

A composition comprising adenosine, lidocaine, $MgSO_4$ 2% CPD in 250 ml of 0.9% NaCl is provided. The concentration of each of the components in the composition may be as follows; 80 ml Bag of the Solution 0.4 g Adenosine base (USP)=0.4 g base (0.4/267.24×1000/80=18.71 mM)

0.8 g Lidocaine HCl (USP) 20 mg/ml=125 ml (2.5/270.80×1000/80=36.92 mM)

8 g $MgSO_4$ (USP) 50% soln (2M)=16 ml (16/80×2M=400 mM)

CPD** 2%

** CPD contains in 100 ml 0.9% NaCl (USP)=to 80 ml

TOTAL VOLUME 80 ml

Citric Acid (Monohydrate), 0.327 g

MW 210.14

Conc=0.327/210.14×1000/100=0.01556 M (15.56 mM)

Sodium Citrate (Dihydrate), 2.630 g

MW 294.1

Conc=2.63/294.1×1000/100=0.0894 M (89.4 mM)

Monobasic Sodium Phosphate (Monohydrate), 0.222 g

MW 119.98

Conc=0.222/119.98×1000/100=0.01850 M (18.5 mM)

Dextrose (Anhydrous), 2.550 g

MW 180.1

Conc=2.550/180.1×1000/100=0.258 M (141.6 mM)

Therefore the final concentrations of the components of the 2% CPD in the above-mentioned 80 ml bag of the solution are as follows:

Citric acid: 1.6 ml/80 ml×15.56 mM=0.3112 mM Na-Citrate: 1.6 ml/80 ml×89.4 mM=1.788 mM Total citrate (TC) 2.0992 mM Na-Phosphate: 1.6 ml/80 ml×18.5 mM=0.37 mM Dextrose: 1.6 ml/80 ml×141.6 mM=2.832 mM.

40b: Preparation of ALM-CPD Solution 2

Typically, in preparing this solution the following method was followed:

Amounts of components of the composition:

Adenosine powder 0.4 g

Lidocaine Hydrochloride 0.8 g

Magnesium sulfate 50% solution (w/w)—16 ml

Sodium citrate dihydrate 0.04208 g

Citric acid monohydrate 0.005232 g

Sodium phosphate monobasic anhydrous 0.003088 g

Dextrose anhydrous powder 0.03712 g

Sodium chloride 0.9% solution for total final volume of 80 ml

Method:

1. Approximately 40 mL (50% of the volume) of the NaCl solution was placed into a vessel with stirring.
2. The adenosine base powder was added with stirring until dissolved.
3. The lidocaine HCl was added with stirring until dissolved.
4. The magnesium sulfate solution was added with stirring.
5. The sodium citrate dihydrate, citric acid monohydrate, sodium phosphate monobasic anhydrous powder and dextrose anhydrous powder were added with stirring until dissolved.
6. The pH of the solution was checked and adjusted if necessary to between 7.2 and 7.5 (preferably 7.4).
7. When the solids were completely dissolved, the solution was made up to 80 ml with 0.9% NaCl solution and filtered through a 0.22 micron filter into a sterile bag.

40c: Use of ALM-CPD Solution

The composition may be administered by a bolus to the blood to provide a contact concentration at the heart. A bolus of the composition is diluted up to 1 L of blood to provide the following heart contact concentrations:

Arrest Induction 25 mL/1000 whole blood (induction)

A=0.468 mM

L=0.923 mM

M=10 mM

TC=0.053 mM; or 20 ml/1000 whole blood (induction)

A=0.374 mM

L=0.738 mM

M=8.0 mM

TC=0.042 mM

Note that when a 25 ml bolus is used for arrest in 1000 m: of blood 0.07 mM of dextrose is added. This addition adds only a 1.3% increase to blood glucose (typically 5 mM). Increasing blood glucose is known to have adverse effects.

Maintenance if Required 15 ml/1000 ml

A=0.281 mM

L=0.554 mM

M=5.6 mM

Reanimation (10 min before X-clamp removal—rewarm heart and reanimate)

2.0 ml/1000 (reanimation)

A=37 µM

L=74 µM

M=0.8 mM

SC=0.3 µM

Example 41: Directions for the Use of ALM-CPD Solution for Cardioplegia (See Example 40 Above for Composition of this Solution)

Table 12 below describes the blood flow rates and ALM-CPD solution sequence used in the treatment of both adult and pediatric patients with ALM-CPD solution. Oxygenated whole blood is provided to the patient at a flow rate as indicated in column 2 of the Table. The whole blood is combined with ALM-CPD solution solution through a Y-adapter just prior to administration. The Polar Shot is supplied to the Y-adapter by either a Quest MPS system or a syringe pump. At the beginning of the treatment (induction), a warm solution of ALM-CPD solution is administered for 1 minute at different flow rates for adult and pediatric patients as described in the Table. After the warm solution is administered, a cold solution of ALM-CPD solution is administered for 3 minutes. The contact concentrations for induction, maintenance and reanimation between the two methods of delivery (Quest MPS or Syringe pump) are the same or similar. The data in Table 12 may be changed by the skilled person to suit their own preferences. For example, Instead of warm induction some skilled persons may prefer colder induction temperatures and the range could be between 2 and 32° C. Some skilled persons may also prefer warm throughout induction and maintenance and higher concentrations of polarshot may be required for maintenance and more frequent intermittent infusions (i.e. every 20 min).

Following the induction period, additional ALM-CPD solution solution is provided to the patient to maintain arrest (maintenance). The time interval between administering doses of ALM-CPD solution during maintenance and the amount of ALM-CPD solution administered during maintenance is to be determined between the surgeon and perfusionist, although the Table below provides a guide as to the volume per minute recommended during maintenance.

TABLE 12

| | | ALM Sequence | | |
|---|---|---|---|---|
| | Whole Blood Flow Rate | Quest MPS | Syringe Pump | |
| Adult | ml/min | *ml/L | ml/min | ml/hr |
| Induction | | | | |
| Warm (1 min) | 350 | 20 (1 min) | 7 | 420 |
| Cold (3 min) | | 15 (3 min) | 5.25 | 315 |
| | | 10 (1 min) | 3.5 | 210 |
| Maintenance (intermittent) ***Cold every 20 to 50 min. | 250 | 10-15 90 sec | 2.5-3.75 | 150-225 |
| Reanimation Warm | 250 | 1.0-2.0 for 2 min | 0.25 to 0.50 | 15 to 30 |
| Whole Blood ONLY X-Clamp removal | 250 | 0 for 2 min | 0 | 0 |

| | Whole Blood | ALM Sequence | | |
|---|---|---|---|---|
| | Flow Rate | Quest MPS | Syringe Pump | |
| Pediatric** | ml/min | **ml/L | ml/min | ml/hr |
| Induction | | | | |
| Warm (1 min) | 80-100 | 20 (1 min) | 1.6-2.0 | 96-120 |
| Cold (3 min) | | 15 (2 min) | 1.2-1.5 | 72-90 |
| | | 10 (1 min) | 0.8-1.0 | 48-60 |
| Maintenance Cold (every 20-50 min) | 80-100 | 10-15 90 sec | 0.8-1.5 | 48-90 |
| Reanimation Warm | 80-100 | 1.0-2.0 for 2 min | 0.08-0.20 | 4.8 to 12 |
| Whole Blood ONLY X-Clamp removal | 80-100 | 0 for 2 min | 0 | 0 |

Warm is normothermia; Cold is 4° C. (Delivery Temperature): Whole Blood Flow Rate = Cardioplegia Blood Flow Rate (ml/min)
*ml/L = ml of ALM per Liter of whole blood; ml/min or ml/hour are suggested rates for syringe pump settings.
**If pediatric patients are hypotensive reduce induction and maintenance to 10 ml/L and its respective rate in ml/min or ml/hr
***Time interval between doses of cardioplegia for cold-maintenance will be determined between the surgeon and perfusionist.
Quest MPS is the Quest MPS2 Myocardial Protection System which is a patented device to delivery cardioplegia to the heart Example 42: Clinical Use of ALM with 2% CPD) Using the Quest MPS Cardioplegia Delivery System. No Extra Potassium was Used to Arrest the Heart The results set out in Table 13 below were obtained using the method described in Example 41. All patients had Spontaneous Return of Sinus Rhythm after the Operation. None experienced Ventricular Fibrillation after cross-clamp release.

Notes on the following terms in Table 13 are set out below.

TABLE 13

| Age | Gender | Condition | Comorbidities | Arrest Time (sec) | Cross clamp time (min) | Bypass Time (min) | Comments |
|---|---|---|---|---|---|---|---|
| Pediatric | | | | | | | |
| 3.3 kg | Male | *Tetrology of Fallot Repair | None | <10 | 55 | 151 | Serum K+ stable at 3.7 mM. Total volume was 6 ml. Heart totally silent during maintenance. Return sinus after 90 sec |
| 5 days old | Male | Single ventricle, dextrocardia | None | 15 | 37 | 201 | Single dose of 4 ml cardioplegia. Deep hypothermic total circulatory arrest for 25 min |
| 9 Month | Male 9.2 kg | Tetrology of Fallot Repair | None | 10 | 57 | 107 | 2 ml bolus of ALM a given as pretreatment in the aortic root prior to bypass (cross-clamp). Heart temp 11° C. at end induction. After 25 min 18° C. |
| 4 year | Male 15.9 kg | Partial AV canal | None | 12 | — | — | Patient was extubated on the table |
| 11 year | Male | ***Ross Procedure | None | 19 | 107 | 177 | 1 minute of antegrade warm. Heart arrested in 19 seconds (aortic insufficiency). Came back after 1 min. Switched to retrograde. Excellent. |
| Adult (years) | | | | | | | |
| 54 | Female | Mitral Valve replacement | Chronic renal failure | 20 | 154 | 183 | Return of left ventricular function to normal |
| 67 | Male | Mitral Valve replacement | Chronic renal failure | 15 | — | — | No activity between doses. No post-op Atrial Fibrillation |
| 55 | Male | CABG | None | 12-15 | 127 | — | No activity between doses |
| 83 | Female | Aortic Valve Replacement Mitral Valve Replacement Tricuspid Valve Repair + Maze | — | 12 | — | 225 | Average time between maintenance doses was 55 min. Very complicated case. |

*Tetralogy of Fallot is a rare, complex heart defect. It occurs in about 5 out of every 10,000 babies and equal incidence in males and females. Tetralogy of Fallot involves four heart defects: 1) ventricular septal defect (VSD), 2) pulmonary stenosis 3) Right ventricular hypertrophy, 4) overriding aorta where the aorta is located between the left and right ventricles, directly over the VSD. As a result, oxygen-poor blood from the right ventricle flows directly into the aorta instead of into the pulmonary artery. Tetralogy of Fallot leads to death if not surgically repaired as not enough blood is able to reach the lungs and body.
** CABG = coronary artery bypass graft
***Ross Procedure or "switch operation" is a specialized aortic valve surgery where the patient's diseased aortic valve is replaced with his or her own pulmonary valve. The pulmonary valve is then replaced with cryopreserved cadaveric pulmonary valve.

Example 43: Small Volume Resuscitation Using Hypertonic Saline ALM with and without a Form of Citrate after 40% Blood Loss and 60 Min Shock in the Rat In Vivo: Higher Pulse Pressure (PP) During Resuscitation Indicates Improved Left Ventricular Function in Compared to Control METHOD Male Sprague Dawley rats (300-400 g) were fed ad libitum with free access to water and housed in a 12-hr light-dark cycle. Animals were anesthetized with an intraperitoneal (IP) injection of 100 mg/kg sodium thiopentone (Thiobarb). After Thiobarb anesthesia, rats were positioned in the supine position on a custom designed cradle. A tracheotomy was performed and the animals artificially ventilated at 90-100 strokes per min on humidified room air using a Harvard Small Animal Ventilator (Harvard Apparatus, Mass., USA) to maintain blood $pO_2$, $pCO_2$ and pH in the normal physiological range. Rectal temperature was monitored using a rectal probe inserted 5 cm from the rectal orifice before, during and following shock and resuscitation, and previous experiments show the temperature ranges between 37 to 34° C. The left femoral vein and artery was cannulated using PE-50 tubing for drug infusions and blood pressure monitoring (UFI 1050 BP coupled to a MacLab) and the right femoral artery was cannulated for bleeding. Lead II electrocardiogram (ECG) leads were implanted subcutaneously on the left and right front legs and grounded to the back leg. Rats were stabilized for 10 minutes prior to blood withdrawal. Hemorrhagic shock was induced by withdrawing blood from the femoral artery at an initial rate of ~1 ml/min then decreasing to ~0.4 ml/min over 20 min. Initially blood was withdrawn slowly into a 10 ml heparinized syringe (0.2 ml of 1000 U/ml heparin) to reduce MAP to between 35 and 40 mmHg. If MAP increased, more blood was withdrawn to maintain its low value, and the process was continued over a 20 min period. The resuscitations were 0.3 ml intravenous bolus of 7.5% NaCL adenosine, lidocaine-HCL, magnesium sulphate (ALM) per rat with no citrate phosphate dextrose (CPD) compared with 0.3 ml intravenous bolus of 3.0% NaCL adenosine, lidocaine-HCL, magnesium sulphate (ALM) with 0.1% CPD per rat. The stock composition of ALM solution was 1 mM Adenosine, 3 mM Lidocaine-HCl and 2.5 mM magnesium sulphate of which 0.3 ml was injected IV into the femoral vein after 40% blood loss and 60 min of shock. In the 0.3 ml the amounts of ALM in mg/kg rat are 0.24 mg/kg adenosine, 0.73 mg/kg lidocaine-HCl and 0.27 mg/kg MgSO$_4$. After administration of 0.3 ml bolus hemodynamics was monitored over a 60 min period.

MAIN RESULTS: It was shown that the presence of small volume resuscitation with CPD produced a larger difference in systolic and diastolic pressure known as the pulse pressure. The literature reports that a larger pulse pressure correlated with a higher stroke volume defined as volume of blood ejected from the left ventricle per heart beat. This funding of a 2.5 fold increase in pulse pressure with hypertonic saline ALM and CPD led to improvement in stroke volume and heart function during 60 min hypotensive resuscitation.

Notes on the following terms in Table 14 are set out below

TABLE 14

| | Hemodynamic Parameter (#) | | | | | |
|---|---|---|---|---|---|---|
| Units | HR bpm | SP | DP mmHg | MAP | PP | RPP mmHgx bpm |
| 0.3 ml of 7.5% NaCl ALM per rat | | | | | | |
| Baseline | 331 | 123 | 91 | 102 | 32 | 35676 |
| 20 min Bleed | 273 | 45 | 35 | 38 | 10 | 12285 |
| 60 min Shock | 283 | 50 | 33 | 38 | 17 | 13242 |
| Resuscitation (0.3 ml bolus fluid volume per rat) | | | | | | |
| 2 min Resuscitation | 278 | 51 | 36 | 41 | 15 | 14178 |
| 5 min Resuscitation | 283 | 56 | 41 | 56 | 15 | 15845 |
| 10 min Resuscitation | 284 | 58 | 40 | 41 | 18 | 16472 |
| 15 min Resuscitation | 285 | 59 | 40 | 46 | 19 | 16660 |
| 30 min Resuscitation | 285 | 71 | 45 | 54 | 26 | 20237 |
| 45 min Resuscitation | 290 | 74 | 49 | 50 | 20 | 21650 |
| 60 min Resuscitation | 297 | 76 | 52 | 60 | 24 | 22563 |
| 0.3 ml of 3% NaCl ALM with 0.1% citrate phosphate dextrose (CPD) per rat | | | | | | |
| Baseline | 329 | 138 | 107 | 115 | 31 | 46700 |
| 20 min Bleed | 293 | 47 | 38 | 40 | 13 | 13771 |
| 60 min Shock | 315 | 54 | 30 | 40 | 24 | 17010 |
| Resuscitation (0.3 ml bolus fluid volume per rat) | | | | | | |
| 2 min Resuscitation | 297 | 79 | 42 | 52 | 37 | 23463 |
| 5 min Resuscitation | 306 | 85 | 44 | 57 | 41 | 26010 |
| 10 min Resuscitation | 304 | 89 | 45 | 60 | 44 | 27056 |
| 15 min Resuscitation | 316 | 89 | 42 | 59 | 47 | 28124 |
| 30 min Resuscitation | 336 | 98 | 53 | 65 | 45 | 32928 |
| 45 min Resuscitation | 339 | 106 | 53 | 73 | 53 | 35934 |
| 60 min Resuscitation | 336 | 114 | 62 | 78 | 52 | 38304 |

| | Comments |
|---|---|
| Hemodynamic Parameter (#) | ***Pulse Pressure Difference. A larger stroke volume produces a larger pulse pressure at any given compliance. PP is used clinically as an indicator of stroke volume in a number of critical care states including blood loss. |
| Units | |
| Baseline | Identical Pulse Pressure at Baseline |
| 20 min Bleed | Identical Pulse Pressure after 20 min bleed |
| 60 min Shock | Similar PP prior to resuscitation |

TABLE 14-continued

| Resuscitation (0.3 ml bolus fluid volume per rat) | |
|---|---|
| 2 min Resuscitation | Present invention 2.5 fold higher Pulse Pressure indicating improved left ventricular function |
| 5 min Resuscitation | Present invention 2.5 fold higher Pulse Pressure. |
| 10 min Resuscitation | Present invention 2.4 fold higher Pulse Pressure |
| 15 min Resuscitation | Present Invention 2.5 fold higher PP |
| 30 min Resuscitation | Present Invention 1.7 fold higher PP |
| 45 min Resuscitation | Present Invention 2.7 fold higher PP |
| 60 min Resuscitation | Present Invention 2.2 fold higher PP |

(#) HR = heart rate, SP = arterial systolic pressure, DP = arterial diastolic pressure, MAP = mean arterial blood pressure, PP = pulse pressure (Systolic minus diastolic arterial pressure is a clinican index of stroke volume of the left ventricle), RPP = rate pressure product.
**ALM is adenosine, lidocaine and magnesium are the identical concentrations in bolus administered in controls and present invention Example 44: Pretreatment Prior to Operation A 9 month old pediatric patient (9.2 kg, 67 cm) suffering Tetralogy of Fallot (TAF) was administered a 2 mL bolus of ALM-CPD solution (adenosine 18.71 mM, lidocaine HCl 36.92 mM, magnesium sulfate 400 mM, 2% CPD in 0.9% NaCl) into the aortic root prior to cross clamp (that is, before removing the heart from the circulation and placing on cardiopulmonary bypass) to provide whole body protection against the trauma of surgery. The total bypass time was 107 min and the patient was cross clamped for 57 min. The patient recovered with a spontaneous heart rhythm and came off bypass without any clinical issues.

Example 45: Pretreatment Prior to Operation

In a 32 year old female undergoing tricuspid value repair, was administered a 10 mL bolus of ALM-CPD solution (adenosine 18.71 mM, lidocaine HCl 36.92 mM, magnesium sulfate 400 mM, 2% CPD in 0.9% NaCl) into the aortic root prior to cross clamp (that is, before removing the heart from the circulation and placing on cardiopulmonary bypass) to provide whole body protection against the trauma of surgery. The 10 ml bolus of ALM-CPD solution was administered over a 5 min period giving rise to small bradycardia then quick return to normal heart rate. The operation was completed in less than 2 hours, the heart spontaneously returned electrical rhythm and the patient was weaned off bypass without any clinical issues.

Example 46: Treatment with Adenosine, Lidocaine and Mg$^{2+}$ During Endotoxemia Induces Reversible Hypotension, Improves Cardiac and Pulmonary Function and Exerts Anti-Inflammatory Effects Background:
Adenosine, lidocaine and Mg$^{2+}$ (ALM) has demonstrated cardioprotective and resuscitative properties in cardiac arrest and hemorrhagic shock. This study evaluates whether ALM also demonstrates protective properties in an endotoxemic porcine model.

Introduction
Sepsis is associated with a high mortality due to the development of cardiovascular dysfunction, lung injury and multi-organ failure. The acute pathophysiology underlying the clinical features of sepsis is believed to be associated with an early systemic pro-inflammatory response followed by an anti-inflammatory phase. During the pro-inflammatory phase the innate immune system is activated in response to microorganisms leading to production of cytokines, reactive oxygen species, and activation of leukocytes.

The combination of adenosine and lidocaine is cardioprotective and is currently used as a cardioplegia in cardiac surgery. Adenosine and lidocaine, individually and in combination, have also been reported to synergistically suppress neutrophil inflammatory functions. The cardioprotective and anti-inflammatory properties of adenosine-lidocaine were confirmed in a porcine model of cardiac arrest. In addition, the combination of adenosine, lidocaine and magnesium (ALM) has been reported to improve cardiovascular, hemodynamic and pulmonary function and reduce whole body oxygen consumption (VO2) following severe hemorrhagic shock. Since cardiovascular dysfunction and respiratory failure are the most frequent causes of early death in septic patients the aim of this study was to investigate the effects of ALM on these systems in a porcine model of systemic inflammation.

It was hypothesized that intervention with ALM may improve cardiovascular and pulmonary function and reduce inflammation in response to lipopolysaccharide in a porcine model. The primary outcome measures were cardiac and pulmonary function while renal function was evaluated as a safety outcome.

Materials and Methods

Animal preparation: Sixteen female crossbred Landrace/Yorkshire/Duroc pigs (35-40 kg) were fasted overnight, but allowed free access to water. Anesthesia was induced with midazolam (20 mg) and s-ketamin (250 mg) and maintained with fentanyl (60 µg·kg-1·h-1) and midazolam (6 mg·kg-1·h-1) as used in previous studies. The animals were intubated and ventilated using pressure control ventilation with volume guaranteed (S/5 Avance, Datex Ohmeda, Madison, Wis., USA) at a positive end-expiratory pressure of 5 cm H2O, FiO2 of 0.4, and a tidal volume of 10 ml/kg. Ventilation rate was adjusted to maintain PaCO2 between 41-45 mmHg. The body temperature was maintained around 38-38.5° C. All animals received a bolus of isotonic saline 10 ml/kg at baseline and a maintenance rate of 15 ml·kg-1·h-1 during lipopolysaccharide infusion.

Surgical Preparations and Monitoring: Vascular sheaths were inserted into the carotid artery and both external jugular veins. A pressure-volume (PV) catheter (SciSense, London, Ontario, Canada) was inserted into the left ventricle through the right carotid artery. A pulmonary artery catheter (CCOmbo, Edwards Lifesciences, Irvine, Calif., USA) was inserted into pulmonary artery through the right external jugular vein to monitor Cardiac output (CO) and core temperature. A PTS® sizing balloon (NMT Medical, Boston Mass., USA) was inserted in the left external jugular vein and positioned into the vena cava to occlude venous return during P-V measurements. A bladder catheter was placed for urine collection.

Systemic vascular resistance (dyn·s/cm5) was calculated as: 80·(mean arterial pressure (MAP)–central venous pressure)/CO while pulmonary vascular resistance (PVR, dyn·s/cm5) was calculated as 80·(MPAP–PCWP)/CO, where MPAP=Mean Pulmonary Arterial pressure and PCWP=Pulmonary Capillary Wedge Pressure.

Figure 29:
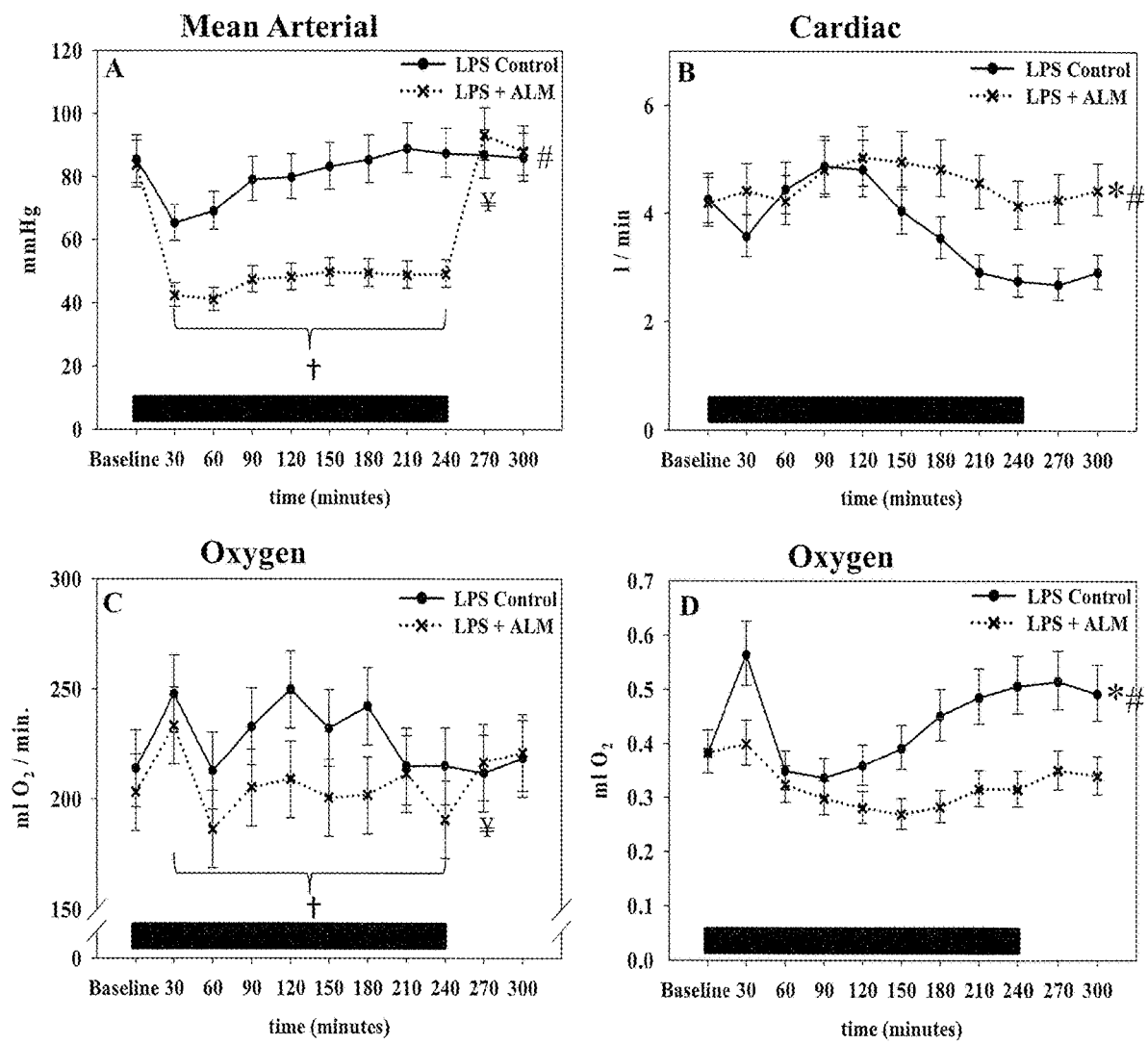
FIG. 29 shows graphs of the results of the experiments described in Example 46.

Experimental Protocol:

After instrumentation, each animal, was randomly assigned to one of two groups: Group 1) Control (n=8); Group 2) ALM (n=8)(FIG. 29). Randomization was performed by drawing pieces of paper from a bag by a lab technician also responsible for the ALM treatment. The primary investigators were blinded to group assignments. Unblinding was performed after data analysis. After randomization endotoxemia was induced by infusion of *Escherichia coli* lipopolysaccharide (0111: B4, Sigma-Aldrich, Broendby, Denmark, lot: 011m4008) at a rate of 1 µg·kg-1·h-1 for 5 hours. In both groups, if MPAP increased to the level of MAP during the first hour of infusion where MPAP levels are at the highest, epinephrine (0.002 mg) was given to avoid circulatory collapse and death as reported in previous studies. In the event of hypoxia (PaO2<12 kPa) FiO2 was increased to first 0.60 and if inadequate to 0.80.

ALM Treatment:

Doses were determined by previous studies and pilot experiments using a three-tier ALM strategy. As lipopolysaccharide infusion was started animals were loaded with a bolus infusion of ALM(1) (Adenosine (0.82 mg/kg), lidocaine (1.76 mg/kg) and magnesium sulfate (0.92 mg/kg)); this was followed by a continuous infusion of ALM(2) using adenosine (300 µg kg-1·min-1), lidocaine (600 µg·kg-1·min-1) and magnesium sulfate (336 µg·kg-1·min-1) for an hour, after which the formulation was decreased to adenosine (240 µg·kg-1·min-1), lidocaine (480 µg·kg-1·min-1) and magnesium sulfate (268 µg-kg-1·min-1) (ALM3) to minimize hypotension. For continuous infusion, drugs were dissolved in 1 liter of NaCl. In the control group saline was used a vehicle infusion and was turned off after 4 hours. Observation was continued for a total of 5 hours.

Oxygen Consumption:

VO2 was calculated as the product of the arterial—mixed venous oxygen content difference and cardiac output (CO) as previously described. Oxygen delivery is calculated as the product of cardiac output and arterial oxygen content, while oxygen extraction ratio is calculated as the ratio of arterial-venous difference and arterial oxygen content.

Analysis of Blood and Urine Samples:

Arterial blood gas analysis was performed every half hour (ABL700, Radiometer, Broenshoej, Denmark). Blood plasma and urine samples were collected hourly. Blood samples were analyzed for creatinine, while urinary samples were analyzed for creatinine, protein and N-acetyl-β-D-glucosaminidase (NAGase) activity as previously reported. Urinary levels of Neutrophil gelatinase-associated lipocalin (NGAL) were determined using a commercially available enzyme-linked immunosorbent assay kit (BioPorto Diagnostics A/S, Gentofte, Denmark). NGAL and NAGase are both markers of tubular injury. Intra- and inter-assay precisions were 2.71 and 6.27% respectively. NAGase activity, protein and NGAL concentrations in urine were divided by urinary creatinine concentrations to correct for urine output.

Multiplex Cytokine Analysis:

The concentration of the cytokines Interleukin (IL)-6, IL-10, and Tumor necrosis factor-α (TNF-α) were determined using a commercially available kit (Procarta® Porcine Cytokine Assay Kit, Panomics, USA. Detection limits were, 4.39 µg/ml for IL-6, 15.41 pg/ml for IL-10, and 14.45 pg/ml for TNF-α. Inter-assay variations were 4-13%, and intra-assay variations were 1-5%.

Leukocyte Superoxide Production:

Blood samples were collected hourly and the number of leukocytes was quantified using Automated Hematology Analyzer (KX-21N, Sysmex Europe GmbH, Norderstedt, Germany). Leukocyte superoxide anion ($'O_2'$) generation was quantified using lucigenin-enhanced chemiluminescence. Each whole blood sample was divided into 2 aliquots: 1) whole blood alone, 2) whole blood+0.2 mg/ml opsonized zymosan. The '$O_2$' component of the overall signal was demonstrated by adding superoxide dismutase (3 mg/ml, Sigma Chemicals, St. Louis, Mo., USA). Lucigenin-enhanced chemiluminescence was recorded over 15 min in a Luminometer (Autolumat LP9507, Berthold Tech, Bad Wildbad, Germany) and expressed as relative light units per $10^6$ leukocytes. Data at different time points are expressed as a percentage of baseline chemiluminescence.

Pulmonary:

The alveolar-arterial oxygen difference [(A-a) was calculated using the simplified alveolar gas equation (PAO$_2$= $(P_{ATM}-P_{H2O})$*FIO$_2$–PaCO$_2$/R], where PaO2 is the alveolar partial pressure of oxygen, $P_{ATM}$ is the atmospheric pressure, $P_{H2O}$ is the saturated vapor pressure of Water (49.7 mmHg), F10$_2$ is the inspired fraction of oxygen, PaCO$_2$ is the arterial partial pressure of carbon dioxide, and R is the respiratory quotient (0.8). Wet/dry lung tissue weight ratio: representative samples of the right upper lung were weighed (wet weight) and placed in an oven at 70° C. until no further weight loss (dry weight).

Cardiac:

Real-time PV loops were obtained using the ADVantage™ system (SciSense, London, Ontario, Canada) which uses an admittance catheter to simultaneously measure left-ventricular pressure and admittance. Data were continuously recorded using a multi-channel acquisition system and Labchart software (ADInstruments, Oxford, UK). The following pressure-derived data were recorded: end-systolic pressure, end diastolic pressure, time constant of isovolumic relaxation Tau ($\tau$), maximum rate of pressure development over time (dP/dt$_{max}$), and maximum rate of pressure decrease over time (dP/dt$_{min}$). Preload was reduced by inflating the vena caval sizing catheter during respiratory apnea to obtain declining left-ventricular PV loops from which the load-independent indices of contractility were calculated: preload recruitable stroke work (PRSW), end-systolic pressure-volume relationship (ESPVR or Ees), and end-diastolic pressure-volume relationship. Arterial-ventricular coupling was described as the ratio of the Ees and the arterial elastance (Ea), i.e. (Ea/Ees). The optimal $E_A/E_S$ ratio is approximately 1 and a deviation from this indicates a decrease in arterial-ventricular coupling efficiency and cardiac performance.

Statistical Analysis:

For continuous variables a two-way repeated measures analysis of variance (ANOVA) was used to analyze data for time-dependent and between-group differences. It was determined a priori to perform post-hoc pairwise comparisons at baseline and at the end of the study; comparisons beyond this were adjusted for multiple compassions (Sidak). The repeated measurements analysis of variance (ANOVA) was a priori divided into analysis of 1) the entire study period and 2) the four hour ALM infusion period. The assumptions of the models were investigated by inspecting scatter plots of the residuals versus fitted values and normal quantile plots of the residuals and data were logarithmically transformed when necessary. If data despite logarithmical transformation did not fulfill assumptions for repeated measurements ANOVA they were analyzed using multivariate repeated measurements ANOVA (MANOVA).

All variables are presented on the original scale of measurement as mean/median and 95% confidence intervals. Two-tailed P-values less than 0.05 were considered statistically significant.

That 8 pigs were included in each group was based on power calculations with data from 6 pilot studies with respect to 1) peak TNF-$\alpha$ levels at 90 min and 2) a change in VO$_2$ from before/after infusion was discontinued (TNF-$\alpha$: Diff: 3353 µg/ml; sd=1480; $\alpha$=0.05 and $\beta$=0.1, n=5: VO$_2$: Diff: 79 ml oxygen/min; sd control=54/alm=29; $\alpha$=0.05 and $\beta$=0.1, n=7). Power calculations were performed with TNF-$\alpha$ and VO$_2$ since we wanted to investigate whether the known anti-inflammatory and metabolic lowering effects of ALM would translate into an improvement with regards to the primary endpoints cardiac and pulmonary function. The analyses were performed using Stata 12.1 (StataCorp LP, Collage Station, Tex., USA).

Results:

Hemodynamics:

ALM infusion resulted in a significantly lower MAP during the 4 hour treatment period (FIG. 30A). At the end of ALM infusion MAP immediately returned to control group values. The lower MAP during infusion of ALM was due to a lower systemic vascular resistance (Table 1) despite a significantly higher cardiac output (FIG. 30B).

At the end of the study both heart rate and stroke volume (SV) were significantly higher in the ALM group vs. the control group (Table 15). The use of intravenous epinephrine was protocol-driven to avoid circulatory collapse and death if MPAP was equal to or greater than MAP during the first 60 min. A significantly lower dose of epinephrine was administered according to this protocol in the ALM group (ALM Median 0 µg [0-0.2] µg vs. Control Median 0.6 µg [Range:0-2.4], p=0.025)

TABLE 15

Systemic Hemodynamic variables

| | Baseline | 30 min | 60 min | 90 min | 120 min | 150 min | 180 min | 210 min | 240 min | 270 min | 300 min |
|---|---|---|---|---|---|---|---|---|---|---|---|
| Systolic blood pressure (mmHg) | | | | | | | | | | | |
| Control | 103 | 83 | 89 | 99 | 98 | 102 | 102 | 106 | 102 | 102 | 102 |
| ALM | 105 | 67 | 69 | 76 | 77 | 77 | 75 | 74 | 75 | 113 | 109 |
| Diastolic blood pressure (mmHg) | | | | | | | | | | | |
| Control | 69 | 58 | 55 | 62 | 63 | 67 | 71 | 75 | 75 | 74 | 72 |
| ALM | 66 | 31 | 29 | 32 | 33 | 35 | 35 | 36 | 36 | 76 | 71 |
| Heart rate (min$^{-1}$) | | | | | | | | | | | |
| Control | 69 | 83 | 84 | 74 | 73 | 77 | 75 | 70 | 69 | 70 | 71 |
| ALM | 69 | 70 | 72 | 76 | 81 | 84 | 84 | 81 | 80 | 84 | 84 |
| Systemic vascular resistance (dyn · s/cm$^5$) | | | | | | | | | | | |
| Control | 1526 | 1242 | 1141 | 1177 | 1210 | 1501 | 1768 | 2245 | 2327 | 2357 | 2145 |
| ALM | 1500 | 607 | 635 | 652 | 644 | 689 | 710 | 742 | 816 | 1630 | 1472 |

TABLE 15-continued

Systemic Hemodynamic variables

| | Baseline | 30 min | 60 min | 90 min | 120 min | 150 min | 180 min | 210 min | 240 min | 270 min | 300 min |
|---|---|---|---|---|---|---|---|---|---|---|---|
| Pulmonary vascular resistance (dyn · s/cm$^5$) | | | | | | | | | | | |
| Control | 131 | 688 | 461 | 331 | 318 | 481 | 585 | 656 | 665 | 640 | 567 |
| ALM | 154 | 173 | 165 | 190 | 246 | 314 | 324 | 333 | 330 | 351 | 300 |
| Stroke volume (ml/beat) | | | | | | | | | | | |
| Control | 63 | 46 | 54 | 67 | 67 | 54 | 48 | 43 | 40 | 39 | 42 |
| ALM | 61 | 65 | 60 | 65 | 63 | 59 | 58 | 57 | 52 | 52 | 53 |
| Temperature (° C.) | | | | | | | | | | | |
| Control | 38.1 | 38.5 | 38.6 | 38.7 | 38.7 | 38.7 | 38.6 | 38.6 | 38.6 | 38.5 | 38.5 |
| ALM | 38.4 | 38.6 | 38.5 | 38.6 | 38.6 | 38.6 | 38.6 | 38.6 | 38.6 | 38.4 | 38.5 |

\* Significant time/group interaction during hypotensive resuscitation (ANOVA)
\# Significant time/group interaction during reperfusion (ANOVA)
† Significant difference at 60 min of hypotensive resuscitation

TABLE 16

Oxygen Consumption variables

| | Baseline | 30 min | 60 min | 90 min | 120 min | 150 min | 180 min | 210 min | 240 min | 270 min | 300 min |
|---|---|---|---|---|---|---|---|---|---|---|---|
| Arterial oxygen content (ml 0$_2$/L blood) | | | | | | | | | | | |
| Control | 131 | 122 | 137 | 142 | 145 | 146 | 151 | 151 | 154 | 153 | 151 |
| ALM | 126 | 129 | 135 | 143 | 147 | 149 | 147 | 147 | 146 | 145 | 146 |
| Venous oxygen content (ml 0$_2$/L blood) | | | | | | | | | | | |
| Control | 81 | 53 | 89 | 94 | 93 | 89 | 83 | 78 | 76 | 74 | 77 |
| ALM | 77 | 77 | 91 | 100 | 106 | 109 | 106 | 101 | 100 | 95 | 97 |
| Oxygen delivery (ml 0$_2$/L blood) | | | | | | | | | | | |
| Control | 556 | 436 | 607 | 692 | 696 | 592 | 533 | 438 | 423 | 410 | 441 |
| ALM | 527 | 569 | 571 | 686 | 742 | 740 | 710 | 670 | 602 | 619 | 648 |
| Arterial – venous difference (ml 0$_2$/L blood) | | | | | | | | | | | |
| Control | 50 | 69 | 48 | 48 | 52 | 57 | 68 | 73 | 78 | 78 | 74 |
| ALM | 48 | 51 | 44 | 42 | 41 | 40 | 42 | 46 | 46 | 51 | 50 |

\* Significant time/group interaction during hypotensive resuscitation (ANOVA)
\# Significant time/group interaction during reperfusion (ANOVA)
† Significant difference at 60 min of hypotensive resuscitation

TABLE 17

Systemic Arterial gas and Metabolic Variables

| | Baseline | 30 min | 60 min | 90 min | 120 min | 150 min | 180 min | 210 min | 240 min | 270 min | 300 min |
|---|---|---|---|---|---|---|---|---|---|---|---|
| Arterial pH | | | | | | | | | | | |
| Control | 7.48 | 7.48 | 7.44 | 7.44 | 7.44 | 7.42 | 7.41 | 7.41 | 7.41 | 7.41 | 7.41 |
| ALM | 7.48 | 7.48 | 7.45 | 7.44 | 7.41 | 7.41 | 7.40 | 7.40 | 7.40 | 7.40 | 7.40 |
| PaO$_2$ (mmHg) | | | | | | | | | | | |
| Control | 24.2 | 15.8 | 20.5 | 20.9 | 19.2 | 15.6 | 14.7 | 14.7 | 16.9 | 16.7 | 15.3 |
| ALM | 24.5 | 23.1 | 23.2 | 22.6 | 22.3 | 22.6 | 22.2 | 21.7 | 20.0 | 20.2 | 19.6 |
| PaCO$_2$ (mmHg) | | | | | | | | | | | |
| Control | 5.7 | 5.5 | 5.8 | 5.8 | 5.8 | 5.9 | 6.0 | 6.0 | 5.8 | 5.8 | 5.9 |
| ALM | 5.7 | 5.5 | 5.7 | 5.7 | 5.9 | 5.8 | 5.9 | 5.7 | 5.8 | 6.0 | 6.0 |

TABLE 17-continued

Systemic Arterial gas and Metabolic Variables

|  | Baseline | 30 min | 60 min | 90 min | 120 min | 150 min | 180 min | 210 min | 240 min | 270 min | 300 min |
|---|---|---|---|---|---|---|---|---|---|---|---|
| $ETCO_2$ (mmHg) | | | | | | | | | | | |
| Control | 43 | 42 | 45 | 45 | 44 | 43 | 42 | 41 | 40 | 40 | 40 |
| ALM | 45 | 42 | 45 | 45 | 45 | 44 | 45 | 44 | 44 | 44 | 44 |
| $HCO_3^-$ (mmol/L) | | | | | | | | | | | |
| Control | 31.4 | 30.5 | 29.1 | 28.7 | 28.7 | 27.8 | 27.6 | 27.1 | 26.9 | 26.6 | 26.8 |
| ALM | 31.4 | 30.3 | 29.0 | 28.1 | 27.4 | 27.0 | 26.6 | 26.5 | 26.1 | 26.4 | 26.6 |
| Hemoglobin (mmol/L) | | | | | | | | | | | |
| Control | 5.7 | 5.5 | 6.0 | 6.3 | 6.5 | 6.6 | 6.9 | 6.9 | 6.9 | 6.9 | 6.9 |
| ALM | 5.5 | 5.7 | 5.9 | 6.3 | 6.5 | 6.6 | 6.5 | 6.5 | 6.5 | 6.5 | 6.5 |
| Lactate (mmol/L) | | | | | | | | | | | |
| Control | 0.8 | 0.8 | 1.1 | 1.1 | 1.2 | 1.2 | 1.3 | 1.3 | 1.3 | 1.2 | 1.1 |
| ALM | 0.7 | 1.0 | 1.2 | 1.2 | 1.2 | 1.2 | 1.2 | 1.1 | 1.1 | 1.0 | 0.8 |

\* Significant time/group interaction during hypotensive resuscitation (ANOVA)
\# Significant time/group interaction during reperfusion (ANOVA)
† Significant difference at 60 min of hypotensive resuscitation

TABLE 18

Cardiac Function Variables

|  | Baseline | 30 min | 60 min | 90 min | 120 min | 150 min | 180 min | 210 min | 240 min | 270 min | 300 min |
|---|---|---|---|---|---|---|---|---|---|---|---|
| ESPVR slope (mmHg/mL) | | | | | | | | | | | |
| Control | 1.01 | | 0.88 | 0.69 | 0.64 | 0.73 | 0.72 | 0.81 | 0.89 | 0.94 | 0.88 |
| ALM | 0.86 | | 1.05 | 0.79 | 0.79 | 0.81 | 0.74 | 0.78 | 0.73 | 0.82 | 0.89 |
| ESPVR $V_0$ intercept (ml) | | | | | | | | | | | |
| Control | −38 | | −40 | −64 | −63 | −51 | −47 | −25 | −10 | −5 | 0 |
| ALM | −48 | | −7 | −25 | −26 | −29 | −31 | −23 | −30 | −39 | −33 |
| EDPVR slope (mmHg/mL) | | | | | | | | | | | |
| Control | 0.11 | | 0.14 | 0.12 | 0.12 | 0.13 | 0.12 | 0.13 | 0.12 | 0.13 | 0.11 |
| ALM | 0.10 | | 0.14 | 0.12 | 0.12 | 0.12 | 0.13 | 0.13 | 0.13 | 0.12 | 0.10 |
| EDPVR $V_0$ intercept (ml) | | | | | | | | | | | |
| Control | 64 | | 61 | 64 | 76 | 89 | 71 | 73 | 58 | 72 | 67 |
| ALM | 55 | | 49 | 56 | 51 | 54 | 41 | 57 | 58 | 61 | 55 |
| PRSW slope (mmHg * mL/mL) | | | | | | | | | | | |
| Control | 70 | | 50 | 51 | 42 | 43 | 38 | 40 | 33 | 34 | 36 |
| ALM | 70 | | 72 | 64 | 61 | 57 | 56 | 48 | 58 | 66 | 61 |
| PRSW $V_0$ intercept (ml) | | | | | | | | | | | |
| Control | 33 | | 24 | 26 | 10 | 23 | 25 | 45 | 41 | 51 | 51 |
| ALM | 27 | | 43 | 46 | 43 | 38 | 41 | 43 | 52 | 37 | 45 |
| End-Diastolic Pressure (mmHg) | | | | | | | | | | | |
| Control | 10 | | 12 | 16 | 14 | 14 | 13 | 14 | 14 | 14 | 14 |
| ALM | 11 | | 15 | 16 | 16 | 15 | 14 | 14 | 15 | 14 | 13 |
| Tau (msec) | | | | | | | | | | | |
| Control | 32 | | 30 | 35 | 35 | 37 | 38 | 41 | 44 | 44 | 44 |
| ALM | 31 | | 33 | 31 | 30 | 32 | 33 | 35 | 36 | 37 | 36 |
| Aortic elastance (mmHg/ml) | | | | | | | | | | | |
| Control | 1.3 | | 1.3 | 1.2 | 1.2 | 1.5 | 1.6 | 1.9 | 2.1 | 2.2 | 1.9 |
| ALM | 1.2 | | 0.9 | 0.8 | 0.9 | 0.9 | 0.9 | 1.1 | 1.1 | 1.6 | 1.5 |

TABLE 19

| Renal function and Plasma Cytokines | | | | | | | | | | |
|---|---|---|---|---|---|---|---|---|---|---|
| | Baseline | 30 min | 60 min | 90 min | 120 min | 150 min | 180 min | 210 min | 240 min | 300 min |
| Urinary Protein/creatinine ratio | | | | | | | | | | |
| Control | 7.5 | | 7.6 | | 9.4 | | 10.1 | | 10.2 | 11.1 |
| ALM | 9.1 | | 8.4 | | 14.1 | | 24.3 | | 19.5 | 14.7 |
| Urinary NAGase/creatinine ratio | | | | | | | | | | |
| Control | 2.2 | | 2.2 | | 2.2 | | 1.8 | | 1.8 | 2.2 |
| ALM | 2.1 | | 2.1 | | 3.0 | | 6.3 | | 6.5 | 3.0 |
| IL-6 (pg/ml) | | | | | | | | | | |
| Control | 6 | 5 | 4 | 32 | 107 | 168 | | 221 | 174 | 83 |
| ALM | 4 | 4 | 6 | 45 | 177 | 272 | | 339 | 266 | 90 |
| IL-10 (pg/ml) | | | | | | | | | | |
| Control | 5 | 10 | 327 | 391 | 215 | 213 | | 392 | 419 | 315 |
| ALM | 6 | 14 | 303 | 463 | 341 | 297 | | 347 | 354 | 383 |

Metabolic:

As a consequence of the higher cardiac output global oxygen delivery was significantly greater in the ALM group (Table 16). However, the average whole body $VO_2$ during the infusion period was significantly lower than for controls (ALM: 205 [95% CI:192-217] ml oxygen/min vs. control: 231 [95% CI:219-243] ml oxygen/min, FIG. 30C) while it immediately returned to control group values after cessation of ALM treatment.

The oxygen extraction ratio was unchanged in the ALM group supporting a favourable oxygen supply/demand status (FIG. 30D). In direct contrast, the ratio increased over time in the control group consistent with inadequate delivery of oxygen.

Lactate was significantly lower in the ALM group at the end of the study (Table 17).

Pulmonary:

Infusion of lipopolysaccharide caused a characteristic increase in MPAP with a peak at 30 min; this increase was avoided in the ALM group (FIG. 31A). ALM maintained a significantly lower MPAP during the entire study. There was an initial peak in PVR at 30 min in the control group but this was not seen in the ALM group (Table 15). PVR continued to be lower during the entire study in the ALM group.

Alveolar-arterial oxygen difference was maintained in the ALM group while it increased over time in the control group with a significant difference at the end of the study (FIG. 31B). Similarly, $PaO_2/FiO_2$ ratio was maintained in ALM group, while it decreased over time in the control group, and ended at a significantly higher level in the ALM group (FIG. 31C). Treatment with ALM significantly reduced mean pulmonary wet/dry ratio when compared to the control group (FIG. 31D).

Figure 32:
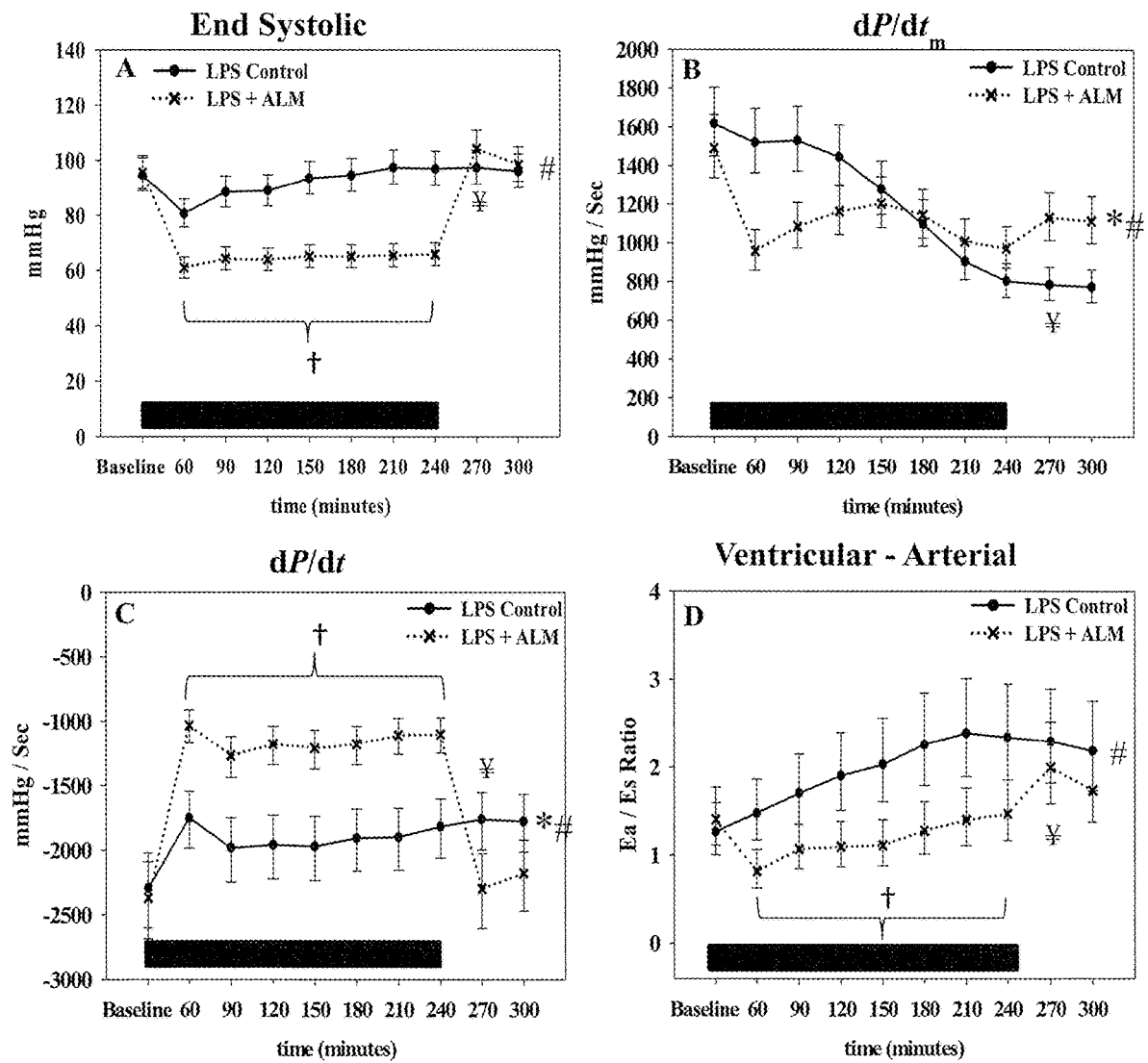
FIG. 32 shows graphs of the results of the experiments described in Example 46.
Figure 33:
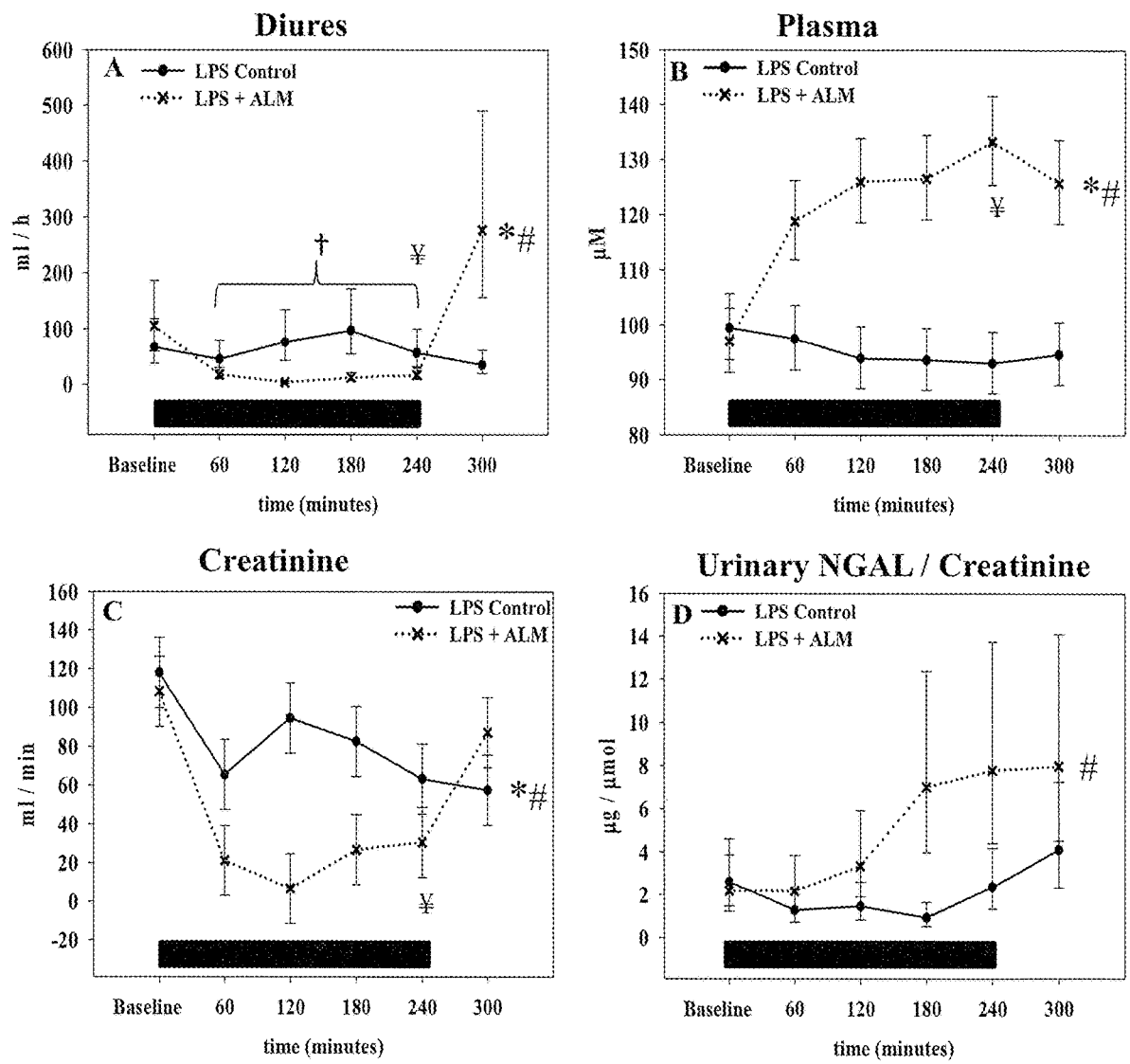
FIG. 33 shows graphs of the results of the experiments described in Example 46.

Cardiac:

The slope of the ESPVR, also named the end-systolic elastance (Ees), did not change significantly over time in either group (FIG. 32AB, Table 18). However, a rightward shift of the volume axis intercept (Vo) was observed in the control group consistent with decreased contractility; this shift was prevented in the ALM group (FIG. 32AB/Table 18). The slope of the PRSW, an index of overall cardiac performance, decreased in the control group but this was preserved in the ALM group (FIG. 32CD, Table 18). In both groups there was a rightward shift in the intercept of PRSW with no significant group difference at the end of the study. Another index of cardiac contractility dP/dtmax was significantly higher at the end of the study when compared to the control group, at equal pressures (FIG. 33AB). The end-diastolic pressure-volume relationship did not change significantly over time and there was no group difference (data not shown). However diastolic function evaluated by dP/dt-min and Tau was significantly improved in the ALM group (FIG. 33C/Table 18). Arterial-ventricular coupling (Ea/Ees) increased progressively in the controls during the course of the experiment consistent with mismatched coupling. This was not observed in the ALM group during ALM infusion, whereas the Ea/Es ratio increased to control group levels after infusion was discontinued (FIG. 33D).

Renal:

Urine output decreased significantly during infusion of ALM (FIG. 34A), but the production increased rapidly after ALM was discontinued resulting in a significantly higher urine output in the ALM group when compared to controls at the end of the study. Despite these temporal differences, there was no significant difference in total urine production during the entire study (ALM: 487[95% CI:236-738] ml vs. control: 544[95% CI:300-788] ml). Plasma creatinine levels increased steadily in the ALM group during infusion (FIG. 34B). After the infusion of ALM was discontinued, there was an immediate decrease in plasma creatinine. Creatinine levels remained 33% higher at the end of the study in the ALM group.

The higher plasma creatinine level during ALM infusion was due in part to decreased creatinine clearance. However, creatinine clearance was significantly higher in the ALM group when compared to controls after infusion was discontinued (FIG. 34C). Both urinary protein/creatinine ratio and NAGase/creatinine ratio increased in the ALM group during ALM infusion but returned to values comparable to the control group after infusion was turned off (Table 19). There was a significantly different development over time between groups with regards to urinary NGAL/creatinine ratio; however no significant group difference existed at the end of the study. (FIG. 34D). Overall markers of renal dysfunction increased in the ALM group during infusion of ALM, but returned to control group levels after the infusion, with the exception of higher plasma creatinine levels and an increase in creatinine clearance in the ALM group compared with controls.

Inflammation:

Infusion of lipopolysaccharide caused a characteristic increase in plasma cytokines (Table 5). Peak TNF-α levels after 90 min of lipopolysaccharide were significantly lower in the ALM group (Control/ALM ratio: 1.63[95% CI:1.11-2.38]; p=0.02). No significant difference existed between groups with regards to IL-6 or IL-10. Total blood leukocyte count decreased over time, with no group differences. In vitro superoxide anion production was significantly lower in the ALM group when compared to the control group.

The present study has shown that treatment with ALM in an endotoxemic porcine model induced a reversible hypotensive state with significantly higher oxygen delivery and lower systemic vascular resistance than lipopolysaccharide controls. Furthermore, infusion of ALM attenuated the lipopolysaccharide-induced increase in whole body $VO_2$, improved cardiac function, increased $PaO_2/FiO_2$ with lower lung wet/dry ratios, and reduced inflammation indicated by lower TNF-α and superoxide anion production.

ALM Treatment

The treatment regime and dosing of ALM was determined from published rat and porcine hemorrhage studies, and from pilot studies in the lipopolysaccharide porcine model. An intravenous bolus of ALM was administered at the start of lipopolysaccharide infusion as a loading dose to increase concentrations in the vascular compartment, followed by constant infusion. After 60 min, the ALM infusion dose was reduced to minimize further hypotension based on our pilot studies, and as shown in FIG. 30A. Magnesium sulfate was added to adenosine-lidocaine (making ALM) based on its ability to improve hemodynamics and correct coagulopathy in a rat model of hemorrhagic shock.

In animal models of LPS infusion and polymicrobial peritonitis, the individual components of A, L or M has previously demonstrated a number of beneficial effects on organ function and survival. It has been shown that lidocaine infusion improved 7 day survival, and reduced TNF-α production, neutrophil infiltration and apoptosis. However, in hemorrhagic shock and trauma it has been shown that it is the unique combination of ALM that exerts synergistic effects related to hemodynamic stability, myocardial salvage and neutrophil activation, which were not conferred by the individual drugs alone.

Hemodynamic Response to ALM Treatment

According to the Surviving Sepsis Campaign guidelines patients with hypotension should be resuscitated to target a MAP above 65 mmHg to ensure adequate tissue perfusion. These guidelines are highly relevant for patients with severe sepsis or septic shock who are hypotensive, have cardiac dysfunction with increasing levels of lactate. This is not the case in this experimental model. In the present study, ALM induced a reversible hypotensive state with a MAP of 47 mmHg that under normal clinical circumstances would require immediate action. This study has further shown that this hypotensive state was stable and was associated with an increase in cardiac and pulmonary function, increased oxygen delivery and normal lactate levels. Interestingly, using the same anesthesia and same size pigs, the inventor has previously shown that a single bolus of ALM during resuscitation, despite the vasodilatory properties of each of its component, increased MAP from a shock state of 37 mmHg to ~48 mmHg after severe hemorrhage with significantly lower blood lactate levels than controls. Similarly, in the present study, despite a MAP of 47 mmHg in normovolemic ALM pigs, cardiac function was improved and lactate levels were significantly lower than in controls over the 4 hour period. It is concluded that the ALM-induced hypotensive state during lipopolysaccharide infusion had no signs of severe whole body ischemia.

Despite that the infusion was turned off after 4 hours, the protective effect on cardiac and pulmonary function was maintained at the end of study, implying that the protective effect of the treatment is also related to the activation of downstream signaling mechanisms outlasting the infusion period. The nature of these signaling mechanisms has to be determined in further studies.

Cardiac

In the current study lipopolysaccharide infusion impaired both systolic and diastolic function, and arterial-ventricular coupling. Systolic dysfunction was evident in controls by a rightward shift of the ESPVR and a decrease in dP/dtmax and PRSW. Diastolic dysfunction was evident by an increase in Tau and dP/dtmin. The present study did not investigate the cellular mechanisms of lipopolysaccharide-induced dysfunction, but these may include lipid peroxidation, abnormal calcium handling, production of inflammatory cytokines, and autonomic dysfunction. Treatment with ALM resulted in a significant and clinically relevant improvement in all measured cardiac functional parameters after 5 hours of observation. The reduction in neutrophil activation and TNF-α release with ALM may be a mechanism underlying cardioprotection as these mediators are known to depress myocardial function.

In this study lipopolysaccharide infusion increased the Ea/Ees ratio in the control group over time as reported in other studies, which indicates a decrease in coupling efficiency and cardiac performance. This increase in the Ea/Ees ratio was prevented in the ALM group during the infusion period only. The decrease in SV and apparent loss in arterial-ventricular coupling efficiency observed in controls may be linked to a higher MPAP, and possibly right heart dysfunction contributing to a lower SV. Since Ees was unchanged in the ALM group, the lower Ea/Ees ratio was due largely to a significantly lower Ea (end-systolic pressure/SV) relative to controls. Hence, ALM optimizes arterial-ventricular coupling with a reduced MPAP and a higher stroke volume.

Pulmonary

Intravenous administration of lipopolysaccharide is a widely used and relevant model of acute lung injury. In the present study acute lung injury was evident in controls by a decrease in $PaO_2/FiO_2$, an increase in the alveolar-arterial oxygen difference, a higher MPAP and an increase in wet/dry ratio. Treatment with ALM improved pulmonary status as manifested by significantly higher $PaO_2/FiO_2$ ratio, a lower alveolar-arterial oxygen difference, lower MPAP and lower wet/dry ratio. At the end of the study, the difference in $PaO_2/FiO_2$ ratio was 129[95% CI:73-184]% higher in the ALM pigs, which we regard as a clinical relevant difference. Following lipopolysaccharide infusion, pulmonary dysfunction and the increase in wet/dry ratio is most likely related to a combination of elevated microvascular pressure and increased vascular permeability.

The improvement in wet/dry ratio and oxygenation with ALM treatment may relate to both a reduction in PVR and a reduction in vascular permeability. It has been shown in an endotoxemic porcine model that adenosine alone infusion reduced extravascular lung water content without a reduction in MPAP, suggesting a fall in wet/dry ratio may in part be related to preserved endothelial permeability. In this study, this is consistent with the observed significant decrease in TNF-α production and leukocyte superoxide anion production, which are known mediators of endothelial dysfunction. However, treatment with ALM also caused a significant reduction in PVR, supporting this contention that the improvement in pulmonary function is related to both improved vascular permeability and a reduction in reduction in peripheral vascular resistance.

Acute Kidney Injury

Figure 34:
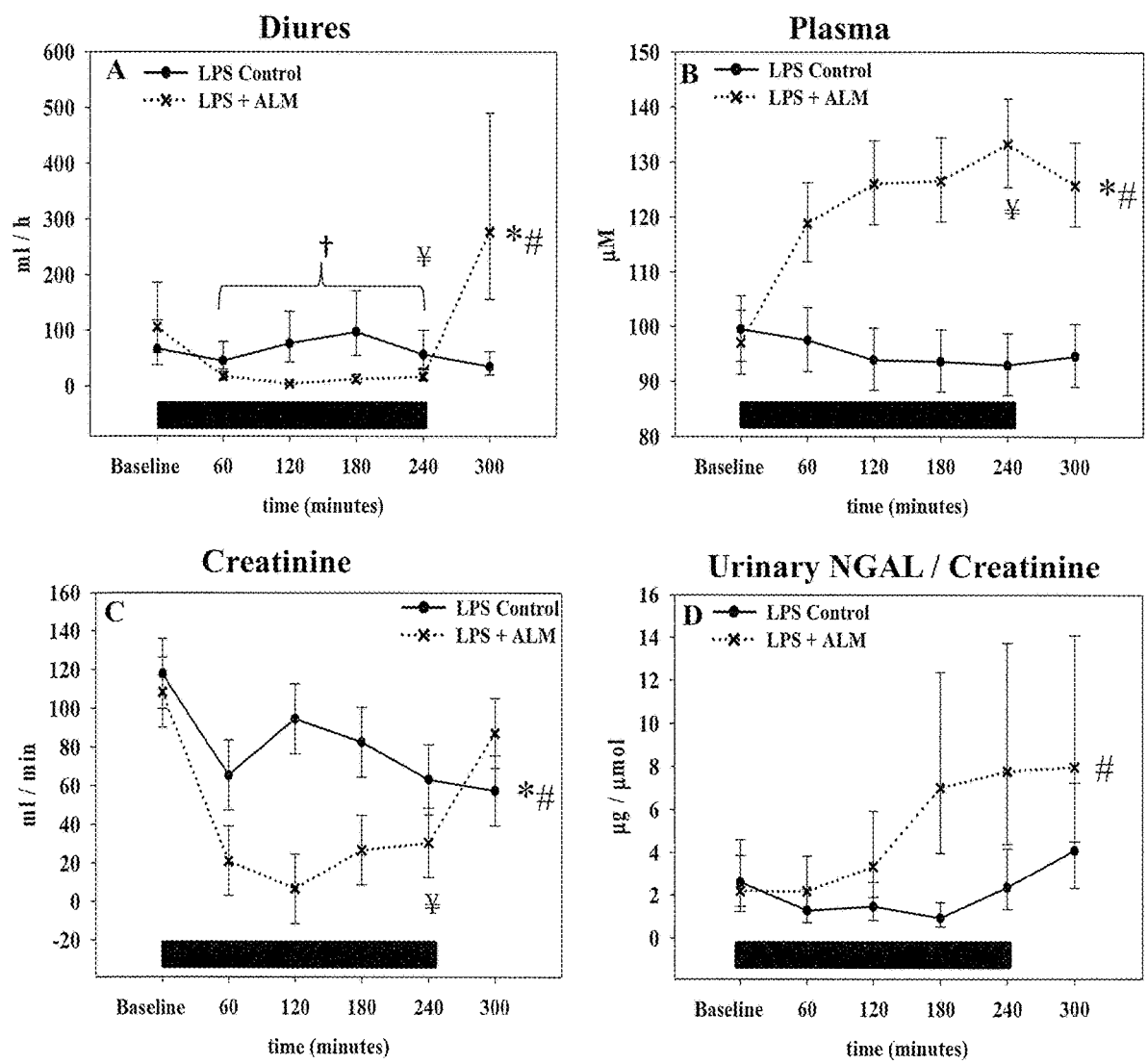
FIG. 34 shows graphs of the results of the experiments described in Example 46.

Previous animal studies have demonstrated that targeting a lower MAP resulted in a higher incidence of acute kidney injury, which is why renal function was meticulously evaluated using several parameters. Adenosine, for example, is believed to be involved in regulation of tubuloglomerular feedback, and infusion in humans increases renal blood flow and lowers the glomerular filtration rate. The adenosine-mediated decrease in glomerular filtration rate is mediated by post-glomerular arteriole vasodilation reducing filtration pressure but preserving renal blood flow. In the present study, during ALM infusion urine output and creatinine clearance decreased while plasma creatinine and the excretion of urinary markers of kidney dysfunction were increased (FIG. 34). The increase in plasma creatinine during infusion was related to a decrease in excretion probably mediated by post-glomerular arteriole vasodilation and a drop in filtration pressure; however the high creatinine clearance, and the decrease in plasma creatinine and normalization of urinary markers after ALM was discontinued indicates that the kidneys were well perfused during the hypotensive period and normally functioning after restoration of blood pressure. In conclusion, LM-induced hypotension resulted in a temporary decrease in renal function; however this appeared to normalize after the ALM treatment was discontinued despite higher plasma creatinine levels and an increase in creatinine clearance compared with controls. Longer observation times are needed to evaluate whether creatinine levels would normalize over time and to fully assess the relationship between renal function and ALM treatment.

Oxygen Consumption and Delivery

Previous studies in septic patients have demonstrated that whole body VO2 is increased compared to healthy controls. VO2 increased in the control group in the present study. In contrast, infusion of ALM maintained VO2 at a significantly lower set-point than controls, along with significantly higher oxygen delivery and a higher arterial-venous oxygen difference. The VO2-lowering effect of ALM disappeared immediately after cessation of the infusion, indicating that the effect was directly related to the treatment. This is consistent with a previous study of porcine hemorrhagic shock in which the combination of adenosine and lidocaine reduced whole body VO2 by 27% after return of shed blood during resuscitation.

In this study, it is possible that ALM reduced VO2 in part by blunting the hypermetabolic effects of elevated catecholamine levels via anti-adrenergic receptor modulation. While plasma lactate levels increased in controls, lactate levels were consistently lower in the ALM, consistent with an improved oxygen supply-demand balance. It is recognized that the small difference in lactate levels may be clinically irrelevant, however, a recent clinical study demonstrated that even mild hyperlactatemia, similar to that observed in controls, was associated with worse outcome in critically ill patients.

Summary of Results:

Infusion of ALM lowered mean arterial pressure during the 4 hour infusion period (ALM: 47[95% CI:44-50] mmHg vs. control: 79[95% CI:75-85] mmHg, p<0.0001). After cessation of ALM mean arterial pressure immediately returned to control group values (ALM: 88[95% CI:81-96] mmHg vs. control: 86[95% CI:79-94] mmHg, p=0.72). Whole body $VO_2$ was significantly lower during ALM infusion when compared to controls (ALM: 205 [95% CI:189-221] ml oxygen/min vs. control: 231 [95% CI:215-247] ml oxygen/min, p=0.016). ALM treatment reduces pulmonary injury evaluated by $PaO_2/FiO_2$ ratio (ALM: 388[95% CI:349-427] vs. control: 260[95% CI:221-299], p=0.0005). Furthermore, preload recruitable stroke work was preserved in the ALM group (ALM: 61[95% CI:51-74] mmHg · ml/ml control: 36[95% CI:30-43] mmHg·ml/ml, p<0.001). Creatinine clearance was significantly lower during ALM infusion but reversed after cessation of infusion. ALM reduced tumor necrosis factor-α peak levels (ALM 7121 [95% CI:5069-10004] pg/ml vs. control 11596[95% CI:9083-14805] pg/ml, p=0.02)

Conclusion

The present study demonstrates that treatment with ALM in an endotoxemic porcine model: 1) induces a state of reversible hypotension with improved oxygen delivery, cardiac and pulmonary function; 2) reduces whole body $VO_2$; 3) reduces neutrophil activation and TNF-α release; and 4) causes a modest transient drop in renal function that is reversed after the treatment is stopped. In this porcine model of endotoxemia ALM treatment induces a reversible hypotensive and hypometabolic state, improves cardiac and pulmonary functions and attenuates tumor necrosis factor-α levels.

Example 47: Small-Volume 7.5% NaCl
Small-Volume 7.5% NaCl Adenosine, Lidocaine, and Mg2+ has Multiple Benefits During Hypotensive and Blood Resuscitation in the Pig Following Severe Blood Loss: Rat to Pig Translation Objectives: Currently, there is no effective small-volume fluid for traumatic hemorrhagic shock. The objective was to translate small-volume 7.5% NaCl adenosine, lidocaine, and Mg2+ hypotensive fluid resuscitation from the rat to the pig.

Design: Pigs (35-40 kg) were anesthetized and bled to mean arterial pressure of 35-40 mm Hg for 90 minutes, followed by 60 minutes of hypotensive resuscitation and infusion of shed blood. Data were collected continuously.

Setting: University hospital laboratory.

Subjects: Female farm-bred pigs.

Interventions: Pigs were randomly assigned to a single IV bolus of 4 mL/kg 7.5% NaCl+adenosine, lidocaine and Mg2+ (n=8) or 4 mL/kg 7.5% NaCl (n=8) at hypotensive resuscitation and 0.9% NaCl±adenosine and lidocaine at infusion of shed blood.

Measurements and Main Results: At 60 minutes of hypotensive resuscitation, treatment with 7.5% NaCl+adenosine, lidocaine, and Mg2+ generated significantly higher mean arterial pressure (48 mm Hg [95% CI, 44-52] vs 33 mm Hg [95% CI, 30-36], p<0.0001), cardiac index (76 mL/min/kg [95% CI, 63-91] vs 47 mL/min/kg [95% CI, 39-57], p=0.002), and oxygen delivery (7.6 mL 02/min/kg [95% CI, 6.4-9.0] vs 5.2 mL 02/min/kg [95% CI, 4.4-6.2], p=0.003) when compared with controls. Pigs that received adenosine, lidocaine, and Mg2+/adenosine and lidocaine also had significantly lower blood lactate (7.1 mM [95% CI, 5.7-8.9] vs 11.3 mM [95% CI, 9.0-14.1], p=0.004), core body temperature (39.3° C. [95% CI, 39.0-39.5] vs 39.7° C. [95% CI, 39.4-39.9]), and higher base excess (−5.9 mEq/L [95% CI, −8.0 to −3.8] vs −11.2 mEq/L [95% CI, −13.4 to −9.1]). One control died from cardiovascular collapse. Higher cardiac index in the adenosine, lidocaine, and Mg2+/adenosine and lidocaine group was due to a two-fold increase in stroke volume. Left ventricular systolic ejection times were significantly higher and inversely related to heart rate in the adenosine, lidocaine, and Mg2+/adenosine and lidocaine group. Thirty minutes after blood return, whole-body oxygen consumption decreased in pigs that received adenosine, lidocaine, and Mg2+/adenosine and lidocaine (5.7 mL 02/min/kg [95% CI, 4.7-6.8] to 4.9 mL 02/min/kg [95% CI, 4.2-5.8]), whereas it increased in controls (4.2 mL 02/min/kg [95% CI, 3.5-5.0] to 5.8 mL 02/min/kg [95% CI, 4.9-5.8], p=0.02). After 180 minutes, pigs in the adenosine, lidocaine, and Mg2+/adenosine and lidocaine group had three-fold higher urinary output (2.1 mL/kg/hr [95% CI, 1.2-3.8] vs 0.7 mL/kg/hr [95% CI, 0.4-1.2], p=0.001) and lower plasma creatinine levels.

Conclusion: Small-volume resuscitation with 7.5% NaCl+adenosine, lidocaine, and Mg2+/adenosine and lidocaine provided superior cardiovascular, acid-base, metabolic, and renal recoveries following severe hemorrhagic shock in the pig compared with 7.5% NaCl alone.

Hemorrhage is the leading cause of death on the battlefield and accounts for 30-40% of deaths in the civilian population in relation to trauma with one-third to one-half occurring in the prehospital environment. Permissive or delayed hypotensive resuscitation using small-volume infusions in contrast to high-volume fluid resuscitation strategies has gained increasing acceptance on the battlefield and at some level 1 trauma centers in the United States.

The concept of hypotensive resuscitation can be traced back to 1918, when it was suggested that targeting a systolic pressure of 70-80 mm Hg to avoid losing more "blood that is sorely needed." This "limited" fluid approach was endorsed in the Second World War and lay dormant for many decades. In 2011, further support of the concept came from a prospective, randomized human trial, which showed that targeting a mean arterial pressure (MAP) of 50 mm Hg, rather than 65 mm Hg, was safe, reduced transfusion requirements, and lowered the risk of early coagulopathic bleeding.

Pharmacologic combinational agents such as adenosine and lidocaine (AL) and adenosine, lidocaine, and $Mg^{2+}$ (ALM) may improve outcomes if added as a supplement to resuscitation fluids. ALM at high doses is currently used in cardiac surgery to arrest the heart in a polarized state and at lower doses is used to reanimate or resuscitate the heart and prevent reperfusion injury. It is the lower dose in hypertonic saline that is being examined in animal models following trauma and in this study. In 2011, Letson and Dobson showed that small-volume bolus (1 mL/kg) hypertonic saline (7.5% NaCl) with ALM gently raised MAP into the hypotensive range following severe (40%) to massive (60%) blood loss and shock in rats. In 2012, this group further showed that "the same solution" fully corrected coagulopathy in a rat model of 40% blood loss. Previously, we reported that a bolus of ALM at fluid resuscitation significantly reduced crystalloid fluid requirements by 40% (volume-sparing effect) with improved cardiac function during 30 minutes of hypotensive resuscitation in a porcine model of severe hemorrhagic shock. Furthermore, we demonstrated that infusion of AL during blood resuscitation transiently reduces whole-body oxygen consumption ($Vo_2$) and improved cardiac and renal function.

The aim of this study is to confirm and extend the findings from the rat studies using small-volume bolus hypertonic (7.5%) saline resuscitation (4 mL/kg) with or without ALM to the porcine model of 75% blood loss. We hypothesize that treatment with 7.5% NaCl+ALM at hypotensive resuscitation and 0.9% NaCl+AL at blood return exerts beneficial effects through improved hemodynamic rescue and improved cardiorenal function.

Materials and Methods
Animal Preparation

Eighteen female crossbred Landrace/Yorkshire/Duroc pigs (35-40 kg) were fasted overnight but were allowed free access to water. Anesthesia was induced with midazolam (20 mg) and s-ketamine (250 mg) and maintained with a continuous infusion of fentanyl (60 μg/kg/hr) and midazolam (6 mg/kg/hr). The animals were intubated and volume-control ventilated (S/5 Avance; Datex Ohmeda, Madison, Wis.) with a positive end-expiratory pressure of 5 cm $H_2O$, $FIo_2$ of 0.35, and a tidal volume of 10 mL/kg. Ventilation rate was adjusted to maintain $Paco_2$ between 41 and 45 mm Hg. The body temperature was kept around 38-38.5° C. at baseline, while no heating or cooling was applied during bleeding and resuscitation. All animals received 0.9% saline at a maintenance rate of 10 mL/kg/hr during surgery and the base line period, but it was turned off at the start of bleeding. Despite carefully being warmed, infusion of hypertonic saline and reinfusion of warm shed blood resulted in a transient decrease in core temperature, which may have triggered shivering in a number of pigs. Shivering is known to increase $Vo_2$, an endpoint in the current study, which is why a bolus of the neuromuscular blocking agent (rocuronium 1.25 mg/kg) was infused at these time points.

Surgical Preparations and Monitoring

A pressure catheter (Millar Instruments, Houston, Tex.,) was inserted into the left ventricle (LV) through the carotid artery. A pulmonary artery catheter (CCOmbo, Edwards Lifesciences, Irvine, Calif.) was inserted through the jugular vein to monitor cardiac index and core temperature. Through the femoral artery, a pigtail catheter (Medtronic, Minneapolis, Minn.) was placed in the LV for injection of microspheres. All catheters were positioned under fluoroscopic guidance, and animals were treated with 200 U/kg of heparin and supplemented (100 U/kg) after 90 and 180 minutes to maintain patency of the multiple catheters. A bladder catheter was placed for urine collection. Systemic vascular resistance index (SVRI) (dyn·s/$cm^5$/kg) was calculated using the following equation: SVRI=80·(MAP−central venous pressure [CVP])/cardiac index. All animals were stabilized for 1 hour before the start of the experiment.

Experimental Protocol

Figure 35:
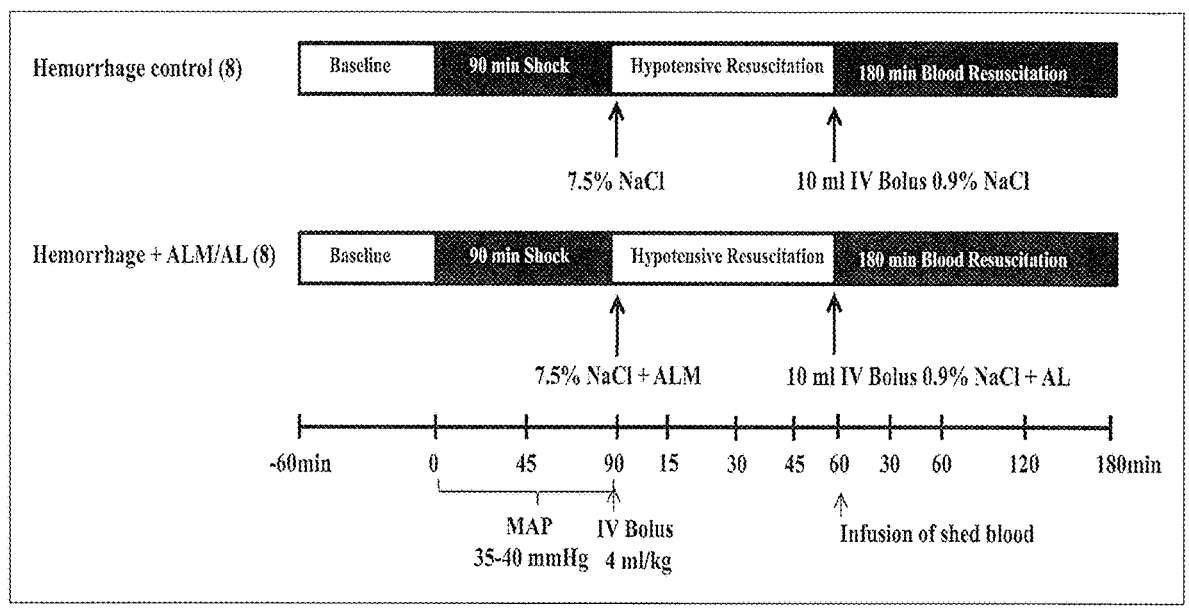
FIG. 35 shows a schematic diagram of the experimental protocol for Example 47.

After instrumentation, each animal was randomly assigned in a blinded manner: group 1, hemorrhage control (n=8) and group 2, hemorrhage+ALM/AL (n=8) (FIG. 35). Animals were bled to a MAP of 40 mm Hg at a rate of 2.15 mL/kg/min over 7 minutes and then 1.15 mL/kg/min over the remaining period. Animals were kept at a MAP of 35-40 mm Hg for 90 minutes by withdrawing or infusing shed blood as needed. The shed blood was stored in a citrated glucose solution at 38° C.

Following 90 minutes of hemorrhagic shock, animals were resuscitated. Animals in the treatment group received a low concentration of the ALM (adenosine [0.54 mg/kg], lidocaine [1.63 mg/kg], and $MgSO_4$ [0.6 mg/kg]) suspended in the 4 mL/kg 7.5% hypertonic saline, whereas those in the nontreatment groups were administered only 4 mL/kg 7.5% hypertonic saline. Upon bolus administration of ALM over 5 minutes (~1 mL/min/kg), a period of transient hypotension was observed after which MAP slowly increased into the hypotensive range. Hypotension was not observed in the hypertonic saline alone (control) group. After 60 minutes of permissive hypotension, the shed blood volume was reinfused at a rate of 60 mL/min and the pigs were observed for 3 hours. At the start of blood resuscitation, a higher concentration of AL (adenosine [1 mg/kg] and lidocaine [2 mg/kg]) dissolved in 10 mL 0.9% NaCl was infused in treatment group during the first minutes, whereas the non-treatment group received just 10 mL of 0.9% NaCl.

The rationale for administering a second bolus during shed blood return was taken from previous studies and from the strategy of preventing organ dysfunction following hemorrhagic shock due to reperfusion injury. Reperfusion injury occurs with both fluid and blood resuscitation, and if therapy is delayed, the protective effect on reperfusion injury is abrogated, that is, what happens first must be treated first. Hence, the second bolus was administered to target reperfusion injury specifically during blood resuscitation and to provide additional hemodynamic support, attenuate whole-body $Vo_2$, and improve renal function.

Whole-Body $Vo_2$ $Vo_2$ was calculated as the product of the arterial—mixed venous oxygen content difference and cardiac index. The oxygen content (C) was calculated by the following formula: $C=(1.36 \times Hb \times So_2+0.003 \times Po_2)$, where Hb is the hemoglobin concentration (g/dL), $So_2$ is the oxygen saturation, and $Po_2$ is the partial pressure of oxygen. Arterial and mixed venous blood gases were collected halfway during the shock phase and every 30 minutes for the remainder of the experiment (ABL 725: Radiometer, Copenhagen, Denmark).

Regional Blood Flow

Regional organ blood flow in the heart, kidney, liver, and skeletal muscle was measured by neutron-activated microspheres (BioPhysics Assay Laboratory, Worcester, Mass.). Organ blood flow is expressed as mL/min/g.

Analysis of Blood and Urine Samples

Blood plasma was analyzed for creatinine according to standard procedures (Siemens Clinical Methods for ADVIA 1650). Intra- and interassay precisions were below 3.0 and 4.0 coefficient of variation (CV) %, respectively. Urine was analyzed for creatinine and total protein (pyrogallol red method according to standard procedures, Siemens Clinical Methods for ADVIA 1650). Intra- and interassay precisions were below 2.7 and 3.7 CV %, respectively. Urinary N-acetyl-P-D-glucosaminidase (NAG) activity (EC 3.2.1.30) was determined by a kinetic, fluorometric assay. Matrix for standards and control material was heat denatured urine from pigs. Intra- and interassay precision was 5.0 and 5.7 CV %, respectively. NAG and protein concentration in urine is divided by urinary creatinine concentrations. Creatinine clearance as a marker of glomerular filtration was calculated using the following formula: Clearance=V U/P, where V is urine volume period, U is creatinine concentration in the sampled urine, and P is creatinine concentration in plasma in the period of urine sampling.

Cardiac Function

The pressure catheter transducer output was fed to a Pressure Control Unit (Millar Instruments). Data were collected using data acquisition software (NOTOCHORD HEM, Paris, France). Pressure-derived data were analyzed throughout the study: end-systolic pressure, end-diastolic pressure, maximum rate of pressure development over time (dP/dtmax), maximum negative rate of pressure decrease over time ($dP/dt_{min}$), and ejection times.

Statistical Analysis

It was predetermined to analyze the data in three temporal phases: 1) the entire study, 2) the fluid resuscitation phase, and 3) the blood resuscitation phase as previously reported. The differences in baseline values and mean/median levels were analyzed using Student t test. For continuous variables, a repeated measurements analysis of variance (ANOVA) was used to analyze data for time-dependent and between-group differences. The assumptions of the models were investigated by inspecting scatter plots of the residuals versus fitted values and normal quantile plots of the residuals. If data did not fulfill assumptions for ANOVA, they were analyzed using multivariate ANOVA. Non-normally distributed data were transformed on a logarithmic scale to ensure normality and constant variation between animals over time. All variables are presented on the original scale of measurement as mean/median and 95% CI. In case of logarithmic transformation, the difference between groups is expressed as a ratio with 95% CI ((log(a)–log(b)=log(a/b)).

The number of pigs was based on power calculations with respect to the a priori determined primary endpoint MAP after 60 minutes of permissive hypotension. With an absolute difference of 19 mm Hg (SD=10) between groups in four pilots, we estimated that seven pigs in each group would be needed to provide a statistical power of 90% to detect a two-tailed a value of 0.05. In a previous experiment, two pigs developed irreversible shock during permissive hypotension, and hence, a total number of eight pigs were included in each group. Two-tailed p values of less than 0.05 were considered statistically significant. The analyses were performed using Stata 11.2 (StataCorp LP, Collage Station, Tex.).

Results

Experimental Model

Total blood loss was 49.1 mL/kg (95% CI, 44.8-53.5) in the hemorrhage control group and 49.0 mL/kg (95% CI, 43.9-54.1) in the ALM/AL group, corresponding to 73% of total blood volume. One animal was excluded due to pericarditis whereas one animal went into ventricular fibrillation during hemorrhagic shock before group assignment and was excluded; eight pigs in each group were included in the final analysis. No significant group differences existed at 90 minutes of bleeding.

Hypotensive Resuscitation

Figure 36:
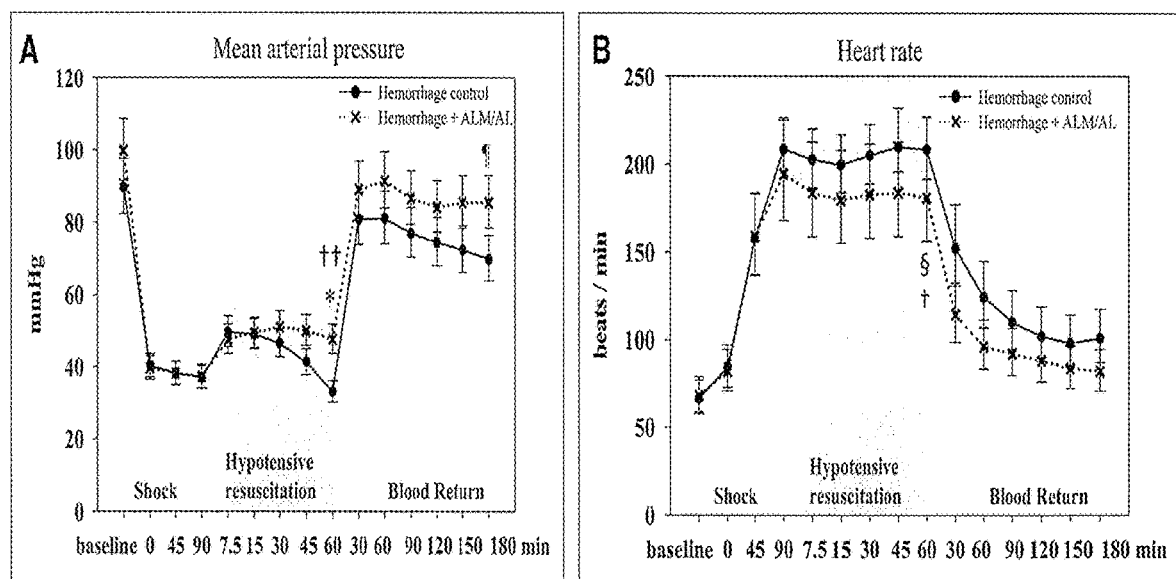
FIG. 36 shows graphs showing the effect of treatment with adenosine, lidocaine, and Mg2+ (ALM)/adenosine and lidocaine (AL) on mean arterial pressure (MAP) (A) and heart rate (HR) (B).

A single bolus of 4 mL/kg 7.5% NaCl (control) resulted in a rapid increase in MAP peaking after 7.5 minutes followed by a steady decline to 33 mm Hg (95% CI, 30-36) at 60 minutes (FIG. 36A). In contrast, a bolus of 4 mL/kg 7.5% NaCl+ALM increased and stabilized MAP reaching 48 mm Hg (95% CI, 44-52) (ratio, 1.45 [95% CI, 1.28-1.64]; p<0.001 vs control group) at 60 minutes of hypotensive resuscitation. The higher MAP was due to both significantly higher systolic and diastolic pressures in the ALM/AL group (Table 20).

The higher MAP in the ALM/AL group at 60 minutes was also associated with a significantly higher pH (7.28 [95% CI, 7.25-7.32] vs 7.21 [95% CI, 7.17-7.24]; ratio, 1.01 [95% CI, 1.00-1.02]; p=0.028), a higher base excess (−5.9 mEq/L [95% CI, −8.0 to −3.8] vs −11.2 mEq/L [95% CI, −13.4 to −9.1]; difference, −5.4 [95% CI, −8.9 to −2.0]; p=0.0047), and lower plasma lactate (7.1 mM [95% CI, 5.7-8.9] vs 11.3 mM [95% CI, 9.0--14.1]; ratio, 0.63 [95% CI, 0.46-0.86]; p=0.004) (Table 21) compared with controls, Interestingly, heart rate (HR) was significantly lower in ALM/AL versus the control group (FIG. 368). Core temperature was also lower in the ALM/AL group during hypotensive resuscitation with a significance at 60 minutes (39.3 [95% CI, 39.0-39.5] vs 39.7 [95% CI. 39.4-39.9]; difference, 0.38 [95% CI, 0.01-0.74]; p<0.05) (Table 20). During the last 30 minutes of hypotensive resuscitation, there was an increase in plasma hemoglobin and potassium levels in controls, but the increase was not observed in the ALM/AL group (Table 21).

Figure 37:
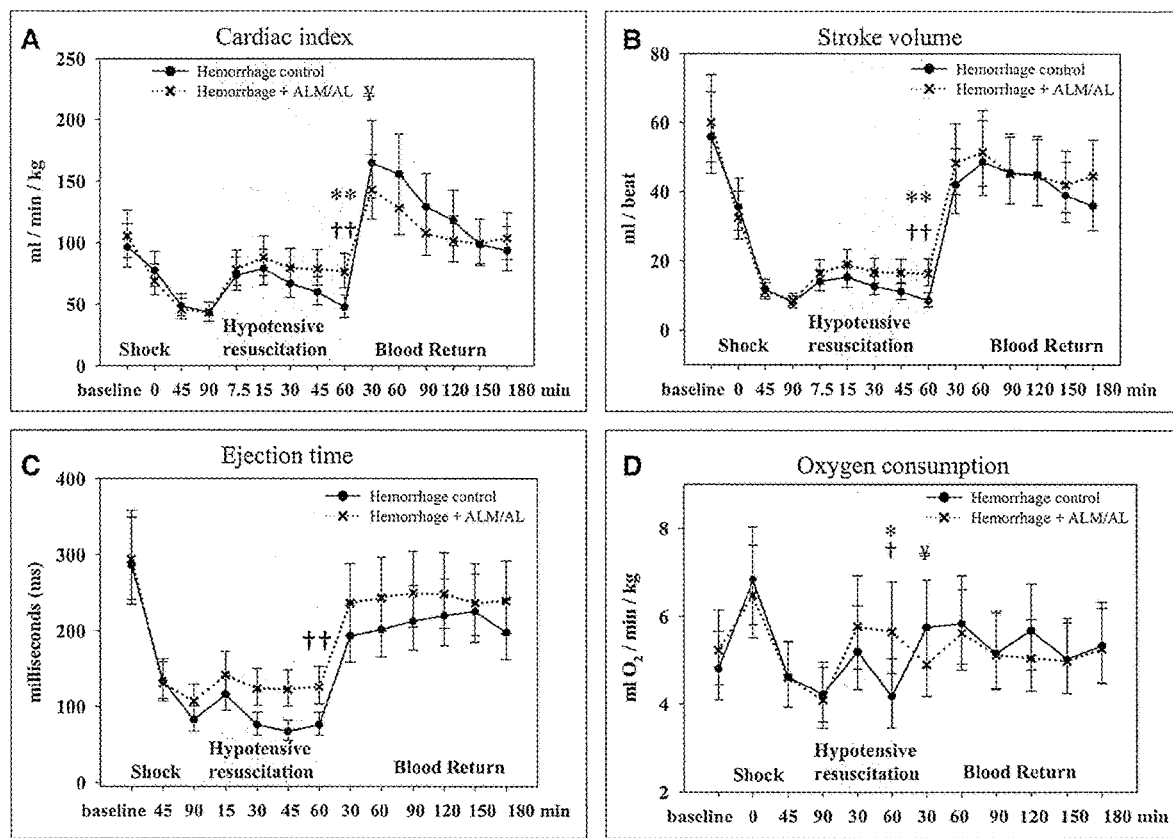
FIG. 37 shows graphs showing cardiac index (A), stroke volume (B), ejection time (C), and oxygen consumption ($Vo_2$) (D) during both hypotensive resuscitation and after infusion blood.

Cardiac index and stroke volume were significantly higher (cardiac index: ratio, 1.66 [95% CI, 1.21-2.28] and stroke volume: ratio, 1.91 [95% CI, 1.37-2.67]) in the ALM/AL group at the end of hypotensive resuscitation (FIG. 37, A and B). Ejection time was also higher in the ALM/AL group.

TABLE 20

Systemic Hemodynamic Variables and Central Temperature at Baseline and During the Bleeding, Hypotensive Resuscitation, and Blood Reperfusion Phases

| | Bleeding | | | |
|---|---|---|---|---|
| | Baseline | 0 Min | 45 Min | 90 Min |
| Systolic arterial pressure, mm Hg | | | | |
| Hemorrhage | 109 (100-119) | 59 (54-64) | 60 (55-66) | 69 (63-75) |
| Hemorrhage + ALM/AL[a] | 118 (108-130) | 57 (52-63) | 56 (52-62) | 61 (56-67) |
| Diastolic arterial pressure, mm Hg | | | | |
| Hemmorhage | 73 (65-82) | 31 (28-35) | 29 (26-32) | 27 (24-30) |
| Hemorrhage + ALM/AL[a] | 83 (74-83) | 29 (36-33) | 29 (26-33) | 27 (24-30) |
| Central venous pressure, mm HG | | | | |
| Hemorrhage | 10 (9-12) | 5 (5-6) | 4 (3-5) | 4 (3-4) |
| Hemorrhage + ALM/AL | 8 (7-9) | 5 (4-6) | 4 (3-4) | 4 (4-5) |
| Systemic vascular resistance index, dyn-s/cm$^5$/kg | | | | |
| Hemorrhage | 44 (36-55) | 24 (20-30) | 37 (30-46) | 41 (34-51) |
| Hemorrhage + ALM/AL | 47 (39-57) | 27 (22-33) | 40 (33-50) | 40 (33-50) |
| Temperature, ° C. | | | | |
| Hemorrhage | 38.2 37-9-38.4 | 38.7 (38.4-38.9) | 39.4 (39.1-39.6 | 39.5 (39.2-39.7) |
| Hemorrhage + ALM/AL | 38.2 (37.9-38.5) | 38.8 (38.5-39.1) | 39.4 (39.1-39.6) | 39.5 (39.2-39.7) |

| | Hypotensive Resuscitation | | | | |
|---|---|---|---|---|---|
| | 7.5 Min | 15 Min | 30 Min | 45 Min | 60 Min |
| Systolic arterial pressure, mm Hg | | | | | |
| Hemorrhage | 85 (78-93) | 83 (76-91) | 85 (78-93) | 77 (70-84) | 65 (59-71) |
| Hemorrhage + ALM/AL[a] | 78 (71-85) | 77 (70-84) | 84 (76-92) | 81 (74-89) | 79 (72-87)[b] |
| Diastolic arterial pressure, mm Hg | | | | | |
| Hemmorhage | 37 (33-41) | 37 (33-41) | 35 (31-39) | 30 (27-34) | 24 (21-27) |
| Hemorrhage + ALM/AL[a] | 34 (30-38) | 34 (30-38) | 36 (32-40) | 36 (32-41) | 33 (30-37)[b] |
| Central venous pressure, mm HG | | | | | |
| Hemorrhage | 5 (4-6) | 5 (5-6) | 5 (4-6) | 5 (4-5) | 5 (4-6) |
| Hemorrhage + ALM/AL | 6 (5-7) | 6 (5-6) | 5 (5-6) | 5 (4-6) | 5 (5-6) |
| Systemic vascular resistance index, dyn-s/cm$^5$/kg | | | | | |
| Hemorrhage | 32 (26-40) | 30 (24-37) | 33 (27-41) | 33 (26-40) | 29 (24-36) |
| Hemorrhage + ALM/AL | 29 (23-35) | 27 (22-33) | 31 (25-38) | 31 (25-38) | 30 (24-37) |
| Temperature, ° C. | | | | | |
| Hemorrhage | 39.0 (38.7-39.3) | 39.1 (38.9-39.4) | 39.3 (39-39.5) | 39.5 (39.2-39.8) | 39.7 (39.4-39.9) |
| Hemorrhage + ALM/AL | 38.8 (38.5-39.0) | 38.9 (38.6-39.1) | 39.1 (38.8-39.3) | 39.2 (38.9-39.4) | 39.3 (39.0-39.5)[b] |

TABLE 20-continued

Systemic Hemodynamic Variables and Central Temperature at Baseline and During the Bleeding, Hypotensive Resuscitation, and Blood Reperfusion Phases

| | Blood Reperfusion | | | | | |
|---|---|---|---|---|---|---|
| | 30 Min | 60 Min | 90 Min | 120 Min | 150 Min | 180 Min |
| Systolic arterial pressure, mm Hg | | | | | | |
| Hemorrhage | 112 (102-123) | 105 (95-116) | 100 (91-110) | 105 (96-116) | 96 (87-1058) | 92 (83-101) |
| Hemorrhage + ALM/AL[a] | 112 (102-122) | 112 (102-122) | 109 (99-119) | 108 (98-118) | 109 (100-120) | 106 (97-116)[c] |
| Diastolic arterial pressure, mm Hg | | | | | | |
| Hemmorhage | 56 (50-63) | 59 (52-67) | 58 (51-65) | 56 (50-63) | 55 (49-62) | 53 (47-60) |
| Hemorrhage + ALM/AL[a] | 66 (59-74) | 72 (65-81) | 69 (62-77) | 66 (58-74) | 67 (60-75) | 67 (60-75)[c] |
| Central venous pressure, mm HG | | | | | | |
| Hemorrhage | 9 (8-11) | 8 (7-10) | 8 (7-9) | 8 (7-10) | 9 (7-10) | 9 (7-10) |
| Hemorrhage + ALM/AL | 11 (9-12) | 10 (9-12) | 9 (8-10) | 9 (8-11) | 9 (8-10) | 9 (8-10) |
| Systemic vascular resistance index, dyn-s/cm$^5$/kg | | | | | | |
| Hemorrhage | 23 (19-29) | 25 (21-32) | 29 (23-36) | 30 (24-37) | 35 (28-43) | 35 (28-43) |
| Hemorrhage + ALM/AL | 29 (24-36) | 34 (28-42) | 39 (31-48) | 39 (32-49) | 41 (33-51) | 40 (32-49) |
| Temperature, ° C. | | | | | | |
| Hemorrhage | 38.7 (38.4-39) | 38.9 (38.6-39.1) | 39.0 (38.7-39.3) | 39.2 (38.9-39.4) | 39.3 (39-39.5) | 39.3 (39-39.5) |
| Hemorrhage + ALM/AL | 38.5 (38.2-38.7) | 38.8 (38.5-39) | 38.9 (38.7-39.2) | 39.0 (38.7-39.2) | 39.0 (38.7-39.2) | 39.0 (38.7-39.2)[c] |

Table 20 Notes:
ALM = adenosine, lidocaine, and Mg$^{2+}$, AL = adenosine and lidocaine.
[a]Significant time/group interaction during hypotensive resuscitation (analysis of variance).
[b]Significant difference at 60 min of hypotensive resuscitation.
[c]Significant difference at the end of the experiment.
Data presented as median (95% CI) except for temperature which is presented as mean (95% CI).

TABLE 21

Arterial Gas Data and Metabolic Variables During the Study ALM = adenosine, lidocaine, and Mg2+, AL = adenosine and lidocaine, Data presented as median (95% CI) except for HCO3− and sodium which are presented as mean (95% CI).

| | Bleeding | | | | Hypotensive Resuscitation | |
|---|---|---|---|---|---|---|
| | Baseline | 0 Min | 45 Min | 90 Min | 30 Min | 60 Min |
| Arterial pH | | | | | | |
| Hemorrhage | 7.45 (7.45-7.48) | 7.43 (7.39-7.47) | 7.32 (7.28-7.36) | 7.23 (7.19-7.27) | 7.21 (7.17-7.25) | 7.21 (7.17-7.24) |
| Hemorrhage + ALM/AL[a,c] | 7.46 (7.42-7.50) | 7.45 (7.41-7.49) | 7.34 (7.30-7.38) | 7.26 (7.22-7.29) | 7.26 (7.23-7.30) | 7.28 (7.25-7.32)[b] |
| Pao$_2$/F1O$_2$ ratio | | | | | | |
| Hemorrhage | 454 (431-478) | 451 (429-475) | 402 (382-424) | 392 (372-413) | 427 (406-450) | 413 (392-437) |
| Hemorrhage + ALM/AL[a,c] | 465 (442-490) | 448 (426-472) | 393 (373-414) | 399 (379-421) | 449 (426-472) | 443 (421-466) |
| HCO$_3$ (mmol/L) | | | | | | |
| Hemorrhage | 29 (27-30) | 28 (26-29) | 22 (21-24) | 17 (15-19) | 17 (15-18) | 15 (14-17) |
| Hemorrhage + ALM/AL[a] | 29 (27-31) | 28 (26-30) | 23 (22-25) | 19 (17-21) | 19 (17-21) | 19 (18-21)[c,d] |

TABLE 21-continued

Arterial Gas Data and Metabolic Variables During the Study ALM = adenosine, lidocaine, and Mg2+, AL = adenosine and lidocaine, Data presented as median (95% CI) except for HCO3– and sodium which are presented as mean (95% CI).

| | | | Base excess | | | |
|---|---|---|---|---|---|---|
| Hemorrhage | 4.8 (2.7-6.9) | 3.4 (1.3-5.5) | −2.4 (−4.4 to −0.3) | −9.0 (−11.1 to −6.9) | −9.6 (−11.7 to −7.5) | −11.2 (−13.4 to −9.1) |
| Hemorrhage + ALM/AL[c] | 5.3 (3.2-7.3) | 4.0 (1.9-6.1) | −1.2 (−3.3 to 0.9) | −6.7 (−8.8 to −4.6) | −6.3 (−8.4 to −4.2) | −5.9 (−8.0 to −3.8)[b] |
| | | | Lactate (mmol/L) | | | |
| Hemorrhage | 0.5 (0.4-0.7) | 0.9 (0.7-1.2) | 4.6 (3.4-6.3) | 9.0 (6.6-12.2) | 9.1 (6.7-12.3) | 11.3 (9-14.1) |
| Hemorrhage + ALM/AL[a] | 0.5 (0.4-0.7) | 0.8 (0.6-1.1) | 3.7 (2.7-5.0) | 7.3 (5.4-10.0) | 7.1 (5.2-9.7) | 7.1 (5.7-8.9)[b] |
| | | | Hemoglobin (mmol/L) | | | |
| Hemorrhage | 5.4 (5.0-5.7) | 5.4 (5.0-5.7) | 5.0 (4.7-5.3) | 5.2 (4.9-5.5) | 4.5 (4.2-4.8) | 4.8 (4.4-5.1) |
| Hemorrhage + ALM/AL[a] | 0.5 (5.1-5.7) | 5.4 (5.1-5.8) | 5.2 (4.8-5.5) | 5.2 (4.9-5.6) | 4.4 (4.1-4.7) | 4.3 (4.0-4.6)[b] |
| | | | Sodium (mmol/L) | | | |
| Hemorrhage | 138 (137-139) | 137 (135-138) | 136 (135-137) | 137 (136-139) | 149 (148-150) | 147 (146-148) |
| Hemorrhage + ALM/AL[c] | 138 (137-140) | 137 (136-138) | 136 (134-137) | 137 (136-138) | 147 (146-148) | 147 (146-149) |
| | | | Potassium (mmol/L) | | | |
| Hemorrhage | 3.7 (3.4-4.0) | 3.9 (3.6-4.2) | 4.6 (4.2-4.9) | 4.9 (4.5-5.3) | 4.2 (3.9-4.5) | 5.6 (5.2-6.0) |
| Hemorrhage + ALM/AL[a,c] | 3.7 (3.5-4.0) | 4.0 (3.7-4.3) | 4.4 (4.1-4.8) | 4.5 (4.2-4.8) | 4.0 (3.7-4.3) | 4.4 (4.1-4.7)[b] |
| | | | Glucose (mmol/L) | | | |
| Hemorrhage | 5.5 (4.4-7.0) | 8.2 (6.5-10.5) | 13.2 (10.4-16.8) | 10.3 (8.1-13.2) | 7.0 (5.5-9.0) | 5.9 (4.6-7.6) |
| Hemorrhage + ALM/AL | 5.7 (4.5-7.2) | 8.0 (6.2-10.1) | 14.1 (11.1-18.0) | 12.7 (10.0-16.2) | 9.6 (7.6-12.3) | 8.9 (7.0-11.3)[b] |
| | | | Plasma protein (g/L) | | | |
| Hemorrhage | 47.8 (44.8-51.0) | | | 40.5 (38-43.2) | | 36.5 (34.1-39) |
| Hemorrhage + ALM/AL | 47.3 (44.3-50.5) | | | 38.3 (35.9-40.9) | | 35.3 (33-37.6) |

| | Blood Reperfusion | | | | | |
|---|---|---|---|---|---|---|
| | 30 Min | 60 Min | 90 Min | 120 Min | 150 Min | 180 Min |
| | | | Arterial pH | | | |
| Hemorrhage | 7.20 (7.16-7.24) | 7.25 (7.21-7.29) | 7.31 (7.27-7.34) | 7.35 (7.31-7.39) | 7.36 (7.33-7.40) | 7.38 (7.34-7.42) |
| Hemorrhage + ALM/AL[a,c] | 7.31 (7.27-7.34)[b] | 7.34 (7.30-7.37)[b] | 7.34 (7.34-7.41) | 7.40 (7.36-7.44) | 7.41 (7.37-7.45) | 7.40 (7.36-7.43) |
| | | | Pao$_2$/F1o$_2$ ratio | | | |
| Hemorrhage | 432 (409-456) | 428 (405-452) | 423 (400-446) | 398 (377-420) | 410 (388-433) | 419 (397-443) |
| Hemorrhage + ALM/AL[a,c] | 472 (448-497) | 452 (429-476) | 443 (421-467) | 445 (423-469) | 448 (425-472) | 441 (419-465)[d] |
| | | | HCO$_3$ (mmol/L) | | | |
| Hemorrhage | 16 (14-18) | 18 (16-20) | 20 (18-22) | 22 (20-24) | 25 (23-26) | 25 (23-26) |
| Hemorrhage + ALM/AL[a] | 20 (18-22)[b] | 22 (20-24)[b] | 24 (22-26)[b] | 25 (24-27)[b] | 25 (24-28) | 26 (24-28) |
| | | | Base excess | | | |
| Hemorrhage | −10.1 (−12.2 to −7.9) | −7.9 (−10.1 to −5.8) | −4.9 (−7.1 to −2.8) | −2.7 (−4.8 to −0.5) | −1.2 (−3.4 to −0.9) | −0.3 (−1.9 to −2.4) |
| Hemorrhage + ALM/AL[c] | −4.9 (−7.0 to −2.8)[b] | −2.9 (−5.0 to −0.8)[b] | −0.3 (−2.4 to −1.8)[b] | −1.2 (−0.9 to −3.3)[b] | −1.8 (−0.3 to −3.9) | −1.9 (−0.2 to −4.0) |
| | | | Lactate (mmol/L) | | | |
| Hemorrhage | 10.2 (7.4-14.1) | 8.5 (6.1-11.7) | 6.2 (4.5-8.6) | 4.0 (2.9-5.6) | 2.6 (1.9-3.6) | 1.8 (1.3-2.5) |

TABLE 21-continued

Arterial Gas Data and Metabolic Variables During the Study ALM = adenosine, lidocaine, and Mg2+, AL = adenosine and lidocaine, Data presented as median (95% CI) except for HCO3– and sodium which are presented as mean (95% CI).

| | | | | | | |
|---|---|---|---|---|---|---|
| Hemorrhage + ALM/AL[a] | 6.5 (4.8-8.9) | 4.5 (3.3-6.1[b]) | 2.8 (2.0-3.8)[b] | 1.6 (1.2-2.2)[b] | 1.0 (0.8-1.4)[b] | 1.2 (0.9-1.6) |

Hemoglobin (mmol/L)

| | | | | | | |
|---|---|---|---|---|---|---|
| Hemorrhage | 5.9 (5.5-6.3) | 5.9 (5.5-6.3) | 5.9 (5.5-6.4) | 5.8 (5.5-6.2) | 5.8 (5.5-6.3) | 5.9 (5.5-6.3) |
| Hemorrhage + ALM/AL[a] | 5.4 (5.0-5.7) | 5.6 (5.2-5.9) | 5.6 (5.2-6.0) | 5.5 (5.1-5.9) | 5.5 (5.1-5.9) | 5.6 (5.2-6.0) |

Sodium (mmol/L)

| | | | | | | |
|---|---|---|---|---|---|---|
| Hemorrhage | 147 (146-148) | 146 (144-147) | 145 (143-146) | 144 (143-146) | 144 (142-145) | 144 (142-145) |
| Hemorrhage + ALM/AL[c] | 146 (145-147) | 146 (144-147) | 145 (144-147) | 145 (144-146) | 145 (144-146) | 145 (144-146) |

Potassium (mmol/L)

| | | | | | | |
|---|---|---|---|---|---|---|
| Hemorrhage | 4.2 (3.9-4.5) | 4.5 (4.1-4.8) | 4.9 (4.5-5.3) | 5.1 (4.7-5.5) | 5.0 (4.6-5.4) | 5.4 (5.0-5.9) |
| Hemorrhage + ALM/AL[a,c] | 4.4 (4.1-4.8) | 4.6 (4.3-5.0) | 4.9 (4.5-5.2) | 5.0 (4.6-5.3) | 4.9 (4.6-5.3) | 4.9 (4.6-5.3) |

Glucose (mmol/L)

| | | | | | | |
|---|---|---|---|---|---|---|
| Hemorrhage | 7.1 (5.6-9.2) | 5.9 (4.6-7.5) | 5.2 (4.0-6.7) | 5.1 (4.0-6.6) | 4.6 (3.5-5.9) | 4.5 (3.5-5.8) |
| Hemorrhage + ALM/AL | 87 (6.9-11.0) | 5.9 (4.6-7.5) | 6.1 (4.8-7.7) | 5.3 (4.1-6.7) | 5.1 (4.1-6.7) | 4.9 (3.9-6.3) |

Plasma protein (g/L)

| | | | | | | |
|---|---|---|---|---|---|---|
| Hemorrhage | | 47.1 (44-50.3) | | 47 (44-50.3) | | 47.6 (44.5-50.9) |
| Hemorrhage + ALM/AL | | 44.1 (41.4-47.1) | | 43.6 (40.9-46.6) | | 44.8 (42-47.9) |

Table 21 Notes:
[a]Significant time/group interaction during hypotensive resuscitation (analysis of variance [ANOVA]),
[b]Significant difference between groups.
[c]Significant time/group interaction during reperfusion (ANOVA).
[d]Significant difference in mean levels between groups after blood resuscitation.

TABLE 22

Parameters of Systemic Oxygen Consumption and Creatinine Clearance

| | Bleeding | | | | Hypotensive Rescuscitation | |
|---|---|---|---|---|---|---|
| | Baseline | 0 Min | 45 Min | 90 Min | 30 Min | 60 Min |

Arterial oxygen content, mL O$_2$/L blood

| | | | | | | |
|---|---|---|---|---|---|---|
| Hemorrhage | 123 (115-131) | 123 (116-131) | 115 (107-122) | 118 (111-124) | 103 (97-110) | 109 (103-106) |
| Hemorrhage + ALM/AL[a] | 125 (118-133) | 124 (116-132) | 118 (110-125) | 119 (112-125) | 102 (96-109) | 100 (93-106)[b] |

Venous oxygen content, mL O$_2$/L blood

| | | | | | | |
|---|---|---|---|---|---|---|
| Hemorrhage | 72 (63-81) | 34 (26-43) | 18 (10-27) | 19 (13-24) | 25 (20-30) | 17 (12-23) |
| Hemorrhage + ALM/AL | 75 (66-84) | 30 (21-38) | 16 (7-25) | 19 (13-24) | 29 (24-34) | 25 (20-30)[b] |

Oxygen delivery mL O$_2$/L blood/kg

| | | | | | | |
|---|---|---|---|---|---|---|
| Hemorrhage | 11.8 (10-14) | 9.5 (8-11.3) | 5.5 (4.7-6.6) | 5.1 (4.3-6) | 6.9 (5.8-8.1) | 5.2 (4.4-6.2) |
| Hemorrhage + ALM/AL[a] | 13.2 (11.1-15.6) | 8.5 (7.2-10.1) | 5.4 (4.5-6.3) | 5.1 (4.3-6.1) | 8.1 (6.8-9.6) | 7.6 (6.4-9)[b] |

Arterial – venous difference, mL O$_2$/L blood

| | | | | | | |
|---|---|---|---|---|---|---|
| Hemorrhage | 51 (43-60) | 89 (81-97) | 96 (88-105) | 99 (91-108) | 78 (70-87) | 92 (83-100) |
| Hemorrhage + ALM/AL[a] | 50 (42-59) | 94 (86-103) | 102 (93-110) | 99 (90-108) | 73 (65-82) | 74 (66-83)[b] |

TABLE 22-continued

Parameters of Systemic Oxygen Consumption and Creatinine Clearance

Creatinine clearance, mL/min

|  |  |  |  |
|---|---|---|---|
| Hemorrhage | 74 (40-137) | 6 (4-12) | 4 (2-8) |
| Hemorrhage + ALM/AL | 81 (45-144) | 7 (4-12) | 7 (4-13) |

Blood Reperfusion

|  | 30 Min | 60 Min | 90 Min | 120 Min | 150 Min | 180 Min |
|---|---|---|---|---|---|---|
| *Arterial oxygen content, mL O$_2$/L blood* | | | | | | |
| Hemorrhage | 133 (125-141) | 134 (126-142) | 134 (126-143) | 132 (124-140) | 133 (125-141) | 135 (127-143) |
| Hemorrhage + ALM/AL[a] | 124 (116-132) | 128 (120-135) | 128 (121-136) | 126 (118-134) | 126 (118-134) | 128 (120-136) |
| *Venous oxygen content, mL O$_2$/L blood* | | | | | | |
| Hemorrhage | 97 (87-106) | 94 (85-103) | 92 (82-101) | 83 (74-92) | 81 (72-90) | 77 (68-87) |
| Hemorrhage + ALM/AL | 89 (80-97) | 83 (74-92) | 80 (71-89) | 75 (66-84) | 75 (66-84) | 76 (68-85) |
| *Oxygen delivery mL O$_2$/L blood/kg* | | | | | | |
| Hemorrhage | 22.2 (18.6-26.6) | 21.1 (17.6-25.2) | 17.6 (14.7-21) | 15.8 (13.2-18.9) | 13.2 (11-15.8) | 12.7 (10.6-15.8) |
| Hemorrhage + ALM/AL[a] | 17.6 (14.9-20.9)[b] | 16.3 (13.7-19.3) | 13.7 (11.6-16.3) | 12.7 (10.7-15.1) | 12.5 (10.5-14.8) | 13.2 (11.1-15.6) |
| *Arterial − venous difference, mL O$_2$/L blood* | | | | | | |
| Hemorrhage | 36 (27-45) | 39 (30-48) | 43 (34-51) | 49 (40-58) | 51 (42-60) | 57 (48-66) |
| Hemorrhage + ALM/AL[a] | 35 (27-44)[d] | 45 (36-53) | 58 (49-66) | 51 (43-60) | 51 (43-59) | 52 (43-60) |
| *Creatinine clearance, mL/min* | | | | | | |
| Hemorrhage |  | 15 (8-29) |  | 14 (7-26) |  | 12 (7-23) |
| Hemorrhage + ALM/AL |  | 26 (15-46) |  | 29 (16-52) |  | 39 (22-69)[c] |

Table 22 Notes:
ALM = adenosine, lidocaine, and Mg$^{2+}$, AL = adenosine and lidocaine.
[a]Significant time/group interaction during hypotensive resuscitation (analysis of variance).
[b]Significant difference at 60 min of hypotensive resuscitation.
[c]Significant difference at the end of the study (Student t test).
[d]t test on difference from start of blood infusion to 30 min after blood infusion.
Data presented as mean (95% CI) except for oxygen delivery and creatinine clearance presented as median (95% CI).

FIG. 37C). Wholebody Vo$_2$ was higher during hypotensive resuscitation in the ALM/AL group compared with the control group (FIG. 37D). The difference was due to a higher oxygen delivery in the ALM/AL group (7.6 mL O$_2$/min/kg [95% CI, 6.4-9] vs 5.2 mL O$_2$/min/kg [95% CI, 4.4-6.2]; ratio, 1.45 [95% CI, 1.13-1.86]; p=0.003) despite control animals attempting to compensate with significantly higher arterial-venous (AV) difference (74 mL O$_2$/L [95% CI, 66-83] vs 92 mL 02/L [95% CI, 83-100] blood at 60 min; difference, 17 [95% CI, 6-29]; p=0.003) (Table 22). Associated with greater cardiac index, stroke volume, and LV ejection time in the ALM/AL group, there was a significantly higher LV end-systolic pressure (LVESP) at 60 minutes (FIG. 38A) with no significant differences in either LV end-diastolic pressure (LVEDP), dP/dtmax, or dP/dtmin (FIG. 38B-D). There were no significant differences in SVRI between groups during hypotensive resuscitation (Table 20).

Blood Resuscitation

Infusion of warm shed blood and a 10 mL IV bolus of 0.9% NaCl±AL led to a rapid restoration of MAP with higher values being maintained in the ALM/AL group (FIG. 36A). At 180 minutes, the MAP for the ALM/AL group was significantly higher (85 mm Hg [95% CI, 78-93]) than that of the controls (70 mm Hg [95% CI, 64-76]; ratio, 1.21 [95% CI, 1.05-1.41]; p=0.011) due to significant increases in both arterial systolic pressure and diastolic pressure (Table 20).

The mean SVRI during the entire reperfusion phase tended to be higher in the ALM/AL group (36.8 dyn s/cm$^5$/kg [95% CI, 31.4-43.1] vs 28.2 dyn s/cm$^5$/kg [95% CI, 21.6-36.8]; ratio, 1.30 [95% CI, 1.0-1.7]; p=0.052) (Table 20). The mean level of Pao$_2$/Flo$_2$ as an index of arterial oxygenation efficiency was significantly increased in the ALM/AL group during the blood return period (449% [95% CI, 435-463] vs 418% [95% CI, 399-439]; ratio, 1.07 [95% CI, 1.02-1.13]; p=0.0093) (Table 21).

Arterial pH continued to be significantly higher in the ALM/AL group when compared with controls 90 minutes into reperfusion while HCO$_3$ was higher 120 minutes into reperfusion. No significant difference existed at 180 minutes (Table 21). Infusion of shed blood caused a significantly higher increase in cardiac index in controls when compared with the ALM/AL group (FIG. 37A). After 30 minutes of blood return, whole-body Vo$_2$ significantly increased in controls by 34% (4.2 mL O$_2$/min/kg [95% CI, 3.5-5.0] to 5.8 mL O$_2$/min/kg [95% CI, 4.9-6.8]) (FIG. 37D). This was associated with a higher oxygen delivery for the same AV oxygen difference when compared to the ALM/AL group at this time (Table 22). In contrast, whole-body Vo$_2$ decreased in ALM/AL pigs (5.7 mL O$_2$/min/kg [95% CI, 4.7-6.8] to 4.9 mL O$_2$/min/kg [95% CI, 4.2-5.81]; ratio, 1.52 [95% CI, 1.07-2.15]; p=0.02 vs control group); during this crossover in Vo$_2$, pH and base excess were higher and lactates were lower in the ALM/AL group suggesting that lower Vo$_2$ did not reflect compromised oxygen demand. No difference in Vo$_2$ between groups was observed at 60 minutes after infusion of blood or during the remainder of the study.

Figure 38:
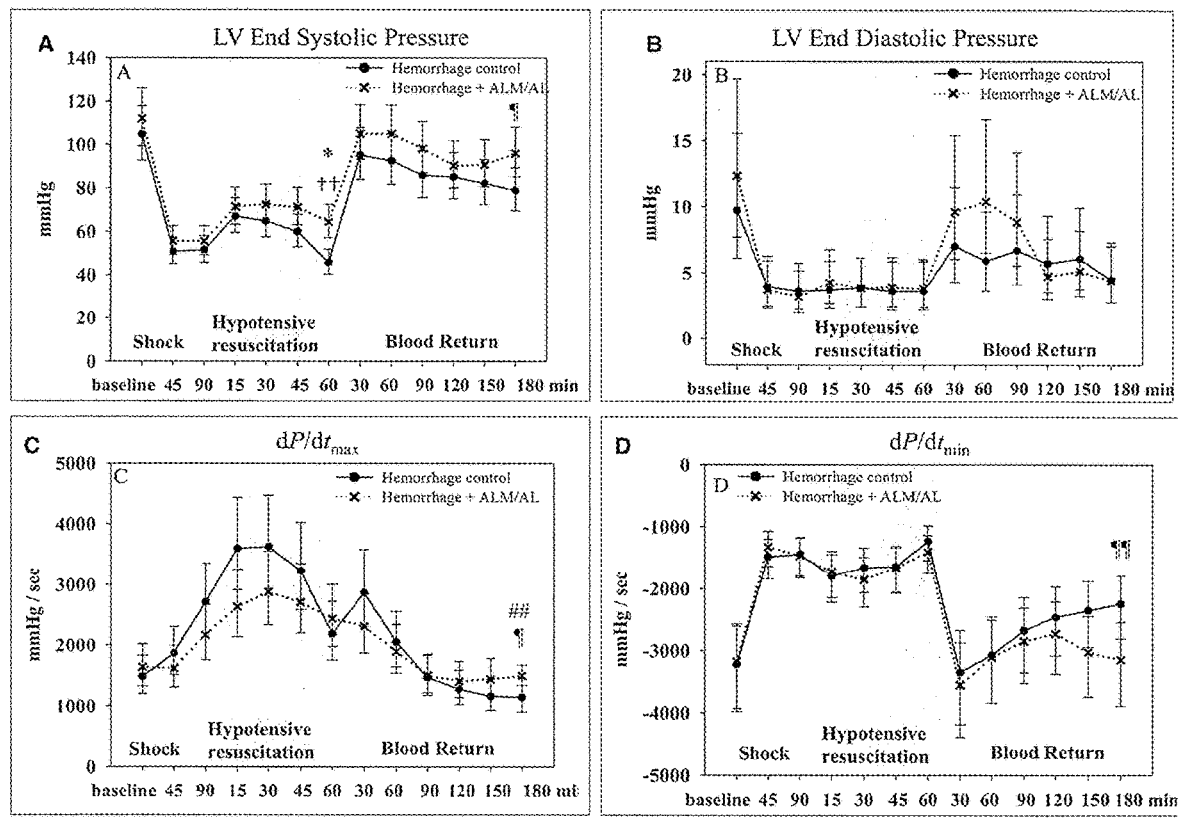
FIG. 38 shows graphs showing cardiac function data during the experiment. Left ventricular (LV) end-systolic pressure (A) and LV end-diastolic pressure (B) measured throughout the course of the experiment. (C) The maximum positive development of ventricular pressure over time (dP/dtmax) as a marker of cardiac systolic function. And (D), The maximum negative development of ventricular pressure over time (dP/dtmin) as a marker of cardiac diastolic function.

LVESP was significantly higher in the ALM/AL group during blood return, a difference that continued for 180 minutes (FIG. 38A). No significant group differences in dP/dt$_{max}$ and dP/dt$_{min}$ were found during the early period of blood reperfusion; however, the ALM/AL group generated significantly higher dP/dt$_{max}$ values and significantly lower dP/dt$_{min}$ values at the end of the study (FIG. 38, C and D).

Renal Function

Figure 39:
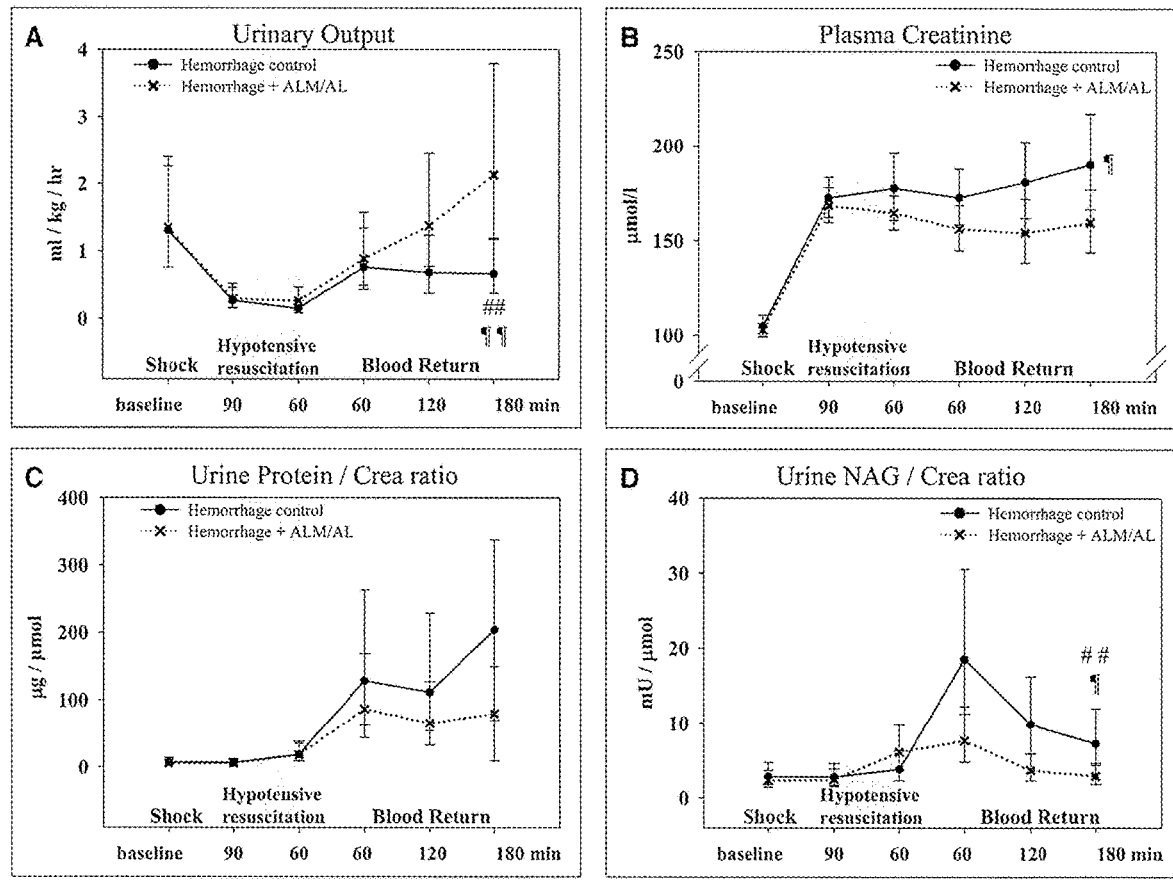
FIG. 39 shows graphs showing the renal variables urine output, plasma creatinine, urine protein to creatinine, and urine n-acetyl-β-d-glucosaminide (NAG) to creatinine ratio throughout the course of the experiment. (A) Urine output measured after 90 min of hemorrhagic shock and then every hour during the remainder of the experiment. (B) Plasma creatinine as a marker of global kidney function. (C) Urine protein to urinary creatinine ratio as a marker of glomerular injury. D, Urine NAG to urinary creatinine ratio as a marker of proximal tubular injury. Data presented as median (95% CI).
Figure 40:
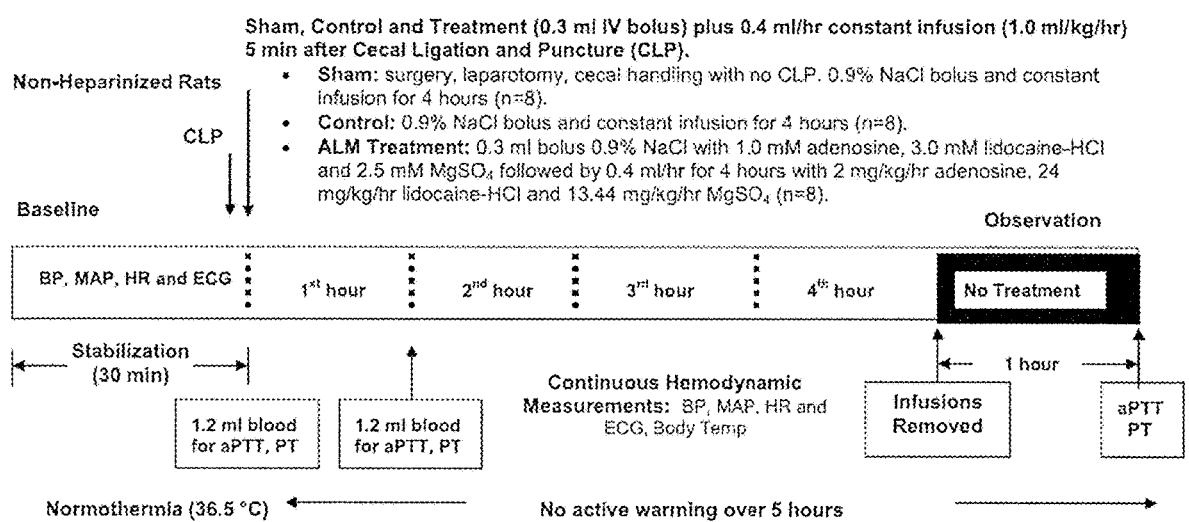
FIG. 40 shows a schematic representation of the in vivo rat protocol of severe polymicrobial sepsis.

During the 60-minute hypotensive resuscitation period, urine output was higher in the ALM/AL group (0.26 mL/kg/hr [95% CI, 0.15-0.47] vs 0.15 mL/kg/hr [95% CI, 0.08-0.26]; ratio, 1.76 mL/kg/hr [95% CI, 0.78-3.97]; p=0.171) when compared with controls (FIG. 39A). However, this difference was not significantly different from zero along with plasma creatinine, urine protein/creatinine, or urine NAG/creatinine ratios at the end of hypotensive resuscitation (FIG. 39B-D). Following infusion of shed blood urine output increased in both groups but it was three-fold higher in the ALM/AL group (2.13 mL/kg/hr [95% CI, 1.19-3.79] vs 0.66 mL/kg/hr [95% CI, 0.38-1.17]; ratio, 3.21 mL/kg/hr [95% CI, 1.42-7.21]; p=0.005). This increase was accompanied by a lower plasma creatinine (160 μmol/L [95% CI. 144-177] vs 190 μmol/L [95% CI. 167-217]; ratio, 1.19 μmol/L [95% CI, 1.02-1.39]; p=0.027), protein/creatinine ratio (79 μg/μmol [95% CI, 9-150] vs 204 μg/μmol [95% CI, 70-338]; ratio, 2.93 μg/μmol [95% CI, 0.78-11.07]; p=0.0593), NAG/creatinine ratio (2.9 mU/μmol [95% CI, 1.8-4.6] vs 7.3 mU/μmol [95% CI, 4.4-12.0]; ratio, 2.49 mU/μmol [95% CI, 1.12-5.53]; p=0.028), and creatinine clearance ratio (39 mL/min [95% CI, 22-69] vs 12 mL/min [95% CI, 7-23]; ratio, 3.15 mL/min [95% CI, 1.35-7.34]; p=0.008) (FIG. 39 and Table 22).

Blood Flow

Hemorrhagic shock resulted in blood flow being maintained to the myocardium in both groups, whereas blood flow to the kidney and liver fell by about 80% and 20%, respectively (Table 23). There were no significant differences between the groups throughout the study.

TABLE 23

Regional Organ Blood Flow Measured by Microspheres at Four Time Points During the Study

|  | Baseline | 45 Minute Bleeding | 30 Minute Hypotensive Resuscitation | 45 Minute Blood Reperfusion |
|---|---|---|---|---|
| Heart (mL/min/g) | | | | |
| Hemorrhage | 1.14 (0.74-1.76) | 1.32 (0.86-2.09) | 3.12 (1.96-4.95)$^a$ | 3.83 (2.41-6.09)$^a$ |
| Hemorrhage + ALM/AL | 1.23 (0.8-1.88) | 0.88 (0.59-1.31) | 2.77 (1.85-4.14) | 3.13 (2.04-4.81)$^a$ |
| Kidney (mL/min/g) | | | | |
| Hemorrhage | 3.1 (2.2-4.3) | 0.7 (0.5-0.9)$^a$ | 1.0 (0.7-1.4)$^a$ | 2.7 (1.9-3.7) |
| Hemorrhage + ALM/AL | 2.3 (1.7-3.2) | 0.5 (0.4-0.7)$^a$ | 1.9 (1.0-1.8) | 2.1 (1.5-2.9) |
| Liver (mL/min/g) | | | | |
| Hemorrhage | 0.28 (0.15-0.53) | 0.22 (0.12-0.41) | 0.34 (0.18-0.64) | 0.37 (0.2-0.7) |
| Hemorrhage + ALM/AL | 0.27 (0.14-0.51) | 0.21 (0.12-0.38) | 0.27 (0.15-0.48) | 0.27 (0.14-0.54) |
| Skeletal muscle (mL/min/g) | | | | |
| Hemorrhage | 0.04 (0.2-0.06) | 0.08 (0.02-0.05) | 0.04 (0.02-0.08) | 0.12 (0.06-0.25) |
| Hemorrhage + ALM/AL | 0.05 (0.03-0.08) | 0.02 (0.01-0.04)$^a$ | 0.06 (0.03-0.09) | 0.15 (0.08-0.29) |

ALM = adenosine, lidocaine, and Mg$^{2+}$, AL = adenosine and lidocaine.
$^a$Significant compared to baseline.
Data presented as median [95% CI].

DISCUSSION

Currently, there is no effective small-volume fluid for hypotensive resuscitation in the civilian or military prehospital environment. Outcomes for small-volume 7.5% NaCl with or without 6% dextran and fluids containing hetastarch have been disappointing. This study shows that a single IV bolus of 4 mL/kg 7.5% NaCl+ALM administered after 90 minutes of severe hemorrhagic shock in the pig produced significantly better hemodynamics, cardiodynamics plasma metabolic markers, higher oxygen delivery and whole-body Vo$_2$, and a significantly lower HR during hypotensive resuscitation compared with 7.5% NaCl alone. Thirty minutes after the return of shed blood, whole-body Vo2: significantly decreased in the ALM/AL group, whereas it increased in the control group. There were continued improvements in hemodynamic and renal indices in the ALM/AL group compared with controls over 180 minutes. These findings confirm and extend the previous findings in the rat model.

Hypotensive Resuscitation

Small-volume 7.5% NaCl+ALM gently increased MAP to around 50 mm Hg (systolic blood pressure, 79 mm Hg [95% CI, 72-87]; diastolic blood pressure, 33 mm Hg [95% CI, 30-37]) at 60 minutes. In direct contrast, MAP in control pigs began to fall sharply after 30 minutes and decreased to preshock values at 60 minutes, with one death from cardiovascular collapse (FIG. 36A and Table 20). This gentle rise of MAP using 7.5% NaCl+ALM has been reported previously by us in rats following severe to catastrophic hemorrhagic shock. The increase in MAP from 35 to 40 mm Hg to around 50 mm Hg in rat and pig is consistent with the goal of establishing a radial pulse at a systolic pressure of 60-80 mm Hg, a goal which is supported by blood pressure targets in a prospective, randomized trial. Higher pressures in the ALM/AL group in our study were also sustained during blood resuscitation (FIG. 36A and Table 20). It is concluded that small-volume 7.5% NaCl alone was not optimal in the pig (and rat) model of hypotensive resuscitation, a finding that is consistent with the recent randomized, multicenter trial that reported no significant benefit of 250 mL 7.5% NaCl or 7.5% NaCl 6% Dextran-70 compared with normal saline for early resuscitation of hemorrhagic shock.

A higher MAP in the ALM pigs was accompanied by a significantly higher cardiac index than controls (FIG. 37A). An interesting question arises: How does a 4 mL/kg bolus of 7.5% NaCl ALM (~8% of shed blood) resuscitate the animal after removal of ~2 L of blood and 90-minute shock? It would not be expected that such a small volume would be able to sustain an increase in preload at 60 minutes, and this was confirmed by little or no change in LVEDP or CVP (preload index) (FIG. 38B and Table 20), yet stroke volume in ALM pigs was two-fold higher (FIG. 37B). There was also no change in $dP/dt_{min}$ (diastolic function) (FIG. 38D) or SVRI (afterload index) (Table 20) compared with controls. It is proposed that the increase in stroke volume during hypotensive resuscitation occurred from ALM's effect to 1) decrease HR (FIG. 36B), possibly via resetting of the CNS vagosympathetic balance to the heart, and 2) increase LV systolic ejection time (FIG. 37C). This effect of ALM would permit greater volumes of blood in the LV to be ejected per beat compared with controls and lead to higher stroke volumes. The inverse relationship between HR and LV ejection time was first reported in humans in 1874. In conclusion, ALM increased stroke volume, and therefore MAP, by lowering HR and prolonging both LV ejection times with significantly higher LVESP.

The contributions of the individual components of ALM in the setting of shock are not known, although in rats adenosine+$Mg^{2+}$ or lidocaine+$Mg^{2+}$ alone failed to increase MAP or stroke volume while AL alone fails to correct coagulopathy. Adenosine alone has been shown to improve depressed myocardial contractility following hemorrhagic shock in rabbits and inhibit the heart's positive inotropic response to isoprenaline in dogs in vivo (i.e., lower $dP/dt_{max}$).

Similarly, a lidocaine bolus has been shown to decrease $dP/dt_{max}$ and lower oxygen demand in rabbits in vivo, and $MgSO_4$ has been shown to suppress isoproterenol-induced Pi-adrenergic desensitization and prevent LV dysfunction in dogs in vivo.

Metabolic Function.

During hypotensive resuscitation, oxygen delivery was significantly higher in the ALM animals versus controls despite a significantly lower hemoglobin concentration at 60 minutes (Table 21). The higher oxygen delivery was associated with improved metabolic and blood acid-base status in ALM-treated animals. Markers of whole-body ischemia (blood lactate, base-excess, and plasma potassium) were all significantly higher at abnormal levels in controls indicating that oxygen delivery was insufficient to sustain cellular function in the controls, while these markers of whole-body ischemia were lower at 60 minutes in ALM/AL-treated animals, suggesting the maintenance of whole-body metabolic balance. Core body temperature was also significantly lower in the ALM/AL treatment group at 60 minutes and may reflect ALM-induced differences in thermoregulatory control set point (Table 20).

Whole Blood/AL Resuscitation

Figure 30:
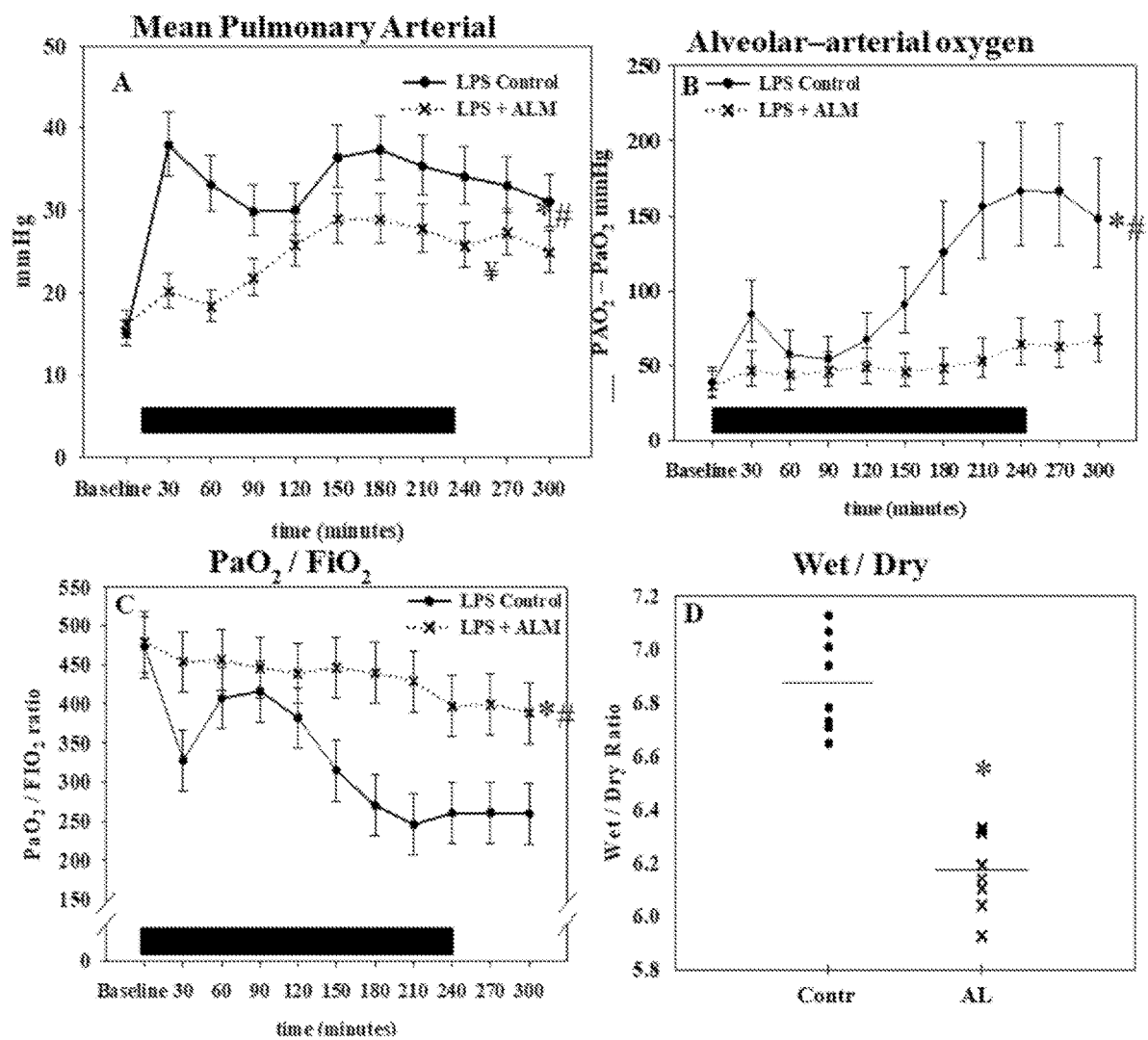
FIG. 30 shows graphs of the results of the experiments described in Example 46.

Two other standout features during blood resuscitation were 1) a crossover in whole-body $Vo_2$ at 30 minutes (fell from 5.7 mL/min/kg [95% CI, 4.7-6.8] to 4.9 mL/min/kg [95% CI, 4.2-5.8] in ALM/AL pigs, yet in controls it increased from 4.2 mL/min/kg [95% CI, 3.5-5.0] to 5.8 mL/min/kg [95% CI, 4.9-6.8]) and 2) a three-fold increase in urine output, lower plasma creatinine, lower urine protein/creatinine, lower urine NAG/creatinine ratios, and higher creatinine clearance in the ALM/AL pigs at 180 minutes compared with controls indicating global kidney and proximal tubule protection (FIG. 30).

A 27% reduction in whole-body $Vo_2$ in pigs has previously been reported by us after AL was administered at the return of shed blood following hypotensive resuscitation with 7.5% NaCl+ALM and Ringers-acetate to maintain a target MAP of 50 mm Hg for 30 minutes. In this study, the $Vo_2$-lowering effect of ALM/AL may be caused by a lower demand and a cumulative lower oxygen debt at blood resuscitation, supported by lower levels of markers of whole-body ischemia. Oxygen debt is the cumulative difference between the baseline (normal) $Vo_2$ and $Vo_2$ at any given time point and is used during hemorrhagic shock as an endpoint for shock. At blood resuscitation, $Vo_2$ may have increased in the control group due to repayment of oxygen debt, whereas it decreases in the ALM/AL group since a part of the oxygen debt was repaid already during hypotensive resuscitation and due to a possible oxygen demand lowering effect of AL.

In this study, the earlier repayment of oxygen debt may have prevented organ impairment compared with controls (Table 20), since faster repayment of oxygen debt has been linked to improved organ function.

The difference in response to ALM during hypotensive resuscitation ($Vo_2$ and delivery increases) and AL at blood resuscitation $Vo_2$ decreases) may be related to 1) different doses administered during the two phases or 2) timing of administration since the integrated physiological response to either low-volume fluid or high-volume blood infusion may be different.

It is interesting that despite a significant three-fold increase in urine output in ALM/AL animals, renal blood flow paradoxically fell by ~20% at 45 minutes blood return compared with controls (Table 23). This decrease in renal (and liver) blood flow may relate to the whole-body $Vo_2$ decrease (FIG. 28D) and a reduced need to repay the oxygen debt associated with resuscitation compared with controls. The effect of ALM/AL on regional blood flow, multiple organ protection, and repayment of oxygen debt requires further investigation.

Clinical and Military Significance

Emergency first responder teams or combat medics have a limited range of options for resuscitating and stabilizing civilians or combatants following massive hemorrhage. Blackbourne et al recently wrote: "Although the widespread training of medics in tactical combat casualty care (TCCC) has clearly saved lives, the use of saline and colloid starch by medics on the battlefield does not represent a significant technological advance in ability since saline was first used for resuscitation in 1831" (30). Low-volume 7.5% NaCl/ALM may fill this capability gap as it has the advantage of not requiring colloids and represents a reduction in the cube/resuscitation over current fluids.

Conclusions

Small-volume 7.5% NaCl ALM affords superior resuscitation benefits and hemodynamic stability following severe hemorrhagic shock in pigs. The multiple benefits may imply improved autonomic control of restorative and homeostatic functions. ALM resuscitation may have applications in the pre-hospital environment and mass casualty situations.

Example 48: Adenosine, Lidocaine, and Magnesium Induce a Reversible Hypotensive State, Reduce Lung Edema, and Prevent Coagulopathy in the Rat Model of Polymicrobial Sepsis Adenosine, Lidocaine, and Magnesium Induce a Reversible Hypotensive State, Reduce Lung Edema, and Prevent Coagulopathy in the Rat Model of Polymicrobial Sepsis Background:

No drug therapy has demonstrated improved clinical outcomes in the treatment of sepsis. Adenosine, lidocaine, and magnesium (ALM) bolus has been shown to be cardioprotective and to restore coagulopathy in different trauma states. We hypothesized that ALM therapy may improve hemodynamics, protect the lung, and prevent coagulopathy in a rat sepsis model.

Methods:

Nonheparinized, anesthetized Sprague-Dawley rats (350-450 g, n=32) were randomly assigned into (1) sham (without sepsis), (2) saline controls, and (3) ALM treatment. Sepsis was induced by cecal ligation and puncture. A 0.3-mL bolus was administered intravenously, followed by a 4-hour intravenous infusion (1 mL/kg/h), and hemodynamics (mean arterial pressure [MAP], systolic arterial pressure, diastolic arterial pressure, heart rate [HR]) and body temperature (BT) were monitored. Coagulation was assessed using prothrombin time and activated partial thromboplastin time (aPTT).

Results:

Shams displayed progressive falls in their MAP, HR, and BT as well as a prolonged aPTT, which were related to surgery, not infection.

At 4 hours, the controls showed more pronounced falls in MAP (33%), HR (17%), and BT (3.3-C), and MAP continued to fall after the infusion was stopped. In contrast, ALM treatment resulted in a rapid fall in MAP from 111 mm Hg to 73 mm Hg at 30 minutes ($p<0.05$ all groups), and MAP was 59 mm Hg at 240 minutes ($p<0.05$ sham), which was immediately corrected after 4 hours ($p<0.05$ control). HR paralleled MAP changes in ALM rats, and BT was significantly higher than that of the controls but not of the shams. ALM rats had no arrhythmias compared with the controls or shams and had significantly lower lung wet-dry ratios. Prothrombin time in the saline controls at 1 hour and 5 hours was prolonged but not in the shams or ALM rats. aPTT at 1 hour in the sham, control, and ALM groups was 158 t 41 seconds, 161 t 41 seconds, and 54 t 23 seconds and at 5 hours was 104 t 43 seconds, 205 t 40 seconds, and 33 t 3 seconds ($p<0.05$), respectively.

Conclusion:

An ALM bolus/infusion induces a stable, hypotensive hemodynamic state with no arrhythmias, significantly less pulmonary edema, and a higher BT and prevents coagulopathy compared with the controls.

Severe sepsis is a leading cause of global morbidity and mortality, claiming more than 8 million lives every year. Sepsis involves an infection that activates the systemic inflammatory and coagulation systems, leading to organ dysfunction and failure.

Cardiovascular dysfunction is characterized by decreased contractility, hypotension, decreased systemic resistance, and ventricular hyporesponsiveness to vasopressors or fluid therapy.

Mortality rates in patients who have cardiac dysfunction can be 70% to 90%, compared with 20% in those without cardiovascular involvement. New therapies are urgently required to support cardiovascular function and maintain tissue oxygen delivery during sepsis and halt the progression of the inflammatory, coagulation, and metabolic cascades.

Previously, it has been shown that a small intravenous bolus of 7.5% NaCl with adenosine and lidocaine and magnesium ($Mg^{2+}$) (ALM) resuscitated mean arterial pressure (MAP) into a hypotensive range following severe hemorrhagic shock in rat and pig. The ALM concept, at high concentrations, is used as a polarizing cardioplegia in cardiac surgery, an idea that was borrowed from the 'tricks' of natural hibernators, and at lower concentrations, it resuscitates the heart, with potent antiarrhythmic and antiischemic anti-inflammatory and coagulative restorative properties following hemorrhagic shock and cardiac arrest. Given the intimate connection between severe infection and cardiac dysfunction as well as inflammation and coagulation imbalances, this study investigates the effect of a small bolus and infusion of ALM in a rat model of cecal polymicrobial sepsis.

Materials and Methods

Animals and Reagents

Nonheparinized, 12-hour fasted, male Sprague-Dawley rats (350-450 g) were anesthetized with an intraperitoneal injection of 100-mg/kg sodium thiopentone (Thiobarb) (ethics approval number A1905).

Adenosine, lidocaine-HCl, $MgSO_4$ (anhydrous) and other chemicals were obtained from Sigma-Aldrich (New South Wales. Australia) Thiobarb and Lethabarb for euthanasia (325 mg/mL) were obtained from Lyppards (Townsville, Queensland, Australia).

Surgical Protocol

Anesthetized animals were placed in a customized cradle, a tracheostomy was performed, and rats were ventilated at 90 to 100 strokes per minute on humidified room air using a Harvard Small Animal Ventilator. Rectal temperatures and lead II electrocardiography (ECG) were recorded. The left femoral vein and artery were cannulated (PE-50 tubing) for infusions and blood pressure monitoring, and the right femoral artery and vein were cannulated for blood sampling and infusions. All cannulae contained citrate-phosphate-dextrose solution (0.14/mL, Sigma). Rats were stabilized for 10 minutes before cecal ligation and puncture (CLP), and any animal that was difficult to anesthetize, proarrhythmic, or hemo-dynamically unstable before CLP was excluded.

Experimental Design

Figure 31:
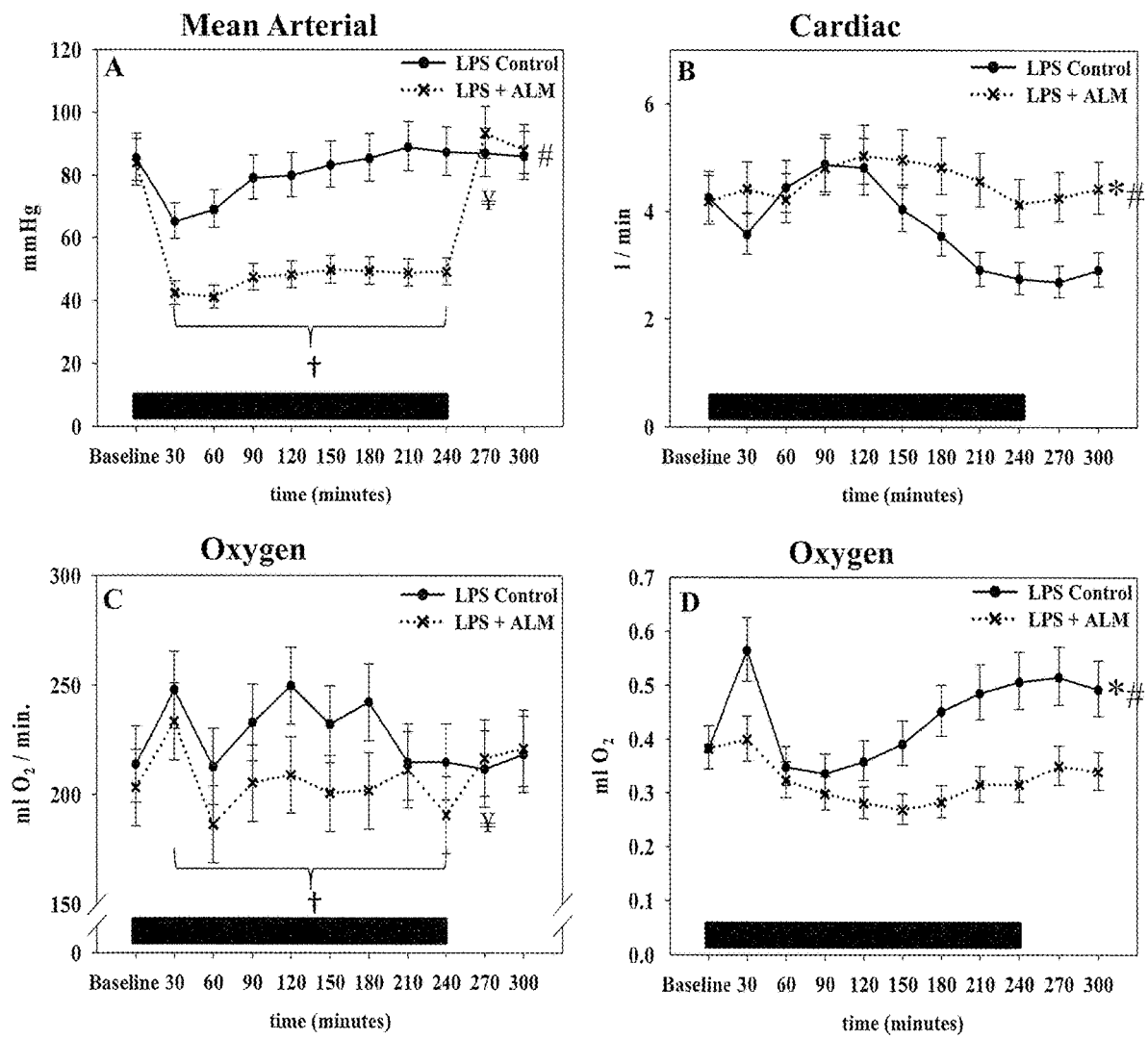
FIG. 31 shows graphs of the results of the experiments described in Example 46.

Rats were randomly assigned to one of three groups: (1) 0.9% NaCl sham animals (n=8), (2) 0.9% NaCl control (n=8), and (3) 0.9% NaCl ALM (n=8) (FIG. 31). CLP was performed using the method of Wichterman et al. Briefly, the cecum was located through a 5.0-cm midline laparotomy and ligated immediately below the ileocecal valve. It was then punctured with an 18-gauge needle four times through-and-through (eight holes) with a droplet of stool milked through each puncture to ensure patency. The abdominal cavity was surgically closed in two layers. Sham animals were subjected to laparotomy and cecum isolation and handling but no CLP.

Five minutes following ligation, control and sham animals received 0.3-mL bolus of normal saline (0.9% NaCl) through the left femoral vein and a 4-hour infusion of normal saline through the right femoral vein (0.4 mL/h per rat). ALM animals received 0.3-mL bolus of 1-mM adenosine, 3-mM lidocaine, and 2.5-mM $MgSO_4$ in 0.9% NaCl from our small-volume resuscitation studies. The ALM infusion solution was developed from rat and pig pilot studies and was composed of adenosine 12 mg/kg per hour, lidocaine 24 mg/kg per hour, and $MgSO_4$ 13.44 mg/kg per hour. MAP, systolic arterial pressure (SAP), diastolic arterial pressure (DAP), heart rate (HR), ECG, and body temperature (BT) were recorded at baseline, 5 minutes, 10 minutes, and 15 minutes after ligation; every 15 minutes for 4 hours; and for another 60 minutes after the infusion was stopped.

Prothrombin and Activated Partial Thromboplastin Times

Blood was sampled at 1 hour and 5 hours for coagulation studies as described by Letson et al.[18] Prothrombin time (PT) and activated partial thromboplastin time (aPTT) plasma measurements were performed in triplicate. Baseline values were obtained from an additional eight anesthetized rats.

Lung Wet Weight and Dry Weight Ratios

The middle and lower lobes of the left lung were removed, weighed, and dried in an oven for 24 hours at 70-C and reweighed to determine the wet-dry lung ratio. The ceca were isolated and removed at the end of the 5 hours for gross pathophysiologic examination.

Statistical Analysis

SPSS Statistical Package 20 (IBM, Armonk, N.Y.) was used for all analysis. Data were evaluated between groups using a one-way analysis of variance, in conjunction with Levene test of homogeneity to ensure that the assumption of equal variance was met. Analysis of variance was followed by Tukey honestly significant difference post hoc test. Two-way independent t tests were used to evaluate the hemodynamic and coagulation changes within treatment groups, again in conjunction with Levene test of homogeneity. All values are expressed as mean t SEM, and statistical significance was defined as p<0.05

Results

Hemodynamic

Figure 42:
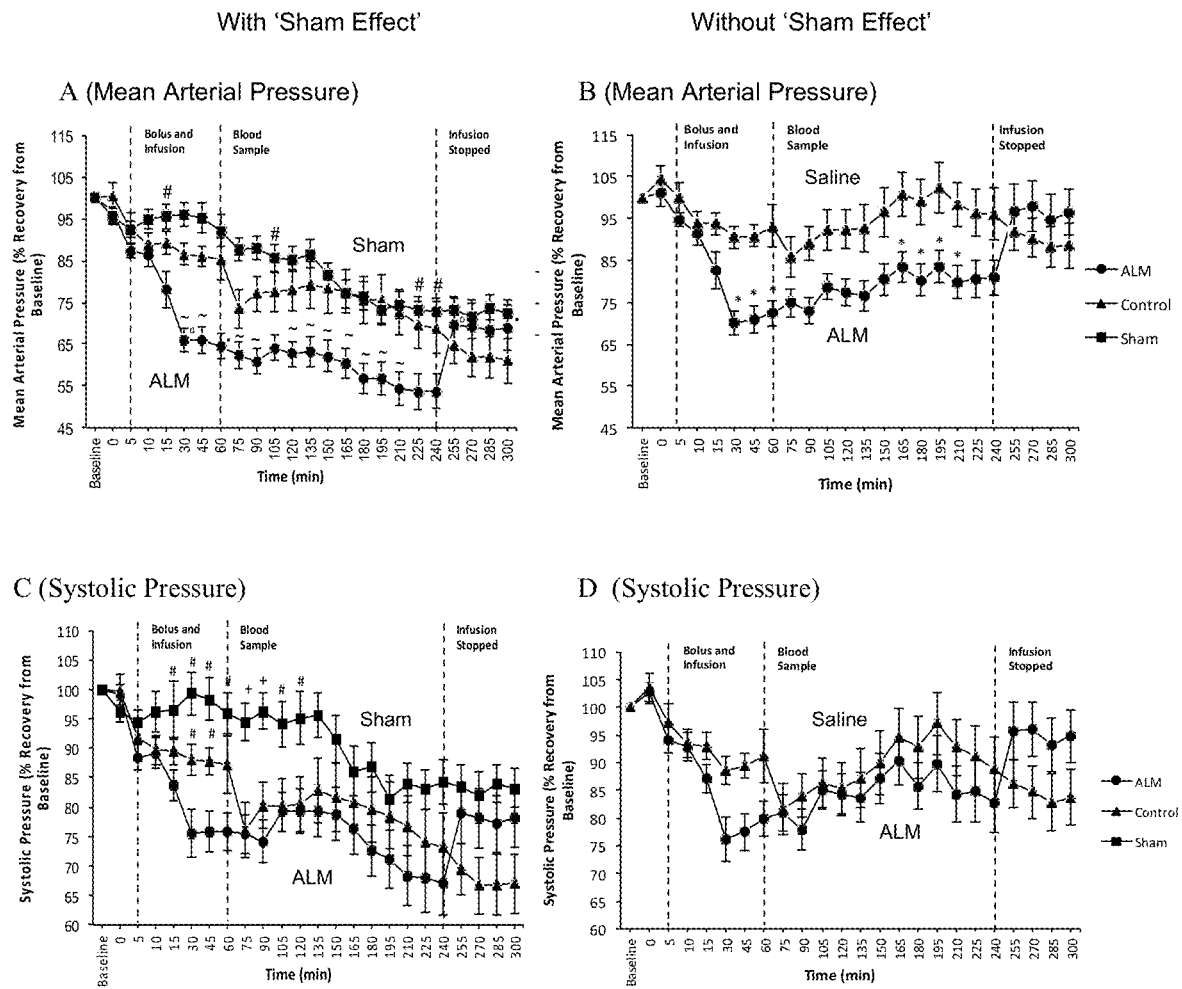
FIG. 42 shows graphs showing the effect of 0.9% NaCl ALM on the MAP (A) and without the effect of shams (B); SAP (C) and without the effect of shams (D) during 5 hours of CLP in a rat model of polymicrobial sepsis.
Figure 43:
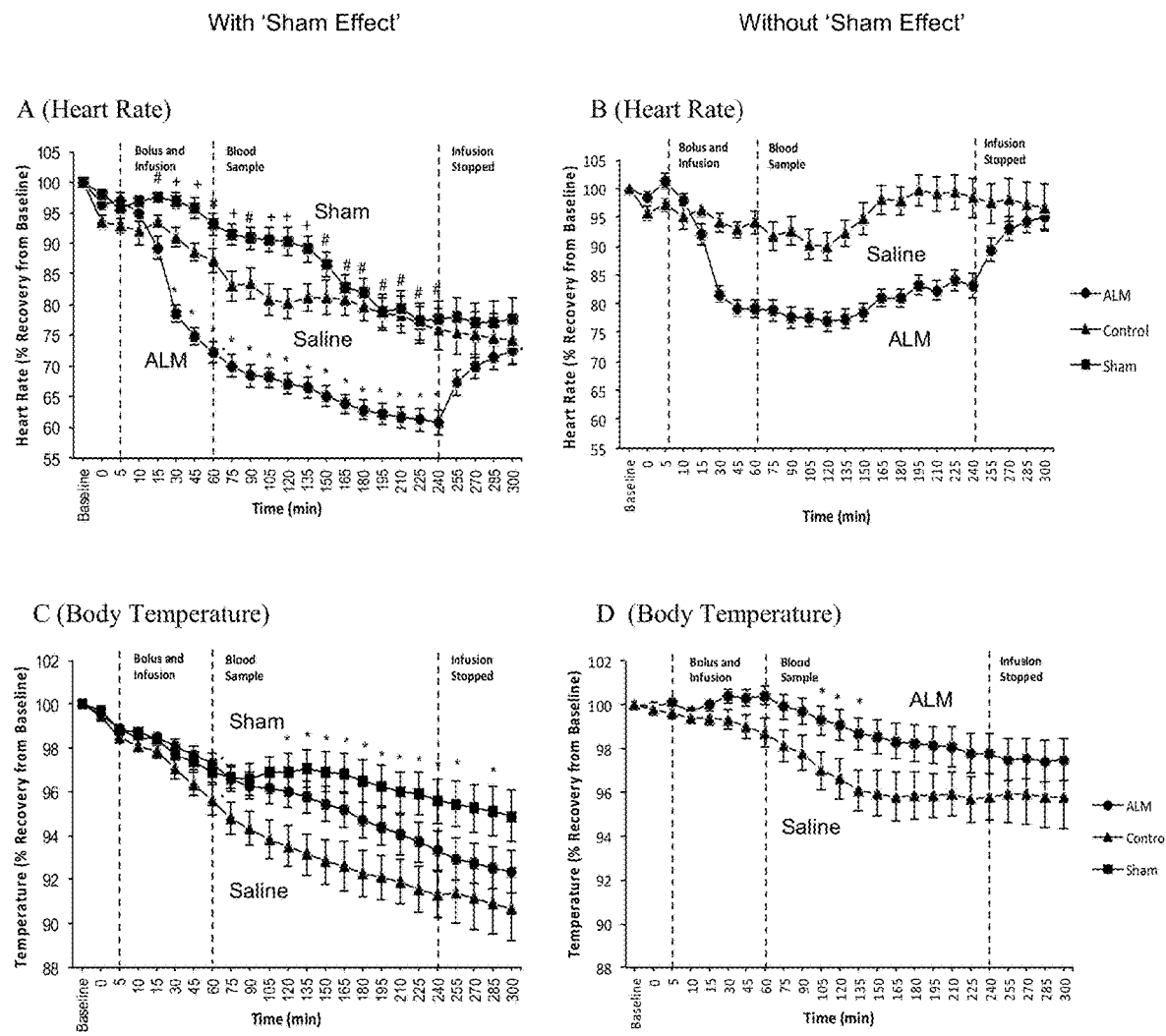
FIG. 43 shows graphs showing the effect of 0.9% NaCl ALM treatment on HR (A) and without the effect of shams (B). Rectal temperature (C) and without the effect of shams (D) during 5 hours of CLP in a rat model of polymicrobial sepsis.

Hemodynamics and temperature at baseline were not significantly different among the groups (FIG. 41 and; FIGS. 42 and 43). MAP in the sham, control, and ALM rats fell by approximately 10% from baseline before bolus administration (FIG. 42A). After the bolus administration, no changes in MAP occurred in the shams during the next 60 minutes, whereas it decreased by 85% of the baseline in the controls (non-significant). After 135 minutes, MAP in the shams slowly decreased and reached 72% of the baseline at 240 minutes. Saline controls also decreased slowly to 68% of the baseline at 240 minutes (FIG. 41 and FIG. 42A). After stopping the infusion, no further change in MAP of the shams occurred. MAP in the controls, however, continued to fall (from 68 mm Hg to 61 mm Hg) (FIG. 41 and, FIG. 42A). Sham systolic and diastolic pressures at 240 minutes fell to 84% and 66% of the baseline, respectively, and control systolic and diastolic pressures fell to 74% and 66%, respectively (FIG. 42B, and FIG. 41). At 60 minutes, as a blood sample was withdrawn, control MAP and SAP fell rapidly for 15 minutes then slowly recovered (FIGS. 42A and C). With the sham effect subtracted, saline controls defended their MAP within 15% of the baseline (FIG. 42B). FIG. 42D shows the effect of shams removed from SAP in the controls. During 30 minutes of ALM infusion, MAP fell rapidly and was significantly lower than that of the controls and shams, and when the infusion was removed, it immediately rebounded from 59 mm Hg to 77 mm Hg (FIG. 41 and, FIGS. 42A and B). ALM rats recovered 69% MAP, 78% SAP, and 63% DAP at 300 minutes. The ALM fall in DAP at 30 minutes was significantly lower than that of the controls and shams.

Incidence and Duration of Ventricular Arrhythmias

Seventy-five percent of the shams and saline controls experienced arrhythmias (Table 25). The number of arrhythmias in saline controls was nearly ninefold higher than that of the shams, and they had 13 times longer durations. In contrast, ALM-treated rats experienced no arrhythmias, which was significantly different from the shams and controls (Table 25).

Change in HR

HR in the sham animals was stable in the first 45 minutes, then decreased by 5%, and was 80% of the baseline at 240 minutes (FIG. 41, and FIGS. 43A and B). HRs in the saline controls were consistently lower than the shams (FIG. 43A). In contrast, HR in the ALM-treated rats fell to 70% of the baseline at 60-minute infusion and continued to decrease during the infusion period, then immediately rebounded after the stopping the infusion. FIG. 43B shows that HR in ALM rats after sham subtraction was consistently lower (approximately 15%) than that of the controls during the 240-minute infusion period.

Change in BT

BT in the sham animals fell by 3% in the first hour, stabilized during the next 2 hours, then progressively decreased to 95% of the baseline at 20 minutes (33.8-C) (FIG. 41 and, FIG. 43C).

ALM treatment tracked the sham changes in the first 60 minutes then slowly decreased after 90 minutes. In contrast, the saline controls had significantly lower than that of the shams after 60 minutes of infusion. BTs for the shams, controls, and ALM treatments at 240 minutes were 34-C, 32.3-C (p<0.05 from shams), and 33.6-C, respectively (FIG. 41 and, FIGS. 43C and D). With sham BT subtracted, the rate of decrease in ALM rats' temperature after 100 minutes was 0.005-C/min or half of the rate of the controls for 150 minutes and then both stabilized after the infusion was stopped (FIG. 43D).

Lung Water Content

Lung wet weight: dry weight ratios for the ALM and sham groups were 4.85 t 0.07 and 4.56 t 0.13, respectively. The controls had a significantly higher wet-dry ratio of 5.43 t 0.11 compared with the sham and ALM groups.

PT and aPTT

Figure 44:
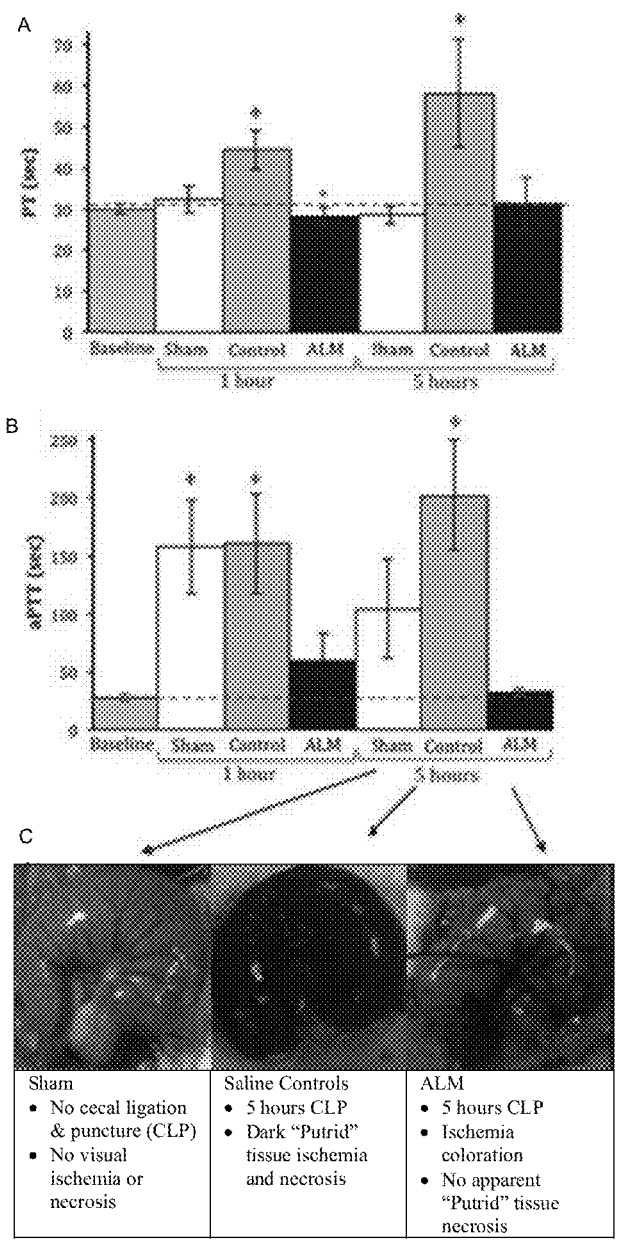
FIG. 44 shows graphs and photographs showing the effect of 0.9% NaCl ALM treatment on plasma clotting times at baseline, 1 hour, and 5 hours following CLP (n=8 each). PT (A), aPTT (B), and representative photographs (C) of gross pathophysiologic examinations of the cecum in the shams, saline controls, and ALM-treated rats after 5 hours.

Baseline PT was 29.9 t 0.5 seconds (n=8) and similar to published values of 27 t 0.4 seconds (n=23). PTs at 1 hour in the sham, control, and ALM groups were 32 t 3 seconds, 44 t 5 seconds (p<0.05), and 28 t 2 seconds and at 5 hours were 29 t 2 seconds, 58 t 13 seconds (p<0.05), and 31 t 6 seconds, respectively (FIG. 44A). Baseline aPTT was 27.5 t 3.4 seconds (n=8). aPTTs at 1 hour in the sham, control, and ALM groups were 158 t 41 seconds, 161 t 43 seconds, and 60t23 seconds (p<0.05) and at 5 hours were 104 t 43 seconds, 202 t 48 seconds, and 3 t 3 seconds (p<0.05), respectively (FIG. 44B).

Discussion

Despite significant advances in medical care, severe infection and septic shock remain a major global unmet need.

In rats with CLP, ALM bolus/infusion induced a rapid hypotensive state with no arrhythmias and an immediate hemodynamic rebound after 4 hours. The ALM-treated rats also had significantly lower pulmonary edema, near-normal BTs, and prevention or correction of coagulopathy compared with the controls.

Separating the Trauma of Surgery From Infection

Sham animals did not receive CLP yet showed progressive falls in MAP, HR, and BT as well as a prolongation of aPTT (Table 1) These changes must therefore be related to the perioperative trauma. Clinically, a laparotomy is classified as a major surgery, and incision-related trauma is known to prime and activate local and peritoneal monocytes/macrophages and neutrophils, which can lead to a systemic inflammatory response and coagulopathy. The fall in BT was probably related to the Thiobarb anesthesia as barbiturates inhibit brain activity and decrease BT in rats.

ALM-Induced Reversible Hypotension

In contrast to the controls, ALM induced a rapid, reversible hypotensive state, with a 15% to 25% fall in SAP and a 20% to 35% fall in DAP (FIG. 41 and, FIG. 42A-D), and this was similar to that reported in the porcine model of LPS-endotoxin infusion. In pigs. ALM-induced hypotension was accompanied by a higher cardiac output, a lower systemic vascular resistance, a higher tissue 02 delivery, a lower mean pulmonary arterial pressure, a higher ventricular-arterial coupling efficiency, and a lower whole body 02 consumption compared with the saline controls. The higher cardiac output in ALM pigs was associated with 66% lower end systolic pressures, 30% lower $dp/dT_{max}$, twofold higher $dp/dT_{min}$, and 1.5 times higher preload recruitable stroke work compared with the saline controls, indicating improved diastolic and systolic function.

However, unlike HR in the pig, which was maintained over 5 hours, this study showed a close coupling between the fall in MAP and HR over 4 hours (FIGS. 42B and 43B). Since MAP=HR×stroke volume (SV)×total peripheral resistance (TPR), the close coupling in our rat model implies an ALM-induced hypotension control of HR with very minimal change to SV or TPR, whereas in the pig, it was shown that TPR played a more dominant role.

Another interesting finding in our study was a rapid 10% fall in MAP and 20% fall in SAP in controls at 60 minutes to 75 minutes when 1.2-mL blood (approximately 5% blood volume for the 350-g rat) was withdrawn for coagulation assessment (FIGS. 42B and D). Since the HR fall contributed to 30% of the fall in MAP (FIG. 43B), the other 70% must have come from either a fall in SV or TPR or a combination of both. This rapid fall in MAP suggests that blood pressure in the controls was not as tightly regulated as the ALM-treated rats and may be caused by an infection-related loss of arterial baroreceptor reflex sensitivity and lower HR variability. A loss of barosensitivity would be consistent with previous studies which showed an impairment of autonomic control of heart function and TPR in rats during polymicrobial sepsis. Baroreceptor impairment in controls may also be responsible for the lack of rebound of MAP (and HR) after the drug infusions were stopped at 240 minutes (FIGS. 42 and 43A and B).

ALM Bolus/Infusion Prevented Ventricular Arrhythmias

This study found that 75% of the sham rats and 75% of the saline controls experienced arrhythmias. However, the saline controls had nine times the number of arrhythmias as the shams and 13 times longer durations (Table 25). In contrast, the ALM-treated rats showed no arrhythmias. The absence of arrhythmias in the ALM rats has been reported before in a number of other trauma models including (1) 30-minute regional myocardial ischemia, (2) small-volume resuscitation after 8-minute asphyxial cardiac arrest, and (3) after severe-to-catastrophic blood loss and shock. The underlying mechanisms for the antiarrhythmic effects of ALM are not known but may be related to the drug's energy demand-lowering effects, anti-inflammatory properties, and/or absence of triangulation of repolarization of ventricular action potential.

ALM Reduced Pulmonary Edema

ALM infusion was also associated with significantly reduced pulmonary edema compared with the controls (4.85 t0.07 vs. 5.43 t 0.11). Acute pulmonary edema results from fluid redistribution and alveolar respiratory distress. Given the short time frame of our study and nonfailing hemodymamics in the controls, the higher lung water content probably arose from an inflammatory, not a cardiogenic, etiology. In 2013, we also reported that ALM infusion led to a significantly lower wet-dry ratio in the upper and lower lobes in the pig model of LPS endotoxemia, a higher $Pao_2/FIo_2$, a lower alveolar-arterial oxygen difference, less neutrophil infiltration, and significantly lower mean pulmonary artery pressures compared with the saline controls.

ALM Defended Higher BTs than Saline Controls

Taking into consideration the sham effects, there was a 2.5% temperature drop in ALM-treated rats and 4.2% fall in the saline controls over the 300 minutes. ALM rats defended BT at significantly higher values at a number of time points (FIGS. 43C and D), and this was suggestive of the subtle differences in the ability of ALM to regulate normal temperature through a different hypothalamic response (or vasoconstriction) to CLP. While fever is a common clinical symptom of patients with infection, approximately 10% of patients do present with hypothermia, with a twofold increase in mortality.

ALM Prevented Coagulopathy at 1 Hour and 5 Hours

Based on laboratory studies, blood coagulation is arbitrarily divided into the extrinsic, intrinsic, and common pathways.

The extrinsic pathway is believed to be the most important to initiate the clot formation, and the intrinsic pathway is involved more with the elongation and life history of the clot. Four standout results were as follows: (1) shams' aPTT (but not PT) was significantly higher than baseline after 1 hour and 5 hours; (2) saline controls' aPTT and PT were significantly higher at both time points; and (3) ALM prevented PT from changing at 1 hour and 5 hours (FIG. 44A) and reduced the rise of aPTT at 1 hour (40% of the controls) and fully corrected it at 5 hours (FIG. 44B). Gross pathology of the ligated isolated ceca following the experiment showed putrid tissue necrosis with surface blood vessel thrombosis in the controls compared with the ALM-treated rats, with no evidence of injury in the shams (FIG. 44C).

Since shams did not undergo CLP, the sixfold increase in aPTT from baseline must be related to the surgical preparation, not infection (FIG. 44A). The increase in aPTT was identical to the saline controls at 1 hour, and this hypocoagulopathy in the shams was partially corrected by 60% at 5 hours, whereas the aPTT in the saline controls continued to rise (FIGS. 44A and B). The high aPTT and intrinsic pathway activation in both the shams and the saline controls therefore were caused by the trauma of surgery, which may be linked to the hyperacute phase of inflammation after the first incision. We also found that in the shams, the PT or extrinsic pathway was not activated. However, in the saline controls, PT increased presumably from the early effect of the infection and was 60 seconds at 5 hours (FIG. 44A). Thus, in the saline controls, the early effect of infection was to increase PT but not aPTT at 1 hour.

Of potential clinical interest, ALM prevented an infection-related activation of the extrinsic pathway (PT) (FIG. 44A), partially corrected a trauma-induced aPTT at 1 hour (by 53%), and fully corrected it at 5 hours (FIG. 44B). In the controls, it is not known if the infection-related hypocoagulopathy involved consumption of coagulation factors from disseminated intravascular coagulation, fibrinogen depletion, or tissue hypoxia-linked activation of the protein C pathways.

Conclusion

We conclude that an ALM bolus/infusion in the rat CLP model induces a stable, hypotensive hemodynamic state with no arrhythmias, significantly less pulmonary edema, and a higher BT and prevents or corrects coagulopathy compared with controls

REFERENCES

Kruger, T., Weigand, E., Hoffmann, I., Blettner, M., Aebert, H., 2011. Cerebral Protection During Surgery for Acute Aortic Dissection Type A Results of the German Registry for Acute Aortic Dissection Type A (GERAADA). Circulation 124, 434-443.

Malhotra, S. P., Hanley, F. L., 2008. Routine Continuous Perfusion for Aortic Arch Reconstruction in the Neonate. Semin Thorac Cardiovasc Surg Pediatr Card Surg Ann 11, 57-60.

Misfield, M., Leontyev, S., Borger, M. A., Gindensperger, O., Lehmann, S., Legare, J. F., Mohr, F. W., 2012. What is the best strategy for brain protection in patients undergoing aortic arch surgery? A single centre experience of 636 patients. Ann Thorac Surg. 93, 1502-1508.

Paxton, E. S., Backus, J., Keener, J., Brophy, R. H., 2013. Shoulder arthroscopy: basic principles of positioning, anaesthesia, and portal anatomy. J Am Acad Orthop Surg. 21, 332-342.

Singh, K., Anderson, E., Harper, J. G., 2011. Overview and management of sternal wound infection. Semin Plast Surg. 25, 25-33.

Tantry, T. P., Muralishankar, B., Adappa K. K., Bhandary, S., Shetty, P., Shenoy, S. P., 2013 Target-controlled infusion (Propofol) versus inhaled anaesthetic (Sevoflurane) in patients undergoing shoulder arthroscopic surgery. Indian J Anaesth. 57 35-40.

Sundelacruz, S., Levin, M., Kaplan, D. L., 2009. Role of Membrane Potential in the Regulation 10 of Cell Proliferation and Differentiation. Stem Cell Rev and Rep 5, 231-246.

Dobson, G. P., and Jones, M. W., 2004. Adenosine and Lignocaine: a new concept in nondepolarising surgical arrest, protection and preservation. J. Thoracic Cardiovas Surgery 127, 794-805.

The invention claimed is:

1. A method of increasing blood pressure in a subject that has suffered a life threatening hypotension comprising the administration of a composition comprising (i) 0.1 to 50 mM of adenosine; 0.1 to 80 mM of lidocaine; (iii) 0.1 to 20 mM of a citrate; and (iv) 0.1 to 2000 mM of a source of magnesium to the subject.

2. A method according to claim 1, in which the citrate is selected from the group consisting of citrate phosphate dextrose (CPD), magnesium citrate, sodium citrate, potassium citrate and sildenafil citrate.

3. A method according to claim 1, wherein the composition further comprises an anti-inflammatory agent.

4. A method according to claim 1, wherein the composition further comprises 0.9 to 3% of an ionic solution.

5. A method according to claim 1, in which components (i), (ii), (iii) and (iv) are administered in one shot as a bolus or in two steps as a bolus followed by infusion.

6. A method according to claim 1, in which the life threatening hypotension or shock suffered by the patient is hemorrhagic shock.

\* \* \* \* \*